US011365263B2

(12) United States Patent
Maderna et al.

(10) Patent No.: US 11,365,263 B2
(45) Date of Patent: Jun. 21, 2022

(54) BIFUNCTIONAL CYTOTOXIC AGENTS CONTAINING THE CTI PHARMACOPHORE

(71) Applicant: PFIZER INC., New York, NY (US)

(72) Inventors: Andreas Maderna, San Diego, CA (US); Chakrapani Subramanyam, South Glastonbury, CT (US); Lawrence N. Tumey, Pawcatuck, CT (US); Zecheng Chen, New City, NY (US); Jeffrey M. Casavant, Franklin, CT (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 17/091,097

(22) Filed: Nov. 6, 2020

(65) Prior Publication Data

US 2021/0061923 A1 Mar. 4, 2021

Related U.S. Application Data

(62) Division of application No. 15/070,549, filed on Mar. 15, 2016, now Pat. No. 10,870,706.

(60) Provisional application No. 62/308,242, filed on Mar. 15, 2016, provisional application No. 62/138,505, filed on Mar. 26, 2015, provisional application No. 62/136,223, filed on Mar. 20, 2015.

(51) Int. Cl.
| | |
|---|---|
| *C07K 16/32* | (2006.01) |
| *C07D 519/00* | (2006.01) |
| *C07F 9/6561* | (2006.01) |
| *C07K 5/062* | (2006.01) |
| *C07K 5/09* | (2006.01) |
| *C07B 59/00* | (2006.01) |
| *C07K 16/28* | (2006.01) |
| *C07D 495/04* | (2006.01) |
| *A61K 47/68* | (2017.01) |
| *A61K 47/65* | (2017.01) |

(52) U.S. Cl.
CPC .............. *C07K 16/32* (2013.01); *A61K 47/65* (2017.08); *A61K 47/6803* (2017.08); *A61K 47/6807* (2017.08); *A61K 47/6849* (2017.08); *A61K 47/6863* (2017.08); *A61K 47/6865* (2017.08); *A61K 47/6869* (2017.08); *A61K 47/6871* (2017.08); *C07B 59/002* (2013.01); *C07D 495/04* (2013.01); *C07D 519/00* (2013.01); *C07F 9/6561* (2013.01); *C07K 5/06052* (2013.01); *C07K 5/0815* (2013.01); *C07K 16/2803* (2013.01); *C07K 16/2866* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,225,539 A | 7/1993 | Winter | |
| 5,545,806 A | 8/1996 | Lonberg et al. | |
| 5,569,825 A | 10/1996 | Lonberg et al. | |
| 5,585,089 A | 12/1996 | Queen et al. | |
| 5,591,828 A | 1/1997 | Bosslet et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 2006/0205670 A1 | 9/2006 | Bradshaw et al. | |
| 2009/0118349 A1 | 5/2009 | Szekely et al. | |
| 2015/0209445 A1 | 7/2015 | Maderna et al. | |

FOREIGN PATENT DOCUMENTS

| | | |
|---|---|---|
| DE | 102009051799 A1 | 5/2011 |
| EP | 0359454 A1 | 3/1990 |
| EP | 0404097 A2 | 6/1990 |
| GB | 2344818 A | 6/2000 |
| WO | 8601533 A1 | 3/1986 |
| WO | 8702671 A1 | 5/1987 |
| WO | 9311161 A1 | 6/1993 |
| WO | 9734631 A1 | 9/1997 |
| WO | 2005037992 A2 | 4/2005 |
| WO | 2007038658 A2 | 4/2007 |
| WO | 2010062171 A2 | 6/2010 |
| WO | 2011054837 A2 | 5/2011 |
| WO | 2012059882 A2 | 5/2012 |

(Continued)

OTHER PUBLICATIONS

Muratake et al., "Preparation of Benzene, Furan, and Thiophene Analogs of Duocarmycin SA Employing a Newly-Devised Phenol-Forming Reaction", Chem. Pharm. Bull. 48(10), 1558-1566, 2000.
Schwartz, et al., "A phase I study of bizelesin, a highly potent and selective DNA-interactive agent, in patients with advanced solid malignancies", Annals of Oncology 14, 775-782, 2003.
International Search Report and the Written Opinion of the International Searching Authority, PCT/IB2016/051465.
Better, "*Escherichia coli* Secretion of an Active Chimeric Antibody Fragment", Science, 1988, 240, 1041-1043.
Boger, "Bifunctional Alkylating Agents Derived from Duocarmycin SA: Potent Antitumor Activity with Altered Sequence Selectivity", Bioorganic & Medicinal Chemistry Letters, 2000, 10, 495-498.

(Continued)

*Primary Examiner* — Po-Chih Chen
(74) *Attorney, Agent, or Firm* — Pfizer Inc.

(57) ABSTRACT

The present invention is directed to novel bifunctional CTI-CTI and CBI-CTI dimers of the formula:

$$F^1-L^1-T-L^2-F^2$$

where $F^1$, $L^1$, T, $L^2$ and $F^2$ are as defined herein, useful for the treatment for proliferative diseases, where the inventive dimers can function as stand-alone drugs, payloads in antibody-drug-conjugates (ADCs), and linker-payload compounds useful in connection with the production or administration of such ADCs; and to compositions including the aforementioned dimers, linker-payloads and ADCs, and methods for using these dimers, linker-payloads and ADCs, to treat pathological conditions including cancer.

4 Claims, No Drawings

(56) References Cited

FOREIGN PATENT DOCUMENTS

| WO | 2012162482 A1 | 11/2012 |
| --- | --- | --- |
| WO | 2013041606 A1 | 3/2013 |
| WO | 2013068946 A2 | 5/2013 |
| WO | 2013093809 A1 | 6/2013 |
| WO | 2013149946 A1 | 10/2013 |
| WO | 2013149948 A1 | 10/2013 |
| WO | 2014014478 A1 | 1/2014 |
| WO | 2015023355 A1 | 2/2015 |

OTHER PUBLICATIONS

Brulikova, "DNA Interstrand Cross-Linking Agents and their Chemotherapeutic Potential", Current Medicinal Chemistry, 2012, 19, 364-385.

Ding, "DNA interstrand cross-linking, DNA sequence specificity, and induced conformational changes produced by a dimeric analog of (+)-CC-1065", Anti-Cancer Drug Design, 1991, 6, 427-452.

Ghosh, "Chemical and Biological Explorations of the Family of CC-1065 and the Duocarmycin Natural Products", Current Topics in Medicinal Chemistry, 2009, 9, 1494-1524.

Holliger, ""Diabodies": Small bivalent and bispecific antibody fragments", Proc. Natl. Acad. Sci., USA, 1993, 90, 3444-6448.

Hoogenboom, "By-passing Immunisation Human Antibodies from Synthetic Repertoires of Germline VH Gene Segments Rearranged in Vitro", J Mol. Biol., 1992, 227, 381-388.

Jespers, "Guiding the Selection of Human Antibodies from Phage Display Repertoires to a Single Epitope of an Antigen", Bio/Technology, 1994, 12, 899-903.

Jia, "Design, Synthesis and Cytotoxicity Evaluation of 1-Chloromethyl-5-hydroxy-1,2-dihydro-3H-benz[e]indole (seco-CBI) Dimers", Bioorganic & Medicinal Chemistry, 2000, 8, 1607-1617.

Jones, "Replacing the complementarity-determining regions in a human antibody with those from a mouse", Nature, 1986, 321, 522-525.

Kabat, "Origins of antibody complementarity and specificity-hypervariable regions and minigene hypothesis". Journal of Immunology, 1980, 125, 961-969.

Kleemann, "Renin Inhibitory Pentals Showing Improved Enteral Bioavailability", J. Med. Chem., 1992, 35, 559-567.

Kozbor, "The production of monoclonal antibodies from human lymphocytes", Immunology Today, 1983, 4, 3, 72-79.

Laguzza, "New Antitumor Monoclonal Antibody-Vinca Conjugates LY 203725 and Related Compounds: Design, Preparation, and Representative in Vivo Activity", J. Med. Chem., 1989, 32, 548-555.

Lajiness, "Design, Synthesis, and Evaluation of Duocarmycin O-Amino Phenol Prodrugs Subject to Tunable Reductive Activation", J. Med. Chem., 2010, 53, 7731-7738.

Langer, "New Methods of Drug Delivery", Science, 1990, 249, 1527-1533.

Lee, "Nucleotide Preferences for DNA Interstrand Cross-Linking Induced by the Cyclopropylpyrroloindole Analogue U-77,779", Biochemistry, 1993, 32, 2592-2600.

Lee, "DNA Interstrand Cross-Links Induced by the Cyclopropylpyrroloindole Antitumor Agent Bizelesin Are Reversible upon Exposure to Alkali", Biochemistry, 1993, 32, 9108-9114.

Lee, "Mapping of DNA Alkylation Sites Induced by Adozelesin and Bizelesin in Human Cells by Ligation-Mediated Polymerase Chain Reaction", Biochemistry, 1994, 33, 6024-6030.

Lee, "Replacement of the Bizelesin Ureadiyl Linkage by a Guanidinium Moiety Retards Translocation from Monoalkylation to Coss-Linking Sites on DNA", J. Am. Chem. Soc., 1997, 119, 3434-3442.

Liu, "Production of a mouse-human chimeric monoclonal antibody to CD20 with potent Fc-dependent biologic activity". J. Immunol, 1987, 139, 3521-3526.

Liu, "Chimeric mouse-human IgG1 antibody that can mediate lysis of cancer cells". Proc. Natl. Acad. Sci., 1987, 84, 3439-3443.

Lonberg, "Human Antibodies from Transgenic Mice", Intern. Rev. Immunol., 1995, 13, 65-93.

Macmillian, "Fundamental Relationships between Structure, Reactivity, and Biological Activity for the Duocarmycins and CC-1065". J. Med. Chem., 2009, 52, 5771-5780.

Marks, "By-passing Immunization. Human Antibodies from V-gene Libraries Displayed on Phage". J. Mol. Biol., 1991, 222, 581-597.

Mitchell, "Interstrand DNA Cross-linking with Dimers of the Spirocyclopropyl Alkylating Moiety of CC-1065". J. Am. Chem. Soc , 1989, 111, 6428-6429.

Mitchell, "Synthesis and DNA Cross-Linking by a Rigid CPI Dimer". J. Am. Chem. Soc., 1991, 113, 8994-8995.

Morrison, "Transfectomas Provide Novel Chimeric Antibodies". Science, 1985, 229, 1202-1207.

Nishimura, "Recombinant Human-Mouse Chimeric Antibody Specific for Common Acute Lymphocytic Leukemia Antigen". Cancer Research, 1987, 47, 999-1005.

Oi, "Chimeric Antibodies". BioTechniques, 1986, 4, 3, 214-221.

Olsson, "Human-Human Monoclonal Antibody-Producing Hybridomas: Technical Aspects". Methods in Enzymology, 1982, 92, 3-16.

Pitot, "A Phase I Study of Bizelesin (NSC 615291) in Patents with Advanced Solid Tumors". Clinical Cancer Research, 2002, 8, 712-717.

Presta, "Antibody Engineering". Current Opinion in Structural Biology, 1992, 2, 593-596.

Rahman, "Effect of base sequence on the DNA cross-linking properties of pyrrolobenzodiazepine (PBD) dimers". Nucleic Acids Research, 2011, 39, 13, 5800-5812.

Riechmann, "Reshaping human antibodies for therapy". Nature, 1988, 332, 323-327.

Schwartz, "A phase I study of bizelesin, a highly potent and selective DNA-interactive agent, in patients with advanced solid malignancies".

Shaw, "Mouse/Human Chimeric Antibodies to a Tumor-Associated Antigen: Biologic Activity of the Four Human IgG Sublasses". Journal of the National Cancer Institute, 1988, 80, 19, 1553-1559.

Smellie, "Sequence-Selective Recognition of Duplex DNA through Covalent Interstrand Cross-Linking: Kinetic and Molecular Modeling Studies with Pyrrolobenzodiazepine Dimers". Biochemistry, 2003, 42, 8232-8239.

Sun, "Analysis of the Monoalkylation and Cross-Linking Sequence Specificity of Bizelesin, a Bifunctional Alkylation Agent Related to (+)-CC-1065". J. Am Chem. Soc , 1993, 115, 5925-5933.

Sun, "Chimeric antibody with human constant regions and mouse variable regions directed against carcinoma-associated antigen 17-1A". Proc. Natl. Acad. Sci., 1987, 84, 214-218.

Teng, "Construction and testing of mouse-human heteromyelomas for human monoclonal antibody production". Proc Natl Acad Sci., 1983, 80, 7308-7312.

Thompson, "Determination of the Structural Role of the Internal Guanine-Cytosine Base Pair in Recognition of a Seven-Base-Pair Sequence Cross-Linked by Bizelesin". Biochemistry, 1995, 34, 11005-11016.

Thompson, "Solution Conformation of a Bizelesin A-tract Duplex Adduct: DNA-DNA Cross-linking of an A-tract Straightens Out Bent DNA". J. Mol. Biol., 1995, 252, 86-101.

Tichenor, "Rational Design, Synthesis, and Evaluation of Key Analogues of CC-1065 and the Duocarmycins". J. Am. Chem. Soc., 2007, 129, 14092-14099.

Verhoeyen, "Reshaping Human Antibodies: Grafting an Antilysozyme Activity". Science, 1988, 239, 1534-1536.

Walker, "Preclinical pharmacology of bizelesin, a potent bifunctional analog of the DNA-binding antibiotic CC-1065". Cancer Chemother Pharmacol, 1994, 34, 317-322.

Wood, "The synthesis and in vivo assembly of functional antibodies in yeast". Nature, 1985, 314, 446-449.

Zhao, "Synthesis and Biological Evaluation of Antibody Conjugates of Phosphate Prodrugs of Cytotoxic DNA Alkylators for the Targeted Treatment of Cancer". Journal of Medicinal Chemistry, 2012, 55, 766-782.

(56) References Cited

OTHER PUBLICATIONS

Zhou, "Design and Synthesis of a Novel DNA-DNA Interstrand Adenine-Guanine Cross-Linking Agent". J. Am. Chem. Soc., 2001, 123, 4865-4866.
Grant & Hackh's Chemical Dictionary (5th Ed. 1987) at p. 148.

BIFUNCTIONAL CYTOTOXIC AGENTS CONTAINING THE CTI PHARMACOPHORE

FIELD OF THE INVENTION

The present invention is directed to novel bifunctional CTI-CTI and CBI-CTI dimers useful for the treatment for proliferative diseases. The inventive dimers can function as stand-alone drugs, payloads in antibody-drug-conjugates (ADCs), and linker-payload compounds useful in connection with the production or administration of such ADCs. The present invention further relates to compositions including the aforementioned dimers, linker-payloads and ADCs, and methods for using these dimers, linker-payloads and ADCs, to treat pathological conditions including cancer.

BACKGROUND

Bifunctional analogs that contain two active DNA alkylation motifs (i.e. a CBI or a CPI) contain two alkylation (e.g., two CPI motifs) fused together. Due to the presence of two reactive alkylation motifs these compounds are active DNA cross linkers, whereas compounds with only one alkylation motif (e.g., duocarmycins) are DNA mono-alkylators.

A

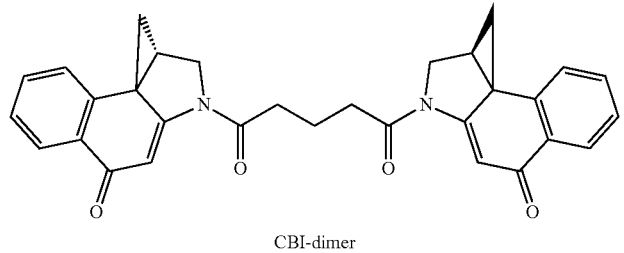

CBI-dimer

B

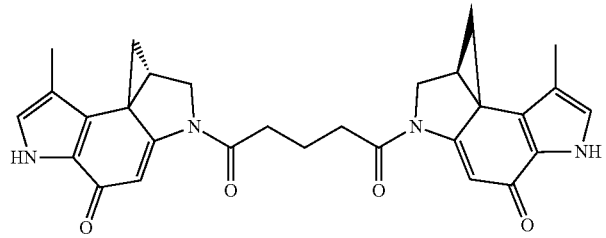

CPI-dimer

C

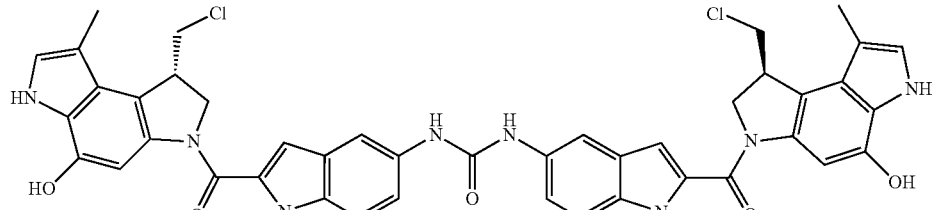

CPI-dimer (Bizelesin)

D

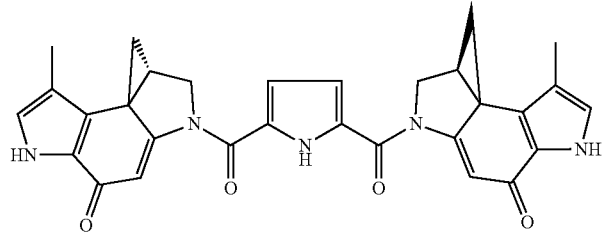

CPI-dimer

The compounds shown above are representative examples from the literature and are reported to be potent cytotoxins: A ("Glycosidic Prodrugs of Highly Potent Bifunctional Duocarmycin Derivatives for Selective Treatment of Cancer", Angew. Chem. Int. Ed. 2010, 49, 7336-7339; "Duocarmycin Analogues Target Aldehyde Dehydrogenase 1 in LungCancer Cells", Angew. Chem. Int. Ed. 2012, 51, 2874-2877; "Bifunctional prodrugs and drugs", WO 2011/054837, DE 10 2009 051 799; "The Two Faces of Potent Antitumor Duocarmycin-Based Drugs: A Structural Dissection Reveals Disparate Motifs for DNA versus Aldehyde Dehydrogenase 1 Affinity", Angew. Chem. Int. Ed. 2013, 52, 1-6; B ("Interstrand DNA Cross-linking with Dimers of the Spirocyclopropyl Alkylating Moiety of CC-1065", J. Am. Chem. SOC. 1989, 11 1, 6428-6429; "CC-1065 analogs having two CPI subunits useful as antitumor agents and ultraviolet light absorbers", Eur. Pat. Appl. (1990), EP 359454, also for compounds C and D; C ("Synthesis and DNA Cross-Linking by a Rigid CPI Dimer", J. Am. Chem. SOC. 1991, 113, 8994-8995; "Nucleotide Preferences for DNA Interstrand Cross-Linking Induced by the Cyclopropylpyrroloindole Analogue U-77,779", Biochemistry 1993, 32, 2592-2600; "Determination of the Structural Role of the Internal Guanine-Cytosine Base Pair in Recognition of a Seven-Base-Pair Sequence Cross-Linked by Bizelesin", Biochemistry 1995, 34, 11005-11016; "Analysis of the Monoalkylation and Cross-Linking Sequence Specificity of Bizelesin, a Bifunctional Alkylation AgentRelated to (+)-CC-1065", J. Am. Chem. SOC. 1993, 115, 5925-5933; "Mapping of DNA Alkylation Sites Induced by Adozelesin and Bizelesin in Human Cells by Ligation-Mediated Polymerase Chain Reaction", Biochemistry 1994, 33, 6024-6030; "DNA Interstrand Cross-Links Induced by the Cyclopropylpyrroloindole Antitumor Agent Bizelesin Are Reversible upon Exposure to Alkali", Biochemistry 1993, 32, 9108-9114; "Replacement of the Bizelesin Ureadiyl Linkage by a Guanidinium Moiety Retards Translocation from Monoalkylation to Cross-Linking Sites on DNA", J. Am. Chem. Soc. 1997, 119, 3434-3442; "DNA interstrand cross-linking, DNA sequence specificity, and induced conformational changes produced by a dimeric analog of (+)-CC-1065", Anti-Cancer Drug Design (1991), 6, 427-452; "A phase I study of bizelesin, a highly potent and selective DNAinteractive agent, in patients with advanced solid malignancies", Ann Oncol. 2003 May; 14(5):775-782; "A Phase I study of bizelesin (NSC 615291) in patients with advanced solid tumors", Clin Cancer Res. 2002, 3, 712-717; "Solution conformation of a bizelesin A-tract duplex adduct: DNA-DNA cross-linking of an A-tract straightens out bent DNA", J Mol Biol. 1995, 252, 86-101; "Preclinical pharmacology of bizelesin, a potent bifunctional analog of the DNA-binding antibiotic CC-1065", Cancer Chemother Pharmacol. 1994, 34, 317-322; and D ("CC-1065 analogs having two CPI subunits useful as antitumor agents and ultraviolet light absorbers", Eur. Pat. Appl. (1990), EP 359454. The active DNA alkylation motif can in principle exist in either a prodrug form that converts to the active drug in the biological medium, or in its active state which does not require further conversion. The prodrug-to-active drug conversion for the bifunctional cross linkers is exemplified in the CBI dimer shown below:

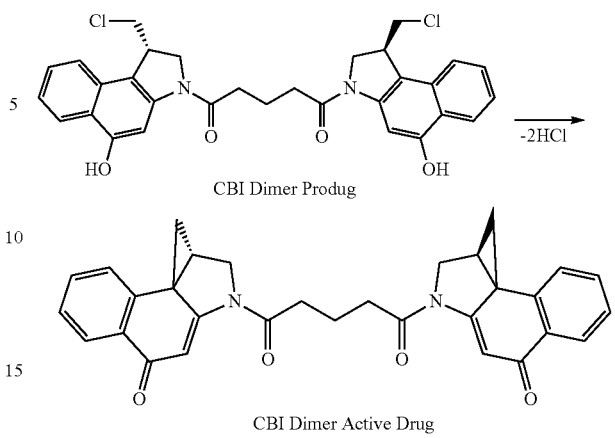

A corresponding conversion takes place for all bifunctional cross linkers that exist in their prodrug states.

Other related bifunctional cross linkers have been reported. ("Chemical and Biological Explorations of the Family of CC-1065 and the Duocarmycin Natural Products", Current Topics in Medicinal Chemistry, 2009, 9, 1494-1524; "DNA interstrand cross-linking agents and their chemotherapeutic potential", Curr Med Chem. 2012, 19, 364-385; "Design and Synthesis of a Novel DNA-DNA Interstrand Adenine-Guanine Cross-Linking Agent", J. Am. Chem. Soc. 2001, 123, 4865-4866; "Effect of base sequence on the DNA cross-linking properties of pyrrolobenzodiazepine (PBD) dimers", Nucleic Acids Res. 2011, 39, 5800-5812; "Sequence-selective recognition of duplex DNA through covalent interstrand cross-linking: kinetic and molecular modeling studies with pyrrolobenzodiazepine dimers", Biochemistry. 2003, 42, 8232-8239; "Bifunctional alkylating agents derived from duocarmycin SA: potent antitumor activity with altered sequence selectivity", Bioorg Med Chem Lett. 2000, 10, 495-498; "Design, Synthesis and Cytotoxicity Evaluation of 1-Chloromethyl-5-hydroxy-1,2-dihydro-3H-benz[e]indole (seco-CBI) Dimers", Bioorganic & Medicinal Chemistry 2000, 8, 1607-1617.

A phosphate pro-drug strategy for monomeric seco-CBI containing cytotoxins has been described by Zhao et al. ("Synthesis and biological evaluation of antibody conjugates of phosphate prodrugs of cytotoxic DNA alkylators for the targeted treatment of cancer", J. Med.

Chem. 2012, 55, 766-782) and Zhang et al. ("Immunoconjugates containing phosphate-prodrugged DNA minor groove binding agents, compositions containing them, and methods of making them and their use for treating cancer", WO 2012/162482).

Certain CBI dimers have recently been described as being useful as ADC Payloads ("I-(Chloromethyl)-2, 3-Dihydro-IH-Benzo[e]indole Dimer Antibody-Drug Conjugate Compounds, and Methods of Use and Treatment", WO2015/023355).

Conjugation of drugs to antibodies, either directly or via linkers, involves a consideration of a variety of factors, including the identity and location of the chemical group for conjugation of the drug, the mechanism of drug release, the structural elements providing drug release, and the structural modification to the released free drug. In addition, if the drug is to be released after antibody internalization, the mechanism of drug release must be consonant with the intracellular trafficking of the conjugate.

While a number of different drug classes have been tried for delivery by antibodies, only a few drug classes have proved efficacious as antibody drug conjugates while maintaining a suitable toxicity profile. One such class is the auristatins, derivatives of the natural product dolastatin 10. Representative auristatins include (N-methylvaline-valine-dolaisoleuine-dolaproine-norephedrine) and (N-methylvaline-valine-dolaisoleuine-dolaproine-phenylalanine). Other related tubulin binding agents include the maytansines (for instance see "Cell-binding agent-maytansinoid conjugates linked via a noncleavable linker, preparation methods, and methods using them for targeting specific cell populations" published as WO 2005/037992). Other cytotoxic drugs that have been employed in linkage with antibodies include DNA-binding drugs such as calicheamicin that causes sequence-specific double-stranded DNA cleavage. Another class of DNA binding cytotoxic drugs employed in ADCs includes dimeric pyrrolobenzodiazepines (for instance see "Preparation of unsymmetrical pyrrolobenzodiazepines dimers for inclusion in targeted conjugates" published as WO2013/041606). Another such class of drug where antibody delivery has been attempted is DNA binding alkylating agents, such as the duocarmycin analog CC-1065 (see "Preparation of CC-1065 analogs and their conjugates for treatment of cancer" published as WO2010/062171) and related compounds (see "Antibody-drug peptide conjugates for use as cytotoxins in cancer treatment" published as WO 2007/038658, and "Immunoconjugates containing phosphate-prodrugged DNA minor groove binding agents, compositions containing them, and methods of making them and their use for treating cancer" published as WO2012/162482). However, these drugs all have limitations relating to disease indications and treatment profile, and thus there remains a need for additional drugs with improved properties deliverable via antibody conjugation. Accordingly, the present invention provides novel ADCs with dimers as payloads.

Another heterocycle that is known to be a potent DNA alkylation motif is represented by the "CTI" group (CTI:1, 2,8,8a-tetrahydro-4H-cyclopropa[c]thieno[3,2-e]indol-4-one, "Fundamental relationships between structure, reactivity, and biological activity for the duocarmycins and CC-1065", J. Med. Chem. 2009, 52(19), 5771-5780, "Rational Design, Synthesis, and Evaluation of Key Analogues of CC-1065 and the Duocarmycins", J. AM. CHEM. SOC. 2007, 129, 14092-14099). CTI containing duocarmycin monomers have been described as ADC payloads ("Synthesis of functionalized thieno-indole derivs. optionally containing a peptidic residue for the treatment of cancer and their use in the preparation of conjugates", WO 2013/149946, "Preparation of new functionalized alkylating agents containing a thieno-indole moiety linked to a DNA-binding moiety for treating cancers and their use in the prepn. of conjugates", WO 2013/149948). The structural differences between "CBI", "CPI" and "CTI" are depicted in the following drawing:

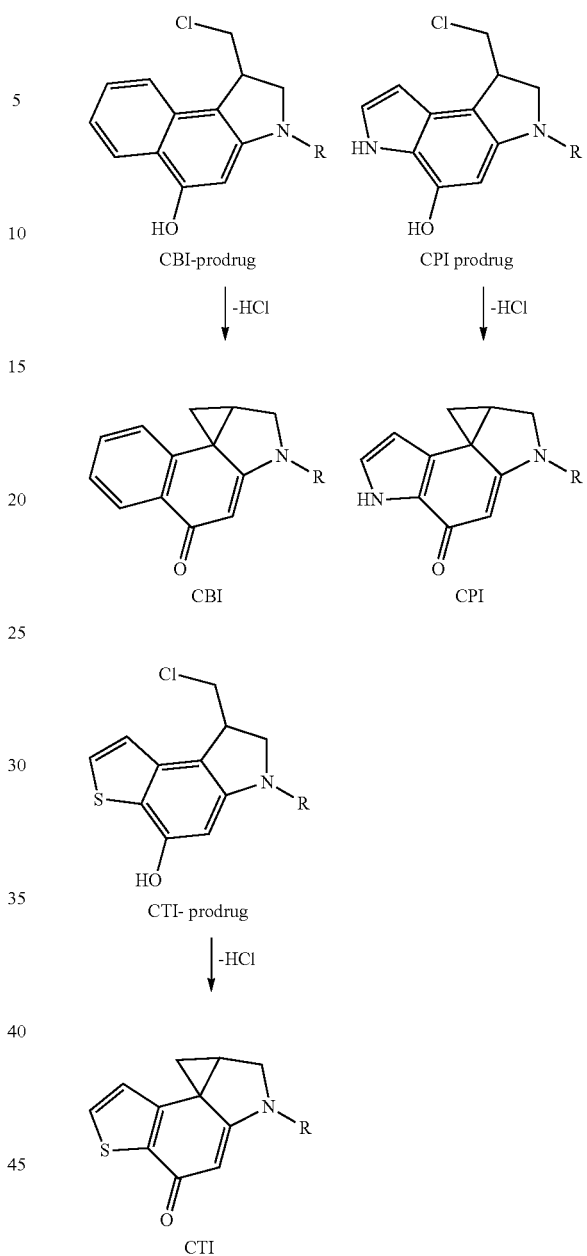

CBI, CPI and CTI's differ in the first aromatic ring with the CBI having a phenyl, the CPI a pyrrole and the CTI a thiophene heterocycle, respectively. The drawing also shows the chloride prodrugs. These prodrugs convert into the active drug in the biological medium under loss of hydrogen chloride. Therefore, both the chloride prodrug and the active cyclopropyl species need to be regarded as equivalent with respect to their biological activity. The concept of the chloride prodrugs for CBI, CPI and related groups has been well documented in the literature ("Design, Synthesis, and Evaluation of Duocarmycin O-Amino Phenol Prodrugs Subject", J. Med. Chem. 2010, 53, 7731-7738, and reference 8 therein.)

With respect to the CTI group, two structural variations are of particular interest, namely the Me-CTI and iso-Me-CTI groups shown in the following drawing:

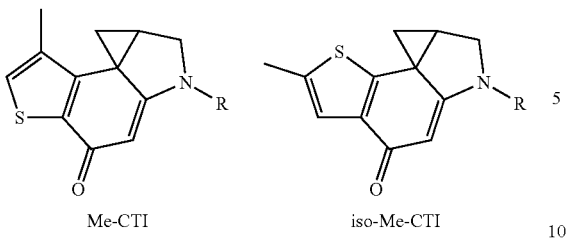

Me-CTI          iso-Me-CTI

Both Me-CTI and iso-Me-CTI groups have been described in context of duocarmycins ("Chemical and biological explorations of the family of CC-1065 and the duocarmycin natural products", Curr Top Med Chem. 2009, 9(16), 1494-1524).

SUMMARY OF THE INVENTION

The invention describes new structural dimer analogs based on the CTI motif. The invention also describes spacer elements for the corresponding CTI dimers and CBI-CTI mixed structures. The term CBI and CTI are used for both the chloride prodrug version as well as the active cyclopropyl species. In addition, linker substitution to these dimeric species are described as well as the preparation of antibody drug conjugates.

No dimers containing the CTI motif are known and the use of CTI dimers in the present invention results in significant changes in chemical reactivity and biological properties as compared to previous described dimer species. Hence, dimers prepared with CTI species represent distinctive drug entities. In this invention, we describe new dimers that contain either two CTI groups or hybrids that bear one CBI and one CTI group. Furthermore, we disclose how these dimer species are connected to suitable linker molecules for the attachment to antibodies.

More specifically, the present invention is directed to cytotoxic dimers comprising CTI/CTI-based and/or CTI/CBI-based (including seco forms of CBI and CTI, as detailed herein) dimers, to antibody drug conjugates comprising such dimers, and to methods for using the same to treat cancer and other indications. Both CTI and CBI structures can be represented by their seco form and can be substituted and derivatized as detailed herein. In addition, the phenol function in seco-forms can be derivatized with acetate groups. The phenolic acetate functions are functionally equivalent to the phenol as the acetate groups easily hydrolize to give the free phenols in biological medium.

Thus, the present invention relates to compounds and pharmaceutical compositions containing them, to their preparation, and to uses for the compounds, primarily but not exclusively anti-cancer agents. According to one aspect, the present invention relates to "payload" compound of Formula I:

$$F^1\text{-}L^1\text{-}T\text{-}L^2\text{-}F^2 \quad \text{(Formula I)}$$

or a pharmaceutically acceptable salt or solvate thereof, wherein:

$F^1$ and $F^2$ are each independently selected from ring systems A, B, C, D, E, F, G and H:

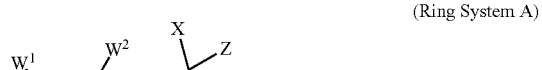
(Ring System A)

(Ring System B)

(Ring System C)

(Ring System D)

(Ring System E)

(Ring System F)

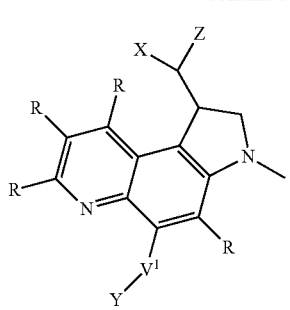
(Ring System G)

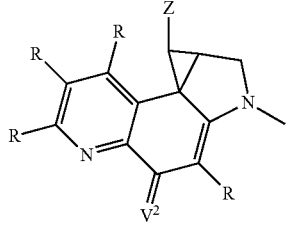
(Ring System H)

where:
at least one of the ring systems A, B, C and D is present;
each R is independently selected from the group consisting of H, —C$_1$-C$_{20}$ alkyl, —C$_2$-C$_6$ alkenyl, —C$_2$-C$_6$ alkynyl, halo, deuterium, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears;
each V$^1$ is independently a bond, O, N(R) or S, for each ring system in which V appears;
each V$^2$ is independently O, N(R) or S, for each ring system in which V$^2$ appears;
W$^1$ and W$^2$ are each independently H, —C$_5$ alkyl, -phenyl, —C(O)OR, —C(O)SR, —C(O)NHN(R)$_2$ or —C(O)N(R)$_2$ for each ring system in which W$^1$ and W$^2$ appear;
each X is independently —OH, —O-acyl, azido, halo, cyanate, thiocyanate, isocyanate, thioisocyanate, or

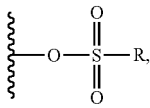

for each ring system in which X appears;
each Y is independently selected from the group consisting of H, —C$_1$-C$_6$ alkyl-R$^A$, C(O)R$^A$, —C(S)R$^A$, C(O)OR$^A$, —S(O)$_2$OR$^A$, —C(O)N(R$^A$)$_2$, —C(S)N(R$^A$)$_2$, a carbohydrate, glycosyl, —NO$_2$, —PO(OR$^A$)$_2$, an amino acid, and a peptide (for instance a peptide that is cleaved by proteases such as cathepsins and matrix metalloproteinases) for each ring system in which Y appears, wherein each R$^A$ is independently selected from the group consisting of H, —C$_1$-C$_{20}$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclyl and —C$_1$-C$_{20}$ alkylN(R)$_2$, wherein said —C$_1$-C$_{20}$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclyl and —C$_1$-C$_{20}$ alkylN(R)$_2$ are optionally substituted with 1 to 3 substitutents independently selected from R;
each Z is independently selected from the group consisting of H, —C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, —C(O)OH, —C(O)NHNH$_2$, and —C(O)-halo, and wherein said C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, —C(O)OH, —C(O)NHNH$_2$ and —C(O)-halo are each optionally substituted with 1 to 3 substituents independently selected from R, for each ring system in which Z appears;
L$^1$ and L$^2$ are each independently selected from a direct bond, carbonyl, or a carbonyl acyl group bonded to F$^1$ or F$^2$ at the acyl moiety, where the carbonyl acyl group is selected from the group consisting of:

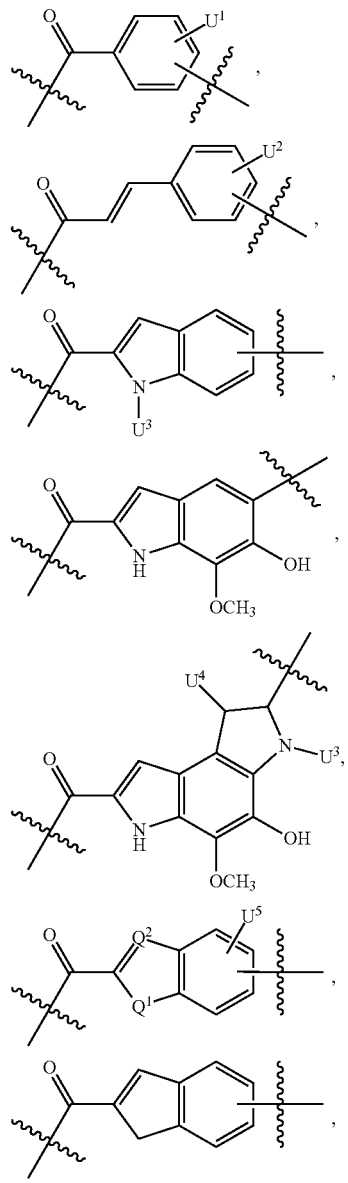

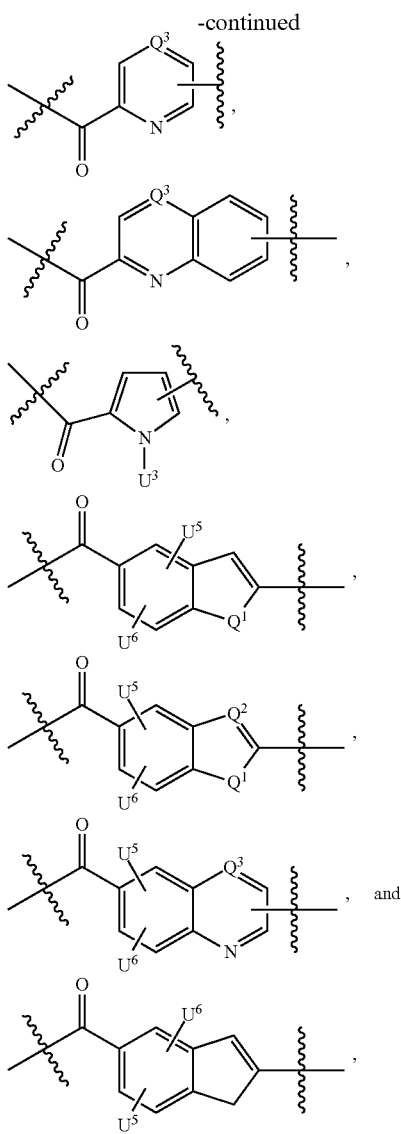

wherein
U$^1$ is selected from H, —CH$_3$, —OH, —OCH$_3$, —NO$_2$, —NH$_2$, —NHNHAc, —NHNHC(O)CH$_3$, —NHC(O)phenyl or -halo,
U$^2$ is H, —OH or —OCH$_3$,
U$^3$ is H, —CH$_3$ or —C$_2$H$_5$,
U$^4$ is H or CH$_3$S—,
U$^5$ and U$^6$ are each independently selected from H, -halo, —C$_1$-C$_4$ alkyl, —C$_1$-C$_3$ alkoxy, —C$_1$-C$_6$ dialkylamino, —NO$_2$, —NHC(O)C$_1$-C$_{10}$ alkyl, —OH, —NH$_2$, —NHC(O)NH$_2$, —NHC(O)CH$_3$ or —NHC(O)phenyl,
Q$^1$ is —O—, —S—, or —NH—, and
Q$^2$ and Q$^3$ are each independently —CH— or —N—;
T is selected from:
—NHC(O)—,
—C(O)NH—,
—C(O)O—,
—OC(O)—,
—NR$^B$-T$^1$-NR$^C$— where R$^B$ and R$^C$ are each independently H or —C$_1$-C$_8$ alkyl, or together R$^B$ and R$^C$ join to form a ring and together are (CH$_2$)$_{2-3}$, where T$^1$ is selected from the group consisting of —C(O)—, —C(O)(CH$_2$)$_n$C(O)— where n is an integer from 0 to 50 and —C(O)PhC(O)— where Ph is 1,3- or 1,4-phenylene, and where T$^1$ is optionally substituted with 1-2 R, —C(O)hetC(O)— wherein het is a mono-, bi-, or tricyclic heteroaryl of 5 to 12 members, containing one, two, or three heteroatoms independently selected from O, N, S, P and B, wherein het is optionally substituted with 1 to 8 substituents each independently selected from the group consisting of —C$_1$-C$_8$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclcl, —NH$_2$, —NHR$^D$ and —NO$_2$, and said optional substituents on het are optionally substituted with R$^E$, wherein each R$^D$ is independently selected from the group consisting of H, —C$_1$-C$_8$ alkyl, —C(O)—C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, and —C(O)-halo, optionally substituted with R$^E$, wherein each R$^E$ is independently selected from the group consisting of H, —C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, and —C(O)-halo, and wherein each R$^E$ is optionally substituted with 1 to 3 substitutents independently selected from R, —C(A$^1$)X$^1$-T$^2$-X$^1$C(B$^1$)—, where T$^2$ is:

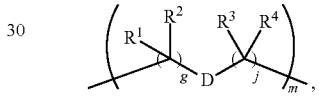

wherein each X$^1$ is independently a bond, —NR$^E$—, —O— or —S—, wherein A$^1$ and B$^1$ are each independently =O or =S, wherein R$^1$, R$^2$, R$^3$, and R$^4$ are each independently R$^E$ or R$^1$ and R$^2$ form a ring system, or R$^3$ and R$^4$ form a ring system, or both R$^1$ and R$^2$, and R$^3$ and R$^4$, each independently form ring systems, or R$^1$ and R$^3$ form a ring system, or R$^2$ and R$^4$ form a ring system, or both R$^1$ and R$^3$, and R$^2$ and R$^4$, each independently form ring systems, where said ring systems are independently selected from —C$_1$-C$_{10}$ heterocyclyl or —C$_3$-C$_8$ carbocyclcl, or R$^1$, R$^2$, R$^3$ and R$^4$ are each bonds to different carbons on D, wherein g and j are each independently an integer from 0 to 50 and m is an integer from 1 to 50, and wherein D is a bond or is selected from the group consisting of —S—, —C$_1$-C$_8$ alkylene-, —C$_6$-C$_{14}$ arylene-, —C$_6$-C$_{14}$ heteroarylene-, —C$_1$-C$_8$ heteroalkylene-, -aralkylene-, —C$_1$-C$_{10}$ heterocyclo and —C$_3$-C$_8$ carbocyclo, where said —C$_1$-C$_8$ alkylene-, —C$_6$-C$_{14}$ arylene-, —C$_6$-C$_{14}$ heteroarylene-, —C$_1$-C$_8$ heteroalkylene-, -aralkylene-, —C$_1$-C$_{10}$ heterocyclo and —C$_3$-C$_8$ carbocyclo are optionally substituted with —R$^E$, —C(O)R$^E$, —(O)OR$^E$, —N(R$^E$)$_2$, —N(R)C(O)R$^E$ or —N(R)C(O)OR$^E$, and is additionally optionally substituted by 1 to 2 R, and -G$^1$-T$^2$-G$^2$-, where G$^1$ and G$^2$ are each independently —S(O)X$^1$— or —S(O)$_2$X$^1$—.

In embodiments of the invention variable n is 0 to 50, preferably 0 to 25, preferably 0 to 10, and preferably 1-5. Preferably, variable n may be 0, 1, 2, 3, 4 or 5.

In other embodiments of the invention the variable —Y— is C(O)N(R$^A$)$_2$ or C(S)N(R$^A$)$_2$ where one R$^A$ is hydrogen or —C$_1$-C$_{20}$ alkyl and the other R$^A$ is —C$_1$-C$_{20}$ alkyl-N(R)$_2$, such that the structure:

is formed, where A is oxygen or sulphur.

As noted above, embodiments of the present invention include those where $R^1$, $R^2$, $R^3$ and $R^4$ are each bonds to different carbons on D. When D is a 6-membered carbocyclic ring (bold, below), this embodiment may take the form of a cubane:

Other forms of cubanes (for instance substituted forms as outlined herein) and non-cubanes are also possible and included within the invention.

According to another aspect of the invention there is provided a "linker-payload" compound of Formula IIA:

L-P     (Formula IIA)

or a pharmaceutically acceptable salt or solvate thereof, wherein:

P is:

$F^1$-$L^1$-T-$L^2$-$F^2$ wherein:

$F^1$ and $F^2$ are each independently selected from ring systems A, B, C, D, E, F, G and H:

(Ring System A)

(Ring System B)

(Ring System C)

(Ring System D)

(Ring System E)

(Ring System F)

(Ring System G)

(Ring System H)

where:
at least one of the ring systems A, B, C and D is present;
each R is independently selected from the group consisting of H, —$C_1$-$C_{20}$ alkyl, —$C_2$-$C_6$ alkenyl, —$C_2$-$C_6$ alkynyl, halo, deuterium, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears;

each V$^1$ is independently a bond, O, N(R) or S, for each ring system in which V$^1$ appears;

each V$^2$ is independently O, N(R) or S, for each ring system in which V$^2$ appears;

W$^1$ and W$^2$ are each independently H, —C$_1$-C$_5$ alkyl, -phenyl, —C(O)OR, —C(O)SR, —C(O)NHN(R)$_2$ or —C(O)N(R)$_2$ for each ring system in which W$^1$ and W$^2$ appear;

each X is independently selected from —OH, —O-acyl, azido, halo, cyanate, thiocyanate, isocyanate, thioisocyanate, or

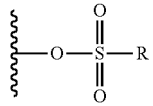

for each ring system in which X appears:

each Y is independently selected from a bond, H, —C(O)R$^A$, C(S)R$^A$, C(O)OR$^A$, —S(O)$_2$OR$^A$, —C(O)N(R$^A$)$_2$, —C(S)N(R$^A$)$_2$, a carbohydrate such as glycosyl, —NO$_2$, —P(O)(OR$^A$)$_2$, an amino acid and a peptide (in particular a peptide that is cleaved by proteases such as cathepsins and matrix metalloproteinases) for each ring system in which Y appears, wherein each R$^A$ is independently selected from H, —C$_1$-C$_{20}$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclyl, —C$_1$-C$_{20}$ alkylN(R)$_2$, —C$_1$-C$_{20}$ alkylene, —C$_1$-C$_8$ heteroalkylene, —C$_6$-C$_{14}$ arylene, aralkylene, —C$_1$-C$_{10}$ heterocyclo, —C$_3$-C$_8$ carbocyclo and —C$_1$-C$_{20}$ alkylN(R)—, and R$^F$ where said R$^A$ iso optionally substituted with 1 to 3 substituents independently selected from R, and wherein one Y is divalent and is bonded to L, R$^F$ is —N(R$^6$)QN(R$^5$)C(O)— and is bonded to L at the carbonyl adjacent N(R$^5$), wherein R$^5$ and R$^6$ are each independently selected from the group consisting of H, —C$_1$-C$_8$ alkyl, —C$_1$-C$_8$ heteroalkyl, —C$_6$-C$_{14}$ aryl, -aralkyl, —C$_1$-C$_{10}$ heterocyclyl and —C$_3$-C$_8$ carbocyclyl, or R$^5$ or R$^6$ joins with a substituted carbon on Q to form a —C$_1$-C$_{10}$ heterocyclic or —C$_6$-C$_{14}$ heteroaryl ring, or R$^5$ and R$^6$ join together to form a —C$_1$-C$_{10}$ heterocyclic or —C$_6$-C$_{14}$ heteroaryl ring system, and where Q is —C$_1$-C$_8$ alkylene-, —C$_1$-C$_8$ heteroalkylene-, —C$_6$-C$_{14}$ arylene-, -aralkylene-, —C$_1$-C$_8$ heterocyclo- or —C$_3$-C$_8$ carbocyclo-, wherein Q, R$^5$ and R$^6$ are each independently optionally substituted with 1 to 3 substituents independently selected from R;

each Z is independently selected from the group consisting of H, —C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, —C(O)OH, —C(O)NHNH$_2$ and —C(O)-halo, and wherein said C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, —C(O)OH, —C(O)NHNH$_2$ and —C(O)-halo are each optionally substituted with 1 to 3 substitutents independently selected from R, for each ring system in which Z appears;

L$^1$ and L$^2$ are each independently selected from a direct bond, carbonyl, or a carbonyl acyl group bonded to F$^1$ or F$^2$ at the acyl moiety, where the carbonyl acyl group is selected from the group consisting of:

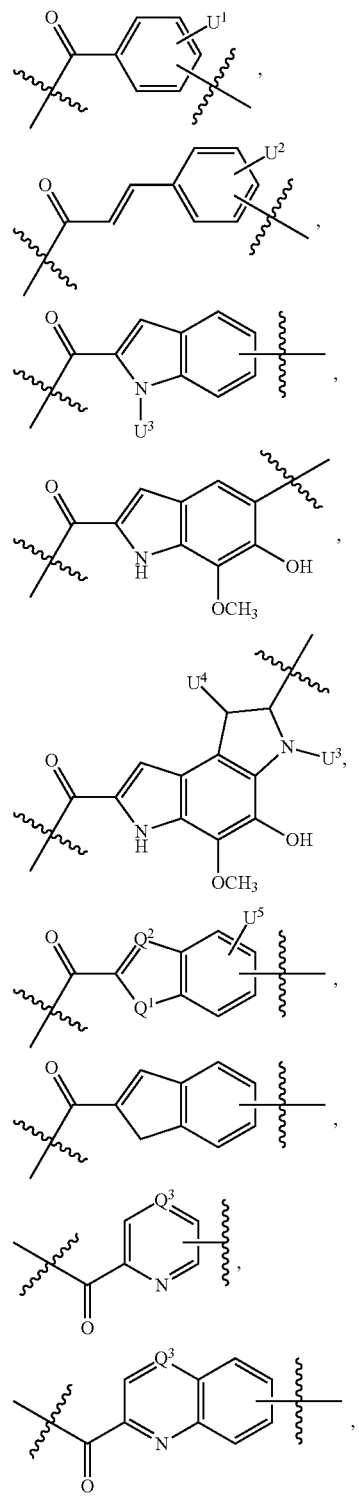

-continued

[chemical structure: pyrrole with carbonyl and U³]

[chemical structure: benzofuran with U⁵, U⁶, Q¹]

[chemical structure: benzoxazole with U⁵, U⁶, Q¹, Q²]

[chemical structure: quinoline-type with U⁵, U⁶, Q³] , and

[chemical structure: indene-type with U⁵, U⁶]

wherein
$U^1$ is selected from H, —CH$_3$, —OH, —OCH$_3$, —NO$_2$, —NH$_2$, —NHNHAc, —NHNHC(O)CH$_3$, —NHC(O)phenyl or -halo,
$U^2$ is H, —OH or —OCH$_3$,
$U^3$ is H, —CH$_3$ or —C$_2$H$_5$,
$U^4$ is H or CH$_3$S—,
$U^5$ and $U^6$ are each independently selected from H, -halo, —C$_1$-C$_4$ alkyl, —C$_1$-C$_3$ alkoxy, —C$_1$-C$_6$ dialkylamino, —NO$_2$, —NHC(O)C$_1$-C$_{10}$ alkyl, —OH, —NH$_2$, —NHC(O)NH$_2$, —NHC(O)CH$_3$ or —NHC(O)phenyl,
$Q^1$ is —O—, —S— or —NH—, and
$Q^2$ and $Q^3$ are each independently —CH— or —N—;
T is selected from:
—NHC(O)—,
—C(O)NH—,
—C(O)O—,
—OC(O)—,
—NR$^B$-T$^1$-NR$^C$— where R$^B$ and R$^C$ are each independently H or —C$_1$-C$_8$ alkyl, or together R$^B$ and R$^C$ join to form a ring and together are (CH$_2$)$_{2-3}$, where T$^1$ is selected from the group consisting of —C(O)—, —C(O)(CH$_2$)$_n$C(O)— where n is an integer from 0 to 50 and —C(O)PhC(O)— where Ph is 1,3- or 1,4-phenylene, and where T$^1$ is optionally substituted with 1-2 R,
—C(O)hetC(O)— wherein het is a mono-, bi-, or tricyclic heteroaryl of 5 to 12 members, containing one, two, or three heteroatoms independently selected from O, N, S, P and B, where het is optionally substituted with 1 to 8 substituents each independently selected from the group consisting of —C$_1$-C$_8$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclycl, —NH$_2$, —NHR$^D$ and —NO$_2$, and said optional substituents on het are optionally substituted with R$^E$, wherein each R$^D$ is independently selected from the group consisting of H, —C$_1$-C$_8$ alkyl, —C(O)—C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, and —C(O)-halo, optionally substituted with R$^E$,
wherein each R$^E$ is independently selected from the group consisting of H, —C$_1$-C$_8$ alkyl, —C$_1$-C$_8$ heteroalkyl, -aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, and —C(O)-halo, and wherein each R$^E$ is optionally substituted with 1 to 3 substituents independently selected from R,
—C(A')X$^1$-T$^2$-X$^1$C(B$^1$)—, where T$^2$ is:

[chemical structure showing (R¹R²C)$_g$-D-(R³R⁴C)$_j$-$_m$]

wherein each $X^1$ is independently a bond, —NR$^E$—, —O— or —S—, wherein A$^1$ and B$^1$ are each independently =O or =S, wherein R$^1$, R$^2$, R$^3$, and R$^4$ are each independently R$^E$ or R$^1$ and R$^2$ form a ring system, or R$^3$ and R$^4$ form a ring system, or both R$^1$ and R$^2$, and R$^3$ and R$^4$, each independently form ring systems, or R$^1$ and R$^3$ form a ring system, or R$^2$ and R$^4$ form a ring system, or both R$^1$ and R$^3$, and R$^2$ and R$^4$, each independently form ring systems, where said ring systems are independently selected from —C$_1$-C$_{10}$ heterocyclyl or —C$_3$-C$_8$ carbocyclyl, or R$^1$, R$^2$, R$^3$ and R$^4$ are each bonds to different carbons on D, wherein g and j are each independently an integer from 0 to 50 and m is an integer from 1 to 50, and wherein D is a bond or is selected from the group consisting of —S—, —C$_1$-C$_8$ alkylene-, —C$_6$-C$_{14}$ arylene-, —C$_6$-C$_{14}$ heteroarylene-, —C$_1$-C$_8$ heteroalkylene-, -aralkylene, —C$_1$-C$_{10}$ heterocyclo and —C$_3$-C$_8$ carbocyclo, where said —C$_1$-C$_8$ alkylene-, —C$_6$-C$_{14}$ arylene-, —C$_6$-C$_{14}$ heteroarylene-, —C$_1$-C$_8$ heteroalkylene-, -aralkylene, —C$_1$-C$_{10}$ heterocyclo and —C$_3$-C$_8$ carbocyclo are optionally substituted with —R$^E$, —C(O)R$^E$, C(O)OR$^E$, —N(R$^E$)$_2$, —N(R)C(O)R$^E$ or —N(R)C(O)OR$^E$, and is additionally optionally substituted by 1 to 2 R, and -G$^1$-T$^2$-G$^2$-, where G$^1$ and G$^2$ are each independently —S(O)X$^1$— or —S(O)$_2$X$^1$—;
L is L$^A$-L$^B$-(L$^C$)$_{1-3}$, wherein L$^A$ is selected from the group consisting of -halo, —N(R)$_2$, —CON(R)$_2$, —S-aryl optionally substituted with —NO$_2$ or —CON(R)$_2$, —S-heteroaryl optionally substituted with —NO$_2$, alkyl-SO$_2$-heteroaryl, arylSO$_2$-heteroaryl-,

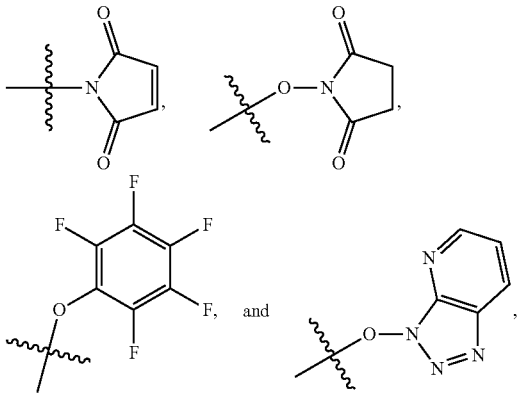

$L^B$ is $L^{B1}$-$L^{B2}$-$L^{B3}$ wherein $L^{B1}$ is absent or is one or more components selected from the group consisting of —C(O)—, —C(S)—, —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-6}$—, —C(O)$C_1$-$C_6$alkylNRC(O)—, —C(O)$C_1$-$C_6$alkyl(OCH$_2$CH$_2$)$_{1-6}$—, —$C_1$-$C_6$alkyl(OCH$_2$CH$_2$)$_{1-6}$—C(O)—, —$C_1$-$C_6$alkyl-S—S—$C_1$-$C_6$alkylNRC(O)CH$_2$—, —$C_1$-$C_6$alkyl(OCH$_2$CH$_2$)$_{1-6}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR-phenyl-O—$C_1$-$C_6$alkyl-C(O)—, —C(O)—$C_1$-$C_6$alkyl(OCH$_2$CH$_2$)$_{1-6}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-6}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl- and (—CH$_2$—CH$_2$—O—)$_{1-20}$, wherein $L^{B2}$ is AA$_{0-12}$, wherein AA is a natural amino acid, a non-natural amino acid or —(CR$^{15}$)$_o$—S—S—(CR$^{15}$)$_p$ where o and p are each independently an integer from 1 to 20, $L^{B3}$ is —PABA-, —PABC—, —C(O)(CH$_2$)$_n$C(O)— or absent;

$L^C$ is absent or independently selected from the group consisting of —$C_1$-$C_6$alkylene-, —NR$C_3$-$C_8$-heterocyclylNR—, —NR$C_3$-$C_8$-carbocyclylNR—, —NR$C_1$-$C_6$alkylNR—, —NR$C_1$-$C_6$alkylene-, —S—, —NR—, —NRNR—, —O(CR$_2$)$_{1-4}$S—S(CR$_2$)$_{1-4}$N(R)—, —NR$C_1$-$C_6$-alkylenephenyleneNR—, —NR$C_1$-$C_6$alkylenephenyleneSO$_2$NR—, —O$C_1$-$C_6$alkylS-S$C_1$-$C_6$alkylC(COOR)NR—, —NRC(COOR)$C_1$-$C_6$alkylS-S$C_1$-$C_6$alkylO—,

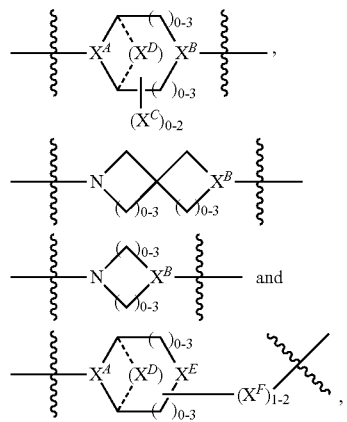

wherein
$X^A$ is CR or N,
$X^B$ is CH, CR(C(R)$_2$)$_{1-3}$NR, CR(C(R)$_2$)$_{1-3}$O, CR(C(R)$_2$)$_{1-3}$C(O)NR, CR—(C(R)$_2$)$_{1-3}$C(O)NRNR, CR(C(R)$_2$)$_{1-3}$SO$_2$NR, CR(C(R)$_2$)$_{1-3}$NRNR, CR(C(R)$_2$)$_{1-3}$NRC(O) or N,
each $X^C$ is R,
each $X^D$ is —(CH$_2$)$_{1-5}$—, or is absent;
$X^E$ is O, S, (R)$_2$, C(R)(C(R)$_2$)$_{1-3}$—NR$_2$ or NR and
each $X^F$ is (C(R)$_2$)$_{1-3}$—NR or C(R)$_2$—(C(R)$_2$)$_{1-3}$—O.

In other embodiments of the invention the variable —Y— is C(O)N(R$^A$)$_2$ or C(S)N(R$^A$)$_2$ where one R$^A$ is hydrogen or $C_1$-$C_{20}$ alkyl and the other R$^A$ is $C_1$-$C_{20}$ alkyl-N(R)—, such that the structure:

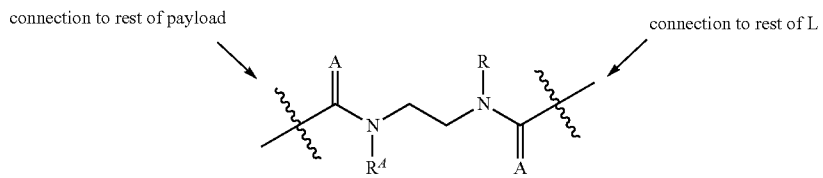

is formed, where each A is independently oxygen or sulphur.

According to still another aspect of the invention there is provided an antibody drug conjugate compound of Formula IIIA:

AB-(L-P)$_{1-20}$ (Formula IIIA)

or a pharmaceutically acceptable salt or solvate thereof, wherein:
AB is an antibody;
P is:

F$^1$-L$^1$-T-L$^2$-F$^2$ wherein:
F$^1$ and F$^2$ are each independently selected from ring systems A, B, C, D, E, F, G and H:

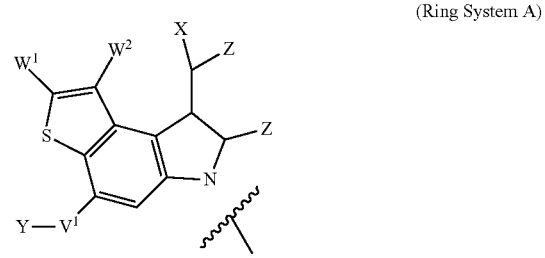

(Ring System A)

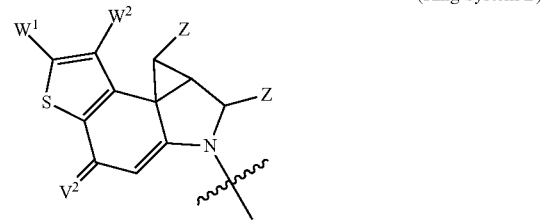

(Ring System B)

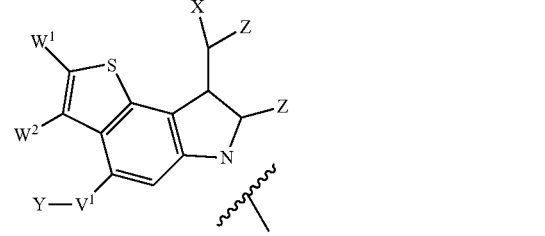

(Ring System C)

-continued

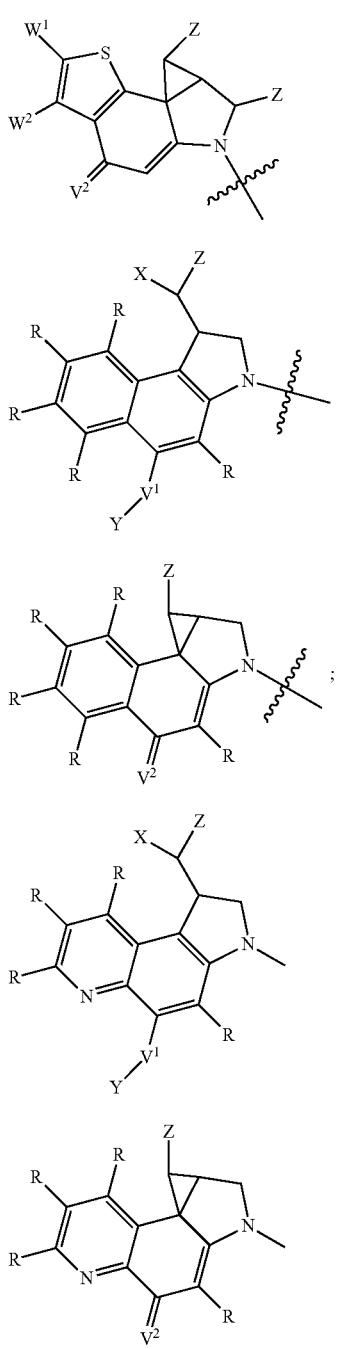

(Ring System D)

(Ring System E)

(Ring System F)

(Ring System G)

(Ring System H)

where:

at least one of the ring systems A, B, C and D is present;

each R is independently selected from the group consisting of H, —$C_1$-$C_{20}$ alkyl, —$C_2$-$C_6$ alkenyl, —$C_2$-$C_6$ alkynyl, halo, deuterium, hydroxyl, alkoxy, —$NH_2$, —NH($C_1$-$C_8$ alkyl), —N($C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —$NO_2$ or —$C_1$-$C_{10}$ heterocyclyl, for each ring system in which R appears;

each $V^1$ is independently a bond, O, N(R) or S, for each ring system in which $V^1$ appears;

each $V^2$ is independently O, N(R) or S, for each ring system in which $V^2$ appears;

$W^1$ and $W^2$ are each independently H, —$C_1$-$C_5$ alkyl, -phenyl, —C(O)OR, —C(O)SR, —C(O)NHN(R)$_2$ or —C(O)N(R)$_2$ for each ring system in which $W^1$ and $W^2$ appear;

each X is independently selected from —OH, —O-acyl, azido, halo, cyanate, thiocyanate, isocyanate, thioisocyanate, or

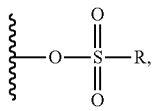

for each ring system in which X appears;

each Y is independently selected from a bond, H, —C(O)$R^A$, C(S)$R^A$, C(O)O$R^A$, —S(O)$_2$$R^A$, —C(O)N($R^A$)$_2$, —C(S)N($R^A$)$_2$, a carbohydrate such as glycosyl, —$NO_2$, —P(O)(O$R^A$)$_2$, an amino acid, and a peptide (in particular a peptide that is cleaved by proteases such as cathepsins and matrix metalloproteinases) for each ring system in which Y appears, wherein each $R^A$ is independently selected from H, —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl, —$C_1$-$C_{20}$ alkylN(R)$_2$, —$C_1$-$C_{20}$ alkylene, —$C_1$-$C_8$ heteroalkylene, —$C_6$-$C_{14}$ arylene, aralkylene, —$C_1$-$C_{10}$ heterocyclo, —$C_3$-$C_8$ carbocyclo and —$C_1$-$C_{20}$ alkylN(R)—, and $R^F$ where said $R^A$ is optionally substituted with 1 to 3 substituents independently selected from R, and wherein one Y is divalent and is bonded to L, $R^F$ is —N($R^6$)QN($R^5$)C(O)— and is bonded to L at the carbonyl adjacent N($R^5$), wherein $R^5$ and $R^6$ are each independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl and —$C_3$-$C_8$ carbocyclyl, or $R^5$ or $R^6$ joins with a substituted carbon on Q to form a —$C_1$-$C_{10}$ heterocyclic or —$C_6$-$C_{14}$ heteroaryl ring, or $R^5$ and $R^6$ join together to form a —$C_1$-$C_{10}$ heterocyclic or —$C_6$-$C_{14}$ heteroaryl ring system, and where Q is —$C_1$-$C_8$ alkylene-, —$C_1$-$C_8$ heteroalkylene-, —$C_6$-$C_{14}$ arylene-, -aralkylene-, —$C_1$-$C_{10}$ heterocyclo- or —$C_3$-$C_8$ carbocyclo-, wherein Q, $R^5$ and $R^6$ are each independently optionally substituted with 1 to 3 substituents independently selected from R;

each Z is independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo, and wherein said $C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo are each optionally substituted with 1 to 3 substitutents independently selected from R, for each ring system in which Z appears;

$L^1$ and $L^2$ are each independently selected from a direct bond, carbonyl, or a carbonyl acyl group bonded to $F^1$ or $F^2$ at the acyl moiety, where the carbonyl acyl group is selected from the group consisting of:

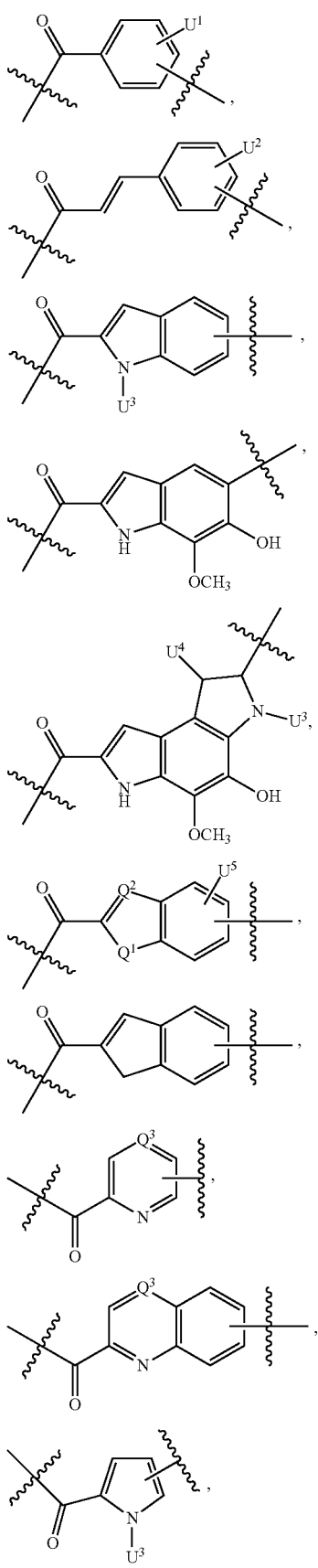

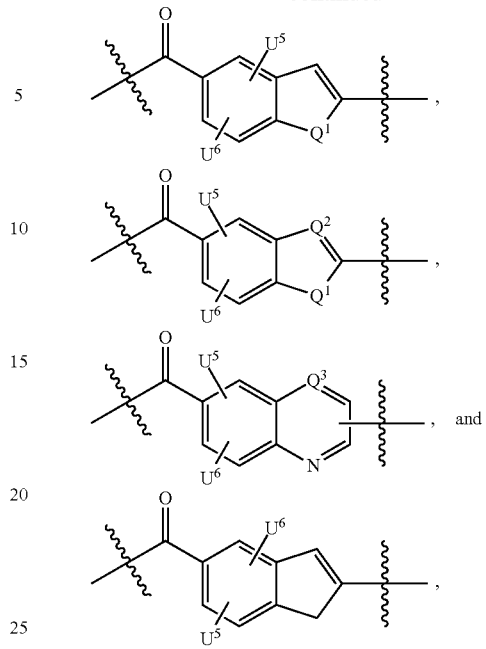

wherein
$U^1$ is selected from H, —CH$_3$, —OH, —OCH$_3$, —NO$_2$, —NH$_2$, —NHNHAc, —NHNHC(O)CH$_3$, —NHC(O)phenyl or -halo,
$U^2$ is H, —OH or —OCH$_3$,
$U^3$ is H, —CH$_3$ or —C$_2$H$_5$,
$U^4$ is H or CH$_3$S—,
$U^5$ and $U^6$ are each independently selected from H, -halo, —C$_1$-C$_4$ alkyl, —C$_1$-C$_3$ alkoxy, —C$_1$-C$_6$ dialkylamino, —NO$_2$, —NHC(O)C$_1$-C$_{10}$ alkyl, —OH, —NH$_2$, —NHC(O)NH$_2$, —NHC(O)CH$_3$ or —NHC(O)phenyl,
$Q^1$ is —O—, —S— or —NH—,
$Q^2$ and $Q^3$ are each independently —CH— or —N—;
T is selected from:
—NHC(O)—,
—C(O)NH—,
—C(O)O—,
—OC(O)—,
—NR$^B$-T-NR$^C$— where R$^B$ and R$^C$ are each independently H or —C$_1$-C$_8$ alkyl, or together R$^B$ and R$^C$ join to form a ring and together are (CH$_2$)$_{2-3}$, where T$^1$ is selected from the group consisting of —C(O)—, —C(O)(CH$_2$)$_n$C(O)— where n is an integer from 0 to 50 and —C(O)PhC(O)— where Ph is 1,3- or 1,4-phenylene, and where T$^1$ is optionally substituted with 1-2 R,
—C(O)hetC(O)— wherein het is a mono-, bi-, or tricyclic heteroaryl of 5 to 12 members, containing one, two, or three heteroatoms independently selected from O, N, S, P and B, where het is optionally substituted with 1 to 8 substituents each independently selected from the group consisting of —C$_1$-C$_8$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclcl, —NH$_2$, —NHR$^D$ and —NO$_2$, and said optional substituents on het are optionally substituted with R$^E$,
wherein each R$^D$ is independently selected from the group consisting of H or —C$_1$-C$_8$ alkyl, —C(O)—C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, and —C(O)-halo, optionally substituted with R$^E$, wherein each $R^E$ is independently selected from the group consisting of H, —$C_1$-$C_8$ alkyl, —$C_1$-$C_8$ heteroalkyl, -aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, and —C(O)-halo, and wherein each $R^E$ is optionally substituted with 1 to 3 substitutents independently selected from R,
—C($A^1$)$X^1$-$T^2$-$X^1$C($B^1$)—, where $T^2$ is:

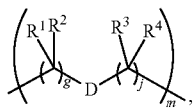

wherein each $X^1$ is independently a bond, —$NR^E$—, —O— or —S—, wherein $A^1$ and $B^1$ are each independently =O or =S, wherein $R^1$, $R^2$, $R^3$, and $R^4$ are each independently $R^E$ or $R^1$ and $R^2$ form a ring system, or $R^3$ and $R^4$ form a ring system, or both $R^1$ and $R^2$, and $R^3$ and $R^4$, each independently form ring systems, or R and $R^3$ form a ring system, or $R^2$ and $R^4$ form a ring system, or both $R^1$ and $R^3$, and $R^2$ and $R^4$, each independently form ring systems, where said ring systems are independently selected from —$C_1$-$C_{10}$ heterocyclyl or —$C_3$-$C_8$ carbocyclycl, or $R^4$, $R^2$, $R^3$ and $R^4$ are each bonds to different carbons on D, wherein g and j are each independently an integer from 0 to 50 and m is an integer from 1 to 50, and wherein D is a bond or is selected from the group consisting of —S—, —$C_1$-$C_8$ alkylene-, —$C_6$-$C_{14}$ arylene-, —$C_6$-$C_{14}$ heteroarylene-, —$C_1$-$C_8$ heteroalkylene-, -aralkylene, —$C_1$-$C_{10}$ heterocyclo and —$C_3$-$C_8$ carbocyclo, where said —$C_1$-$C_8$ alkylene-, —$C_6$-$C_{14}$ arylene-, —$C_6$-$C_{14}$ heteroarylene-, —$C_1$-$C_8$ heteroalkylene-, -aralkylene, —$C_1$-$C_{10}$ heterocyclo and —$C_3$-$C_8$ carbocyclo are optionally substituted with —$R^E$, —C(O)$R^E$, C(O)O$R^E$, —N($R^E$)$_2$, —N(R)C(O)$R^E$ or —N(R)C(O)O$R^E$, and D is additionally optionally substituted by 1 to 2 R, and -$G^1$-$T^2$-$G^2$-, where G and $G^2$ are each independently —S(O)$X^1$— or —S(O)$_2$$X^4$—;
L is $L^A$-$L^B$-($L^C$)$_{1-3}$;
$L^A$ is selected from: a bond to AB, —NR-(bond to AB), -heteroaryl-(bond to AB),

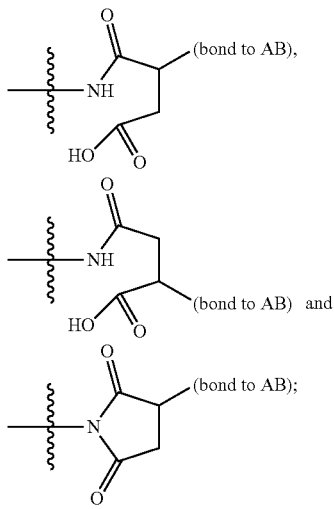

$L^B$ is $L^{B1}$-$L^{B2}$-$L^{B3}$
wherein $L^{B1}$ is absent or is one or more components selected from the group consisting of —C(O)—, —C(S)—, —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-6}$—, —C(O)$C_1$-$C_6$alkylNRC(O)—, —C(O)$C_1$-$C_6$alkyl(OCH$_2$CH$_2$)$_{1-6}$—, —$C_1$-$C_6$alkyl(OCH$_2$CH$_2$)$_{1-6}$—C(O)—, —$C_1$-$C_6$alkyl-S—S—$C_1$-$C_6$alkylNRC(O)CH$_2$—, —$C_1$-$C_6$alkyl(OCH$_2$CH$_2$)$_{1-6}$NR$^C$(O)CH$_2$—, —C(O)$C_1$-$C_6$alkyl-NR$^C$(O)$C_{1-6}$alkyl-, —N=CR-phenyl-O—$C_1$-$C_6$alkyl-, —N=CR-phenyl-O—$C_1$-$C_6$alkyl-C(O)—, —C(O)—$C_1$-$C_6$alkyl(OCH$_2$CH$_2$)$_{1-6}$NR$^C$(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-6}$—NR$^C$(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl- and (—CH$_2$—CH$_2$—O—)$_{1-20}$;
$L^{B2}$ is AA$_{0-12}$, wherein AA is a natural amino acid, a non-natural amino acid or —(CR$^{15}$)$_o$—S—S—(CR$^{15}$)$_p$ where o and p are each independently an integer from 1 to 20,
$L^{B3}$ is —PABA-, —PABC—, —C(O)(CH$_2$)$_n$C(O)— or absent;
$L^C$ is absent or is independently selected from the group consisting of —$C_1$-$C_6$alkylene-, —NR$C_3$-$C_8$-heterocyclylNR—, —NR$C_3$-$C_8$-carbocyclylNR—, —NR$C_1$-$C_6$alkylNR—, —NR$C_1$-$C_6$alkylene-, —S—, —NR—, —NRNR—, —O(CR$_2$)$_{1-4}$S—S(CR$_2$)$_{1-4}$N(R)—, —NR$C_1$-$C_6$-alkylenephenyleneNR—, —NR$C_1$-$C_6$alkylenephenyleneSO$_2$NR—, —O$C_1$-$C_6$alkylS-S$C_1$-$C_6$alkylC(COOR)NR—, —NR$^C$(COOR)$C_1$-$C_6$alkylS-S$C_1$-$C_6$alkylO—,

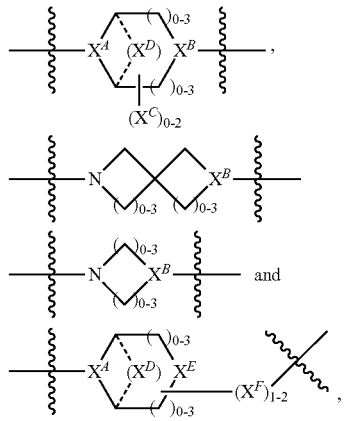

wherein
$X^A$ is CR or N,
$X^B$ is CH, CR(C(R)$_2$)$_{1-3}$NR, CR(C(R)$_2$)$_{1-3}$O, CR(C(R)$_2$)$_{1-3}$C(O)NR, CR—(C(R)$_2$)$_{1-3}$C(O)NRNR, CR(C(R)$_2$)$_{1-3}$SO$_2$NR, CR(C(R)$_2$)$_{1-3}$NRNR, CR(C(R)$_2$)$_{1-3}$NR$^C$(O) or N,
each $X^C$ is R;
each $X^D$ is —(CH)$_{1-5}$—, or is absent;
$X^E$ is O, S, C(R)$_2$, C(R)(C(R)$_2$)$_{1-3}$—NR$_2$ or NR, and
each $X^F$ is (C(R)$_2$)$_{1-3}$—NR or C(R)$_2$—(C(R)$_2$)$_{1-3}$—O.

According to another aspect of the invention there is provided a "linker-payload" compound of Formula IIB:

(Formula IIB)

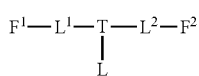

or a pharmaceutically acceptable salt or solvate thereof, wherein:

F¹ and F² are each independently selected from ring systems A, B, C, D, E, F, G and H:

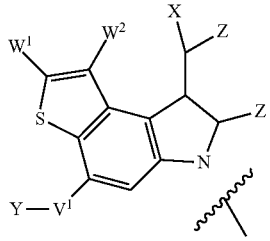
(Ring System A)

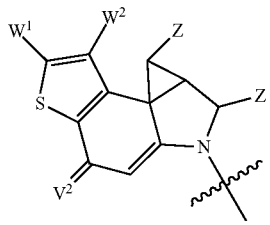
(Ring System B)

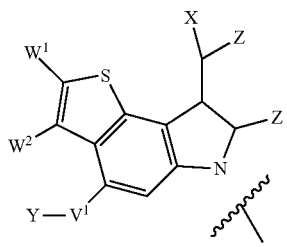
(Ring System C)

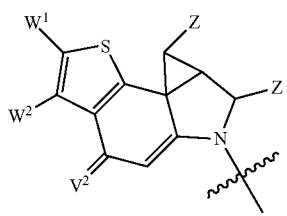
(Ring System D)

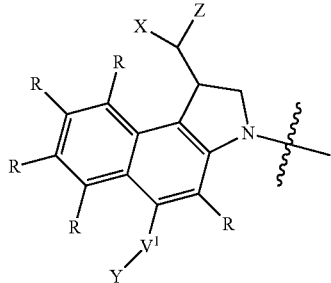
(Ring System E)

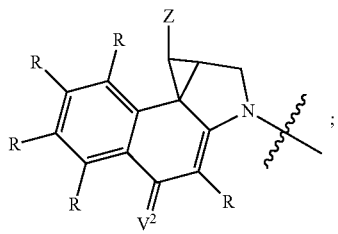
(Ring System F)

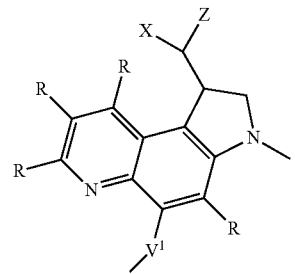
(Ring System G)

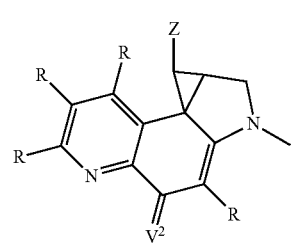
(Ring System H)

where:

at least one of the ring systems A, B, C and D is present;

each R is independently selected from the group consisting of H, —$C_1$-$C_{20}$ alkyl, —$C_2$-$C_6$ alkenyl, —$C_2$-$C_6$ alkynyl, halo, deuterium, hydroxyl, alkoxy, —$NH_2$, —NH($C_1$-$C_8$ alkyl), —N($C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —$NO_2$ or —$C_1$-$C_{10}$ heterocyclyl, for each ring system in which R appears;

each $V^1$ is independently a bond, O, N(R) or S, for each ring system in which $V^1$ appears;

each $V^2$ is independently O, N(R) or S, for each ring system in which $V^2$ appears;

$W^1$ and $W^2$ are each independently H, —$C_1$-$C_5$ alkyl, -phenyl, —C(O)OR, —C(O)SR, —C(O)NHN(R)$_2$ or —C(O)N(R)$_2$ for each ring system in which $W^1$ and $W^2$ appear;

each X is independently —OH, —O-acyl, azido, halo, cyanate, thiocyanate, isocyanate, thioisocyanate, or

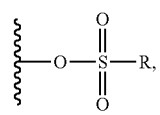

for each ring system in which X appears;

each Y is independently selected from the group consisting of H, —$C_1$-$C_6$ alkyl-$R^A$ —C(O)$R^A$, —C(S)$R^A$, C(O)O$R^A$, —S(O)$_2$O$R^A$, —C(O)N($R^A$)$_2$, —C(S)N($R^A$)$_2$, a carbohydrate such as glycosyl, —$NO_2$, —PO(O$R^A$)$_2$, an amino acid and a peptide (in particular a peptide that is cleaved by proteases such as cathepsins and matrix metalloproteinases) for each ring system in which Y appears, wherein each $R^A$ is independently selected from the group consisting of H, —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl and —$C_1$-$C_{20}$ alkylN(R)$_2$, wherein said —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_0$ carbocyclyl and —$C_1$-$C_{20}$ alkylN(R)$_2$ are optionally substituted with 1 to 3 substitutents independently selected from R;

each Z is independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo, and wherein said $C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo are each optionally substituted with 1 to 3 substitutents independently selected from R, for each ring system in which Z appears;

$L^1$ and $L^2$ are each independently selected from a direct bond, carbonyl, or a carbonyl acyl group bonded to $F^1$ or $F^2$ at the acyl moiety, where the carbonyl acyl group is selected from the group consisting of:

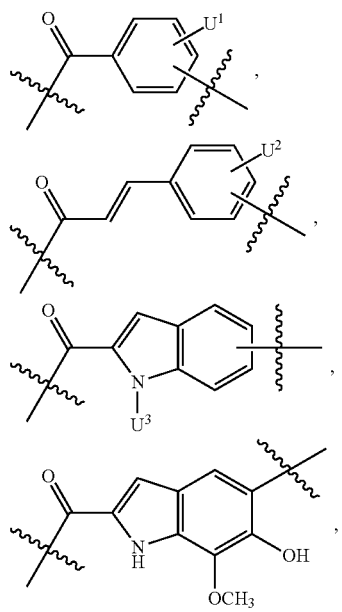

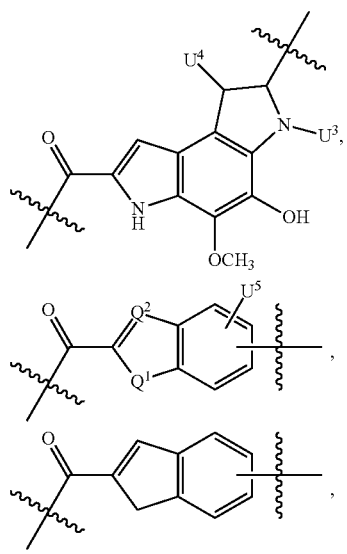

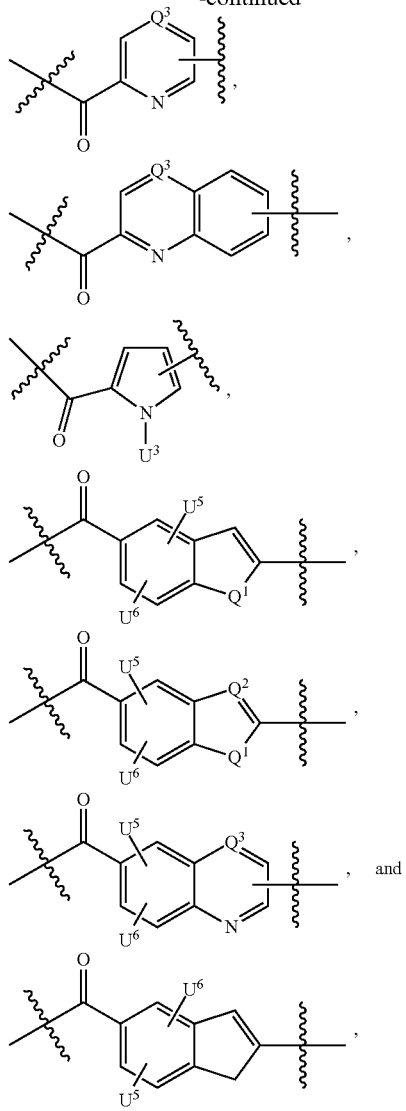

wherein
$U^1$ is selected from H, —CH$_3$, —OH, —OCH$_3$, —NO$_2$, —NH$_2$, —NHNHAc, —NHNHC(O)CH$_3$, —NH—C(O)phenyl or -halo,
$U^2$ is H, —OH or —OCH$_3$,
$U^3$ is H, —CH$_3$ or —$C_2$H$_5$,
$U^4$ is H or CH$_3$S—,
$U^5$ and $U^6$ are each independently selected from H, -halo, —$C_1$-$C_4$ alkyl, —$C_1$-$C_3$ alkoxy, —$C_1$-$C_6$ dialkylamino, —NO$_2$, —NHC(O)$C_1$-$C_{10}$ alkyl, —OH, —NH$_2$, —NHC(O)NH$_2$, —NHC(O)CH$_3$ or —NHC(O)phenyl,
$Q^1$ is —O—, —S— or —NH—, and
$Q^2$ and $Q^3$ are each independently —CH— or —N—;
T is selected from:
—C($A^1$)$X^1$-$T^2$-$X^1$C($B^1$)—, where $T^2$ is:

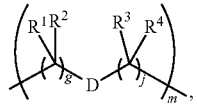

wherein each $X^1$ is independently a bond, —$NR^E$—, —O— or —S—, wherein $A^1$ and $B^1$ are each independently =O or =S, wherein $R^1$, $R^2$, $R^3$, and $R^4$ are each independently $R^E$, or $R^1$ and $R^2$ form a ring system, or $R^3$ and $R^4$ form a ring system, or both $R^1$ and $R^2$, and $R^3$ and $R^4$ each independently form ring systems, or $R^1$ and $R^3$ form a ring system, or $R^2$ and $R^4$ form a ring system, or both $R^1$ and $R^3$, and $R^2$ and $R^4$ each independently form ring systems, where the ring systems are independently selected from —$C_1$-$C_{10}$ heterocyclyl or —$C_3$-$C_8$ carbocyclyl, or $R^1$, $R^2$, $R^3$ and $R^4$ are each bonds to different carbons on D, wherein g and j are each independently an integer from 0 to 50 and m is an integer from 1 to 50, and wherein D is selected from the group consisting of —$C_1$-$C_8$ alkylene-, —$C_6$-$C_{14}$ arylene-, —$C_6$-$C_{14}$ heteroarylene-, —$C_1$-$C_8$ heteroalkylene-, -aralkylene, —$C_1$-$C_{10}$ heterocyclo and —$C_3$-$C_8$ carbocyclo, where said —$C_1$-$C_8$ alkylene-, —$C_6$-$C_{14}$ arylene-, —$C_6$-$C_{14}$ heteroarylene-, —$C_1$-$C_8$ heteroalkylene-, -aralkylene, —$C_1$-$C_{10}$ heterocyclo and —$C_3$-$C_8$ carbocyclo are substituted with one member of the group selected from $N(R^E)C(O)$— where the carbonyl is bonded to L, and —C(O)— where the carbonyl is bonded to L, and additionally optionally substituted by 1 to 2 R;

where each $R^E$ is independently selected from the group consisting of H, —$C_1$-$C_8$ alkyl, —$C_1$-$C_8$ heteroalkyl, -aryl, -aralkyl, —$C_1$-$C_{10}$ heterocyclyl, —$C_3$-$C_8$ carbocyclyl, —$C(O)OC_1$-$C_8$ alkyl, —$C(O)N(C_1$-$C_8$ alkyl)$_2$, and —C(O)-halo, and wherein each $R^E$ is optionally substituted with 1 to 3 substitutents independently selected from R;

L is $L^A$-$L^B$-$(L^C)_{1-3}$;

$L^A$ is selected from -halo, —$N(R)_2$, —$CON(R)_2$, —S-aryl optionally substituted with —$NO_2$ or —$CONR_2$, —S-heteroaryl optionally substituted with —$NO_2$, alkyl-$SO_2$-heteroaryl, aryl$SO_2$-heteroaryl-,

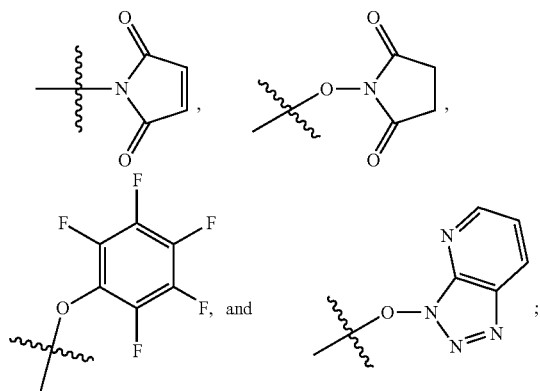

$L^B$ is $L^{B1}$-$L^{B2}$-$L^{B3}$ wherein $L^{B1}$ is absent or is one or more components selected from the group consisting of —C(O)—, —C(S)—, —C(O)NR—, —$C(O)C_1$-$C_6$alkyl-, —$C(O)NRC_1$-$C_6$alkyl-, —$C_1$-$C_6$alkyl($OCH_2CH_2)_{1-5}$—, —$C(O)C_1$-$C_6$alkylNRC(O)—, —$C(O)C_1$-$C_6$alkyl($OCH_2CH_2)_{1-5}$—, —$C_1$-$C_6$alkyl $(OCH_2CH_2)_{1-5}$—C(O)—, —$C_1$-$C_6$alkyl-S—S—$C_1$-$C_6$alkylNRC(O)$CH_2$—, —$C_1$-$C_6$alkyl($OCH_2CH_2)_{1-6}NR^C$ $(O)CH_2$—, —$C(O)C_1$-$C_6$alkyl-$NR^C(O)C_1$-, -alkyl-, —N=CR-phenyl-O—$C_1$-$C_6$alkyl-, —N=CR-phenyl-O—$C_1$-$C_6$alkyl-C(O)—, —C(O)—$C_1$-$C_6$alkyl($OCH_2CH_2)_{1-6}NRC(O)$—, —$C(O)C_1$-$C_6$alkyl-phenyl(NR—C(O) $C_1$-$C_6$alkyl)$_{1-4}$-, —$C(O)C_1$-$C_6$alkyl($OCH_2CH_2)_{1-5}$—$NR^C$ $(O)C_1$-$C_6$alkyl-, —$C_1$-$C_6$alkyl-, —S—, —C(O)—CH $(NR—C(O)C_1$-$C_6$alkyl)-$C_1$-$C_6$alkyl- and ($CH_2$—$CH_2$—O—)$_{1-20}$;

$L^{B2}$ is $AA_{0-12}$, wherein AA is a natural amino acid, a non-natural amino acid or —$(CR^{15})_o$—S—S—$(CR^{15})_p$ where o and p are each independently an integer from 1 to 20, $L^{B3}$ is —PABA-, —PABC—, —$C(O)(CH_2)_nC(O)$— or absent;

$L^C$ is absent or is independently selected from the group consisting of —$C_1$-$C_6$alkylene-, —$NRC_3$-$C_8$-heterocyclylNR—, —$NRC_3$-$C_8$-carbocyclylNR—, —$NRC_1$-$C_6$alkylNR—, —$NRC_1$-$C_6$alkylene-, —S—, —NR—, —NRNR—, —$O(CR_2)_{1-4}S$—S$(CR_2)_{1-4}N(R)$—, —$NRC_1$-$C_5$-alkylenephenyleneNR—, —$NRC_1$-$C_6$alkylenephenyleneSO$_2$NR—, —$OC_1$-$C_6$alkylS-S$C_1$-$C_6$alkylC(COOR)NR—, —$NR^C(COOR)C_1$-$C_6$alkylS-S$C_1$-$C_6$alkylO—,

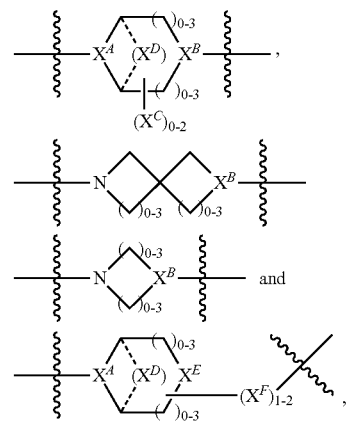

wherein $X^A$ is CR or N, $X^B$ is CH, CR$(C(R)_2)_{1-3}$NR, CR$(C(R)_2)_{1-3}$O, CR $(C(R)_2)_{1-3}$C(O)NR, CR—$(C(R)_2)_{1-3}$C(O)NRNR, CR $(C(R)_2)_{1-3}$SO$_2$NR, CR$(C(R)_2)_{1-3}$NRNR, CR$(C(R)_2)_{1-3}$NR$^C$ (O) or N;

each $X^C$ is R;

each $X^D$ is —$(CH_2)_{1-5}$—, or is absent;

$X^E$ is O, S, $C(R)_2$, $C(R)(C(R)_2)_{1-3}$—NR$_2$ or NR, and each $X^F$ is $(C(R)_2)_{1-3}$—NR or $C(R)_2$—$(C(R)_2)_{1-3}$—O.

According to yet another aspect of the invention there is provided an antibody drug conjugate compound of Formula IIIB:

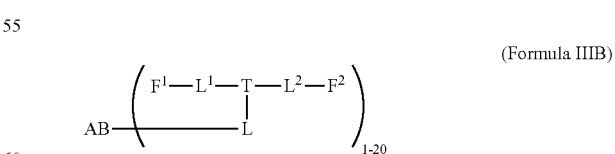

(Formula IIIB)

or a pharmaceutically acceptable salt or solvate thereof, wherein:

AB is an antibody;

$F^1$ and $F^2$ are each independently selected from ring systems A, B, C, D, E, F, G and H:

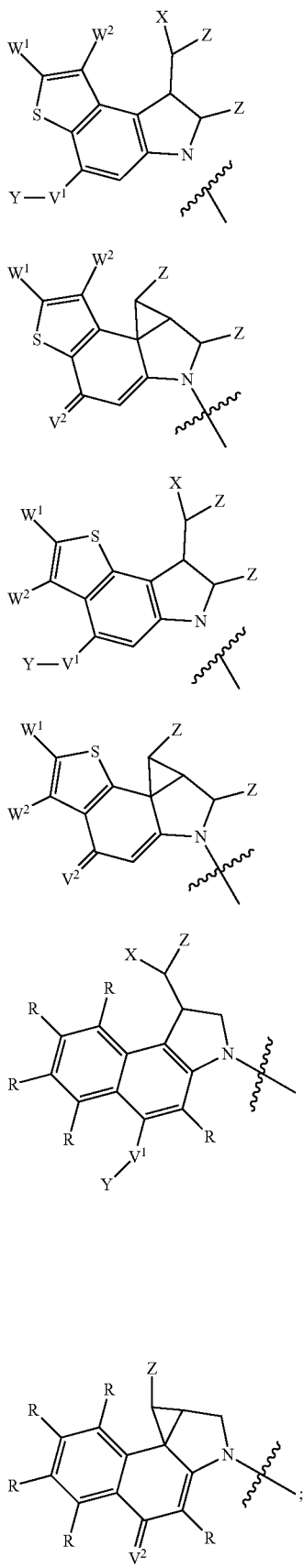

(Ring System A)

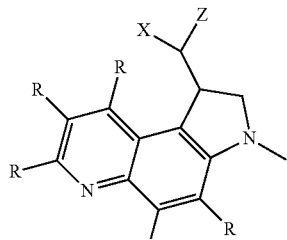

(Ring System B)

(Ring System G)

(Ring System C)

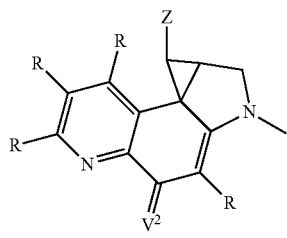

(Ring System D)

(Ring System H)

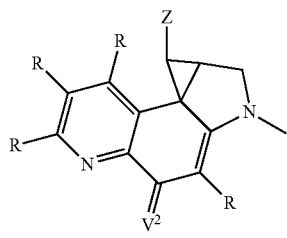

(Ring System E)

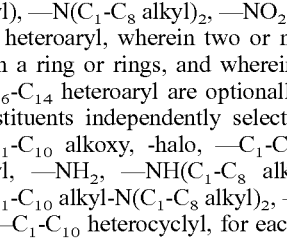

(Ring System F)

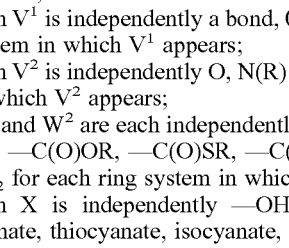

where:

at least one of the ring systems A, B, C and D is present;

each R is independently selected from the group consisting of H, —C$_1$-C$_{20}$ alkyl, —C$_2$-C$_6$ alkenyl, —C$_2$-C$_6$ alkynyl, halo, deuterium, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears;

each V$^1$ is independently a bond, O, N(R) or S, for each ring system in which V$^1$ appears;

each V$^2$ is independently O, N(R) or S, for each ring system in which V$^2$ appears;

W$^1$ and W$^2$ are each independently H, —C$_1$-C$_5$ alkyl, -phenyl, —C(O)OR, —C(O)SR, —C(O)NHN(R)$_2$ or —C(O)N(R)$_2$ for each ring system in which W$^1$ and W$^2$ appear;

each X is independently —OH, —O-acyl, azido, halo, cyanate, thiocyanate, isocyanate, thioisocyanate, or

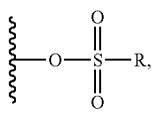

for each ring system in which X appears;

each Y is independently selected from the group consisting of H, —C$_1$-C$_6$ alkyl-R$^A$ —C(O)R$^A$, —C(S)R$^A$, C(O)OR$^A$, —S(O)$_2$OR$^A$, —C(O)N(R$^A$)$_2$, —C(S)N(R$^A$)$_2$, a carbohydrate such as glycosyl, —NO, —PO(OR$^A$)$_2$, an amino acid, and a peptide (in particular a peptide that is cleaved by proteases such as cathepsins and matrix metalloproteinases), for each ring system in which Y appears, wherein each R$^A$ is independently selected from the group consisting of H, —C$_1$-C$_{20}$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclyl and —C$_1$-C$_{20}$ alkylN(R)$_2$, wherein said —C$_1$-C$_{20}$ alkyl, —C$_1$-C$_8$ heteroalkyl, —C$_6$-C$_{14}$ aryl, aralkyl, —C$_1$-C$_{10}$ heterocyclyl, —C$_3$-C$_0$ carbocyclyl and —C$_1$-C$_{20}$ alkylN(R)$_2$ are optionally substituted with 1 to 3 substitutents independently selected from R;

each Z is independently selected from the group consisting of H, —C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, —C(O)OH, —C(O)NHNH$_2$ and —C(O)-halo, and wherein said C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, —C(O)OH, —C(O)NHNH$_2$ and —C(O)-halo are each optionally substituted with 1 to 3 substitutents independently selected from R, for each ring system in which Z appears;

L$^1$ and L$^2$ are each independently selected from a direct bond, carbonyl, or a carbonyl acyl group bonded to F$^1$ or F$^2$ at the acyl moiety, where the carbonyl acyl group is selected from the group consisting of:

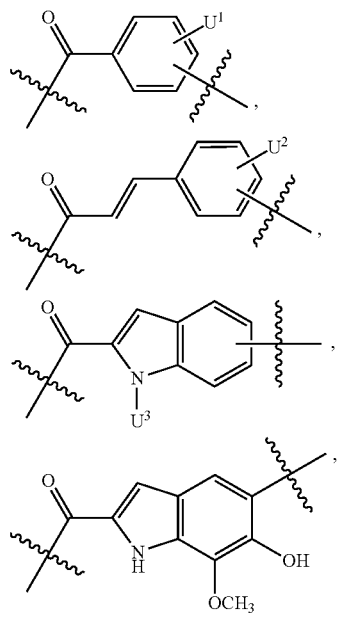

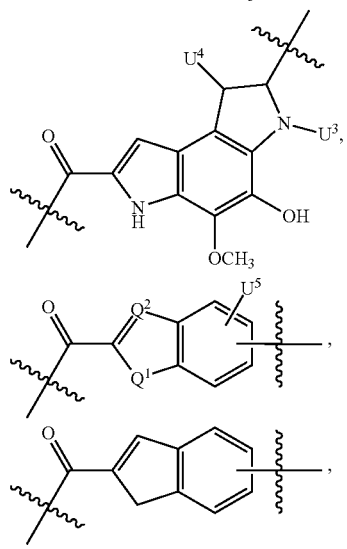

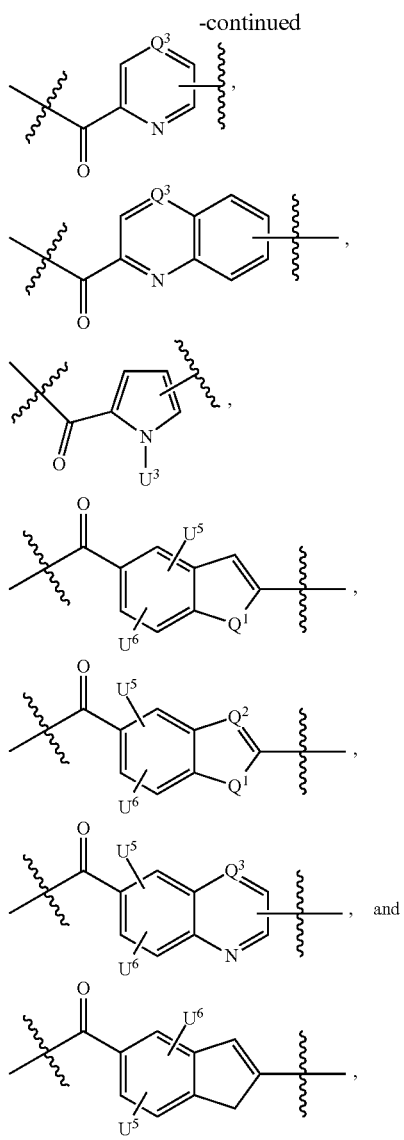

wherein
U$^1$ is selected from H, —CH$_3$, —OH, —OCH$_3$, —NO$_2$, —NH$_2$, —NHNHAc, —NHNHC(O)CH$_3$, —NH—C(O)phenyl or -halo,
U$^2$ is H, —OH or —OCH$_3$,
U$^3$ is H, —CH$_3$ or —C$_2$H$_5$,
U$^4$ is H or CH$_3$S—,
U$^5$ and U$^6$ are each independently selected from H, -halo, —C$_1$-C$_4$ alkyl, —C$_1$-C$_3$ alkoxy, —C$_1$-C$_6$ dialkylamino, —NO$_2$, —NHC(O)C$_1$-C$_{10}$ alkyl, —OH, —NH$_2$, —NHC(O)NH$_2$, —NHC(O)CH$_3$ or —NHC(O)phenyl,
Q$^1$ is —O—, —S— or —NH—, and
Q$^2$ and Q$^3$ are each independently —CH— or —N—;
T is selected from:
—C(A$^1$)X$^1$-T$^2$-X$^1$C(B$^1$)—, where T$^2$ is:

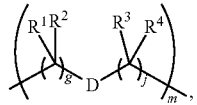

wherein each $X^1$ is independently a bond, —NR$^E$—, —O— or —S—, wherein $A^1$ and $B^1$ are each independently =O or =S, wherein $R^1$, $R^2$, $R^3$, and $R^4$ are each independently $R^E$, or $R^1$ and $R^2$ form a ring system, or $R^3$ and $R^4$ form a ring system, or both $R^1$ and $R^2$, and $R^3$ and $R^4$ each independently form ring systems, or R and $R^3$ form a ring system, or $R^2$ and $R^4$ form a ring system, or both $R^1$ and $R^3$, and $R^2$ and $R^4$ each independently form ring systems, where the ring systems are independently selected from —$C_1$-$C_{10}$ heterocyclyl or —$C_3$-$C_8$ carbocyclycl, or $R^1$, $R^2$, $R^3$ and $R^4$ are each bonds to different carbons on D, wherein g and j are each independently an integer from 0 to 50 and m is an integer from 1 to 50, and wherein D is selected from the group consisting of —$C_1$-$C_8$ alkylene-, —$C_6$-$C_{14}$ arylene-, —$C_6$-$C_{14}$ heteroarylene-, —$C_1$-$C_8$ heteroalkylene-, -aralkylene, —$C_1$-$C_{10}$ heterocyclo and —$C_3$-$C_8$ carbocyclo, where said —$C_1$-$C_8$ alkylene-, —$C_6$-$C_{14}$ arylene-, —$C_6$-$C_{14}$ heteroarylene-, —$C_1$-$C_8$ heteroalkylene-, -aralkylene-, —$C_1$-$C_{10}$ heterocyclo and —$C_3$-$C_8$ carbocyclo are substituted with one member of the group selected from N($R^E$)C(O)— where the carbonyl is bonded to L, and —C(O)— where the carbonyl is bonded to L, and additionally optionally substituted by 1 to 2 R;

where each $R^E$ is independently selected from the group consisting of H, —$C_1$-$C_8$ alkyl, —$C_1$-$C_8$ heteroalkyl, -aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, and —C(O)-halo, and wherein each $R^E$ is optionally substituted with 1 to 3 substitutents independently selected from R;

L is $L^A$-$L^B$-($L^C$)$_{1-3}$;

$L^A$ is selected from: a bond to AB, —NR-(bond to AB), -heteroaryl-(bond to AB),

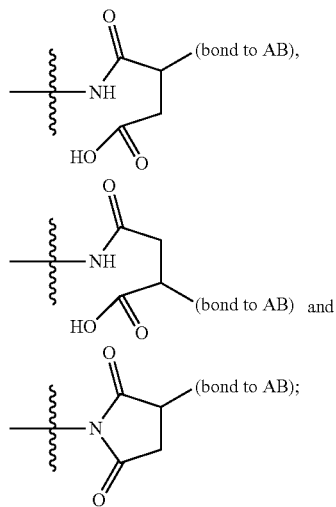

$L^B$ is $L^{B1}$-$L^{B2}$-$L^{B3}$ wherein $L^{B1}$ is absent or is one or more components selected from the group consisting of —C(O)—, —C(S)—, —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-6}$—, —C(O)$C_1$-$C_6$alkylNRC(O)—, —C(O)$C_1$-$C_6$alkyl(OCH$_2$CH$_2$)$_{1-6}$—, —$C_1$-$C_6$alkyl(OCH$_2$CH$_2$)$_{1-6}$—C(O)—, —$C_1$-$C_6$alkyl-S—S—$C_1$-$C_6$alkylNRC(O)CH$_2$—, —$C_1$-$C_6$alkyl(OCH$_2$CH$_2$)$_{1-6}$NR$^C$(O)CH$_2$—, —C(O)$C_1$-$C_6$alkyl-NR$^C$(O)$C_{1-6}$alkyl-, —N=CR-phenyl-O—$C_1$-$C_6$alkyl-, —N=CR-phenyl-O—$C_1$-$C_6$alkyl-C(O)—, —C(O)—$C_1$-$C_6$alkyl(OCH$_2$CH$_2$)$_{1-6}$NR$^C$(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-6}$—NR$^C$(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl- and (—CH$_2$—CH$_2$—O—)$_{1-20}$;

$L^{B2}$ is AA$_{0-12}$, wherein AA is a natural amino acid, a non-natural amino acid or —(CR$^{15}$)$_o$—S—S—(CR$^{15}$)$_p$ where o and p are each independently an integer from 1 to 20, $L^{B3}$ is —PABA-, —PABC—, —C(O)(CH$_2$)$_n$C(O)— or absent;

$L^C$ is absent or is independently selected from the group consisting of —$C_1$-$C_6$alkylene-, —NR$C_3$-$C_8$-heterocyclylNR—, —NR$C_3$-$C_8$-carbocyclylNR—, —NR$C_1$-$C_6$alkylNR—, —NR$C_1$-$C_6$alkylene-, —S—, —NR—, —NRNR—, —O(CR$_2$)$_{1-4}$S—S(CR$_2$)$_{1-4}$N(R)—, —NR$C_1$-$C_6$-alkylenephenyleneNR—, —NR$C_1$-$C_6$alkylenephenyleneSO$_2$NR—, —OC$_1$-$C_6$alkylS-SC$_1$-$C_6$alkylC(COOR)NR—, —NR$^C$(COOR)$C_1$-$C_6$alkylS-SC$_1$-$C_6$alkylO—,

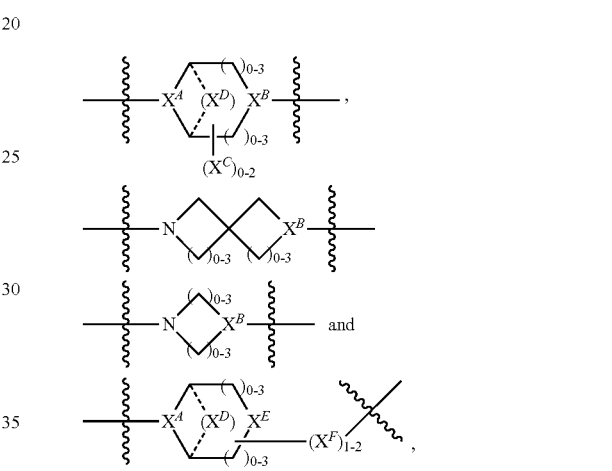

wherein $X^A$ is CR or N, $X^B$ is H, CR(C(R)$_2$)$_{1-3}$NR, CR(C(R)$_2$)$_{1-3}$O, CR(C(R)$_2$)$_{1-3}$C(O)NR, CR—(C(R)$_2$)$_{1-3}$C(O)NRNR, CR(C(R)$_2$)$_{1-3}$SO$_2$NR, CR(C(R)$_2$)$_{1-3}$NRNR, CR(C(R)$_2$)$_{1-3}$NRC(O) or N;

each $X^C$ is R;

each $X^D$ is —(CH$_2$)$_{1-5}$—, or is absent;

$X^E$ is O, S, C(R)$_2$, C(R)(C(R)$_2$)$_{1-3}$—NR$_2$ or NR, and each $X^F$ is (C(R)$_2$)$_{1-3}$—NR or C(R)$_2$—(C(R)$_2$)$_{1-3}$—O.

Additional aspects of the invention include compounds such as those mentioned herein where each R is independently selected from the group consisting of H, deuterium, —$C_1$-$C_{20}$ alkyl and —NH$_2$;

each $V^1$ is independently O or N(R) for each ring system in which $V^1$ appears;

each $V^2$ is independently O or N(R) for each ring system in which $V^2$ appears;

W and $W^2$ are each independently H, —$C_1$-$C_8$ alkyl, —C(O)OR, or —C(O)NR$_2$ for each ring system in which $W^1$ and $W^2$ appear;

each X is independently halo, for each ring system in which X appears;

each Y is independently selected from the group consisting of H, —C(O)$R^A$, —C(O)N($R^A$)$_2$, a carbohydrate such as glycosyl, —NO$_2$, —PO(O$R^A$)$_2$, an amino acid and a peptide (in particular a peptide that is cleaved by proteases such as cathepsins and matrix metalloproteinases) for each ring system in which Y appears, wherein each $R^A$ is independently selected from the group consisting of H, —$C_1$-$C_{20}$ alkyl, —$C_1$-$C_8$ heteroalkyl, —$C_3$-$C_8$ carbocyclyl and —$C_1$-$C_{20}$ alkylN(R)$_2$, wherein said —$C_1$-$C_{20}$ alkyl, —$C_1$-$C_8$ heteroalkyl, —$C_3$-$C_8$ carbocyclyl and —$C_1$-$C_{20}$ alkylN(R)$_2$ are optionally substituted with 1 to 3 substitutents independently selected from R;

$L^1$ and $L^2$ are each independently selected from a direct bond and carbonyl; and T is selected from:
—$NR^B$-$T^1$-$NR^C$— where $R^B$ and $R^C$ are each independently H or —$C_1$-$C_8$ alkyl,
—C(O)hetC(O)— wherein het is a monocyclic heteroaryl of 5 to 12 members, containing one or two heteroatoms independently selected from O, N and S, wherein het is optionally substituted with 1 to 8 substituents each independently selected from the group consisting of —$C_1$-$C_8$ alkyl, —$NH_2$, and —$NH_2$, and said optional substituents on het are optionally substituted with —$C_1$-$C_8$ alkyl, and
—$C(A^1)X^1$-$T^2$-$X^C(B^1)$—, where $T^2$ is:

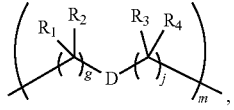

wherein each $X^1$ is a bond, wherein $A^1$ and $B^1$ are each independently =O, wherein $R^1$, $R^2$, $R^3$, and $R^4$ are each independently H or $R^1$ and $R^2$ form a ring system, or $R^3$ and $R^4$ form a ring system, or both $R^1$ and $R^2$, and $R^3$ and $R^4$, each independently form ring systems, or $R^1$ and $R^3$ form a ring system, or $R^2$ and $R^4$ form a ring system, or both $R^1$ and $R^3$, and $R^2$ and $R^4$, each independently form ring systems, where said ring systems are independently selected from —$C_1$-$C_{10}$ heterocyclyl or —$C_3$-$C_0$ carbocyclycl, and wherein D is a bond or is selected from the group consisting of —S—, —$C_1$-$C_8$ alkylene-, —$C_6$-$C_{14}$ arylene-, —$C_6$-$C_{14}$ heteroarylene-, —$C_1$-$C_{10}$ heterocyclo and —$C_3$-$C_8$ carbocyclo, where said —$C_1$-$C_8$ alkylene-, —$C_6$-$C_{14}$ arylene-, —$C_6$-$C_{14}$ heteroarylene-, —$C_1$-$C_{10}$ heterocyclo and —$C_3$-$C_8$ carbocyclo are optionally substituted with —$NH_2$, —N(R)C(O)H or —N(R)C(O)OH.

Additional aspects of the invention include compounds such as those mentioned herein where two or more R optionally join to form a ring or rings.

Additional aspects of the invention include compounds such as those mentioned herein where
each R is independently selected from the group consisting of H, deuterium, —$C_1$-$C_{20}$ alkyl and —$NH_2$;
each $V^1$ is independently O or N(R) for each ring system in which $V^4$ appears;
each $V^2$ is independently O or N(R) for each ring system in which $V^2$ appears;
$W^1$ and $W^2$ are each independently H, —$C_1$-$C_5$ alkyl, —C(O)OR, or —C(O)NR$_2$ for each ring system in which $W^1$ and $W^2$ appear;
each X is independently halo, for each ring system in which X appears;
each Y is independently selected from a bond, H, —C(O)$R^A$, C(S)$R^A$, C(O)O$R^A$, —S(O)$_2R^A$, —C(O)N($R^A$)$_2$, —C(S)N($R^A$)$_2$, a carbohydrate such as glycosyl, —$NO_2$, —P(O)(O$R^A$)$_2$, an amino acid, and a peptide (in particular a peptide that is cleaved by proteases such as cathepsins and matrix metalloproteinases) for each ring system in which Y appears, wherein each $R^A$ is independently selected from H, —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl, —$C_1$-$C_{20}$ alkylN(R)$_2$, —$C_1$-$C_{20}$ alkylene, —$C_1$-$C_8$ heteroalkylene, —$C_6$-$C_{14}$ arylene, aralkylene, —$C_1$-$C_{10}$ heterocyclo, —$C_3$-$C_8$ carbocyclo and —$C_1$-$C_{20}$ alkylN(R)—, and $R^F$ where said $R^A$ is optionally substituted with 1 to 3 substituents independently selected from R, and wherein one Y is divalent and is bonded to L, $R^F$ is —N($R^6$)QN($R^5$)C(O)— and is bonded to L at the carbonyl adjacent N($R^5$), wherein $R^5$ and $R^6$ are each independently selected from the group consisting of H, —$C_1$-$C_8$ alkyl, and —$C_1$-$C_8$ heteroalkyl, or $R^5$ or $R^6$ joins with a substituted carbon on Q to form a —$C_1$-$C_{10}$ heterocyclic or —$C_6$-$C_{14}$ heteroaryl ring, or $R^5$ and $R^6$ join together to form a —$C_1$-$C_{10}$ heterocyclic or —$C_6$-$C_{14}$ heteroaryl ring system, and where Q is —$C_1$-$C_8$ alkylene-, —$C_6$-$C_{14}$ arylene-, or —$C_3$-$C_8$ carbocyclo-, wherein Q, $R^5$ and $R^6$ are each independently optionally substituted with 1 to 3 substituents independently selected from R;

$L^1$ and $L^2$ are each independently selected from a direct bond and carbonyl; and T is selected from:
—$NR^B$-$T^1$-$NR^C$— where $R^B$ and $R^C$ are each independently H or —$C_1$-$C_8$ alkyl,
—C(O)hetC(O)— wherein het is a monocyclic heteroaryl of 5 to 12 members, containing one or two heteroatoms independently selected from O, N and S, wherein het is optionally substituted with 1 to 8 substituents each independently selected from the group consisting of —$C_1$-$C_8$ alkyl, —$NH_2$, and —$NH_2$, and said optional substituents on het are optionally substituted with —$C_1$-$C_8$ alkyl, and
—$C(A^1)X^1$-$T^2$-$X^1C(B^1)$—, where $T^2$ is:

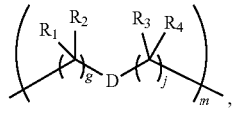

wherein each $X^1$ is a bond, wherein A1 and B1 are each independently =O, wherein $R^1$, $R^2$, $R^3$, and $R^4$ are each independently H or $R^1$ and $R^2$ form a ring system, or $R^3$ and $R^4$ form a ring system, or both $R^1$ and $R^2$, and $R^3$ and $R^4$, each independently form ring systems, or $R^1$ and $R^3$ form a ring system, or $R^2$ and $R^4$ form a ring system, or both $R^1$ and $R^3$, and $R^2$ and $R^4$, each independently form ring systems, where said ring systems are independently selected from —$C_1$-$C_{10}$ heterocyclyl or —$C_3$-$C_0$ carbocyclycl, and wherein D is a bond or is selected from the group consisting of —S—, —$C_1$-$C_8$ alkylene-, —$C_6$-$C_{14}$ arylene-, —$C_6$-$C_{14}$ heteroarylene-, —$C_1$-$C_{10}$ heterocyclo and —$C_3$-$C_8$ carbocyclo, where said —$C_1$-$C_8$ alkylene-, —$C_6$-$C_{14}$ arylene-, —$C_6$-$C_{14}$ heteroarylene-, —$C_1$-$C_{10}$ heterocyclo and —$C_3$-$C_8$ carbocyclo are optionally substituted with —$NH_2$, —N(R)C(O)H or —N(R)C(O)OH.

Additional aspects of the invention include compounds such as those mentioned herein where
each R is independently selected from the group consisting of H, deuterium, —$C_1$-$C_{20}$ alkyl and —$NH_2$;
each $V^1$ is independently O or N(R) for each ring system in which $V^1$ appears;
each $V^2$ is independently O or N(R) for each ring system in which $V^2$ appears;
$W^1$ and $W^2$ are each independently H, —$C_1$-$C_5$ alkyl, —C(O)OR, or —C(O)NR$_2$ for each ring system in which $W^1$ and $W^2$ appear;
each X is independently halo, for each ring system in which X appears;

each Y is independently selected from the group consisting of H, —C(O)R$^A$, —C(O)N(R$^A$)$_2$, a carbohydrate such as glycosyl, —NO$_2$, —PO(OR$^A$)$_2$, an amino acid, and a peptide (in particular a peptide that is cleaved by proteases such as cathepsins and matrix metalloproteinases) for each ring system in which Y appears, wherein each R$^A$ is independently selected from the group consisting of H, —C$_1$-C$_{20}$ alkyl, —C$_1$-C$_8$ heteroalkyl, —C$_3$-C$_8$ carbocyclyl and —C$_1$-C$_{20}$ alkylN(R)$_2$, wherein said —C$_1$-C$_{20}$ alkyl, —C$_1$-C$_8$ heteroalkyl, —C$_3$-C$_8$ carbocyclyl and —C$_1$-C$_{20}$ alkylN(R)$_2$ are optionally substituted with 1 to 3 substitutents independently selected from R;
L$^1$ and L$^2$ are each independently selected from a direct bond and carbonyl; and
T is —C(A$^1$)X$^1$-T$^2$-X$^C$(B$^1$)—, where T$^2$ is:

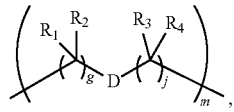

wherein each X$^1$ is a bond, wherein A1 and B1 are each independently =O, wherein R$^1$, R$^2$, R$^3$, and R$^4$ are each independently H or R$^1$ and R$^2$ form a ring system, or R$^3$ and R$^4$ form a ring system, or both R$^1$ and R$^2$, and R$^3$ and R$^4$, each independently form ring systems, or R$^1$ and R$^3$ form a ring system, or R$^2$ and R$^4$ form a ring system, or both R$^1$ and R$^3$, and R$^2$ and R$^4$, each independently form ring systems, where said ring systems are independently selected from —C$_1$-C$_{10}$ heterocyclyl or —C$_3$-C$_8$ carbocyclycl, and wherein D is a bond or is selected from the group consisting of —S—, —C$_1$-C$_8$ alkylene-, —C$_6$-C$_{14}$ arylene-, —C$_6$-C$_{14}$ heteroarylene-, —C$_1$-C$_{10}$ heterocyclo and —C$_3$-C$_8$ carbocyclo, where said —C$_1$-C$_8$ alkylene-, —C$_6$-C$_{14}$ arylene-, —C$_6$-C$_{14}$ heteroarylene-, —C$_1$-C$_{10}$ heterocyclo and —C$_3$-C$_8$ carbocyclo are optionally substituted with —NH$_2$, —N(R)C(O)H or —N(R)C(O)OH.

Additional aspects of the invention include compounds such as those mentioned herein where
L$^A$ is selected from the group consisting of -halo, —N(R)$_2$, —CON(R)$_2$, —S-aryl optionally substituted with —NO$_2$ or —CON(R)$_2$, —S-heteroaryl optionally substituted with —NO$_2$, alkyl-SO$_2$-heteroaryl, arylSO$_2$-heteroaryl-, and

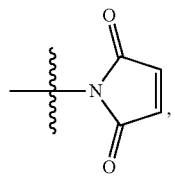 [SMILES: *N1C(=O)C=CC1=O]

L$^B$ is L$^{B1}$-L$^{B2}$-L$^{B3}$ wherein L$^{B1}$ is absent or is one or more components selected from the group consisting of —C(O)—, —C(S)—, —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-5}$—, —C(O)C$_1$-C$_6$alkylNRC(O)—, —C(O)C$_1$-C$_6$alkyl(OCH$_2$CH$_2$)$_{1-5}$—, —C$_1$-C$_6$alkyl(OCH$_2$CH$_2$)$_{1-5}$—C(O)—, —C$_1$-C$_6$alkyl-S—S—C$_1$-C$_6$alkylNRC(O)CH$_2$—, —C$_1$-C$_6$alkyl(OCH$_2$CH$_2$)$_{1-6}$NR$^C$(O)CH$_2$—, —C(O)C$_1$-C$_6$alkyl-NR$^C$(O)C$_1$-C$_6$alkyl-, —C(O)—C$_1$-C$_6$alkyl(OCH$_2$CH$_2$)$_{1-6}$NR$^C$(O)—, —C(O)C$_1$-C$_6$alkyl-phenyl(NR—C(O)C$_1$-C$_6$alkyl)$_{1-4}$-, —C(O)C$_1$-C$_6$alkyl(OCH$_2$CH$_2$)$_{1-5}$—NR$^C$(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl- and (—CH$_2$—CH$_2$—O—)$_{1-20}$, wherein L$^{B2}$ is AA$_{0-12}$, wherein AA is a natural amino acid, a non-natural amino acid or —(CR$^{15}$)$_o$—S—S—(CR$^{15}$)$_p$ where o and p are each independently an integer from 1 to 20, and L$^{B3}$ is —PABA-, —PABC—, —C(O)(CH$_2$)$_n$C(O)— or absent; and L$^C$ is absent.

Additional aspects of the invention include antibody drug conjugates such as those mentioned herein where L$^A$ is selected from: a bond to AB, —NR-(bond to AB), -heteroaryl-(bond to AB),

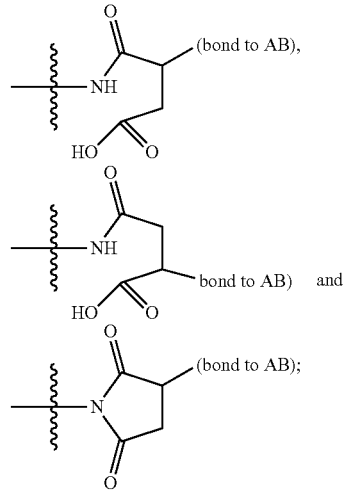

L$^B$ is L$^{B1}$-L$^{B2}$-L$^{B3}$ wherein L$^{B1}$ is absent or is one or more components selected from the group consisting of —C(O)—, —C(S)—, —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-6}$—, —C(O)C$_1$-C$_6$alkylNRC(O)—, —C(O)C$_1$-C$_6$alkyl(OCH$_2$CH$_2$)$_{1-6}$—, —C$_1$-C$_6$alkyl(OCH$_2$CH$_2$)$_{1-6}$—C(O)—, —C$_1$-C$_6$alkyl-S—S—C$_1$-C$_6$alkylNRC(O)CH$_2$—, —C$_1$-C$_6$alkyl(OCH$_2$CH$_2$)$_{1-6}$NR$^C$(O)CH$_2$—, —C(O)C$_1$-C$_6$alkyl-NR$^C$(O)C$_1$-C$_6$alkyl-, —C(O)—C$_1$-C$_6$alkyl(OCH$_2$CH$_2$)$_{1-6}$NR$^C$(O)—, —C(O)C$_1$-C$_6$alkyl-phenyl(NR—C(O)C$_1$-C$_6$alkyl)$_{1-4}$-, —C(O)C$_1$-C$_6$alkyl(OCH$_2$CH$_2$)$_{1-6}$—NR$^C$(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl- and (—CH$_2$—CH$_2$—O—)$_{1-20}$, wherein L$^{B2}$ is AA$_{0-12}$, wherein AA is a natural amino acid, a non-natural amino acid or —(CR$^{15}$)$_o$—S—S—(CR$^{15}$)$_p$ where o and p are each independently an integer from 1 to 20, and L$^{B3}$ is —PABA-, —PABC—, —C(O)(CH$_2$)$_n$C(O)— or absent.

Additional aspects of the invention include compounds such as those mentioned herein where R$^F$ is selected from:

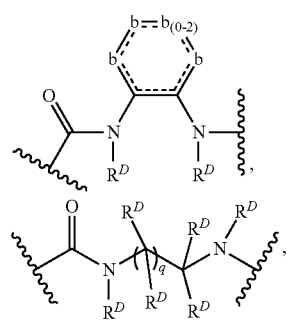

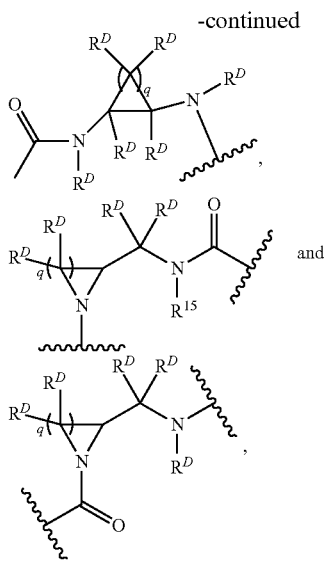

wherein q is 1-10, and each b is independently $CR^D$, N, $NR^D$, O or S.

Additional aspects of the invention include compounds such as those mentioned herein where one or more W is $C_1$-$C_3$ alkyl.

Additional aspects of the invention include compounds such as those mentioned herein where X is chloro.

Additional aspects of the invention include compounds such as those mentioned herein where one Y is H or —C(O)$C_1$-$C_{10}$alkyl.

Additional aspects of the invention include compounds such as those mentioned herein where one or more Z is H.

Additional aspects of the invention include compounds such as those mentioned herein where T is selected from an amide, or amino-tether-amino of the formula —NH—C(O)—NH— or —NH—C(O)-het-C(O)—NH—.

Additional aspects of the invention include compounds such as those mentioned herein where the amide is —C(O)NH— or —NHC(O)—.

Additional aspects of the invention include compounds such as those mentioned herein where het is a heteroaryl selected from pyrrol-2-,5-diyl-, fur-2,5-diyl-, indol-2,5-diyl, benzofuran-2,5-diyl, and 3, 6-dihydrobenzo[1, 2-b:4, 3-b]dipyrrol-2,7-diyl.

Additional aspects of the invention include compounds such as those mentioned herein where $L^1$ and $L^2$ are selected from carbonyl, 2-carbonylindole-5-yl, 2-carbonyl-6-hydroxy-7-methoxyindol-5-yl, 2-carbonyl-1,2,3,6-tetrahydrobenzo[1,2-b:4,3-b]dipyrrol-7-yl, 2-carbonyl-4-hydroxy-5-methoxy-1,2,3,6-tetrahydrobenzo[1,2-b:4,3-b']dipyrrol-7-yl, and 2-carbonyl-4-hydroxy-5-methoxy-1,2,3,6-tetrahydrobenzo[1,2-b:4,3-b']dipyrrol-7-yl.

Additional aspects of the invention are those compounds recited herein where one or more of the following apply: W is methyl; X is a halogen; Y is hydrogen or —COR where R is $C_1$-$C_{10}$alkyl; and Z is hydrogen.

The invention also includes compound as described herein where T is selected from an amide (i.e., —C(O)NH— or —NHC(O)—); or an amino-tether-amino of the formula —NH-T'-NH where T' is carbonyl or —C—(O)-het-C(O)—. Where T is an amino-tether-amino of the formula NH-T'-NH, T' may be carbonyl (i.e., —C—(O)—) or —C(O)-het-C(O)— where het is a heteroaryl selected from pyrrol-2-, 5-diyl-; fur-2, 5-diyl-; indol-2, 5-diyl; benzofuran-2, 5-diyl; or 3, 6-dihydrobenzo[1, 2-b:4, 3-b]dipyrrol-2, 7-diyl.

Also included in embodiments of the invention are those compounds as described herein where $L^1$ and $L^2$ are selected from 2-carbonylindole-5-yl; 2-carbonyl-6-hydroxy-7-methoxyindol-5-yl; 2-carbonyl-1, 2, 3, 6-tetrahydrobenzo[1, 2-b:4, 3-b]dipyrrol-7-yl; 2-carbonyl-4-hydroxy-5-methoxy-1, 2, 3, 6-tetrahydrobenzo[1, 2-b:4, 3-b']dipyrrol-7-yl; and 2-carbonyl-4-hydroxy-5-methoxy-1, 2, 3, 6-tetrahydrobenzo[1, 2-b:4, 3-b']dipyrrol-7-yl.

Another aspect of the invention includes compounds as described herein where $L^A$ is

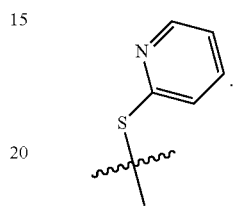

The invention includes, as well, linker-payloads or an antibody-drug-conjugates comprising a radical of the payload compounds described herein.

Importantly, the invention includes pharmaceutical compositions of the compounds, and any pharmaceutically acceptable salts or solvates thereof, described herein, where the pharmaceutical composition includes a pharmaceutically acceptable excipient.

The invention further relates to methods of treating cancer comprising administering to a patient in need thereof a therapeutically effective amount of a one or more of compound described herein, or a pharmaceutical composition or compositions comprising one or more of these compounds.

Some compounds, including payloads, linker-payloads and ADCs depicted herein, are shown in a specific stereoisomeric form. The invention, however, is meant to include all stereoisomeric forms of these compounds. For instance, a compound with two stereoisomeric centers may be depicted as the R, S form of the compound, but the invention conveys all stereoisomeric forms, e.g., R,R; R,S; S,R and S,S.

DETAILED DESCRIPTION

The present invention is directed to cytotoxic bifunctional compounds, to antibody drug conjugates (ADCs) comprising said cytotoxic bifunctional compounds, and to methods for using the same to treat cancer and other pathological conditions. The invention also relates to methods of using such compounds and/or conjugates in vitro, in situ, and in vivo for the detection, diagnosis or treatment of mammalian cells, or associated pathological conditions.

Definitions and Abbreviations

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" (or "Ab") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. An intact antibody has primarily two regions: a variable region and a constant region. The variable region binds to and interacts with a target antigen. The variable region includes a complementary determining region (CDR) that recognizes and binds to a specific binding site on a particular antigen. The constant region may be recognized by and interact with the immune system (see, e.g., Janeway et al., 2001, Immuno. Biology, 5th Ed., Garland Publishing, New York). An antibody can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

The terms "specifically binds" and "specific binding" refer to antibody binding to a predetermined antigen. Typically, the antibody binds with an affinity of at least about $1 \times 10^7$ M$^{-1}$, and binds to the predetermined antigen with an affinity that is at least two-fold greater than its affinity for binding to a non-specific antigen (e.g., BSA, casein) other than the predetermined antigen or a closely-related antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "monoclonal antibodies" specifically includes "chimeric" antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

An "intact antibody" is one which comprises an antigen-binding variable region as well as a light chain constant domain ($C_L$) and heavy chain constant domains, $C_{H1}$, $C_{H2}$, $C_{H3}$ and $C_{H4}$, as appropriate for the antibody class. The constant domains may be native sequence constant domains (e.g., human native sequence constant domains) or amino acid sequence variants thereof.

An intact antibody may have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immuno specifically bind to a target antigen (e.g., a cancer cell antigen, a viral antigen or a microbial antigen).

The term "variable" in the context of an antibody refers to certain portions of the variable domains of the antibody that differ extensively in sequence and are used in the binding and specificity of each particular antibody for its particular antigen. This variability is concentrated in three segments called "hypervariable regions" in the light chain and the heavy chain variable domains. The more highly conserved portions of variable domains are called the framework regions (FRs). The variable domains of native heavy and light chains each comprise four FRs connected by three hypervariable regions.

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (L3) in the heavy chain variable domain; Kabat et al. (Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (142) and 96-101 (H3) in the heavy chain variable domain; Chothia and Lesk, 1987, J. Mol. Biol. 196:901-917). FR residues are those variable domain residues other than the hypervariable region residues as herein defined.

A "single-chain Fv" or "scFv" antibody fragment comprises the V.sub.H and V.sub.L domains of an antibody, wherein these domains are present in a single polypeptide chain. Typically, the Fv polypeptide further comprises a polypeptide linker between the V.sub.H and V.sub.L domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

The term "diabody" refers to small antibody fragments with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., 1993, Proc. Natl. Acad. Sci. USA 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., 1986, Nature 321:522-525; Riechmann et al., 1988, Nature 332:323-329; and Presta, 1992, Curr. Op. Struct. Biol. 2:593-596.

used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of a compound (e.g., a conjugate) by weight of the isolate.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

The term "substantial amount" refers to a majority, i.e. greater than 50% of a population, of a mixture or a sample.

The term "intracellular metabolite" refers to a compound resulting from a metabolic process or reaction inside a cell on an antibody-drug conjugate (ADC). The metabolic process or reaction may be an enzymatic process such as proteolytic cleavage of a peptide linker of the ADC. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an ADC or the like, whereby the covalent attachment, e.g., the linker, between the drug moiety and the antibody is broken, resulting in the free drug, or other metabolite of the conjugate dissociated from the antibody inside the cell. The cleaved moieties of the ADC are thus intracellular metabolites.

The term "bioavailability" refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

The term "cytotoxic activity" refers to a cell-killing, a cytostatic or an anti-proliferative effect of a ADC or an intracellular metabolite of said ADC. Cytotoxic activity may be expressed as the $IC_{50}$ value, which is the concentration (molar or mass) per unit volume at which half the cells survive.

A "disorder" is any condition that would benefit from treatment with a drug or antibody-drug conjugate. This includes chronic and acute disorders or diseases including those pathological conditions which predispose a mammal to the disorder in question. Non-limiting examples of disorders to be treated herein include benign and malignant cancers; leukemia and lymphoid malignancies, neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition or disorder in mammals that is typically characterized by unregulated cell growth. A "tumor" comprises one or more cancerous cells.

Examples of a "patient" include, but are not limited to, a human, rat, mouse, guinea pig, monkey, pig, goat, cow, horse, dog, cat, bird and fowl. In an exemplary embodiment, the patient is a human.

The terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: inhibiting the growth, multiplication or replication of the pathogen that causes the infectious disease and ameliorating one or more symptoms of an infectious disease.

The term "package insert" is used to refer to instructions customarily included in commercial packages of therapeutic products, that contain information about the indication(s), usage, dosage, administration, contraindications and/or warnings concerning the use of such therapeutic products.

As used herein, the terms "cell," "cell line," and "cell culture" are used interchangeably and all such designations include progeny. The words "transformants" and "transformed cells" include the primary subject cell and cultures or progeny derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, CBI refers to 1,2,9,9a-tetrahydro-4H-benzo[e]cyclopropa[c]indol-4-one, or a substituted or derivatized form thereof. CBI can also refer to the seco form of CBI, or seco-CBI, which is also know as 1-(chloromethyl)-2,3-dihydro-1H-benzo[e]indol-5-ol, or a substituted or derivatized form (or forms) thereof.

As used herein, CPI refers to 1,2,8,8a-tetrahydrocyclopropa[c]pyrrolo[3,2-e]indol-4(5H)-one or a substituted or derivatized form thereof. CPI can also refer to the seco form of CPI, or seco-CPI, which is also know as 8-(chloromethyl)-1-methyl-3,6,7,8-tetrahydropyrrolo[3,2-e]indol-4-ol, or a substituted or derivatized form (or forms) thereof.

Unless otherwise indicated, the term "alkyl" by itself or as part of another term refers to a straight chain or branched, saturated hydrocarbon having the indicated number of carbon atoms (e.g., "$C_1$-$C_8$" alkyl refer to an alkyl group having from 1 to 8 carbon atoms). Alkyl groups typically comprise from 1 to 20 carbon atoms, preferably from 1 to 8 carbon atoms, and more preferably from 1 to 4 carbon atoms. When the number of carbon atoms is not indicated, the alkyl group has from 1 to 8 carbon atoms. Representative straight chain $C_1$-$C_8$ alkyls include, but are not limited to, methyl, ethyl, n-propyl, n-butyl, n-pentyl, n-hexyl, n-heptyl and n-octyl; while branched $C_1$-$C_8$ alkyls include, but are not limited to, -isopropyl, -sec-butyl, -isobutyl, -tert-butyl, -isopentyl, and -2-methylbutyl; unsaturated $C_2$-$C_8$ alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl. Reference to "alkyl" herein refers to unsubstituted and substituted moieties as described above.

Unless otherwise indicated, "alkylene," by itself of as part of another term, refers to a saturated, branched or straight chain or cyclic hydrocarbon radical of the stated number of carbon atoms, typically 1-18 carbon atoms, and having two monovalent radical centers derived by the removal of two hydrogen atoms from the same or two different carbon atoms of a parent alkane.) Alkylene groups typically comprise from 1 to 18 carbon atoms, preferably from 1 to 10 carbon atoms, more preferably from 1 to 8 carbon atoms, and most preferably from 1 to 4 carbon atoms. Typical alkylene radicals include, but are not limited to: methylene (—CH$_2$—), 1,2-ethylene —CH$_2$CH$_2$—), 1,3-propylene (—CH$_2$CH$_2$CH$_2$—), 1,4-butylene (—CH$_2$CH$_2$CH$_2$CH$_2$—), and the like. A "$C_1$-$C_{10}$" straight chain alkylene is a straight chain, saturated hydrocarbon group of the formula —(CH$_2$)$_{1-10}$—. Examples of a $C_1$-$C_{10}$ alkylene include methylene, ethylene, propylene, butylene, pentylene, hexylene, heptylene, ocytylene, nonylene and decalene. Reference to "alkylene" herein refers to unsubstituted and substituted moieties as described above.

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Up to two heteroatoms may be consecutive. Heteroalkyl groups typically comprise from 1 to 15 carbon atoms, preferably from 1 to 12 carbon atoms, more preferably from 1 to 8 carbon atoms, and most preferably from 1 to 4 carbon atoms. Reference to "heteroalkyl" herein refers to unsubstituted and substituted moieties as described above.

Unless otherwise indicated, the term "heteroalkylene" by itself or as part of another substituent means a divalent group derived from heteroalkyl (as discussed above). For heteroalkylene groups, heteroatoms can also occupy either or both of the chain termini. Reference to "heteroalkylene" herein refers to unsubstituted and substituted moieties as described above.

The term H or hydrogen herein typically refers to a hydrogen atom comprising a single proton and no neutron, but also includes the hydrogen isotope known as deuterium which comprises a single proton and a single neutron.

Unless otherwise indicated, "aryl," by itself or an part of another term, means a substituted or unsubstituted monovalent carbocyclic aromatic hydrocarbon radical of 5-20, preferably 5-14 or 6-14, carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like. A substituted carbocyclic aromatic group (e.g., an aryl group) can be substituted with one or more, preferably 1 to 5, of the following groups: $C_1$-$C_8$ alkyl, —O—($C_1$-$C_8$ alkyl), —C(O)R$^9$, —OC(O)R$^9$, —C(O)OR$^9$, —C(O)NH$_2$, —C(O)NHR', —C(O)N(R')$_2$, —NHC(O)R', —S(O)$_2$R', —S(O)R', —OH, halogen, —N$_3$, —NH$_2$, —NH(R$^9$), —N(R$^9$)$_2$ and —CN; wherein each R$^9$ is independently selected from —H, $C_1$-$C_8$ alkyl and unsubstituted aryl. In some embodiments, a substituted carbocyclic aromatic group can further include one or more of: —NHC(=NH)NH$_2$, —NHCONH$_2$, —S(=O)$_2$R$^9$ and —SR$^9$. "Arylene" is the corresponding divalent moiety.

"Substituted alkyl" (or "substituted alkylene", "substituted heteroalkyl", or "substituted heteroalkylene") means an the relevant alkyl alkyl-containing group or radical as discussed above in which one or more hydrogen atoms are each independently replaced with a substituent. Typical substituents include, but are not limited to, —X, —$R^{10}$, —O—, —$OR^{10}$, —$SR^{10}$, —S—, —$NR^{10}{}_2$, —$NR^{10}{}_3$, =N $R^{10}$, —$CX_3$, —CN, —OCN, —SCN, —N=C=O, —NCS, —NO, —$NO_2$, =$N_2$, —$N_3$, —N $R^{10}$C(=O)$R^{10}R^{10}$, —C(=O)$NR^{10}{}_2$, —$SO_3{}^-$, —$SO_3H$, —S(=O)$_2R^{10}$, —OS(=O)$_2OR^{10}$, —S(=O)$_2NR^{10}$, —S(=O)$R^{10}$, —OP(=O)(O$R^{10}$)$_2$, —P(=O)(O$R^{10}$)$_2$, —$PO_3{}^{2-}$, $PO_3H_2$, —$AsO_2H_2$, —C(=O)$R^{10}$, —C(=O)X, —C(=S) $R^{10}$, —$CO_2R^{10}$, —$CO_2{}^-$, —C(=S)O$R^{10}$, —C(=O)S$R^{10}$, —C(=S)S$R^{10}$, —C(=O)N$R^{10}{}_2$, —C(=S)N$R^{10}{}_2$, or —C(=N $R^{10}$)N $R^{10}{}_2$, where each X is independently a halogen: —F, —C, —Br, or —I; and each $R^{10}$ is independently —H, $C_1$-$C_{20}$ alkyl, $C_1$-$C_{20}$ heteroalkyl, $C_6$-$C_{20}$ aryl, $C_1$-$C_{10}$ heterocyclyl, a protecting group or a prodrug moiety. Aryl, alkylene and heteroalkylene groups as described above may also be similarly substituted.

Unless otherwise indicated, "aralkyl" by itself or part of another term, means an alkyl group, as defined above, substituted with an aryl group, as defined above.

Unless otherwise indicated, "$C_3$-$C_{10}$ heterocyclyl" by itself or as part of another term, refers to a monovalent substituted or unsubstituted aromatic or non-aromatic monocyclic, bicyclic or tricyclic ring system having from 2 to 10, 2 to 14, or 2-20 carbon atoms, preferably 3 to 8, carbon atoms (also referred to as ring members) and one to four heteroatom ring members independently selected from N, O, P or S, and derived by removal of one hydrogen atom from a ring atom of a parent ring system. One or more N, C or S atoms in the heterocyclyl can be oxidized. The ring that includes the heteroatom can be aromatic or nonaromatic. Aromatic heterocycles are sometimes referred to herein as heteroaryls. Unless otherwise noted, the heterocyclyl is attached to its pendant group at any heteroatom or carbon atom that results in a stable structure. Representative examples of a $C_2$-$C_{10}$ heterocyclyl include, but are not limited to, tetrahyrofuranyl, oxetanyl, pyranyl, pyrrolidinyl, piperidinyl, piperazinyl, benzofuranyl, benzothiophene, benzothiazolyl, indolyl, benzopyrazolyl, pyrrolyl, thiophenyl (thiopene), furanyl, thiazolyl, imidazolyl, pyrazolyl, triazolyl, quinolinyl including moieties such as 1,2,3,4-tetrshyhro-quinolinyl, pyrimidinyl, pyridyl, pyridonyl, pyrazinyl, pyridazinyl, isothiazolyl, isoxazolyl, tetrazolyl, epoxide, oxetane and BODIPY (substituted or unsubstituted). A $C_2$-$C_{10}$ heterocyclyl can be substituted with up to seven groups including, but not limited to, $C_1$-$C_8$ alkyl, $C_1$-$C_8$ heteroalkyl, —$OR^{11}$, aryl, —C(O)$R^{11}$, —OC(O)$R^{11}$, —C(O)O$R^{11}$, —C(O)$NH_2$, —C(O)NH$R^{11}$, —C(O)N($R^{11}$)$_2$, —NHC(O)$R^{11}$, —S(=O)$_2R^{11}$, —S(O)$R^{11}$, halogen, —$N_3$, —$NH_2$, —NH($R^{11}$), —N($R^{11}$)$_2$ and —CN; wherein each $R^{11}$ is independently selected from —H, $C_1$-$C_8$ alkyl, $C_1$-$C_8$ heteroalkyl and aryl. In some embodiments, a substituted heterocyclyl can also include one or more of: —NHC(=NH)$NH_2$, —NHCON$H_2$, —S(=O)$_2R^{11}$ and —S$R^{11}$. Heterocyclo or $C_2$-$C_{10}$ heterocyclo is the corresponding divalent moiety. Divalent aromatic heterocycles are sometimes referred to herein as heteroarylene or $C_2$-$C_{10}$ heteroarylene.

As noted above, aromatic heterocycles are sometimes referred to herein as heteroaryls, and preferably contain 5-14, 6-14, or 6-20 carbon atoms in addition to heteroatoms. Heteroaryls may be monocyclic, bicyclic, or tricyclic ring systems. Representative heteroaryls include but are not limited to triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, and quinoxalinyl. Heteroaryls are optionally substituted. Typical substituents include, but are not limited to, —X, —$R^h$, —O—, —$OR^h$, —$SR^h$, —$S^-$, —$NR^h{}_2$, —$NR^h{}_3$, =$NR^h$, —$CX_3$, —CN, —OCN, —SCN, —N=C=O, —NCS, —NO, —$NO_2$, =$N_2$, —$N_3$, —$NR^h$C(=O)$R^h$, —C(=O)$NR^h{}_2$, —$SO_3{}^-$, —$SO_3H$, —S(=O)$_2$Rh, —OS(=O)$_2OR^h$, —S(=O)$_2NR^h$, —S(=O)$R^h$, —OP(=O)(O$R^h$)$_2$, —P(=O)(O$R^h$)$_2$, —$PO_3{}^{2-}$, $PO_3H_2$, —$AsO_2H_2$, —C(=O)$R^h$, —C(=O)X, —C(=S)$R^h$, —$CO_2$Rh, —$C_{O2}$—, —C(=S)O$R^h$, —C(=O)S$R^h$, —C(=S)S$R^h$, —C(=O)N$R^h{}_2$, —C(=S)N$R^h{}_2$, —C(=NR)N$R^h{}_2$, $C_1$-$C_{20}$ heteroalkyl, $C_6$-$C_{20}$ aryl, $C_3$-$C_8$ heterocyclyl, a protecting group or a prodrug moiety, where each X is independently a halogen: —F, —Cl, —Br, or —I; and each $R^h$ is independently —H or $C_1$-$C_8$ alkyl. Divalent aromatic heterocycles are sometimes referred to herein as heteroarylenes or $C_1$-$C_{10}$ heteroarylenes.

Unless otherwise indicated, "heteroaralkyl" by itself or part of another term, means an alkyl group, as defined above, substituted with an aromatic heterocyclyl group, as defined above. Heteroaralklo is the corresponding divalent moiety.

Unless otherwise indicated, "$C_3$-$C_8$ carbocyclyl" by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative $C_3$-$C_8$ carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(1.1.1.)pentane, and bicyclo(2.2.2.)octane. A $C_3$-$C_8$ carbocyclyl group can be unsubstituted or substituted with up to seven groups including, but not limited to, $C_1$-$C_8$ alkyl, $C_1$-$C_8$ heteroalkyl, —$OR^{11}$, aryl, —C(O)$R^{11}$, —OC(O)$R^{11}$, —C(O)O$R^{11}$, —C(O)$NH_2$, —C(O)NH$R^{11}$, —C(O)N($R^{11}$)$_2$, —NHC(O)$R^{11}$, —S(=O)$_2R^{11}$, —S(=O)$R^{11}$, —OH, -halogen, —$N_3$, —$NH_2$, —NH($R^{11}$), —N($R^{11}$)$_2$ and —CN; where each $R^{11}$ is independently selected from —H, $C_1$-$C_8$ alkyl, $C_1$-$C_8$ heteroalkyl and aryl. "$C_3$-$C_8$ carbocyclo" is the corresponding divalent moiety.

As used herein, an azido substituent refers to —N=N=N; a cyanate substituent refers to —OCN; a thiocyanate substituent refers to —S—CN; an isocyanate substituent refers to —N=C=O; and a thioisocyanate substituent refers to —S—N=C=O.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Glycosyl" refers to the structure:

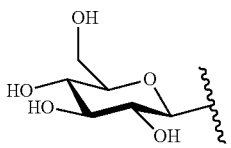

or substituted forms of same, for instance including the references structure substituted to form structures such as:

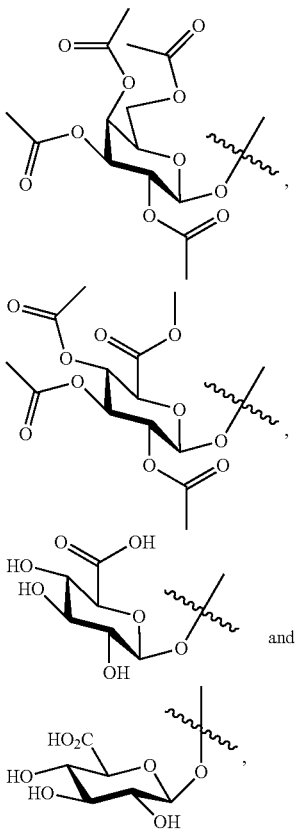

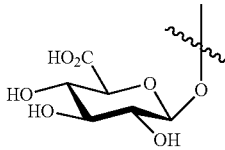

and many others.

Stereochemical definitions and conventions used herein generally follow S. P. Parker, Ed., McGraw-Hill Dictionary of Chemical Terms, McGraw-Hill Book Company, New York (1984); and Eliel and Wilen, Stereochemistry of Organic Compounds, John Wiley & Sons, Inc., New York (1994). Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

As used herein, "—PABA-" or "PABA" refers to the p-aminobenzoic acid and moieties derived therefrom, for instance the structure:

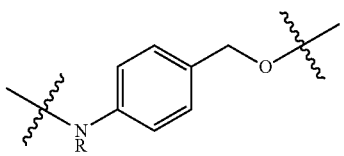

or variants thereof.

As used herein, "—PABC-" or "PABC" refers to p-aminobenzyloxycarbonyl and moieties derived therefrom, for instance the structure:

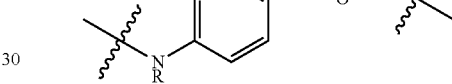

or variants thereof.

An amino acid "derivative" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs of an amino acid with substituted linkages, as well as other modifications known in the art.

A "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

"Protecting group" refers to a moiety that when attached to a reactive group in a molecule masks, reduces or prevents that reactivity. Examples of protecting groups can be found in T. W. Greene and P. G. M. Wuts, Protective Groups in Organic Synthesis, 3rd edition, John Wiley & Sons, New York, 1999, and Harrison and Harrison et al., Compendium of Synthetic Organic Methods, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, iodide), methanesulfonyl (mesyl), p-toluenesulfonyl (tosyl), trifluoromethylsulfonyl(triflate), and trifluoromethylsulfonate.

The phrase "pharmaceutically acceptable salt," as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, malate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and a compound or conjugate of the invention. Examples of solvents that form pharmaceutically acceptable solvates include, but are not limited to, water, isopropanol, ethanol, methanol, DMSO, ethyl acetate, acetic acid, and ethanolamine.

The terms "loading" or "drug loading" or "payload loading" represent or refer to the average number of payloads ("payload" and "payloads" are used interchangeable herein with "drug" and "drugs") per antibody in an ADC molecule. Drug loading may range from 1 to 20 drugs per antibody. This is sometimes referred to as the DAR, or drug to antibody ratio. Compositions of the ADCs described herein typically have DAR's of from 1-20, and in certain embodiments from 1-8, from 2-8, from 2-6, from 2-5 and from 2-4. Typical DAR values are 2, 4, 6 and 8. The average number of drugs per antibody, or DAR value, may be characterized by conventional means such as UV/visible spectroscopy, mass spectrometry, ELISA assay, and HPLC. The quantitative DAR value may also be determined. In some instances, separation, purification, and characterization of homogeneous ADCs having a particular DAR value may be achieved by means such as reverse phase HPLC or electrophoresis. DAR may be limited by the number of attachment sites on the antibody. For example, where the attachment is a cysteine thiol, an antibody may have only one or several cysteine thiol groups, or may have only one or several sufficiently reactive thiol groups through which a Linker unit may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond. Typically, fewer than the theoretical maximum of drug moieties are conjugated to an antibody during a conjugation reaction. An antibody may contain, for example, many lysine residues that do not react with a linker or linker intermediate. Only the most reactive lysine groups may react with a reactive linker reagent.

Generally, antibodies do not contain many, if any, free and reactive cysteine thiol groups which may be linked to a drug via a linker. Most cysteine thiol residues in the antibodies exist as disulfide bridges and must be reduced with a reducing agent such as dithiothreitol (DTT). The antibody may be subjected to denaturing conditions to reveal reactive nucleophilic groups such as lysine or cysteine. The loading (drug/antibody ratio) of an ADC may be controlled in several different manners, including: (i) limiting the molar excess of drug-linker relative to the antibody, (ii) limiting the conjugation reaction time or temperature, and (iii) partial or limiting reductive conditions for cysteine thiol modification. Where more than one nucleophilic group reacts with a drug-linker then the resulting product is a mixture of ADCs with a distribution of one or more drugs moieties per antibody. The average number of drugs per antibody may be calculated from the mixture by, for example, dual ELISA antibody assay, specific for antibody and specific for the drug. Individual ADCs may be identified in the mixture by mass spectroscopy, and separated by HPLC, e. g, hydrophobic interaction chromatography.

Below is a list of abbreviations and definitions that may not otherwise be defined or described in this application: DMSO (refers to dimethyl sulfoxide), HRMS (refers to high resolution mass spectrometry), DAD (refers to diode array detection), TFA (refers to 2,2,2-trifluoroacetic acid or trifluoroacetic acid), TFF (refers to tangential flow filtration), EtOH (refers to ethanol), MW (refers to molecular weight), HPLC (refers to high performance liquid chromatography), prep HPLC (refers to preparative high performance liquid chromatography), etc. (refers to and so forth), trityl (refers 1,1',1"-ethane-1,1,1-triyltribenzene), THF (refers to tetrahydrofuran), NHS (refers to 1-Hydroxy-2,5-pyrrolidinedione), Cbz (refers to carboxybenzyl), eq. (refers to equivalent), n-BuLi (refers to n-butyllithium), OAc (refers to acetate), MeOH (refers to methanol), i-Pr (refers to isopropyl or propan-2-yl), NMM (refers to 4-methylmorpholine), and "-" (in a table refers to no data available at this time).

Divalent moieties and substituents used herein are meant to refer to said moieties or substituents bound or linked in either direction or both directions. For instance, the moiety —C(O)NR— (in the definition of $L^{B1}$, and elsewhere) is meant to convey —C(O)NR— as well as —NR$^C$(O)—, the moiety —C(O)C$_1$-C$_6$alkyl- is meant to convey —C(O)C$_1$-C$_6$alkyl- as well as —C$_1$-C$_6$alkylC(O)—, and so on. More generally, a description of a non-symmetrical divalent moiety linked on its "left" and "right" sides is meant to convey both the moiety as presented (left side of the moiety linked on left side as written, right side of the moiety linked on the right side as written) and the reverse of the moiety as presented (left side of the moiety linked on right side as written, right side of the moiety linked on the left side as written).

The terms "bond" and "absent" are both used herein to describe a variable which does not include an atom or atoms. Thus, where a divalent variable that is "absent" is understood to mean that the adjacent moieties are bound to one another. For example, if $L^{B2}$ is absent it is understood that $L^{B1}$ may be bound to $L^{B3}$; or if $L^{B1}$ and $L^{B2}$ are both absent it is understood that $L^A$ may be bound to $L^{B3}$. Similarly, if a divalent variable is defined as being a "bond" this is understood to mean that there are no atoms present and the adjacent moieties are bound to one another. Thus, for instance, where variable "D" is defined as being a bond it is appreciated that the carbons adjacent D (in the structure defining $T^2$) are bound to one another. An absent monovalent variable is understood to be a hydrogen or an electron pair capable of further covalent bonding.

The Antibody Unit (A, Ab or AB)

As noted above, the term "antibody" (or "A", "Ab" or "AB") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. In addition, while certain aspects of the invention described herein refer to antibody drug conjugates, it is further envisioned that the antibody portion of the conjugate might be replaced with anything that specifically binds or reactively associates or complexes with a receptor, antigen or other receptive moiety associated with a given target-cell population. For example, instead of containing an antibody a conjugates of the invention could contain a targeting molecule that binds to, complexes with, or reacts with a receptor, antigen or other receptive moiety of a cell population sought to be therapeutically or otherwise biologically modified. Example of such molecules include smaller molecular weight proteins, polypeptide or peptides, lectins, glycoproteins, non-peptides, vitamins, nutrient-transport molecules (such as, but not limited to, transferrin), or any other cell binding molecule or substances. In certain aspects, the antibody or other such targeting molecule acts to deliver a drug to the particular target cell population with which the antibody or other targeting molecule interacts.

In another aspect, the present invention relates to an antibody drug conjugate compound of Formulae IIIA or IIIB wherein the antibody AB is selected from: trastuzumab, trastuzumab mutants (for instance the trastuzumab mutants disclosed herein or in international patent application PCT/IB2012/056234), oregovomab, edrecolomab, cetuximab, a humanized monoclonal antibody to the vitronectin receptor ($\alpha_v\beta_3$), alemtuzumab, anti-HLA-DR antibodies including a humanized anti-HLA-DR antibody for the treatment of non-Hodgkin's lymphoma, 1311 Lym-1, anti-HLA-Dr10 antibodies including a murine anti-HLA-Dr10 antibody for the treatment of non-Hodgkin's lymphoma, anti-cd33 antibodies, anti-cd22 antibodies including a humanized anti-CD22 mAb for the treatment of Hodgkin's Disease or non-Hodgkin's lymphoma, labetuzumab, bevacizumab, ibritumomab tiuxetan, ofatumumab, panitumumab, rituximab, tositumomab, ipilimumab, and gemtuzumab.

Heteroatoms that may be present on an antibody unit include sulfur (in one embodiment, from a sulfhydryl group of an antibody), oxygen (in one embodiment, from a carbonyl, carboxyl or hydroxyl group of an antibody) and nitrogen (in one embodiment, from a primary or secondary amino group of an antibody). These hetero atoms can be present on the antibody in the antibody's natural state, for example a naturally-occurring antibody, or can be introduced into the antibody via chemical modification.

In one embodiment, an antibody unit has a sulfhydryl group and the antibody unit bonds via the sulfhydryl group's sulfur atom.

In another embodiment, the antibody has lysine residues that can react with activated esters (such esters include, but are not limited to, N-hydroxysuccinimde, pentafluorophenyl, and p-nitrophenyl esters) and thus form an amide bond consisting of the nitrogen atom of the antibody unit and a carbonyl.

In yet another aspect, the antibody unit has one or more lysine residues that can be chemically modified to introduce one or more sulfhydryl groups. The reagents that can be used to modify lysines include, but are not limited to, N-succinimidyl S-acetylthioacetate (SATA) and 2-Iminothiolane hydrochloride (Traut's Reagent).

In another embodiment, the antibody unit can have one or more carbohydrate groups that can be chemically modified to have one or more sulfhydryl groups.

In yet another embodiment, the antibody unit can have one or more carbohydrate groups that can be oxidized to provide an aldehyde group (see, e.g., Laguzza, et al., 1989, J. Med. Chem. 32(3):548-55). The corresponding aldehyde can form a bond with a reactive site such as, for example, hydrazine and hydroxylamine. Other protocols for the modification of proteins for the attachment or association of drugs are described in Coligan et al., Current Protocols in Protein Science, vol. 2, John Wiley & Sons (2002) (incorporated herein by reference).

When the conjugates comprise non-immunoreactive protein, polypeptide, or peptide units instead of an antibody, useful non-immunoreactive protein, polypeptide, or peptide units include, but are not limited to, transferrin, epidermal growth factors ("EGF"), bombesin, gastrin, gastrin-releasing peptide, platelet-derived growth factor, IL-2, IL-6, transforming growth factors ("TOP"), such as TGF-$\alpha$ and TGF-$\beta$, vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art (e.g., Teng et al., 1983, Proc. Natl. Acad. Sci. USA. 80:7308-7312; Kozbor et al., 1983, Immunology Today 4:72-79; and Olsson et al., 1982, Meth. Enzymol. 92:3-16).

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (for location of the CDR sequences, see, e.g., Kabat et al., 1991, Sequences of Proteins of Immunological Interest, Fifth Edition, National Institute of Health, Bethesda, Md.; Kabat E et al., 1980, J. Immunology 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903). Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan and Carter, 2002, The rise of monoclonal antibodies as therapeutics, In Anti-IgE and Allergic Disease, Jardieu and Fick, eds., Marcel Dekker, New York, N.Y., Chapter 20, pp. 427-469).

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, OVAREX which is a murine antibody for the treatment of ovarian cancer; PANOREX (Glaxo Wellcome, N.C.) which is a murine $IgG_{2a}$ antibody for the treatment of colorectal cancer; Cetuximab ERBITUX (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; CAMPATH I/H (Leukosite, MA) which is a humanized $IgG_1$ antibody for the treatment of chronic lymphocytic leukemia (CLL); SMART ID10 (Protein Design Labs, Inc., CA) which is a humanized anti-HLA-DR antibody for the treatment of non-Hodgkin's lymphoma; ONCOLYM (Techniclone, Inc., CA) which is a radiolabeled murine anti-HLA-Dr10 antibody for the treatment of non-Hodgkin's lymphoma; ALLOMUNE (BioTransplant, CA) which is a humanized anti-CD2 mAb for the treatment of Hodgkin's Disease or non-Hodgkin's lymphoma; and CEACIDE (Immunomedics, NJ) which is a humanized anti-CEA antibody for the treatment of colorectal cancer.

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

The Linker Unit (L)

A linker (sometimes referred to as "[linker]" herein) is a bifunctional compound which can be used to link a drug and an antibody to form an antibody drug conjugate (ADC). Such conjugates are useful, for example, in the formation of immunoconjugates directed against tumor associated antigens. Such conjugates allow the selective delivery of cytotoxic drugs to tumor cells.

In an ADC the linker serves to attach the payload to the antibody.

In one aspect, a second section of the linker unit is introduced which has a second reactive site e.g., an electrophilic group that is reactive to a nucleophilic group present on an antibody unit (e.g., an antibody). Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups. The electrophilic group provides a convenient site for antibody attachment.

In another embodiment, a linker unit has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide. The electrophilic group on an antibody provides a convenient site for attachment to a linker unit.

Amino functional groups are also useful reactive sites for a linker unit because they can react with carboxylic acid, or activated esters of a compound to form an amide linkage. Typically, the peptide-based compounds of the invention can be prepared by forming a peptide bond between two or more amino acids and/or peptide fragments. Such peptide bonds can be prepared, for example, according to the liquid phase synthesis method (see, e.g., Schroder and Lubke, "The Peptides", volume 1, pp 76-136, 1965, Academic Press) that is well known in the field of peptide chemistry.

In the context of the invention, particularly but not limited to linker components such as $L_1$, $L_2$ (including $L_2^A$, $L_2^B$ and $L_2^C$) and $L_3$, the language "selected from one or more of" or "one or more of" indicates that multiple components, which may be the same or different, are or may be arranged sequentially. Thus, for example, $L_3$ may be —$C_{1-6}$alkyl-, —NR— or the other individually listed components, but also —$C_{1-6}$alkyl-NR—, or any other combination of 2 or more listed components.

In another embodiment, a linker unit has a reactive site that can react with antibody nucleophiles, such as cysteins. The reactive site is comprised of a heterocycle that is substituted with a sulfone. The sulfone is then replaced by the antibody nucleophile (i.e. cysteine) and the newly formed bond between the antibody and the heterocycle connects the antibody to the linker. See, WO 2014/144878.

Synthesis of Compounds and Antibody Drug Conjugates Thereof

The compounds and conjugates of the invention can be made using the synthetic procedures outlined below in the Exemplification. As described in more detail below, the compounds and conjugates of the invention can be prepared using a section of a linker unit having a reactive site for binding to the compound. In one aspect, a second section of the linker unit is introduced which has a second reactive site e.g., an electrophilic group that is reactive to a nucleophilic group present on an antibody unit (e.g., an antibody). Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups. The electrophilic group provides a convenient site for antibody attachment.

In another embodiment, a linker unit has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide. The electrophilic group on an antibody provides a convenient site for attachment to a linker unit.

Amino functional groups are also useful reactive sites for a linker unit because they can react with carboxylic acid, or activated esters of a compound to form an amide linkage. Typically, the peptide-based compounds of the invention can be prepared by forming a peptide bond between two or more amino acids and/or peptide fragments. Such peptide bonds can be prepared, for example, according to the liquid phase synthesis method (see, e.g., Schroder and Lubke, "The Peptides", volume 1, pp 76-136, 1965, Academic Press) that is well known in the field of peptide chemistry.

As described in more detail below, the conjugates can be prepared using a section of the linker having a reactive site for binding to a compound of the invention and introducing another section of the linker unit having a reactive site for an antibody. In one aspect, a linker unit has a reactive site which has an electrophilic group that is reactive with a nucleophilic group present on an antibody unit, such as an antibody. The electrophilic group provides a convenient site for antibody attachment. Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups.

In another embodiment, a linker unit has a reactive site which has a nucleophilic group that is reactive with an electrophilic group present on an antibody unit. The electrophilic group on an antibody provides a convenient site for attachment to a linker unit. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide.

In another embodiment of the invention the linkage of the present invention employs an engineered antibody constant domain polypeptide, or a portion thereof, wherein the engineered constant domain comprises at least one amino acid substitution to introduce a cysteine residue useful for conjugation, and wherein the constant domain polypeptide is an engineered human IgG heavy chain constant domain (Cy) polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, I336, E345, Q347, S354, R355, M358, K360, Q362, K370, Y373, D376, A378, E380, K382, Q386, E388, N390, K392, T393, D401, F404, T411, D413, K414, R416, Q418, Q419, N421, M428, A431, L432, T437, Q438, K439, L443, and S444, according to the EU index of Kabat.

In another embodiment of the invention the linkage of the present invention employs an engineered antibody constant domain polypeptide, or a portion thereof, wherein the engineered constant domain comprises at least one amino acid substitution to introduce a cysteine residue useful for conjugation, and wherein the constant domain polypeptide is an engineered human lambda light chain constant domain (CA) polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat.

In yet another embodiment of the invention the linkage of the present invention employs an engineered antibody constant domain polypeptide, or a portion thereof, wherein the engineered constant domain comprises at least one amino acid substitution to introduce a cysteine residue useful for conjugation, and wherein the constant domain polypeptide is an engineered human kappa light chain constant domain (CK) polypeptide, or portion thereof, comprising at least one amino acid substitution selected from the group consisting of A111, K183, and N210, according to the numbering of Kabat.

In yet another embodiment of the invention the linkage of the present invention employs an engineered antibody constant domain polypeptide, or a portion thereof, wherein the engineered constant domain comprises at least one amino acid substitution to introduce a cysteine residue useful for conjugation, and wherein the constant domain polypeptide is an engineered Cy polypeptide, or portion thereof, comprising at least one amino acid sequence selected from the group consisting of an amino acid sequence of SEQ ID NOs:97-100, 102, 104, 107-127, and 129-163, as disclosed in WO2013/093809, which reference is incorporated herein in its entirety.

In still another embodiment of the invention the linkage of the present invention employs an engineered antibody constant domain polypeptide, or a portion thereof, wherein the engineered constant domain comprises at least one amino acid substitution to introduce a cysteine residue useful for conjugation, and wherein the constant domain polypeptide is an engineered CK polypeptide, or portion thereof, comprising at least one amino acid sequence selected from the group consisting of an amino acid sequence of SEQ ID NOs:90, 92, 95, 164, 166, and 169, as disclosed in WO2013/093809, which reference is incorporated herein in its entirety.

In still another embodiment of the invention the linkage of the present invention employs an engineered antibody constant domain polypeptide, or a portion thereof, wherein the engineered constant domain comprises at least one amino acid substitution to introduce a cysteine residue useful for conjugation, and wherein the constant domain polypeptide is an engineered CA polypeptide, or portion thereof, comprising at least one amino acid sequence selected from the group consisting of an amino acid sequence of SEQ ID NOs:172-186, as disclosed in WO2013/093809, which reference is incorporated herein in its entirety.

In another embodiment of the invention the engineered Cy polypeptide mentioned above further comprises at least one mutation selected from the group consisting of a mutation at amino acid position 284, 287, A327, N384, $L^{398}$, and $V^{422}$, according to the EU index of Kabat.

Conjugation with Transglutaminase

In certain embodiments, a compound of the invention may be covalently crosslinked to an Fc-containing or Fab-containing polypeptide engineered with an acyl donor glutamine-containing tag (e.g., Gln-containing peptide tags or Q-tags) or an endogenous glutamine made reactive (i.e., the ability to form a covalent bond as an acyl donor in the presence of an amine and a transglutaminase) by polypeptide engineering (e.g., via amino acid deletion, insertion, substitution, mutation, or any combination thereof on the polypeptide), in the presence of transglutaminase, provided that the compound of the invention comprises an amine donor agent (e.g., small molecule comprising or attached to a reactive amine), thereby forming a stable and homogenous population of an engineered Fc-containing polypeptide conjugate with the amine donor agent being site-specifically conjugated to the Fc-containing or Fab-containing polypeptide through the acyl donor glutamine-containing tag or the exposed/accessible/reactive endogenous glutamine. For example, compounds of the invention may be conjugated as described in International Patent Application Serial No. PCT/IB2011/054899, whose entire contents are incorporated herein by reference. In certain embodiments, to facilitate conjugation of the compound of the invention to an Fc-containing or Fab-containing polypeptide engineered with an acyl donor glutamine-containing tag or an endogenous glutamine made reactive by polypeptide engineering in the presence of transglutaminase, Z is $NH_2$.

Conjugation to the Human Light Chain Kappa Domain Constant Region

In certain embodiments, a compound of the invention may be covalently attached to the side chain of $K^{188}$ of the human light chain kappa domain constant region (CLκ) (full light chain numbering according to Kabat). For example, compounds of the invention may be conjugated as described in U.S. patent application Ser. No. 13/180,204, whose entire contents are incorporated herein by reference. In certain embodiments, to facilitate conjugation to K188 CLκ, Z is

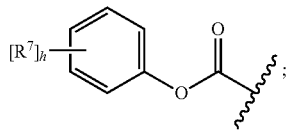

$R^7$ is independently selected for each occurrence from the group consisting of F, Cl, I, Br, $NO_2$, CN and $CF_3$; and h is 1, 2, 3, 4 or 5.

In certain embodiments, the invention provides for a composition comprising a compound of the invention covalently conjugated to an antibody (or antigen binding portion thereof), wherein at least about 50%, or at least about 60%, or at least about 70%, or at least about 80%, or at least about 90% of the compound of the invention in the composition is conjugated to the antibody or antigen binding portion thereof at $K^{188}$ CLκ.

In certain embodiments, the compounds of the invention may be conjugated to the combining site of a catalytic antibody, such as aldolase antibodies, or antigen binding portion thereof. Aldolase antibodies contain combining site portions that, when unencumbered (for example by conjugation), catalyze an aldol addition reaction between an aliphatic ketone donor and an aldehyde acceptor. The contents of US Patent Application Publication No. US 2006/205670 are incorporated herein by reference, in particular pages 78-118 describing linkers, and paragraphs [0153]-[0233] describing antibodies, useful fragments, variants and modifications thereof, h38C2, combining sites and complimentary determining regions (CDRs), and related antibody technology. The term "combining site" includes the CDRs and the adjacent framework residues that are involved in antigen binding.

Compositions and Methods of Administration

In other embodiments, another aspect of the invention relates to pharmaceutical compositions including an effective amount of a compound of the invention and/or antibody drug conjugate thereof and a pharmaceutically acceptable carrier or vehicle. In certain embodiments, the compositions are suitable for veterinary or human administration.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow a compound of the invention and/or antibody drug conjugate thereof to be bioavailable upon administration of the composition to a patient. Compositions can take the form of one or more dosage units, where for example, a tablet can be a single dosage unit, and a container of a compound of the invention and/or antibody drug conjugate thereof in liquid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the a compound of the invention and/or antibody drug conjugate thereof, the manner of administration, and the composition employed.

The pharmaceutically acceptable carrier or vehicle can be solid or particulate, so that the compositions are, for example, in tablet or powder form. The carrier(s) can be liquid. In addition, the carrier(s) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of a compound of the invention and/or antibody drug conjugate thereof that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound of the invention and/or antibody drug conjugate thereof such that a suitable dosage will be obtained. Typically, this amount is at least about 0.01% of a compound of the invention and/or antibody drug conjugate thereof by weight of the composition. In an exemplary embodiment, pharmaceutical compositions are prepared so that a parenteral dosage unit contains from about 0.01% to about 2% by weight of the amount of a compound of the invention and/or antibody drug conjugate thereof.

For intravenous administration, the composition can comprise from about 0.01 to about 100 mg of a compound of the invention and/or antibody drug conjugate thereof per kg of the patient's body weight. In one aspect, the composition can include from about 1 to about 100 mg of a compound of the invention and/or antibody drug conjugate thereof per kg of the patient's body weight. In another aspect, the amount administered will be in the range from about 0.1 to about 25 mg/kg of body weight of a compound of the invention and/or antibody drug conjugate thereof.

Generally, the dosage of a compound of the invention and/or antibody drug conjugate thereof administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

A compound of the invention and/or antibody drug conjugate thereof can be administered by any convenient route, for example by infusion or bolus injection. Administration can be systemic or local. Various delivery systems are known, e.g., encapsulation in liposomes, mieroparticles, microcapsules, capsules, etc., and can be used to administer a compound of the invention and/or antibody drug conjugate thereof. In certain embodiments, more than one compound of the invention and/or antibody drug conjugate thereof is administered to a patient.

In specific embodiments, it can be desirable to administer one or more compounds of the invention and/or antibody drug conjugates thereof locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the compound of the invention and/or antibody drug conjugate thereof can be delivered in a controlled release system, such as but not limited to, a pump or various polymeric materials can be used. In yet another embodiment, a controlled-release system can be placed in proximity of the target of the compound of the invention and/or antibody drug conjugate thereof, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a compound or antibody drug conjugate thereof is administered. Such pharmaceutical carriers can be liquids, such as water and oils, including those of petroleum, animal, vegetable or synthetic origin. The carriers can be saline, and the like. In addition, auxiliary, stabilizing and other agents can be used. In one embodiment, when administered to a patient, the compound or conjugate and pharmaceutically acceptable carriers are sterile. Water is an exemplary carrier when the compound or conjugate are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use. Other examples of suitable pharmaceutical carriers are described in "Remington's Pharmaceutical Sciences" by E. W. Martin.

In an embodiment, the compound of the invention and/or antibody drug conjugate thereof are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a compound of the invention and/or antibody drug conjugate thereof is to be administered by infusion, it can be dispensed, for example, with an infusion bottle containing sterile pharmaceutical grade water or saline. Where the compound of the invention and/or antibody drug conjugate thereof is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer.

Therapeutics Uses of Compounds and Antibody Drug Conjugates Thereof

Another aspect of the invention relates to a method of using the compounds of the invention and antibody drug conjugates thereof for treating cancer.

The compounds of the invention and/or antibody drug conjugates thereof are useful for inhibiting the multiplication of a tumor cell or cancer cell, causing apoptosis in a tumor or cancer cell, or for treating cancer in a patient. The compounds of the invention and/or antibody drug conjugates thereof can be used accordingly in a variety of settings for the treatment of animal cancers. Said conjugates can be used to deliver a compound of the invention to a tumor cell or cancer cell. Without being bound by theory, in one embodiment, the antibody of the conjugate binds to or associates with a cancer-cell or a tumor-cell-associated antigen, and the conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. In certain embodiments, once inside the cell, one or more specific peptide sequences are enzymatically or hydrolytically cleaved by one or more tumor cell or cancer cell-associated proteases, resulting in release of a compound of the invention from the conjugate. The released compound of the invention is then free to migrate within the cell and induce cytotoxic or cytostatic activities. The conjugate also can be cleaved by an intracellular protease to release a compound of the invention. In an alternative embodiment, the compound of the invention is cleaved from conjugate outside the tumor cell or cancer cell, and the compound of the invention subsequently penetrates the cell.

In certain embodiments, the conjugates provide conjugation-specific tumor or cancer drug targeting, thus reducing general toxicity of the compounds of the invention.

In another embodiment, the antibody unit binds to the tumor cell or cancer cell.

In another embodiment, the antibody unit binds to a tumor cell or cancer cell antigen which is on the surface of the tumor cell or cancer cell.

In another embodiment, the antibody unit binds to a tumor cell or cancer cell antigen which is an extracellular matrix protein associated with the tumor cell or cancer cell.

The specificity of the antibody unit for a particular tumor cell or cancer cell can be important for determining those tumors or cancers that are most effectively treated.

Particular types of cancers that can be treated with a compound of the invention and/or antibody drug conjugate thereof, include but are not limited to, carcinomas of the bladder, breast, cervix, colon, endometrium, kidney, lung, esophagus, ovary, prostate, pancreas, skin, stomach, and testes; and blood born cancers including but not limited to leukemias and lymphomas.

Multi-Modality Therapy for Cancer. Cancers, including, but not limited to, a tumor, metastasis, or other disease or disorder characterized by uncontrolled cell growth, can be treated or inhibited by administration of a compound of the invention and/or antibody drug conjugate thereof.

In other embodiments, methods for treating cancer are provided, including administering to a patient in need thereof an effective amount of a compound of the invention and/or antibody drug conjugate thereof and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. A compound of the invention and/or antibody drug conjugate thereof can be administered to a patient that has also undergone surgery as treatment for the cancer.

In some embodiments, the patient also receives an additional treatment, such as radiation therapy. In a specific embodiment, the compound of the invention and/or antibody drug conjugate thereof is administered concurrently with the chemotherapeutic agent or with radiation therapy. In another specific embodiment, the chemotherapeutic agent or radiation therapy is administered prior or subsequent to administration of a compound of the invention and/or antibody drug conjugate thereof.

A chemotherapeutic agent can be administered over a series of sessions. Any one or a combination of the chemotherapeutic agents, such a standard of care chemotherapeutic agent(s), can be administered.

Additionally, methods of treatment of cancer with a compound of the invention and/or antibody drug conjugate thereof are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

The compounds of the invention and/or antibody drug conjugates thereof can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stein cells are harvested and purged of all cancer cells, the animal's remaining bone-marrow cell population is then eradicated via the administration of a high dose of a compound of the invention and/or antibody drug conjugate thereof with or without accompanying high dose radiation therapy, and the stem cell graft is infused back into the animal. Supportive care is then provided while bone marrow function is restored and the patient recovers.

The invention is further described in the following examples, which are in not intended to limit the scope of the invention.

General Methods

Synthetic Experimental Procedures:

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Sea™ products from the Aldrich Chemical Company, Milwaukee, Wis.). Mass spectrometry data is reported from either liquid chromatography-mass spectrometry (LC-MS) or atmospheric pressure chemical ionization (APCI). Chemical shifts for nuclear magnetic resonance (NMR) data are expressed in parts per million (ppm, 6) referenced to residual peaks from the deuterated solvents employed.

For syntheses referencing procedures in other Examples or Methods, reaction Protocol (length of reaction and temperature) may vary. In general, reactions were followed by thin layer chromatography, LC-MS or HPLC, and subjected to work-up when appropriate. Purifications may vary between experiments: in general, solvents and the solvent ratios used for eluents/gradients were chosen to provide appropriate retention times. Unless otherwise specified, reverse phase HPLC fractions were concentrated via lyophilization/Freeze-drying.

Intermediate and final compounds were stored at (0° C.) or room temperature in closed vials or flasks under nitrogen. Compound names were generated with ACD Labs software.

Abbreviations for solvents and/or reagents is based on American Chemical Society guidelines and is highlighted below:

Ac=Acetyl
Boc=N-tert-butoxycarbonyl
CDI=N,N'-Carbonyldiimidazole
DCC=1,3-Dicyclohexylcarbodiimide
DCE=Dichloroethane
DCM=Dichloromethane
DEA=N,N-Diethylamine
DEAD=Diethyl azodicarboxylate
DIAD=Diisopropyl azodicarboxylate
DIBAL-H=Diisobutylaluminium hydride
DIPEA (or) Hunig's Base=N,N-Diisopropylethylamine
DMA=Dimethylacetamide
DMAP=4-Dimethylaminopyridine
DME=Dimethoxyethane
DMF=N,N-Dimethylformamide
DMSO=Dimethyl sulfoxide
DPPA=Diphenylphosphoryl azide
EDCI=1-Ethyl-3-(3-dimethylaminopropyl)carbodiimide
EtOAc=Ethyl acetate
Fmoc=Fluorenylmethyloxycarbonyl
h=hour
HATU=o-(7-azabenzotriazol-1-yl)-N,N,N',N'-tetramethyluronium hexafluorophosphate
HBTU=N,N,N',N'-Tetramethyl-O-(1H-benzotriazol-1-yl)uronium hexafluorophosphate
HOAc=Acetic acid
HOAt=1-Hydroxy-7-azabenzotriazole
HOBt=1-Hydroxybenzotriazole hydrate
LDA=Lithium diisopropylamide
Me=Methyl
MS=Molecular Sieves
MTBE=Methyl tert-butyl ether
n-BuLi=n-Butyllithium
NBS=N-Bromosuccinimide
NMM=N-methyl morpholine
Ph=Phenyl
PPTS=Pyridinium p-Toluenesulfonate
p-TsOH=p-Toluenesulfonic acid
rt=room temperature
TBAI=Tetrabutylammonium Iodide
TEA=Triethylamine
Tf=Trifluoromethanesulfonate
TFA=TFA
THF=Tetrahydrofuran
TPTU=O-(2-Oxo-1(2H)pyridyl)-N,N,N,'N'-tetramethyluronium tetrafluoroborate HPLC and LC-MS Conditions Used for Analysis Protocol A: Column: Waters Acquity UPLC HSS T3, 2.1 mm×50 mm, C18, 1.7 µm; Mobile phase A:0.1% formic acid in water (v/v); Mobile phase B: 0.1% formic acid in acetonitrile (v/v); Gradient: 5% B over 0.1 minute, 5% to 95% B over 2.5 minutes, 95% B over 0.35 minute; Flow rate: 1.25 mL/minute. Temperature: 60° C.; Detection: 200-450 nm; MS (+) range 100-2000 daltons; Injection volume: 5 µL; Instrument: Waters Acquity.

Protocol B: Column: Waters Acquity UPLC HSS T3, C18, 2.1×50 mm, 1.7 µm; Mobile phase A: 0.1% formic acid in water (v/v); Mobile phase B: 0.1% formic acid in acetonitrile (v/v); Gradient: 5% B over 0.1 minute, 5% to 95% B over 1.5 minute, 95% B over 0.35 minute; Flow rate: 1.25 mL/minute. Temperature: 60° C.; Detection: 200-450 nm; MS (+) range 100-2000 daltons; Injection volume: 5 µL; Instrument: Waters Acquity.

HPLC Conditions Used for Purification

Method A: Column: Phenomenex Luna Phenylhexyl 150×21.2 mm, 5 µm; Mobile phase A: 0.02% TFA in water (v/v); Mobile phase B: 0.02% TFA in acetonitrile (v/v); Gradient: 20% B over 1.5 minutes, 20% B to 100% B over 8.5 minutes, then 100% B over 2.0 minutes; Flow rate: 27 mL/minute. Temperature: not controlled; Detection: DAD 210-360 nm; MS (+) range 150-2000 daltons; Instrument: 305 RP Waters Fractional Lynx LCMS Method B: Column: Phenomenex Luna C18, 100×30 mm, 5 µm; Mobile phase A: 0.02% TFA in water (v/v); Mobile phase B: 0.02% TFA in acetonitrile (v/v); Gradient: 20% B over 1.5 minutes, 20% B to 100% B over 8.5 minutes, then 95% B over 2.0 minutes; Flow rate: 30 mL/minute. Temperature: not controlled; Detection: UV 215 nm; Instrument: Gilson Method C: Phenomenex Luna C18, 100×30 mm, 5 µm; Mobile phase A: 0.02% TFA in water (v/v); Mobile phase B: 0.02% TFA in acetonitrile (v/v); Gradient: variable, increasing gradient of B in A over 10 to 20 minutes. Flow rate: 27 to 30 mL/minute. Temperature: not controlled; Detection: UV 215 nm; Instrument: Gilson General Procedures:

General procedure A: To a stirring solution of the mono or diacid, in THF, dichloromethane, or a mixture of both at 0° C., oxalyl chloride (1-2.5 eq.) was added followed by a catalytic amount of DMF. The reaction allowed to stir at 0° C. for several minutes before being allowed to warm to room temperature, and then stir at room temperature for 30 minutes to several hours. The reaction was then concentrated in vacuo. In some cases the crude material was then azeotroped one to several times with heptane, or other relevant solvent or solvents. Crude material was then dried over high vacuum before being used in the next step.

General procedure B: To a stirring solution of the amine (2-2.5 eq.) in THF, dichloromethane, or a mixture of both at 0° C. (or in some cases other relevant solvent or solvents), the acid chloride, or diacid chloride was added followed by pyridine (3-6 eq.), triethylamine (3-6 eq.), or other relevant base (3-6 eq.). The reaction allowed to stir at 0° C. for a few seconds to several minutes before being allowed to warm to room temperature, and then stir at room temperature for 10 minutes to several hours. The reaction was then concentrated in vacuo. In some cases the crude material was then azeotroped one to several times with heptane, or other relevant solvent or solvents. In most cases the crude material was then purified by a described method such as silica chromatography or medium pressure reverse phase C18 chromatography.

Examples

Preparation of (S)-8-(chloromethyl)-1-methyl-7,8-dihydro-6H-thieno[3,2-e]indol-4-yl Acetate (4)

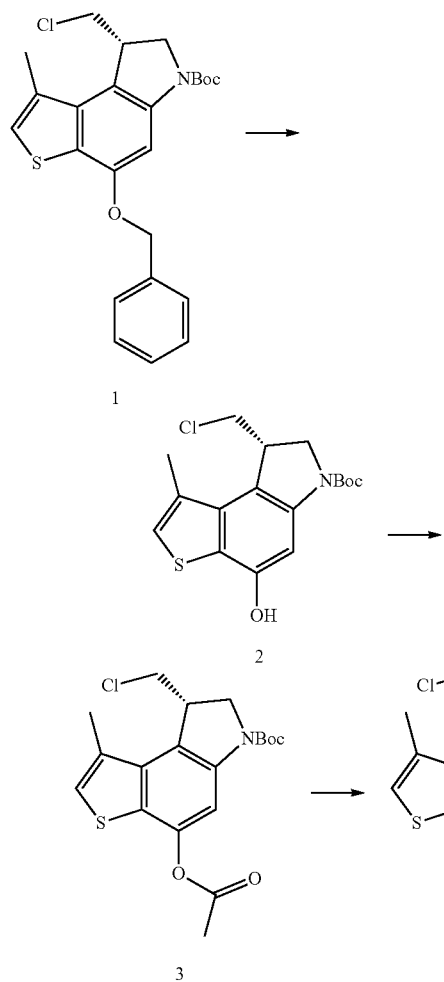

Step 1: Synthesis of tert-butyl (S)-8-(chloromethyl)-4-hydroxy-1-methyl-7,8-dihydro-6H-thieno[3,2-e]indole-6-carboxylate (2). To a stirring solution of tert-butyl (8S)-4-(benzyloxy)-8-(chloromethyl)-1-methyl-7,8-dihydro-6H-thieno[3,2-e]indole-6-carboxylate (1) [prepared as described in *J. Am. Chem. Soc.*, 2007, 129, 14092-14099.] (100 mg, 0.225 mmol) in THF (1.5 mL) was added 10% Pd/C (33 mg) followed by a 25% aqueous solution of ammonium formate (0.15 mL). The solution was stirred for 2 h. The solution was diluted with ether (6 mL) and sodium sulfate was added. The mixture was filtered through Celite and solvent removed in vacuo providing the desired product 2 as a white solid (79 mg, 100%).

Step 2: Synthesis of tert-butyl (S)-4-acetoxy-8-(chloromethyl)-1-methyl-7,8-dihydro-6H-thieno[3,2-e]indole-6-carboxylate (3). tert-Butyl (S)-8-(chloromethyl)-4-hydroxy-1-methyl-7,8-dihydro-6H-thieno[3,2-e]indole-6-carboxylate (2.69 mg, 0.19 mmol) was dissolved in CH$_2$Cl$_2$ (2 ml). Pyridine (46 mg, 0.585 mmol). Acetyl chloride (16 mL, 0.234 mmol) was added and reaction stirred for 2 h. The solvent was removed in vacuo. The crude residue was purified by flash chromatography (0-100% EtOAc/heptane) to provide desired product (45 mg, 58%).

Step 3: Synthesis of (S)-8-(chloromethyl)-1-methyl-7,8-dihydro-6H-thieno[3,2-e]indol-4-yl acetate (4): tert-butyl (S)-4-acetoxy-8-(chloromethyl)-1-methyl-7,8-dihydro-6H-thieno[3,2-e]indole-6-carboxylate (3) (45 mg, 0.11 mmol) was taken up in dioxane (1 mL). 4N HCl in dioxane (1 mL) was added and solution was stirred for 2 h. Solvent was removed to provide crude target material in quantitative yield and the material was used immediately as is.

Preparation of Bicyclo[1.1.1]-1,3-dicarboxylic Acid Chloride (6)

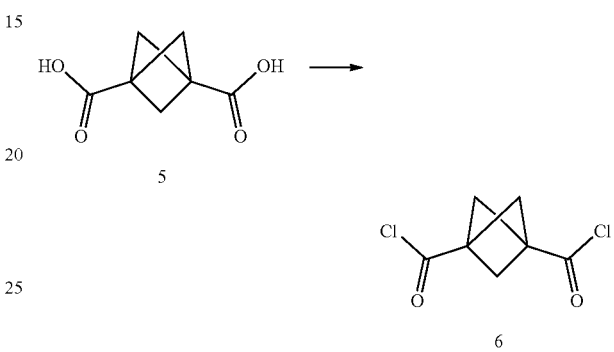

Bicyclo[1.1.1]pentane-1,3-dicarboxylic acid (50 mg) was placed in vial and taken up in THF (1 mL) and a drop of DMF was added. Oxalyl dichloride (122 mg, 0.961 mmol, 0.0825 mL) was added slowly and solution bubbled rapidly. After 2 h the solvent was removed and the diacid chloride 6 was used as is in subsequent reactions.

Preparation of (8S,8'S)-(bicyclo[1.1.1]pentane-1,3-dicarbonyl)bis(8-(chloromethyl)-1-methyl-7,8-dihydro-6H-thieno[3,2-e]indole-6,4-diyl) Diacetate (7)

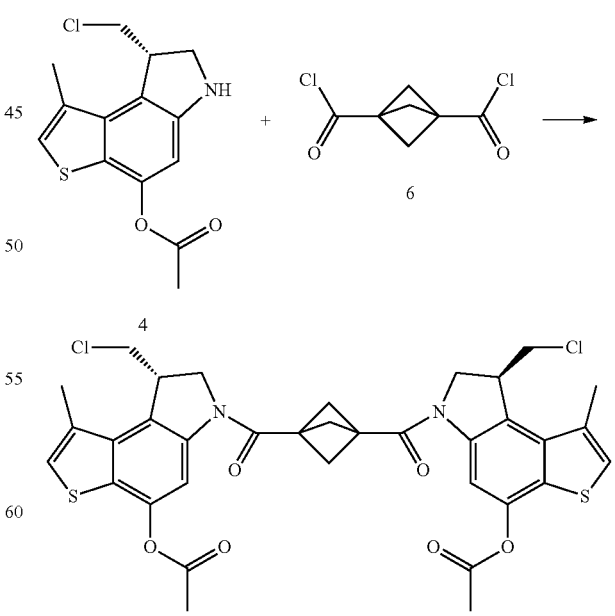

Step 1: (8S,8'S)-(bicyclo[1.1.1]pentane-1,3-dicarbonyl)bis(8-(chloromethyl)-1-methyl-7,8-dihydro-6H-thieno[3,2-e]indole-6,4-diyl) Diacetate (7): The title compound was prepared following general procedure B using 4 (20.0 mg, 0.060 mmol), 6 (5.81 mg, 0.0301 mmol, 0.0301 mL, 1 M in THF), pyridine (14.3 0.181 mmol) and THF (1.0 mL), and purification using Material was purified by medium pressure reverse phase C18 chromatography (Gradient: 0% to 80% acetonitrile in water with 0.02% TFA in each phase) (providing desired product 7. (8.0 mg, 20%). LC-MS (Protocol B): m/z 711.3 [M+H]$^+$, retention time=1.12 minutes Preparation of (R)-8-(chloromethyl)-1-methyl-7,8-dihydro-6H-thieno[3,2-e]indol-4-yl Acetate (11)

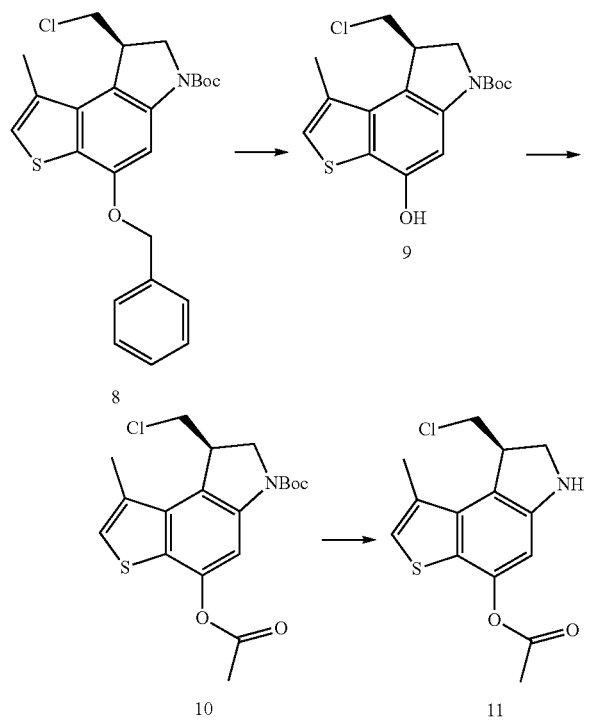

Step 1: Synthesis of tert-butyl (R)-8-(chloromethyl)-4-hydroxy-1-methyl-7,8-dihydro-6H-thieno[3,2-e]indole-6-carboxylate (9). To a stirring solution of tert-butyl (8R)-4-(benzyloxy)-8-(chloromethyl)-1-methyl-7,8-dihydro-6H-thieno[3,2-e]indole-6-carboxylate (8) [prepared as described in *J. Am. Chem. Soc.*, 2007, 129, 14092-14099.] (100 mg, 0.225 mmol) in THF (1.5 mL) was added 10% Pd/C (33 mg) followed by a 25% aqueous solution of ammonium formate (0.15 mL). The solution was stirred for 2 h. The solution was diluted with ether (6 mL) and sodium sulfate was added. The mixture was filtered through Celite and solvent removed in vacuo providing the desired product 9 as a white solid (79 mg, 100%).

Step 2: Synthesis of tert-butyl (R)-4-acetoxy-8-(chloromethyl)-1-methyl-7,8-dihydro-6H-thieno[3,2-e]indole-6-carboxylate (10): tert-Butyl (R)-8-(chloromethyl)-4-hydroxy-1-methyl-7,8-dihydro-6H-thieno[3,2-e]indole-6-carboxylate (2) (69 mg, 0.19 mmol) was dissolved in CH$_2$Cl$_2$ (2 ml). pyridine (46 mg, 0.585 mmol) was added. Acetyl chloride (16 mL, 0.234 mmol) was added and reaction stirred for 2 h. The solvent was removed in vacuo. The crude residue was purified by flash chromatography (0-100% EtOAc/heptane) to provide desired product 10 (53 mg, 69%).

Step 3: Synthesis of (R)-8-(chloromethyl)-1-methyl-7,8-dihydro-6H-thieno[3,2-e]indol-4-yl acetate (11): tert-butyl (R)-4-acetoxy-8-(chloromethyl)-1-methyl-7,8-dihydro-6H-thieno[3,2-e]indole-6-carboxylate (10) (53 mg, 0.13 mmol) was taken up in dioxane (1 mL). 4N HCl in dioxane (1 mL) was added and solution was stirred for 2 h. Solvent was removed to provide crude target material in quantitative yield and the material was used immediately as is Preparation of (8R,8'R)-(bicyclo[1.1.1]pentane-1,3-dicarbonyl)bis(8-(chloromethyl)-1-methyl-7,8-dihydro-6H-thieno[3,2-e]indole-6,4-diyl) diacetate (11).

Preparation of (8R,8'R)-(bicyclo[1.1.1]pentane-1,3-dicarbonyl)bis(8-(chloromethyl)-1-methyl-7,8-dihydro-6H-thieno[3,2-e]indole-6,4-diyl) Diacetate (12)

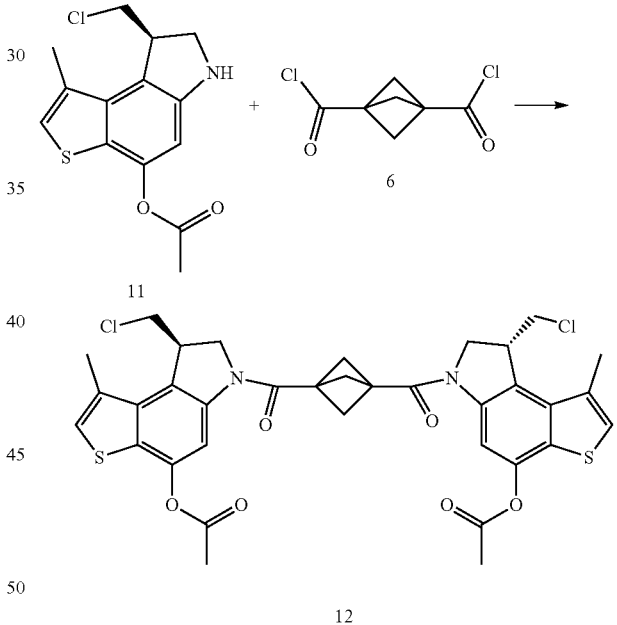

Step 1: Synthesis of (8R,8'R)-(bicyclo[1.1.1]pentane-1,3-dicarbonyl)bis(8-(chloromethyl)-1-methyl-7,8-dihydro-6H-thieno[3,2-e]indole-6,4-diyl) diacetate (12).

The title compound was prepared following general procedure B using 11 (20.0 mg, 0.060 mmol) and 6 (5.81 mg, 0.0301 mmol, 0.0301 mL, 1 M in THF), pyridine (14.3 0.181 mmol) and THE (1.0 mL), and purification using medium pressure reverse phase C$_{18}$ chromatography (Gradient: 0% to 80% acetonitrile in water with 0.02% TFA in each phase) providing desired product 12. (5.9 mg, 14%). LC-MS (Protocol B): m/z 711.2 [M+H]$^+$, retention time=1.12 minutes Preparation of (S)-8-(chloromethyl)-2-methyl-7,8-dihydro-6H-thieno[2,3-e]indol-4-yl Acetate (16)

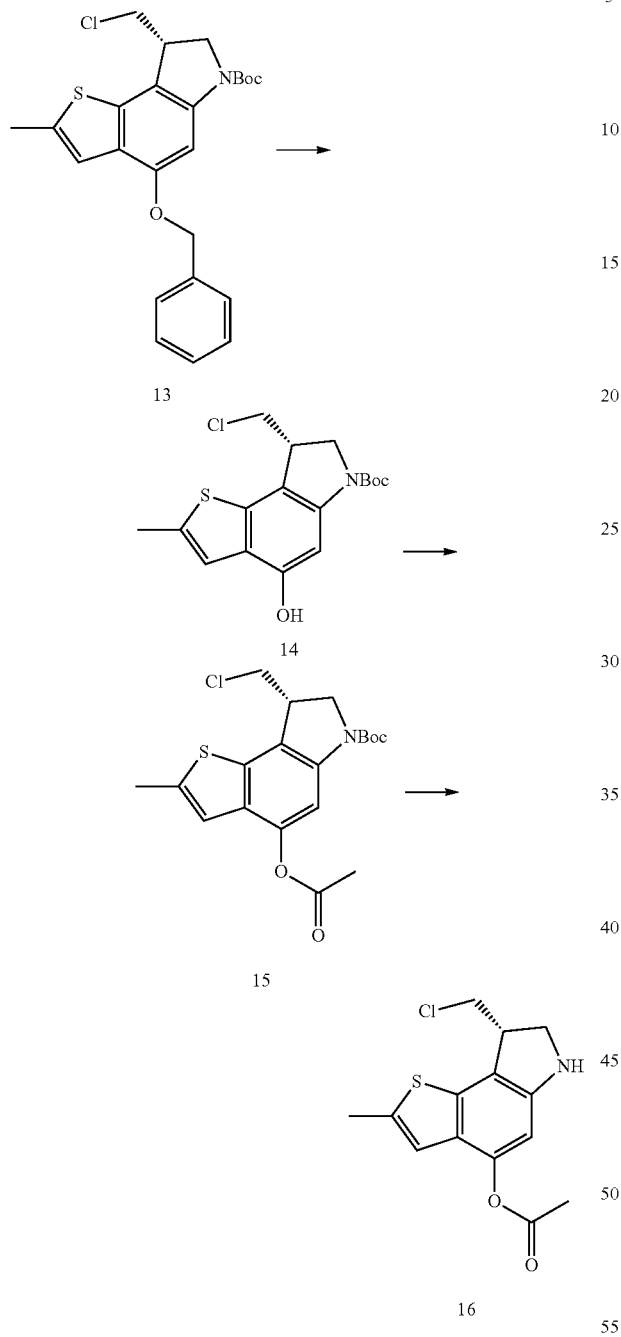

Step 1: Synthesis of tert-butyl (S)-8-(chloromethyl)-4-hydroxy-2-methyl-7,8-dihydro-6H-thieno[2,3-e]indole-6-carboxylate (14): tert-Butyl (S)-4-(benzyloxy)-8-(chloromethyl)-2-methyl-7,8-dihydro-6H-thieno[2,3-e]indole-6-carboxylate (13) [prepared as described in *J. Am. Chem. Soc.*, 2007, 129, 14092-14099.] (250 mg, 0.563 mmol) was taken up in THF (5.63 mL). 10% Pd/C (80 mg) was added. A freshly prepared 25% aqueous Formic acid ammonium salt (500 mg, 2 mmol, 0.5 mL) was added and reaction was stirred for 30 min. The reaction mixture was diluted with ether (15 mL) and $Na_2SO_4$ was added. The solution was filtered through Celite and solvent removed in vacuo to provide the title compound 14 (191 mg, 95%)

Step 2: Synthesis of tert-butyl (S)-4-acetoxy-8-(chloromethyl)-2-methyl-7,8-dihydro-6H-thieno[2,3-e]indole-6-carboxylate (15): tert-butyl (S)-8-(chloromethyl)-4-hydroxy-2-methyl-7,8-dihydro-6H-thieno[2,3-e]indole-6-carboxylate (14, 171 mg, 0.483 mmol) was dissolved in $CH_2Cl_2$ (5.0 mL). Pyridine (213 mg, 2.69 mmol) was added followed by acetyl chloride (114 mg, 1.45 mmol). Reaction was stirred overnight and solution turned orange/brown. The solvent was removed in vacuo leaving a crude orange solid. The crude residue was purified by flash chromatography (0-100% EtOAc/heptane) to provide after solvent removal provided desired product 15 (171.0 mg, 89.4%)

Step 3: Synthesis of (S)-8-(chloromethyl)-2-methyl-7,8-dihydro-6H-thieno[2,3-e]indol-4-yl acetate (16): tert-butyl (S)-4-acetoxy-8-(chloromethyl)-2-methyl-7,8-dihydro-6H-thieno[2,3-e]indole-6-carboxylate (15, 20 mg, 0.051 mmol) was taken up in 4N HCl in dioxane (1 mL). The reaction was allowed to stand overnight and the solvent was removed to provide crude target material 16 in quantitative yield and the material was used immediately Preparation of bicyclo[1.1.1]pentane-1,3-diylbis[carbonyl(8S)-8-(chloromethyl)-2-methyl-7,8-dihydro-6H-thieno[2,3-e]indole-6,4-diyl] Diacetate (17)

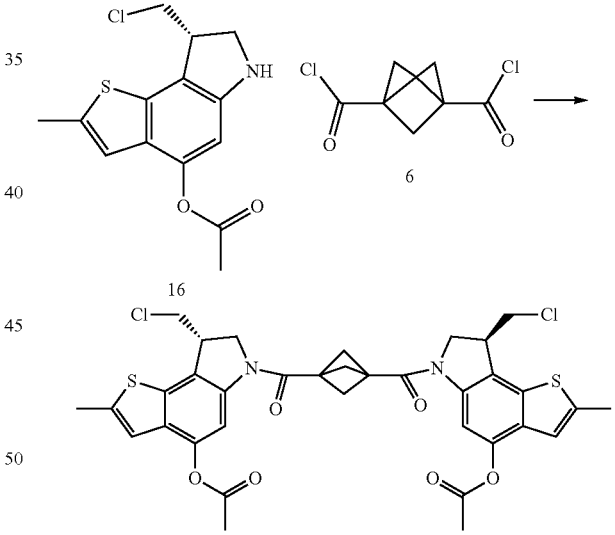

Step 1: Synthesis of bicyclo[1.1.1]pentane-1,3-diylbis[carbonyl(8S)-8-(chloromethyl)-2-methyl-7,8-dihydro-6H-thieno[2,3-e]indole-6,4-diyl] diacetate (17): The title compound was prepared following general procedure B using 16, (17 mg, 0.051) and 6 (4.94 mg, 0.026 mmol, 0.0301 mL, 1 M in THF), pyridine (14.3 0.181 mmol) and THF (1.0 mL), and purification using medium pressure reverse phase C18 chromatography (Gradient: 0% to 80% acetonitrile in water with 0.02% TFA in each phase) providing desired product 17 (10.0 mg, 27%) LC-MS (Protocol B): m/z 711.1 $[M+H]^+$, retention time=1.12 minutes Preparation of (R)-8-(chloromethyl)-2-methyl-7,8-dihydro-6H-thieno[2,3-e]indol-4-yl Acetate (21)

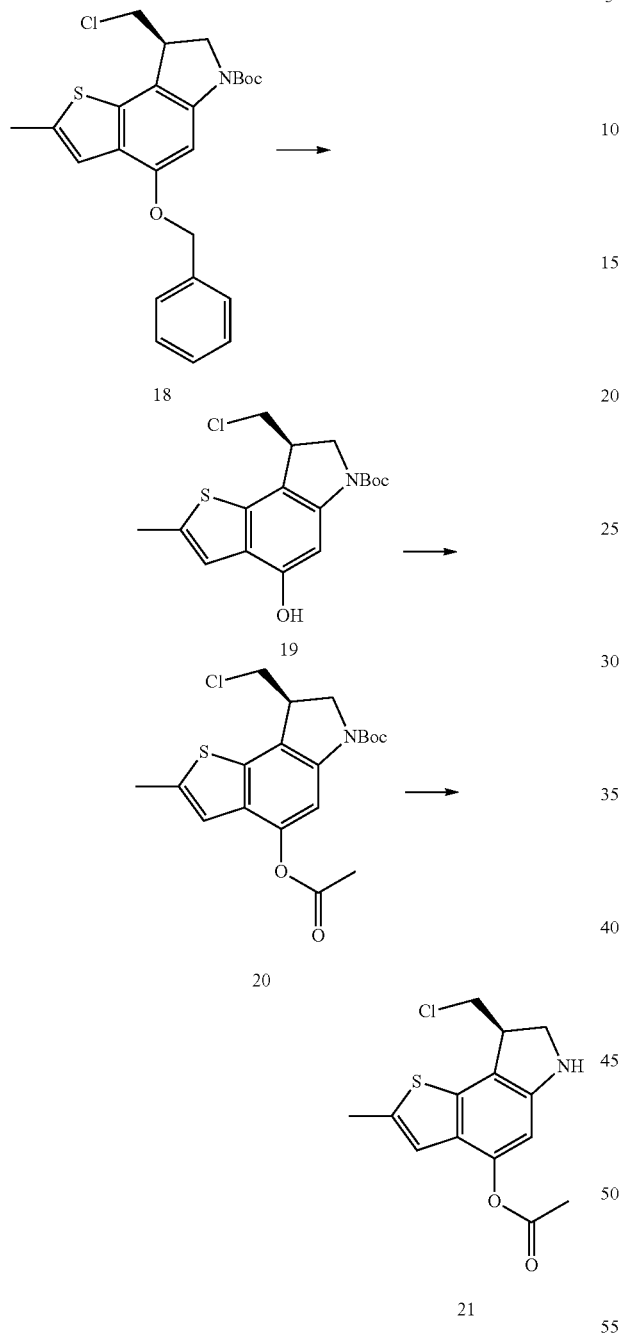

filtered through Celite and solvent removed in vacuo leaving a white solid of crude 19 (156 mg, 78%)

Step 2: Synthesis of tert-butyl (R)-4-acetoxy-8-(chloromethyl)-2-methyl-7,8-dihydro-6H-thieno[2,3-e]indole-6-carboxylate (20): tert-butyl (R)-8-(chloromethyl)-4-hydroxy-2-methyl-7,8-dihydro-6H-thieno[2,3-e]indole-6-carboxylate (19, 136 mg, 0.384 mmol) was dissolved in DCM (5.0 mL). Pyrdine (213 mg, 2.69 mmol) was added followed by acetyl chloride (114 mg, 1.45 mmol). Reaction was stirred overnight and solution turned orange/brown. The solvent was removed in vacuo leaving a crude orange solid. The crude residue was purified by flash chromatography (0-100% EtOAc/heptane) provide after solvent removal provided desired product 20 (113.0 mg, 74%)

Step 3: Synthesis of (R)-8-(chloromethyl)-2-methyl-7,8-dihydro-6H-thieno[2,3-e]indol-4-yl acetate (21): tert-butyl (R)-4-acetoxy-8-(chloromethyl)-2-methyl-7,8-dihydro-6H-thieno[2,3-e]indole-6-carboxylate (20, 25 mg, 0.051 mmol) was taken up in 4N HCl in dioxane (1 mL). The reaction was allowed to stand overnight and the solvent was removed to provide crude target material 21 in quantitative yield and the material was used immediately Preparation of Bicyclo[1.1.1]pentane-1,3-diylbis[carbonyl(8R)-8-(chloromethyl)-2-methyl-7,8-dihydro-6H-thieno[2,3-e]indole-6,4-diyl] Diacetate (22)

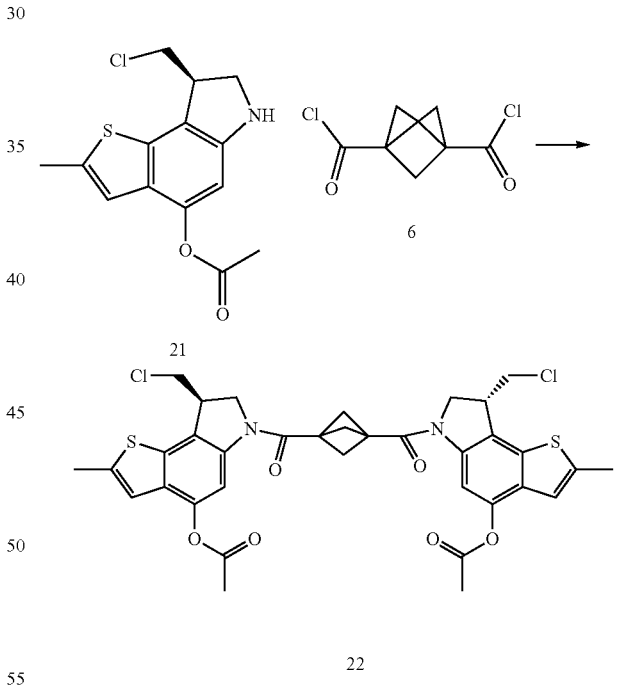

Step 1: Synthesis of tert-butyl (R)-8-(chloromethyl)-4-hydroxy-2-methyl-7,8-dihydro-6H-thieno[2,3-e]indole-6-carboxylate (19): tert-Butyl (R)-4-(benzyloxy)-8-(chloromethyl)-2-methyl-7,8-dihydro-6H-thieno[2,3-e]indole-6-carboxylate (18) [prepared as described in J. Am. Chem. Soc., 2007, 129, 14092-14099.] (250 mg, 0.563 mmol) was taken up in THF (5.63 mL). 10% Pd/C (80 mg) was added. A freshly prepared 25% aqueous Formic acid ammonium salt (500 mg, 2 mmol, 0.5 mL) was added and reaction was stirred for 30 min. The reaction mixture was diluted with ether (15 mL) and Na$_2$SO$_4$ was added. The solution was Step 1: Synthesis of Bicyclo[1.1.1]pentane-1,3-diylbis[carbonyl(8R)-8-(chloromethyl)-2-methyl-7,8-dihydro-6H-thieno[2,3-e]indole-6,4-diyl] diacetate (22): The title compound was prepared following general procedure B using 21, (17 mg, 0.051 mmol) and 6 (4.94 mg, 0.026 mmol, 0.0301 mL, 1 M in THF), pyridine (14.3 0.181 mmol) and THF (1.0 mL), and purification using medium pressure reverse phase C18 chromatography (Gradient: 0% to 80% acetonitrile in water with 0.02% TFA in each phase) providing desired product 22 (8.6 mg, 19%) LC-MS (Protocol B): m/z 711.1 [M+H]$^+$, retention time=1.12 minutes

81

Preparation of (8S,8'S)-glutaroylbis(8-(chloromethyl)-1-methyl-7,8-dihydro-6H-thieno[3,2-e]indole-6,4-diyl) Diacetate (24)

82

Preparation of (8R,8'R)-glutaroylbis(8-(chloromethyl)-1-methyl-7,8-dihydro-6H-thieno[3,2-e]indole-6,4-diyl) Diacetate (25)

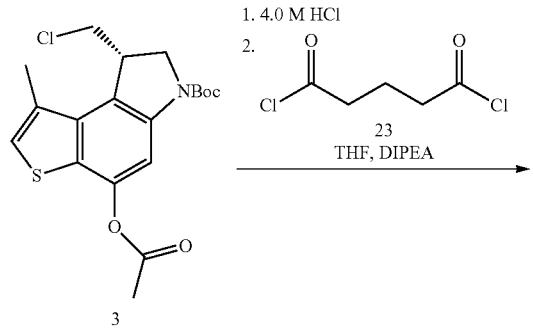

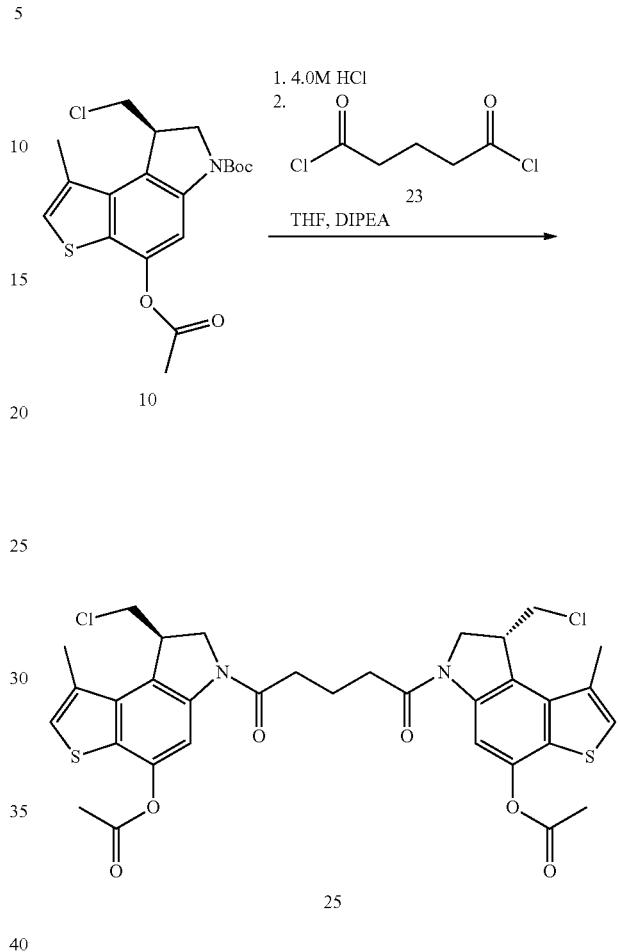

Step 1: Synthesis of (8S,8'S)-glutaroylbis(8-(chloromethyl)-1-methyl-7,8-dihydro-6H-thieno[3,2-e]indole-6,4-diyl) Diacetate (24): A solution of 3 (10 mg, 0.025 mmol) was treated with 4M HCl (0.5 mL in dioxane) at rt for 1 h and concentrated in vacuo The residue was dissolved in THF (2 mL) and glutaryl chloride (2.13 mg, 0.0125 mmol), was added followed by DIPEA (13 uL, 0.074 mmol). The resulting mixture was stirred at rt for 30 min. The reaction mixture was concentrated and the residue was purified by silica gel chromatography using MeOH/DCM (0-10%) to give the product as off-white solid, which was treated with MeOH, filtered to give product 24 as off-white solid 6 mg (70%). LC-MS (Protocol B): m/z 687.1 [M+H]$^+$, retention time=1.11 minutes.

$^1$H NMR (400 MHz, CDCl$_3$) δ=8.24 (s, 2H), 7.13 (s, 2H), 4.36 (d, J=10.5 Hz, 2H), 4.17 (m, 2H), 4.06 (m, 2H), 3.74 (d, J=10.9 Hz, 2H), 3.39 (t, J=10.9 Hz, 2H), 2.80 (m, 2H), 2.66 (m, 2H), 2.55 (s, 6H), 2.37 (s, 6H), 2.22 (m, 2H).

Step 1: Synthesis of (8R,8'R)-glutaroylbis(8-(chloromethyl)-1-methyl-7,8-dihydro-6H-thieno[3,2-e]indole-6,4-diyl) Diacetate (25):

A solution of 10 (10 mg, 0.025 mmol) was treated with 4M HCl (0.5 mL in dioxane) at rt for 1 h and Concentrated in vacuo. The residue was dissolved was dissolved in THF (2 mL), and glutaryl chloride (2.13 mg, 0.0125 mmol) was added followed by Pyridine (12 mg, 0.15 mmol). The resulting mixture was stirred at rt for 4 h., concentrated in vacuo and the residue was purified by reverse phase HPLC (Method C) to give the product 25 as off-white solid 1.5 mg (17%). LC-MS (Protocol B): m/z 687.1 [M+H]$^+$, retention time=1.11

$^1$H NMR (400 MHz, CDCl$_3$)=8.24 (s, 2H), 7.13 (s, 2H), 4.37 (d, J=10.5 Hz, 2H), 4.18 (m, 2H), 4.06 (m, 2H), 3.73 (d, J=10.9 Hz, 2H), 3.39 (t, J=10.9 Hz, 2H), 2.77 (m, 2H), 2.66 (m, 2H), 2.55 (s, 6H), 2.37 (s, 6H), 2.22 (m, 2H).

Preparation of (8S,8'S)-glutaroylbis(8-(chloromethyl)-2-methyl-7,8-dihydro-6H-thieno[2,3-e]indole-6,4-diyl) Diacetate (26)

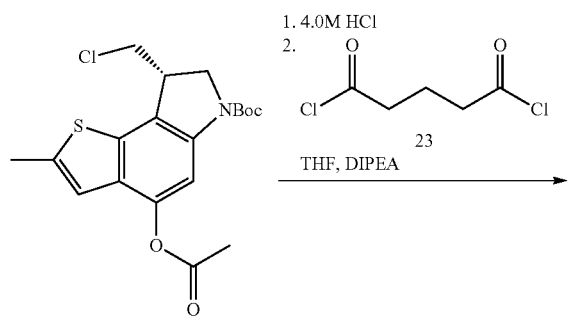

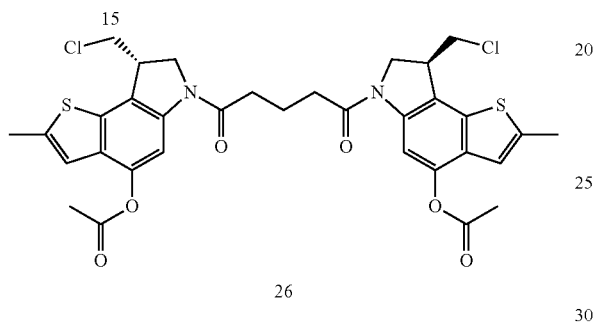

Step 1: (8S,8'S)-glutaroylbis(8-(chloromethyl)-2-methyl-7,8-dihydro-6H-thieno[2,3-e]indole-6,4-diyl) Diacetate (26): A solution of 15 (12 mg, 0.03 mmol) was treated with 4M HCl (0.5 mL in dioxane) at rt for 1 h. and Concentrated in vacuo. The residue was dissolved in THF (2 mL), and glutaryl chloride (2.5 mg, 0.015 mmol) was added followed by DIPEA (16 uL, 0.09 mmol). The resulting mixture was stirred at rt for 30 min, and concentrated in vacuo and the residue was purified by ISCO using MeOH/DCM (0-10%) to give the product 26 as off-white solid 6 mg (60%): LC-MS (Protocol B): m/z 687.1 [M+H]$^+$, retention time=1.11.

$^1$H NMR (400 MHz, CDCl$_3$) δ=8.12 (s, 2H), 6.84 (s, 2H), 4.32 (m, 2H), 4.2 (m, 2H), 4.05 (d, J=10.9 Hz, 2H), 3.93 (m, 2H), 3.62 (m, 2H), 2.68 (br.s., 4H), 2.56 (s, 6H), 2.37 (s, 6H), 2.19 (br.s., 2H).

Preparation of (8S)-8-(chloromethyl)-6-[(3-{[(8S)-8-(chloromethyl)-1-methyl-4-(phosphonooxy)-7,8-dihydro-6H-thieno[3,2-e]indol-6-yl]carbonyl}bicyclo[1.1.1]pent-1-yl)carbonyl]-1-methyl-7,8-dihydro-6H-thieno[3,2-e]indol-4-yl 4-nitrophenyl Carbonate (33)

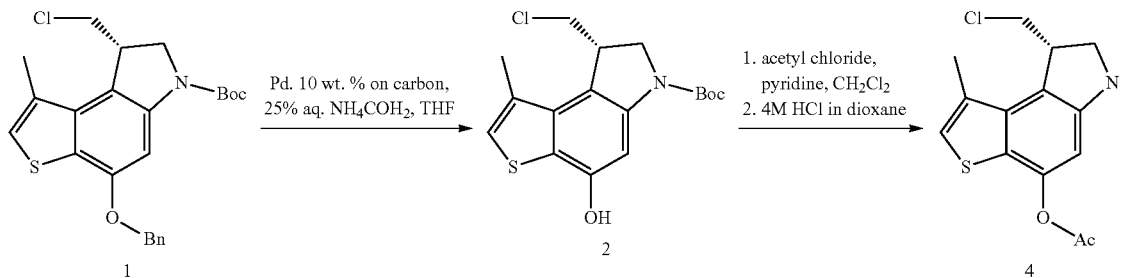

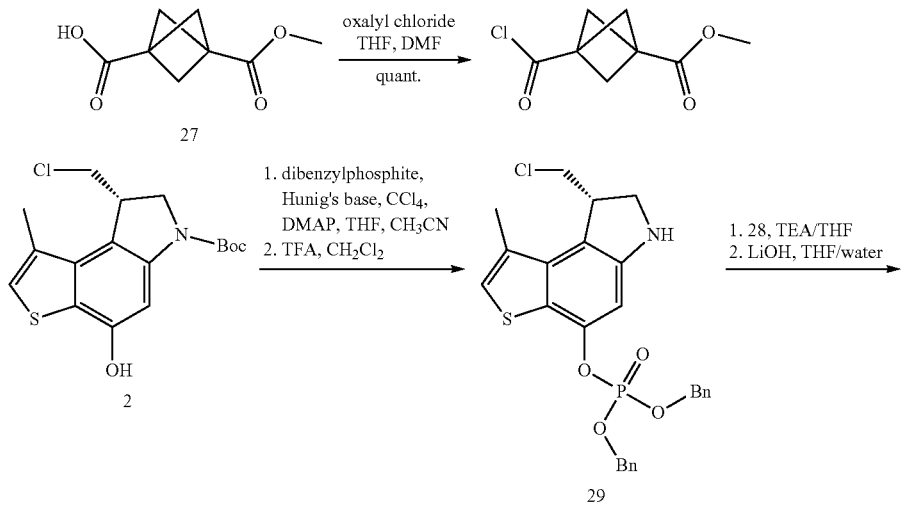

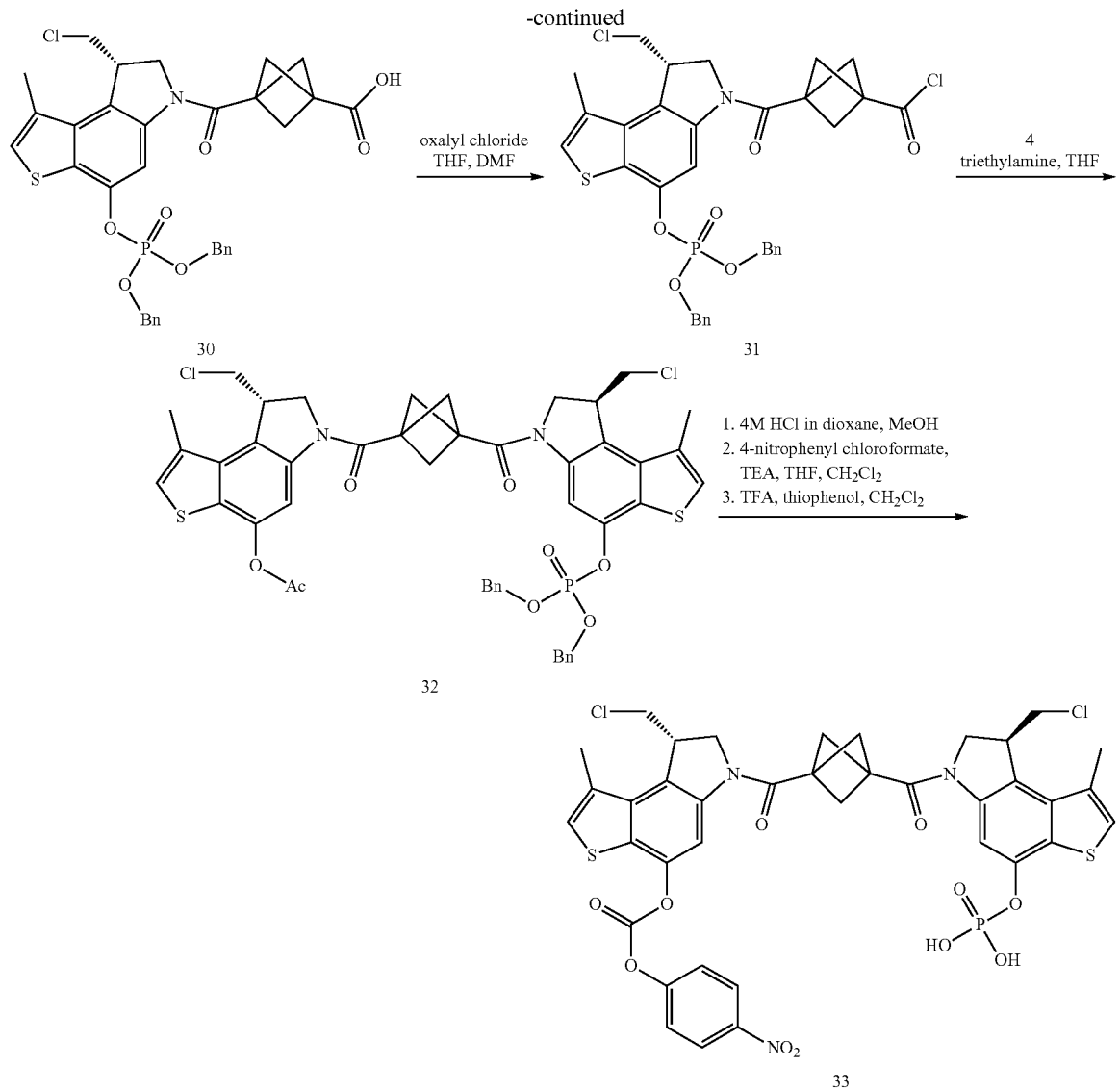

Step 1: Synthesis of tert-butyl (8S)-8-(chloromethyl)-4-hydroxy-1-methyl-7,8-dihydro-6H-thieno[3,2-e]indole-6-carboxylate (2). To a stirring solution of tert-butyl (8S)-4-(benzyloxy)-8-(chloromethyl)-1-methyl-7,8-dihydro-6H-thieno[3,2-e]indole-6-carboxylate 1 [prepared as described in J. Am. Chem. Soc., 2007, 129, 14092-14099.] (575 mg, 1.30 mmol) in 18 mL of THF at 0° C., Palladium 10 wt. % on carbon (250 mg) was added followed by slow dropwise addition of 2.0 mL of 25% ammonium formate in water. The reaction was allowed to stir at 0° C. for ~90 minutes. Reaction was diluted with ether followed by the addition of sodium sulfate. The reaction was filtered through a thin pad of celite, which was then washed twice with ether. The organics where combined and then reduced down before being placed underneath vacuum yielding 2 (458 mg, quantitative) as off white solid. LC-MS (Protocol A): m/z 352.2 [M−H], retention time=1.96 minutes.

Step 2: Synthesis of (8S)-8-(chloromethyl)-1-methyl-7,8-dihydro-6H-thieno[3,2-e]indol-4-yl acetate (4). To a stirring solution of 2 (209 mg, 0.591 mmol) in 8 mL of dichloromethane at 0° C., acetyl chloride (0.0462 mL, 0.650 mmol) was added followed immediately by pyridine (0.0714 mL, 0.886 mmol). The reaction was allowed to stir at 0° C. for ~10 minutes. Reaction was reduced down onto silica. Silica chromatography was then preformed (gradient: 0%-15% acetone in heptanes). Appropriate test tubes where concentrated and placed underneath high vacuum to produce a white solid. To this white solid 4M HCl in dioxane (10 mL, 40 mmol) was added and the reaction was allowed to stir at room temperature for ~90 minutes. Reaction was diluted with heptane, concentrated in vacuo, and then placed underneath high vacuum to produce 4 (170 mg, 80% yield, 2 steps) as a light orange solid. LC-MS (Protocol A): m/z 296.1 [M+H]$^+$, retention time=1.56 minutes. $^1$H NMR (400 MHz, DMSO-$d_6$): δ 7.53 (s, 1H), 7.05 (s, 1H), 4.27-4.19 (m, 1H), 3.93-3.86 (m, 1H), 3.80-3.75 (m, 1H), 3.72-3.64 (m, 2H), 2.54 (s, 3H), 2.37 (s, 3H).

Step 3: Synthesis of methyl 3-(chlorocarbonyl)bicyclo[1.1.1]pentane-1-carboxylate (28). Following general procedure A using 3-(methoxycarbonyl)bicyclo[1.1.1]pentane-1-carboxylic acid 27 (86.8 mg, 0.510 mmol), oxalyl chloride (0.0525 mL, 0.612 mmol), THF (6 mL), and 1 drop of DMF, 28 was prepared as a white solid (97 mg, quant.). Crude 28 was used as is without further purification.

Step 4: Synthesis of dibenzyl (8S)-8-(chloromethyl)-1-methyl-7,8-dihydro-6H-thieno[3,2-e]indol-4-yl phosphate (29). To a stirring solution of 2 (4.5 g, 13.4 mmol) in 8 mL of THF and 8 mL of acetonitrile, carbon tetrachloride (0.997 mL, 10.3 mmol) was added followed by Hunig's base (0.512 mL, 2.94 mmol), dibenzylphosphite (0.974 mL, 4.41 mmol), and DMAP (18 mg, 0.147 mmol). The reaction was allowed to stir at room temperature for ~10 minutes. Reaction was reduced down onto silica. Silica chromatography was then preformed (gradient: 0%-25% acetone in heptanes). Appropriate test tubes where concentrated and placed underneath high vacuum to produce a white solid. Crude material was dissolved in 5 mL of dichloromethane followed by the addition of trifluoroacetic acid (5 mL, 70 mmol). The reaction was allowed to stir at room temperature for 60 seconds, immediately concentrated in vacuo, and then placed underneath high vacuum producing 29 (321 mg, 70% yield, 2 steps) as white and clear, oil and solid mix. LC-MS (Protocol A): m/z 514.1 [M+H]$^+$, retention time=2.14 minutes.

Step 5: Synthesis of 3-{[[(8S)-4-{[bis(benzyloxy)phosphoryl]oxy}-8-(chloromethyl)-1-methyl-7,8-dihydro-6H-thieno[3,2-e]indol-6-yl]carbonyl}bicyclo[1.1.1]pentane-1-carboxylic acid (30). Following general procedure B using 29 (315 mg, 0.502 mmol), 28 (94.6 mg, 0.502 mmol), triethylamine (0.210 mL, 1.50 mmol) and THF (20 mL), and purification using silica gel chromatography (Gradient: 0% to 35% acetone in heptane). Appropriate test tubes where combined and concentrated in vacuo producing a white solid. Material was dissolved in THF (10 mL) followed by the addition of lithium hydroxide dissolved in 2.5 mL of water. The reaction was allowed to stir at room temperature for ~45 minutes. The reaction was diluted with dichloromethane and quenched through the addition of 1N HCl (aq.). Reaction was transferred to a separatory funnel. The organic layer was separated and the aqueous layer was washed twice with dichloromethane. The organic layers where combined, washed once with brine, washed once with water, dried over sodium sulfate, filtered, concentrated in vacuo, and then placed underneath high vacuum producing 30 (178 mg, 57% yield, 2 steps). LC-MS (Protocol A): m/z 652.2 [M+H]$^+$, retention time=1.97 minutes.

Step 6: Synthesis of dibenzyl (8S)-6-{[3-(chlorocarbonyl) bicyclo[1.1.1]pent-1-yl]carbonyl}-8-(chloromethyl)-1-methyl-7,8-dihydro-6H-thieno[3,2-e]indol-4-yl phosphate (31). Following general procedure A using 30 (174 mg, 0.267 mmol), oxalyl chloride (0.0298 mL, 0.347 mmol), THF (5 mL), dichloromethane (1 mL) and 1 drop of DMF, 31 was prepared as a white solid (182 mg, quant.). Crude 31 was used as is without further purification.

Step 7: Synthesis of (8S)-6-[(3-{[(8S)-4-{[bis(benzyloxy) phosphoryl]oxy}-8-(chloromethyl)-1-methyl-7,8-dihydro-6H-thieno[3,2-e]indol-6-yl]carbonyl}bicyclo[1.1.1]pent-1-yl)carbonyl]-8-(chloromethyl)-1-methyl-7,8-dihydro-6H-thieno[3,2-e]indol-4-yl acetate (32). Following general procedure B using 31 (167 mg, 0.249 mmol), 4 (99.3 mg, 0.299 mmol), triethylamine (0.104 mL, 0.747 mmol) and THF (20 mL), and purification using silica gel chromatography (Gradient: 0% to 50% acetone in heptane). Appropriate test tubes where combined and concentrated in vacuo producing 32 (103 mg, 45%) a white solid. LC-MS (Protocol A): m/z 929.3 [M+H]$^+$, retention time=2.44 minutes. $^1$H NMR (400 MHz, DMSO-d$_6$): δ 8.37 (s, 1H), 8.09 (s, 1H), 7.54-7.50 (m, 2H), 7.39-7.33 (m, 10H), 5.23-5.14 (m, 4H), 4.53-4.46 (m, 2H), 4.38-4.25 (m, 4H), 4.02-3.95 (m, 2H), 3.78-3.69 (m, 2H), 2.63 (s, 6H), 2.57-2.53 (m, 6H), 2.39 (s, 3H).

Step 8: Synthesis of (8S)-8-(chloromethyl)-6-[(3-{[(8S)-8-(chloromethyl)-1-methyl-4-(phosphonooxy)-7,8-dihydro-6H-thieno[3,2-e]indol-6-yl]carbonyl}bicyclo[1.1.1]pent-1-yl)carbonyl]-1-methyl-7,8-dihydro-6H-thieno[3,2-e]indol-4-yl 4-nitrophenyl carbonate (33). To a stirring solution of 32 (99 mg, 0.11 mmol) in 6 mL of methanol, 4M HCl in dioxane (6.0 mL, 20 mmol) was added. The reaction was allowed to stir at room temperature for ~15 minutes. Reaction was reduced and then placed underneath high vacuum. To a stirring solution of crude material in 6 mL of dichloromethane and 6 mL of THF at 0° C., p-nitrophenyl chloroformate (38.6 mg, 0.192 mmol) was added followed immediately by triethylamine (0.0742 mL, 0.532 mmol). The reaction was allowed to stir at 0° C. for ~5 minutes and then allowed to warm to room temperature while stirring. The reaction was allowed to stir at room temperature for ~10 minutes. Reaction was reduced down. To a stirring solution of crude material in 3 mL of dichloromethane, a solution of TFA (3.0 mL, 39 mmol) in 3 mL of dichloromethane was added followed by the addition of thiophenol (0.109 mL, 1.06 mmol). The reaction was allowed to stir at room temperature for ~6 hours. Reaction was reduced down. Crude material was diluted with a few milliliters of DMSO and then injected onto a 25 g C18 pre-column (which was previously equilibrated with acetonitrile and then water, with 0.02% TFA in each phase). Material was purified by medium pressure reverse phase C18 chromatography (Gradient: 20% to 65% acetonitrile in water with 0.02% TFA in each phase) with the appropriate test tubes concentrated using a genevac producing 33 (37 mg, 40%, 3 steps) as a white solid. LC-MS (Protocol A): m/z 872.3 [M+H]$^+$, retention time=1.86 minutes. $^1$H NMR (400 MHz, DMSO-d$_6$): δ 8.44 (s, 1H), 8.40-8.33 (m, 3H), 7.78-7.72 (m, 2H), 7.59 (m, 1H), 7.47 (m, 1H), 4.53-4.44 (m, 2H), 4.38-4.22 (m, 4H), 4.04-3.94 (m, 2H), 3.81-3.75 (m, 1H), 3.72-3.65 (m, 1H), 2.62 (s, 6H), 2.58 (s, 3H), 2.54 (s, 3H).

Preparation of N-[1-(2,5-dioxo-2,5-dihydro-1H-pyrrol-1-yl)-21-oxo-3,6,9,12,15,18-hexaoxahenicosan-21-yl]-L-valyl-N~5~-carbamoyl-N-{4-[({methyl[2-(methylamino)ethyl]carbamoyl}oxy) methyl]phenyl}-L-ornithinamide (40)

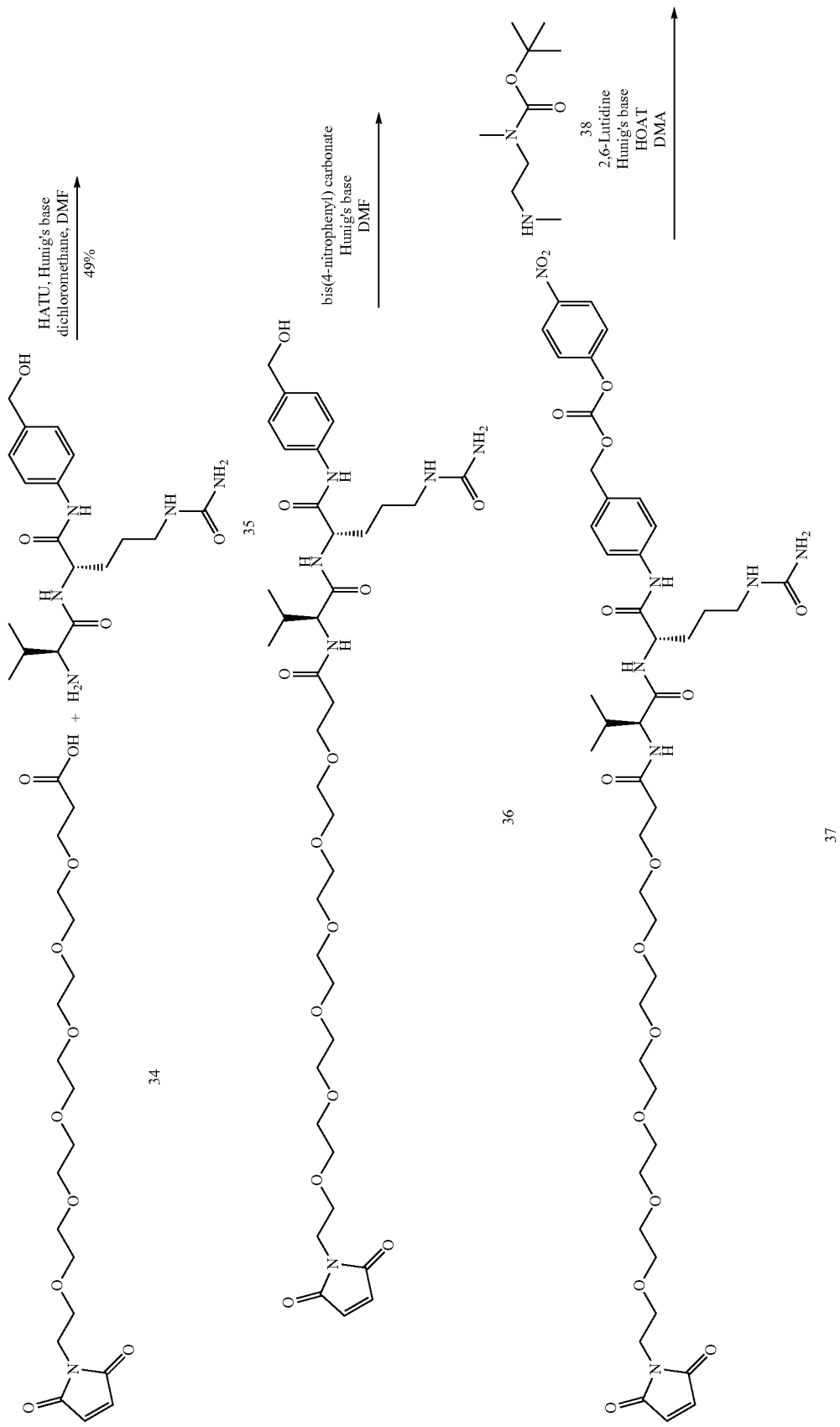

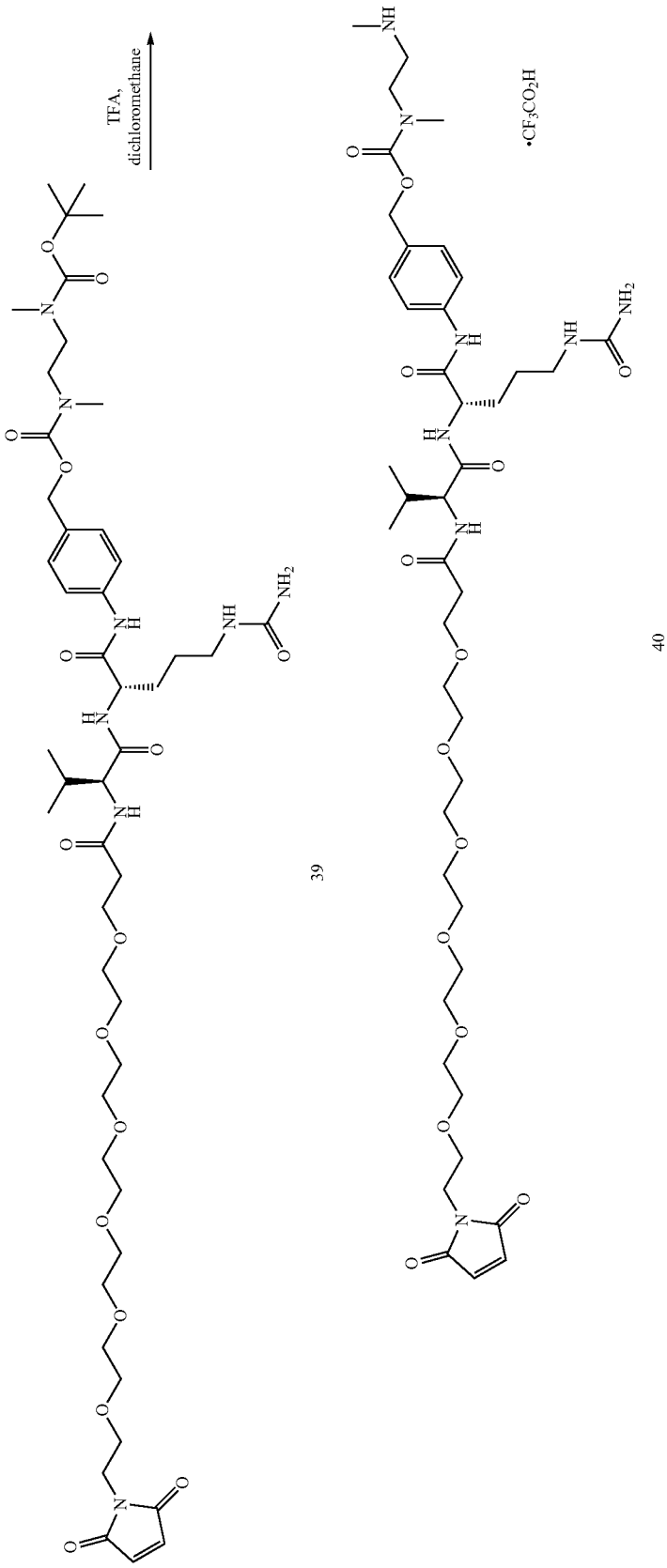

Step 1: Synthesis of N-[1-(2,5-dioxo-2,5-dihydro-1H-pyrrol-1-yl)-21-oxo-3,6,9,12,15,18-hexaoxahenicosan-21-yl]-L-valyl~N~5~-carbamoyl-N-[4-(hydroxymethyl)phenyl]-L-ornithinamide (36). To a round bottom flask containing 1-(2,5-dioxo-2,5-dihydro-1H-pyrrol-1-yl)-3,6,9,12,15,18-hexaoxahenicosan-21-oic acid, 34(628 mg, 1.45 mmol), 20 mL of dichloromethane, 2 mL of DMF, HATU (501 mg, 1.32 mmol) and Hunig's base (0.92 mL, 5.3 mmol) was added. The reaction was allowed to stir at room temperature for 2 minutes before the addition of L-valyl~N~5~-carbamoyl-N-[4-(hydroxymethyl)phenyl]-L-ornithinamide, 35 (500 mg, 1.32 mmol). The reaction was allowed to stir at room temperature for ~90 minutes before being quenched through the addition of TFA. The reaction was concentrated to a smaller volume, diluted with a few mLs of DMSO and then injected onto a 25 g C18 pre-column (which was previously equilibrated with acetonitrile and then water, with 0.02% TFA in each phase). Material was purified by medium pressure reverse phase C18 chromatography (Gradient: 5% to 40% acetonitrile in water with 0.02% TFA in each phase) with the appropriate test tubes concentrated using a genevac producing 36 (514 mg, 49%) as a clear solid. LC-MS (Protocol A): m/z 795.5 [M+H]$^+$, retention time=1.01 minutes.

Step 2: Synthesis of N-[1-(2,5-dioxo-2,5-dihydro-1H-pyrrol-1-yl)-21-oxo-3,6,9,12,15,18-hexaoxahenicosan-21-yl]-L-valyl~N~5~-carbamoyl-N-[4-({[(4-nitrophenoxy)carbonyl]oxy}methyl)phenyl]-L-ornithinamide (37). To a stirring solution of 36 (210 mg, 0.264 mmol) and bis(4-nitrophenyl) carbonate (161 mg, 0.528 mmol) in 4 mL of DMF, Hunig's base (0.096 mL, 0.554 mmol) was added. The reaction was allowed to stir at room temperature for ~2 hours. The reaction was injected onto a 25 g C18 pre-column (which was previously equilibrated with acetonitrile and then water, with 0.02% TFA in each phase). Material was purified by medium pressure reverse phase C18 chromatography (Gradient: 5% to 55% acetonitrile in water with 0.02% TFA in each phase) with the appropriate test tubes concentrated using a genevac producing 37(180 mg, 71%) as a solid. LC-MS (Protocol A): m/z 960.5 [M+H]$^+$, retention time=1.48 minutes.

Step 3: Synthesis of N-[1-(2,5-dioxo-2,5-dihydro-1H-pyrrol-1-yl)-21-oxo-3,6,9,12,15,18-hexaoxahenicosan-21-yl]-L-valyl~N~5~-carbamoyl-N-[4-(4,7,10,10-tetramethyl-3,8-dioxo-2,9-dioxa-4,7-diazaundec-1-yl)phenyl]-L-ornithinamide (39). To a stirring solution of 37 (640 mg, 0.667 mmol) and 38 [prepared as described *J. Med. Chem.* 1992, 33, 559-567] (127 mg, 0.674 mmol) in 6 mL of DMA, 2,6-Lutidine (0.154 mL, 1.33 mmol) was added followed by Hunig's base (0.232 mL, 1.33 mmol) and HOAT (9.1 mg, 0.67 mmol). The reaction was allowed to stir at room temperature for ~15 minutes. The reaction was injected onto a 25 g C18 pre-column (which was previously equilibrated with acetonitrile and then water, with 0.02% TFA in each phase). Material was purified by medium pressure reverse phase C18 chromatography (Gradient: 5% to 40% acetonitrile in water with 0.02% TFA in each phase) with the appropriate test tubes concentrated using a genevac producing 39 (564 mg, 84%) as a wax like white solid. LC-MS (Protocol A): m/z 1009.7 [M+H]$^+$, retention time=1.43 minutes.

Step 4: Synthesis of N-[1-(2,5-dioxo-2,5-dihydro-1H-pyrrol-1-yl)-21-oxo-3,6,9,12,15,18-hexaoxahenicosan-21-yl]-L-valyl~N~5~-carbamoyl-N-{4-[({methyl[2-(methylamino)ethyl]carbamoyl}oxy)methyl]phenyl}-L-ornithinamide (40). To a stirring mixture of 39 (470 mg, 0.466 mmol) in 6 mL of dichloromethane, TFA (3.0 mL, 40 mmol) was added. The reaction was allowed to stir at room temperature for ~10 minutes. Reaction was reduced down. Residue was purified by medium pressure reverse phase C18 chromatography (Gradient: 5% to 30% acetonitrile in water with 0.02% TFA in each phase) with the appropriate test tubes concentrated using a genevac producing 40 (326 mg, 68%) as a white oil/solid mix. LC-MS (Protocol A): m/z 909.8 [M+H]$^+$, retention time=0.91 minutes.

Preparation of N-[1-(2,5-dioxo-2,5-dihydro-1H-pyrrol-1-yl)-21-oxo-3,6,9,12,15,18-hexaoxahenicosan-21-yl]-L-valyl~N~5~-carbamoyl-N-[4-({[(2-{[({(8S)-8-(chloromethyl)-6-[(3-{[({(8S)-8-(chloromethyl)-1-methyl-4-(phosphonooxy)-7,8-dihydro-6H-thieno[3,2-e]indol-6-yl]carbonyl}bicyclo[1.1.1]pent-1-yl)carbonyl]-1-methyl-7,8-dihydro-6H-thieno[3,2-e]indol-4-yl}oxy)carbonyl](methyl)amino}ethyl)(methyl)carbamoyl]oxy}methyl)phenyl]-L-ornithinamide (41)

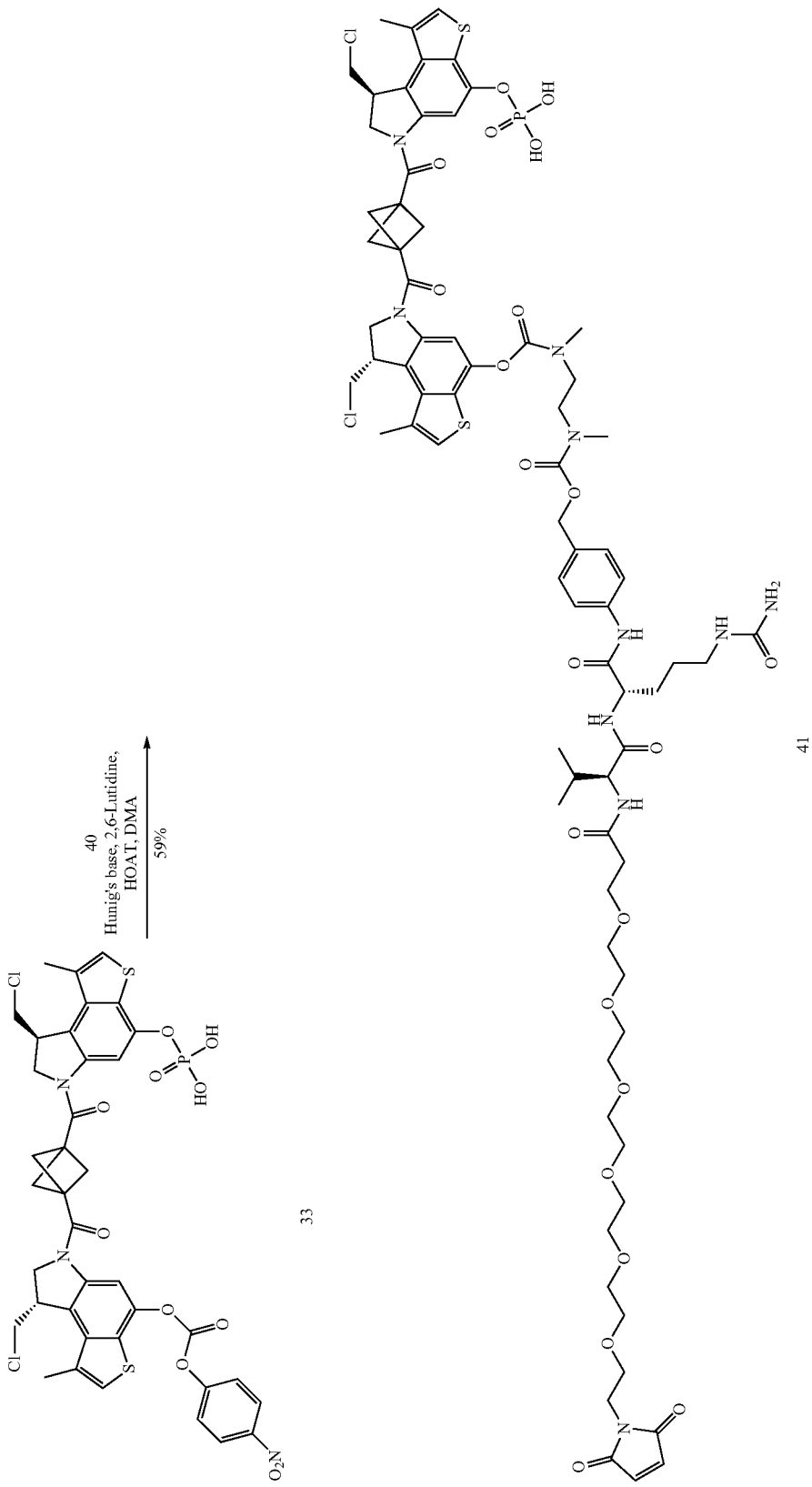

Step 1: Synthesis of N-[1-(2,5-dioxo-2,5-dihydro-1H-pyrrol-1-yl)-21-oxo-3,6,9,12,15,18-hexaoxahenicosan-21-yl]-L-valyl~N~5~-carbamoyl-N-[4-({[(2-{[({(8S)-8-(chloromethyl)-6-[(3-{[(8S)-8-(chloromethyl)-1-methyl-4-(phosphonooxy)-7,8-dihydro-6H-thieno[3,2-e]indol-6-yl]carbonyl}bicyclo[1.1.1]pent-1-yl)carbonyl]-1-methyl-7,8-dihydro-6H-thieno[3,2-e]indol-4-yl}oxy)carbonyl](methyl)amino}ethyl)(methyl)carbamoyl]oxy}methyl)phenyl]-L-ornithinamide (41). To a 2 dram vial containing 33 (8.0 mg, 0.0092 mmol) and 40 (10.3 mg, 0.0101 mmol), 1.0 mL of DMA was added followed by Hunig's base (0.00639 mL, 0.0367 mmol), 2,6-Lutidine (0.00425 mL, 0.0367 mmol) and HOAT (1.25 mg, 0.0367 mmol). The reaction was allowed to stir at room temperature for ~5 minutes. Crude reaction was injected onto a 4 g C18 pre-column (which was previously equilibrated with acetonitrile and then water, with 0.02% TFA in each phase). Material was purified by medium pressure reverse phase C18 chromatography (Gradient: 15% to 50% acetonitrile in water with 0.02% TFA in each phase) followed by a second purification by method A with the appropriate test tubes concentrated using a genevac producing 41 (8.9 mg, 59%) as a white solid. LC-MS (Protocol A): m/z 1642.9 [M+2H]$^+$, retention time=1.61 minutes.

Preparation of LP: (2S,3S,4S,5R,6S)-6-(((S)-8-(chloromethyl)-6-(5-((S)-8-(chloromethyl)-4-(((2-((((4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosan-27-amido)benzyl)oxy)carbonyl)(methyl)amino)ethyl)(methyl)carbamoyl)oxy)-1-methyl-7,8-dihydro-6H-thieno[3,2-e]indol-6-yl)-5-oxopentanoyl)-1-methyl-7,8-dihydro-6H-thieno[3,2-e]indol-4-yl)oxy)-3,4,5-trihydroxytetrahydro-2H-pyran-2-carboxylic Acid (49)

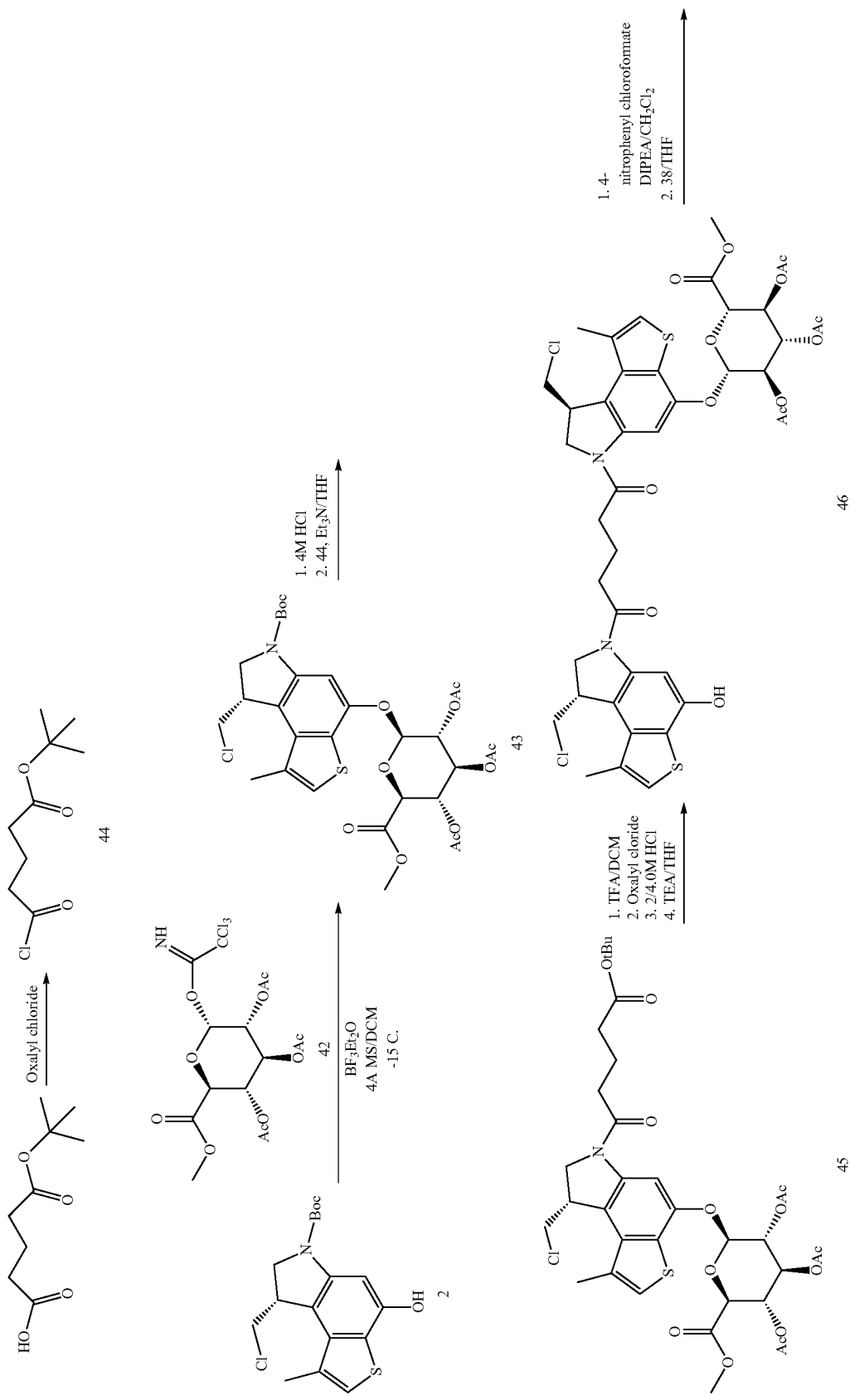

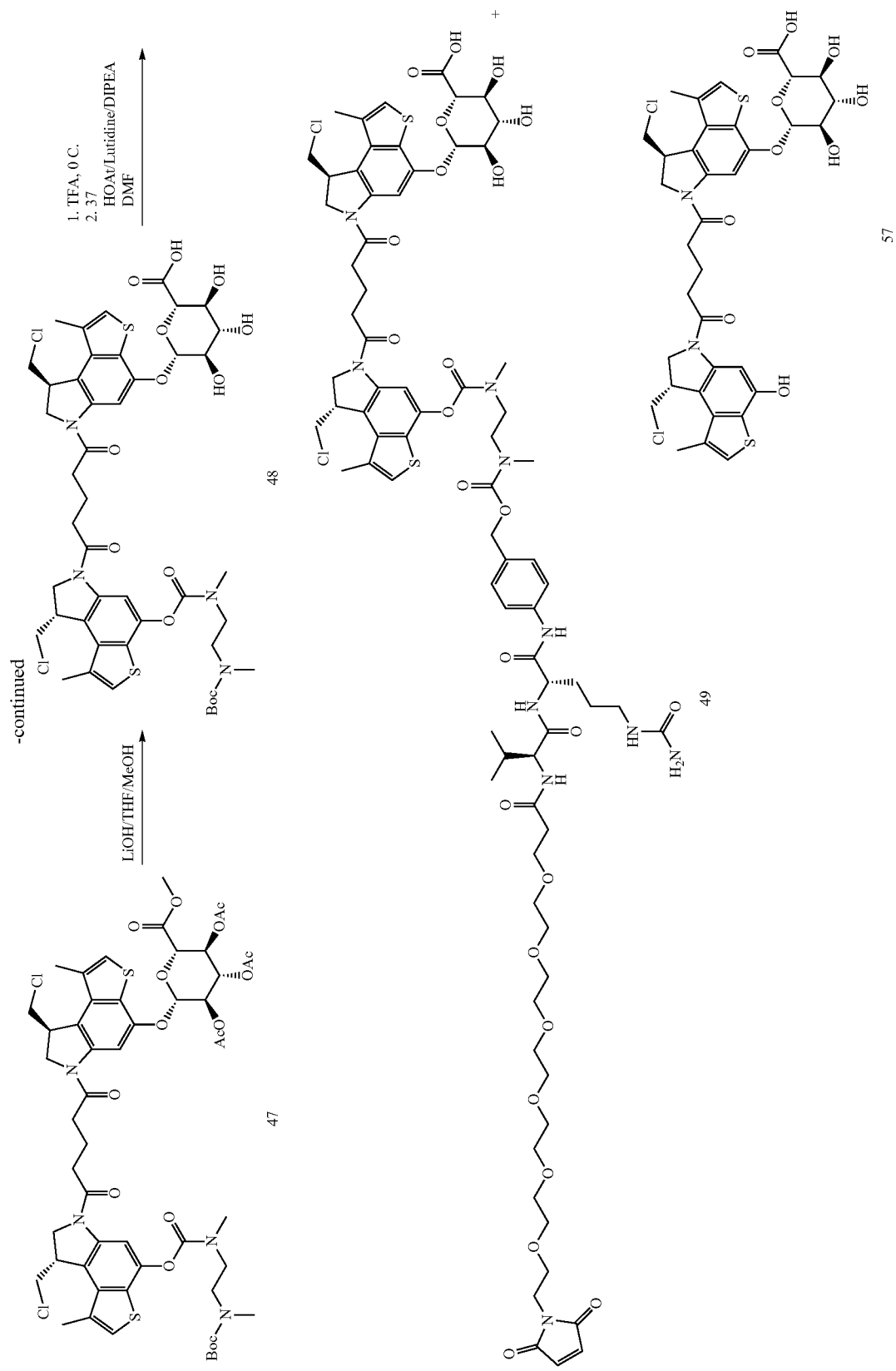

Step 1: Synthesis of tert-butyl 5-chloro-5-oxopentanoate (44): To a solution of 5-(tert-butoxy)-5-oxopentanoic acid (110 mg, 0.58 mmol) in THF (3 mL), was added oxalyl chloride (0.58 mL, 1.2 mmol, 2M in DCM) at 0° C. followed by 1 drop of DMF. The mixture was stirred at 0° C. for 30 min, and concentrated in vacuo to give the corresponding acid chloride 44 as white solid.

Step 2. Synthesis of (2S,3R,4S,5S,6S)-2-(((S)-6-(tert-butoxycarbonyl)-8-(chloromethyl)-1-methyl-7,8-dihydro-6H-thieno[3,2-e]indol-4-yl)oxy)-6-(methoxycarbonyl)tetrahydro-2H-pyran-3,4,5-triyl triacetate (43)

To a solution of 2 (226 mg, 0.64 mmol) in DCM (23 mL), was added 4 A MS (1.17 g, powder, <5 micro, activated), and the mixture was stirred at room temperature for 30 min. To the reaction mixture, alpha-D-glucuronide methyl ester 2,3,4-triacetate 1-2,2,2-trichloroethanimidate (42, 367 mg, 0.77 mmol) was added, and the mixture cooled to −25° C. And a solution of $BF_3.Et_2O$ (0.13 mL, 0.32 mmol) in DCM (10 mL) was added slowly and mixture was stirred at below −20° C. for 1 h. The reaction mixture was filtered and the solution was concentrated in vacuo. The residue was purified by silica gel chromatography using a gradient of 0-60% EtOAc in Heptanes to give the product 43 as a yellow solid 261 mg (61%).

LC-MS (Protocol B): m/z 692.1 (M+Na), retention time=1.09 min. $^1$H NMR (400 MHz, CHLOROFORM-d) δ=7.29 (s, 1H), 7.13 (s, 1H), 5.40 (br. s., 3H), 4.30 (d, J=7.4 Hz, 2H), 4.06-3.92 (m, 2H), 3.85-3.73 (m, 4H), 3.69 (d, J=10.5 Hz, 1H), 3.36 (t, J=10.5 Hz, 1H), 2.56 (s, 3H), 2.10 (s, 6H), 2.08 (s, 3H), 1.62 (s, 9H).

Step 2. Synthesis of (2S,3R,4S,5S,6S)-2-(((S)-6-(5-(tert-butoxy)-5-oxopentanoyl)-8-(chloromethyl)-1-methyl-7,8-dihydro-6H-thieno[3,2-e]indol-4-yl)oxy)-6-(methoxycarbonyl)tetrahydro-2H-pyran-3,4,5-triyl triacetate (45)

A solution of 43 (261 mg, 0.39 mmol) was treated with 4M HCl in dioxane (3 mL) for 1 h. Concentrated in vacuo. and the residue was dissolved in THF (3.0 mL) and a solution of acid chloride 44 (0.58 mmol) in THF (3.0 mL) was added followed by TEA (0.163 mL, 1.2 mmol). The mixture was stirred at 0° C. for 30 min. The mixture was concentrated, and the residue was purified by silica gel chromatography using a gradient of EtOAc (0-70%) in heptanes to give the product as off-white solid 224 mg (78%). LC-MS (Protocol B): m/z 740.2 [M+H]$^+$, retention time=1.07 minutes. $^1$H NMR (400 MHz, CHLOROFORM-d) δ=8.26 (br. s., 1H), 7.13 (s, 1H), 5.45-5.25 (m, 4H), 4.32 (d, J=9.0 Hz, 2H), 4.12 (t, J=8.8 Hz, 1H), 4.05 (d, J=8.6 Hz, 1H), 3.79-3.66 (m, 5H), 3.33 (t, J=10.9 Hz, 1H), 2.63 (d, J=7.0 Hz, 1H), 2.58-2.47 (m, 4H), 2.45-2.35 (m, 2H), 2.06 (m 11H), 1.47 (s, 9H).

Step 3. Synthesis of (2S,3R,4S,5S,6S)-2-(((S)-8-(chloromethyl)-6-(5-((S)-8-(chloromethyl)-4-hydroxy-1-methyl-7,8-dihydro-6H-thieno[3,2-e]indol-6-yl)-5-oxopentanoyl)-1-methyl-7,8-dihydro-6H-thieno[3,2-e]indol-4-yl)oxy)-6-(methoxycarbonyl)tetrahydro-2H-pyran-3,4,5-triyl Triacetate (46)

A solution of 45 (116 mg, 0.16 mmol) was treated with DCM (1.5 mL) and TFA (1 mL) at rt for 1 h, concentrated in vacuo and the residue was dissolved in THF at 0° C., and oxalyl chloride (0.16 mL, 0.32 mmol, 2M in DCM), and DMF (1 drop) were added. The mixture was stirred at 0° C. for 30 min and concentrated in vacuo to give the corresponding acid chloride.

In a separate vial compound 2 (83 mg, 0.24 mmol) was treated with 4M HCl (2 mL) in dioxane at rt for 1 h and concentrated in vacuo was and the residue was dissolved in THF (5 mL) at 0° C., and Et3N (100 uL, 0.78 mmol) was added, followed by a solution of the above acid chloride in THF (5 mL). The mixture was stirred at 0° C. for 20 min. The mixture was concentrated, and the residue was purified by silica gel chromatography using a gradient of EtOAc (0-100%) in heptanes to give the product 46 as off-white solid 114 mg (79%). LC-MS (Protocol B): m/z 919.1 [M+H]$^+$, retention time=1.05 minutes, $^1$H NMR (400 MHz, DMSO-d6) δ=10.41 (s, 1H), 8.22 (s, 1H), 7.93 (s, 1H), 7.47 (s, 1H), 7.38 (s, 1H), 5.81-5.70 (m, 4H), 5.63-5.52 (m, 1H), 5.19 (t, J=8.6 Hz, 1H), 5.12 (t, J=9.8 Hz, 1H), 4.76 (d, J=9.8 Hz, 1H), 4.30-4.16 (m, 3H), 3.86 (m, 2H), 3.68 (s, 3H), 3.64-3.51 (m, 2H), 2.73 (br. s., 1H), 2.62 (m, 2H), 2.50 (s, 6H), 2.10-2.02 (m, 12H).

Step 4. Synthesis of (2S,3R,4S,5S,6S)-2-(((S)-6-(5-((S)-4-(((2-((tert-butoxycarbonyl)(methyl)amino)ethyl)(methyl)carbamoyl)oxy)-8-(chloromethyl)-1-methyl-7,8-dihydro-6H-thieno[3,2-e]indol-6-yl)-5-oxopentanoyl)-8-(chloromethyl)-1-methyl-7,8-dihydro-6H-thieno[3,2-e]indol-4-yl)oxy)-6-(methoxycarbonyl)tetrahydro-2H-pyran-3,4,5-triyl triacetate (47): To a solution of 46 (50 mg, 0.054 mmol) in THF (3 mL) at 0° C., was added a solution of 4-nitrophenyl chloroformate (22 mg, 0.10 mmol) in DCM (0.5 mL), followed by DIPEA (57 uL, 0.33 mmol), and the mixture was stirred at 0° C. for 1 h. To the above mixture was added a solution of 38 [prepared as described J. Med. Chem. 1992, 33, 559-567] (31 mg, 0.16 mmol) in THF (0.5 mL), and the mixture was stirred at 0° C. for 30 min and concentrated in vacuo, and the residue was purified was purified by silica gel chromatography using a gradient of EtOAc (0-100%) in heptanes to give the product 47 as white solid 56 mg (91%). LC-MS (Protocol B): m/z 1150.2 [M+NH$_4$], retention time=1.14 minutes Step 5: Synthesis of (2S,3S,4S,5R,6S)-6-(((S)-6-(5-((S)-4-(((2-((tert-butoxycarbonyl)(methyl)amino)ethyl)(methyl)carbamoyl)oxy)-8-(chloromethyl)-1-methyl-7,8-dihydro-6H-thieno[3,2-e]indol-6-yl)-5-oxopentanoyl)-8-(chloromethyl)-1-methyl-7,8-dihydro-6H-thieno[3,2-e]indol-4-yl)oxy)-3,4,5-trihydroxytetrahydro-2H-pyran-2-carboxylic acid (48): To a solution of 47 (56 mg, 0.049 mmol) in THF/MeOH (1/1, 6 mL) at 0° C., was added a solution of LiOH.H2O (21 mg, 0.49 mmol) in water (0.5 mL). The mixture was stirred at 0° C. for 1 h. Acetic acid (50 mg) was added and the reaction concentrated in vacuo to give crude product 48 as white solid 45 mg (90%). LC-MS (Protocol B): m/z 1014.9 [M+Na], retention time=1.0 minutes Step 6: Synthesis of (2S,3S,4S,5R,6S)-6-(((S)-8-(chloromethyl)-6-(5-((S)-8-(chloromethyl)-4-(((2-((((4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosan-27-amido)benzyl)oxy) carbonyl)(methyl)amino)ethyl)(methyl)carbamoyl)oxy)-1-methyl-7,8-dihydro-6H-thieno[3,2-e]indol-6-yl)-5-oxopentanoyl)-1-methyl-7,8-dihydro-6H-thieno[3,2-e]indol-4-yl)oxy)-3,4,5-trihydroxytetrahydro-2H-pyran-2-carboxylic acid (49) and (8S)-8-(chloromethyl)-6-{5-[(8S)-8-(chloromethyl)-4-hydroxy-1-methyl-7,8-dihydro-6H-thieno[3,2-e]indol-6-yl]-5-oxopentanoyl}-1-methyl-7,8-dihydro-6H-thieno[3,2-e]indol-4-yl beta-D-glucopyranosiduronic acid (57): Compound 48 (23 mg, 0.02 mmol) was treated with pre-cooled TFA (1 mL) at 0° C. for 5 min. and concentrated in vacuo. The residue was dissolved in DMF (2 mL), and compound 37(19 mg, 0.02 mmol), lutidine (14 uL, 0.12 mmol), DIPEA (21 uL, 0.12 mmol) and HOAt (2.7 mg, 0.02 mmol) were added and. the mixture was stirred at 30° C. for 1 h The mixture was purified by reverse phase HPLC (Method C) to give compound 49 as off-white solid 8 mg (20%). LC-MS (Protocol B): m/z 1714.6 [M+H]+, retention time=0.89 minutes and compound 57 as a gum 7 mg (50%): LC-MS (Protocol B): m/z 779.1 [M+H]+, retention time=0.90 minutes Preparation of: (S)-8-(chloromethyl)-6-(5-((S)-8-(chloromethyl)-1-methyl-4-(phosphonooxy)-7,8-dihydro-6H-thieno[3,2-e]indol-6-yl)-5-oxopentanoyl)-1-methyl-7,8-dihydro-6H-thieno[3,2-e]indol-4-yl (4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosan-27-amido)benzyl) ethane-1,2-diylbis(methylcarbamate) (56)

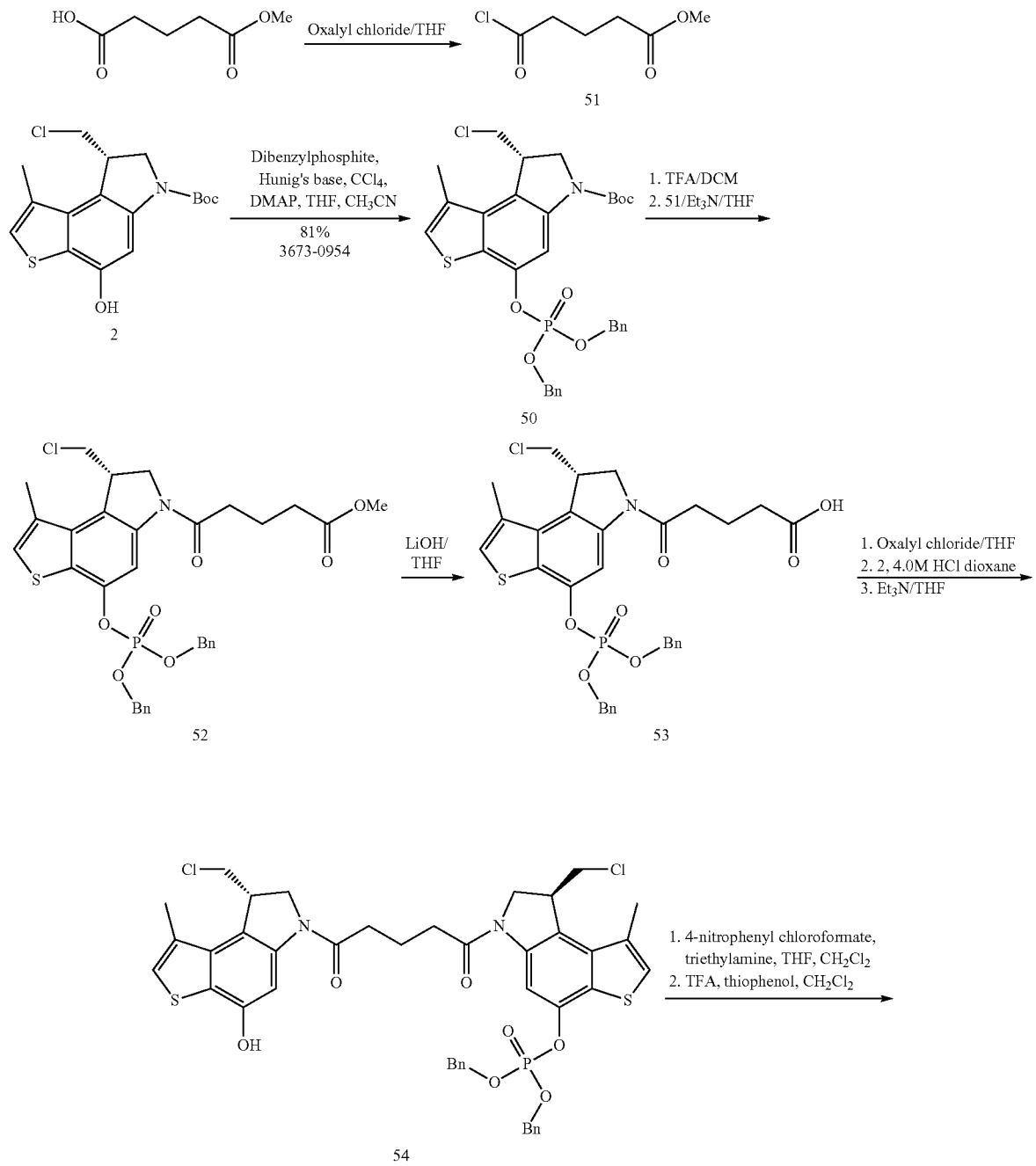

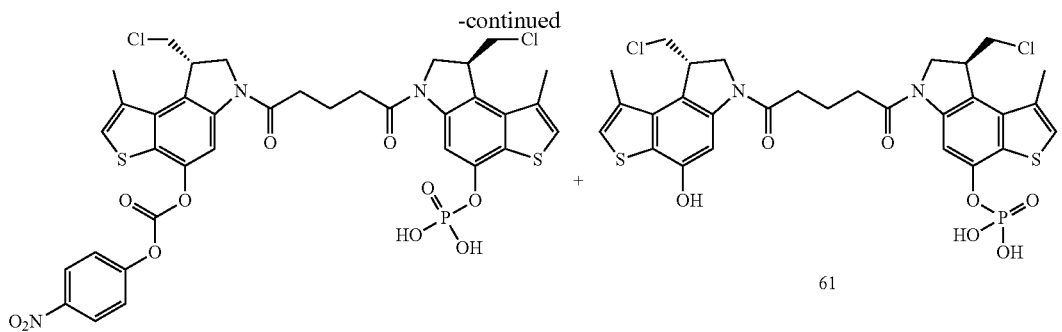

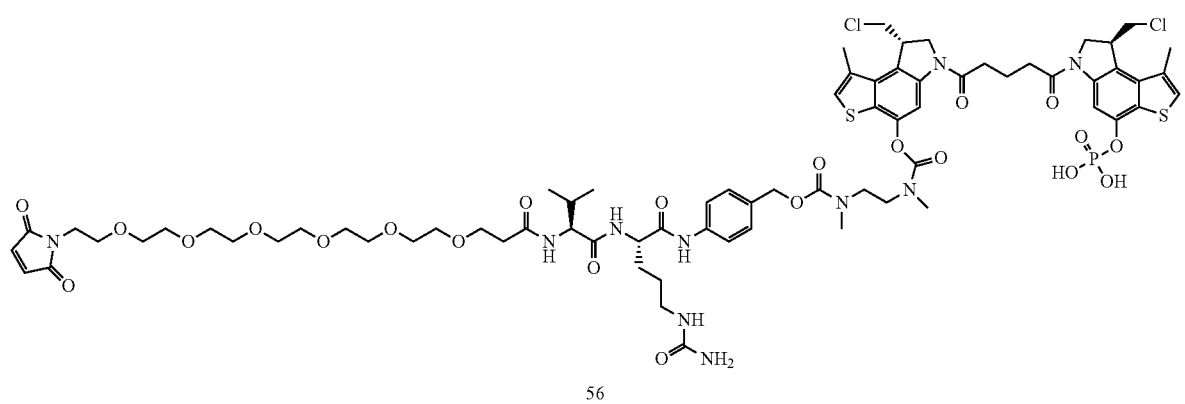

Step 1: Synthesis of methyl 5-chloro-5-oxopentanoate (51): 5-methoxy-5-oxopentanoic acid (128 mg, 0.88 mmol) was dissolved in THF (5 mL) at 0 C, and oxalyl chloride (0.9 mL, 1.8 mmol, 2M in DCM) and DMF (1 drop) were added and the mixture was stirred at 0° C. for 30 min. Concentrated in vacuo to give the correspond acid chloride 51 as white solid which was used without further purification.

Step 2. Synthesis of tert-butyl (S)-4-((bis(benzyloxy)phosphoryl)oxy)-8-(chloromethyl)-1-methyl-7,8-dihydro-6H-thieno[3,2-e]indole-6-carboxylate (50)

To a solution of 2 (260 mg, 0.74 mmol) in ACN (8 mL) and THF (8 mL), was added CCl₄ (1 mL), DIPEA (0.52 mL, 2.94 mmol), dibenylphosphite (1.03 mL, 4.41 mmol), and DMAP (18 mg). The mixture was stirred at rt for 15 min, concentrated in vacuo the residue was purified by silica gel chromatography using a gradient (0-60%) of EtOAc in heptanes to give the product 50 as colorless oil 365 mg (81%). LC-MS (Protocol B): m/z 631.2 [M+H]⁺, retention time=1.18 minutes Step 3. Synthesis of methyl (S)-5-(4-((bis(benzyloxy)phosphoryl)oxy)-8-(chloromethyl)-1-methyl-7,8-dihydro-6H-thieno[3,2-e]indol-6-yl)-5-oxopentanoate (52)

To a solution of 50 (365 mg, 0.58 mmol) in DCM (3 mL) was added TFA (3 mL) and the mixture was stirred at rt for 2 min and concentrated in vacuo. The residue was dissolved in THF (5.0 mL) and a solution of acid chloride 51 (0.88 mmol) in THF (5.0 mL) followed by Et₃N (0.37 mL, 0.24 mmol) was added and the mixture was stirred at 0° C. for 30 min. The reaction was concentrated and the residue was purified by silica gel chromatography using a gradient (0-80%) of EtOAc in heptanes to give the product 52 as colorless oil 240 mg (64%). LC-MS (Protocol B): m/z 642.1 [M+H]⁺, retention time=1.09 minutes Step 4. Synthesis of (S)-5-(4-((bis(benzyloxy)phosphoryl)oxy)-8-(chloromethyl)-1-methyl-7,8-dihydro-6H-thieno[3,2-e]indol-6-yl)-5-oxopentanoic acid (53)

To a solution of 52 (235 mg, 0.37 mmol) in THF (10 mL) at 0° C., added a solution of LiOH/H₂O (155 mg, 3.7 mmol) in water (2.5 mL), and the mixture was stirred at 0° C. for 1.5 h. The mixture was diluted with DCM, acidified by 1M HCl, and organic layer was separated, and the aqueous phase was extracted with DCM tow times. Combined organic phases were dried over MgSO4. The mixture was concentrated in vacuo and the residue which was purified by reverse phase HPLC (Method C) to give the product 53 as off-white foam 27 mg (12%). LC-MS (Protocol B): m/z 628.1 [M+H]⁺, retention time=1.01 minutes Step 5. Synthesis of dibenzyl ((S)-8-(chloromethyl)-6-(5-((S)-8-(chloromethyl)-4-hydroxy-1-methyl-7,8-dihydro- 6H-thieno[3,2-e]indol-6-yl)-5-oxopentanoyl)-1-methyl-7,8-dihydro-6H-thieno[3,2-e]indol-4-yl) phosphate (54)

To a solution of 53 (27 mg, 0.043 mmol) in THF (5 mL), at 0° C., was added oxalyl chloride (0.043 mL, 0.086 mmol, 2M in DCM) and DMF (1 drop). The mixture was stirred at 0° C. for 30 min, and concentrated in vacuo to give the corresponding acid chloride as yellow foam.

In a separate vial, compound 2 (23 mg, 0.064 mmol) was treated with 4M HCl (1 mL) at rt for 1 h, and concentrated in vacuo. The residue was dissolved in THF (5 mL), cooled to 0° C., and added to a solution of the above acid chloride in THF (5 mL) and Et₃N (0.018 mL, 0.13 mmol). The mixture was concentrated in vacuo, and the residue was purified by reverse phase HPLC (Method C) to give the product 54 as an off-white solid 28 mg (75%). LC-MS (Protocol B): m/z 863.2 [M+H]⁺, retention time=1.16 minutes Step 6. Synthesis of (S)-8-(chloromethyl)-6-(5-((S)-8-(chloromethyl)-1-methyl-4-(phosphonooxy)-7,8-dihydro-6H-thieno[3,2-e]indol-6-yl)-5-oxopentanoyl)-1-methyl-7,8-dihydro-6H-thieno[3,2-e]indol-4-yl (4-nitrophenyl) carbonate (55) and (8S)-8-(chloromethyl)-6-{5-[(8S)-8-(chloromethyl)-4-hydroxy-1-methyl-7,8-dihydro-6H-thieno[3,2-e]indol-6-yl]-5-oxopentanoyl}-1-methyl-7,8-dihydro-6H-thieno[3,2-e]indol-4-yl dihydrogen phosphate (61)

To a solution of 54 (40 mg, 0.046 mmol) in THF (5 mL), at 0° C., was added a solution of 4-nitrophenyl chloroformate (19.4 mg, 0.092 mmol) in DCM (0.5 mL), and DIPEA (0.049 mL, 0.28 mmol). The mixture was stirred at 0° C. for 30 min. The reaction was concentrated in vacuo and the residue was purified by silica gel chromatography using a gradient (0-60%) of acetone in heptanesto give intermediate PNP carbonate as white solid 48 mg. It was dissolved in DCM (2 mL), and TFA (2 mL) and thiophenol (0.047 mL, 0.46 mmol) were added and the mixture was stirred at rt for 3 h. The reaction was concentrated in vacuo, and the residue was purified by reverse phase HPLC (Method C) to give 17.8 mg (46%) of the product 55 as white solid (17.8 mg, 46%). LC-MS (Protocol B): m/z 848.2 [M+H]⁺, retention time=1.09 minutes and 5.2 mg (17%) of product 61 as a gum LC-MS (Protocol B): m/z 683.2 [M+H]⁺, retention time=0.93 minutes Step 7. Synthesis of (S)-8-(chloromethyl)-6-(5-((S)-8-(chloromethyl)-1-methyl-4-(phosphonooxy)-7,8-dihydro-6H-thieno[3,2-e]indol-6-yl)-5-oxopentanoyl)-1-methy-7,8-dihydro-6H-thieno[3,2-e]indol-4-yl (4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosan-27-amido)benzyl) ethane-1,2-diylbis(methylcarbamate) (56)

To a solution of 55 (10.5 mg, 0.012 mmol) in DMF (1 mL), was added 40 (13.9 mg, 0.014 mmol), lutidine (0.009 mL, 0.074 mmol), DIPEA (0.013 mL, 0.074 mmol) and HOAt (1.7 mg, 0.012 mmol). The mixture was stirred at rt for 20 min, concentrated in vacuo, and the residue was purified by reverse phase HPLC (Method C) to give product 56 as white foam 12 mg (60%). LC-MS (Protocol B): m/z 1619.6 [M+2H]⁺, retention time=0.95 minutes Preparation of pentacyclo[4.2.0.0⁻2,5⁻.0⁻3,8⁻.0⁻4,7⁻]octane-1,4-diylbis[carbony(8S)-8-(chloromethyl)-1-methyl-7,8-dihydro-6H-thieno[3,2-e]indole-6,4-diyl] Diacetate (60)

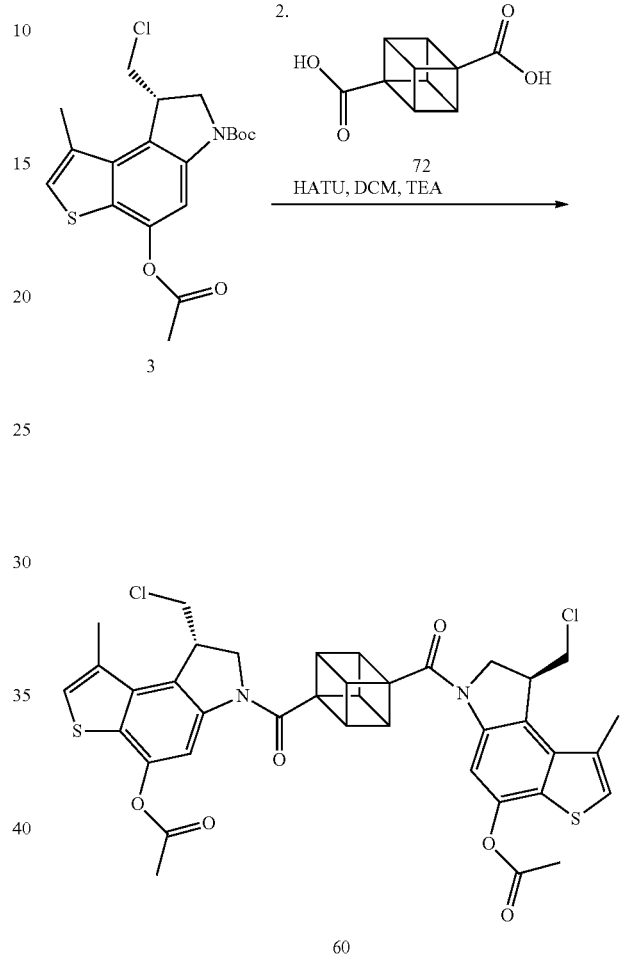

Step 1: Synthesis of pentacyclo[4.2.0.0⁻2,5⁻.0⁻3,8⁻.0⁻4,7⁻]octane-1,4-diylbis[carbonyl(8S)-8-(chloromethyl)-1-methyl-7,8-dihydro-6H-thieno[3,2-e]indole-6,4-diyl]diacetate (60): A solution of 3 (47 mg, 0.12 mmol) was treated with 4M HCl (1.5 mL in dioxane) at rt for 90 min and concentrated in vacuo and the residue was dissolved in DCM (4 mL) and TEA (0.025 mL) and added to a solution of 1,4-Cubanedicarboxylic acid (11.5 mg, 0.06 mmol, 72) was dissolved in 1 mL of anhydrous dichloromethane followed by addition of HATU (47 mg, 0.12 mmol). The reaction was stirred at room temperature for 16 h. The mixture was purified by reverse phase HPLC Column: (Phenomenex Column Luna C18 5 u 150×21.5 mm, Gradient 20%-90% AcCN/Water (with 0.02% AcOH in each) over 20 min (plus an initial 6 minute isocratic time at 20% AcCN/water) with 0.02% to afford 3.1 mg 60 (white solid, 7%). LC-MS (Protocol A): m/z: 747.1 (M+H)+, retention time=2.39 min Preparation of (S)-8-(chloromethyl)-6-(5-((S)-1-(chloromethyl)-5-((S)-2-((S)-2-(6-(2,5-dioxo-2,5-dihydro-1H-pyrrol-1-yl)hexanamido)-3-methylbutanamido)propanamido)-1,2-dihydro-3H-benzo[e]indol-3-yl)-5-oxopentanoyl)-1-methyl-7,8-dihydro-6H-thieno[3,2-e]indol-4-yl Dihydrogen Phosphate (62)
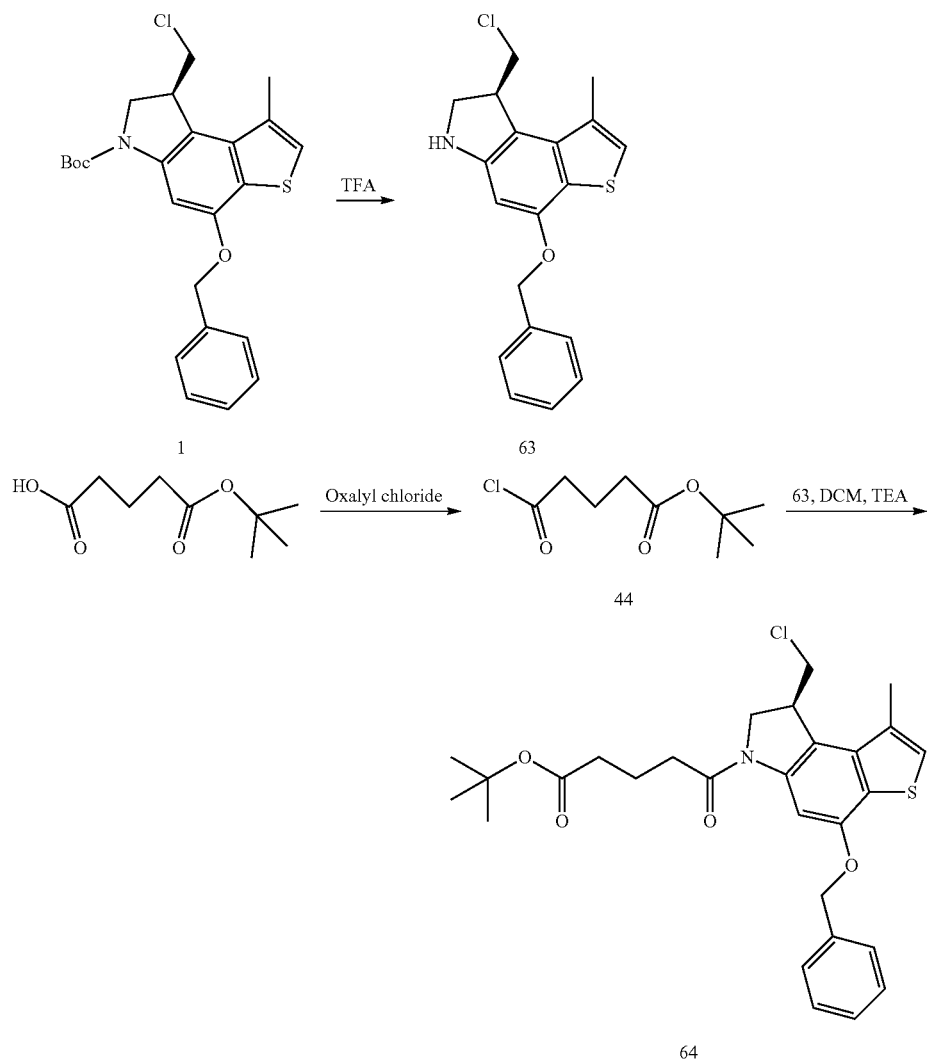
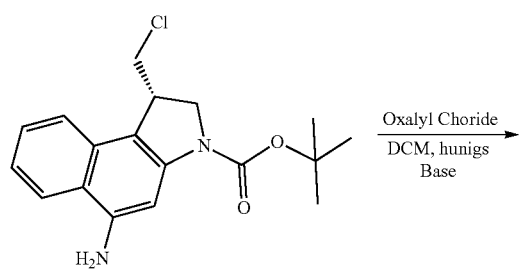

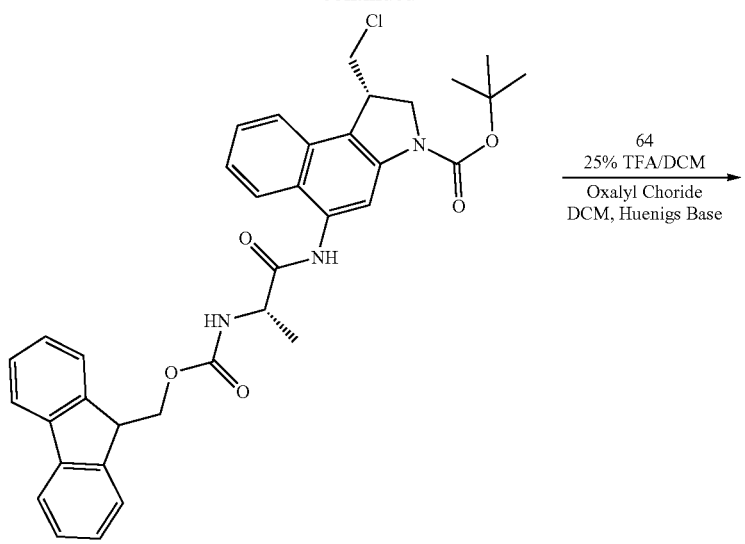
66
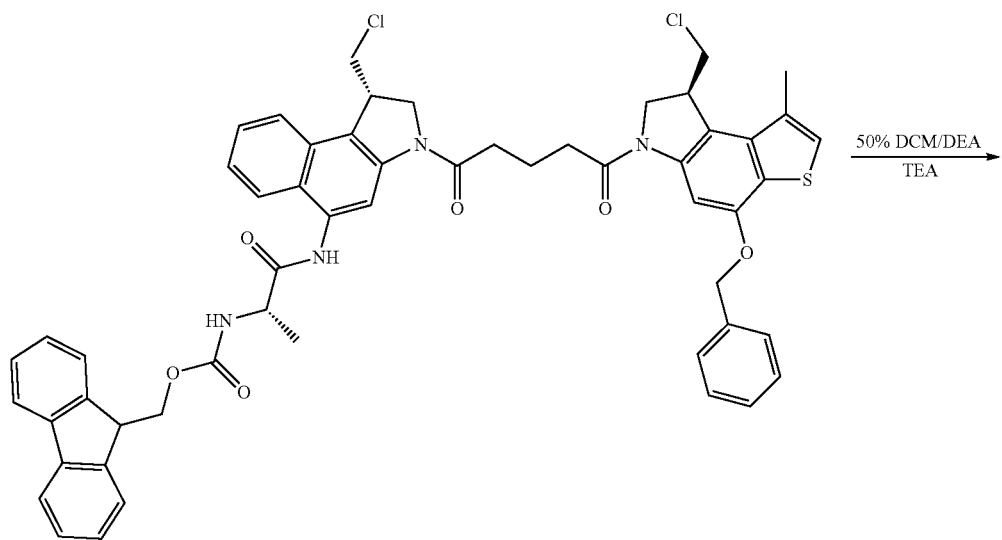
67

-continued
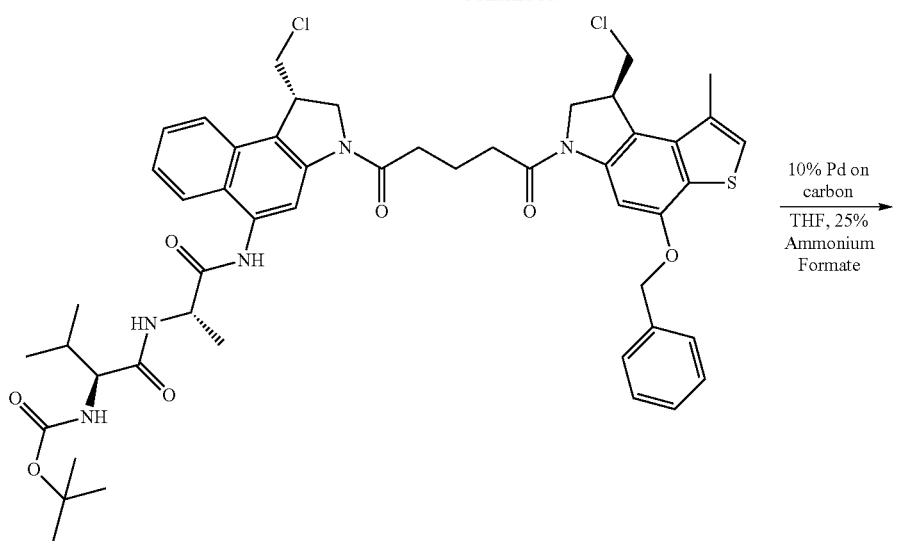
68
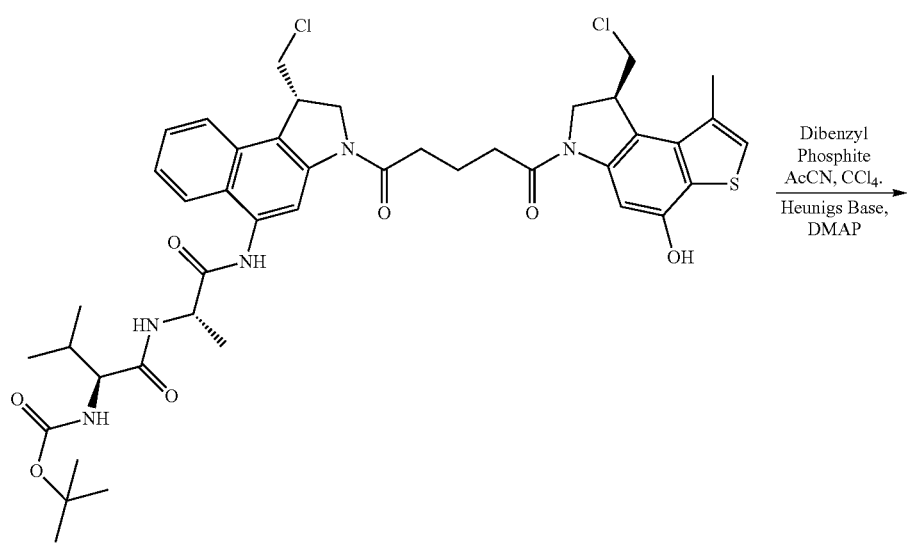
69

-continued
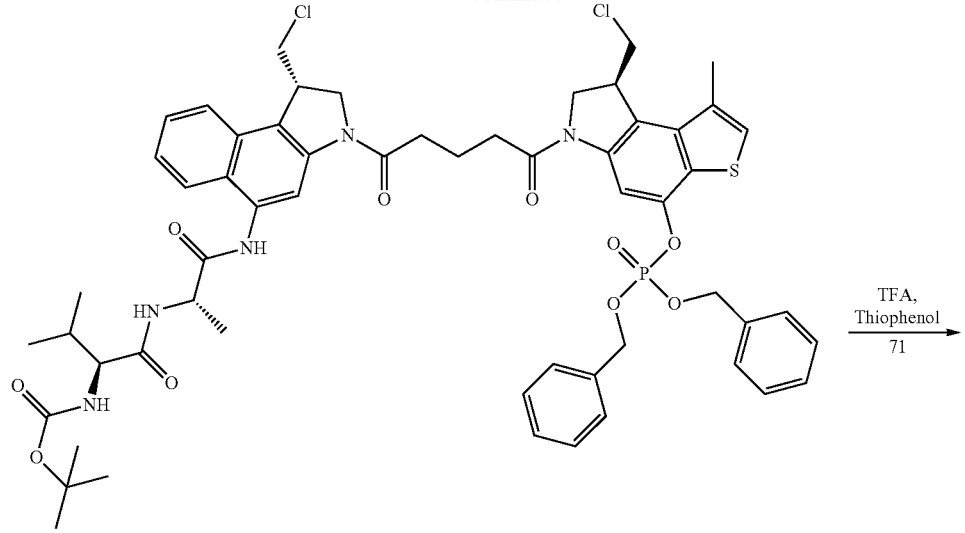
70
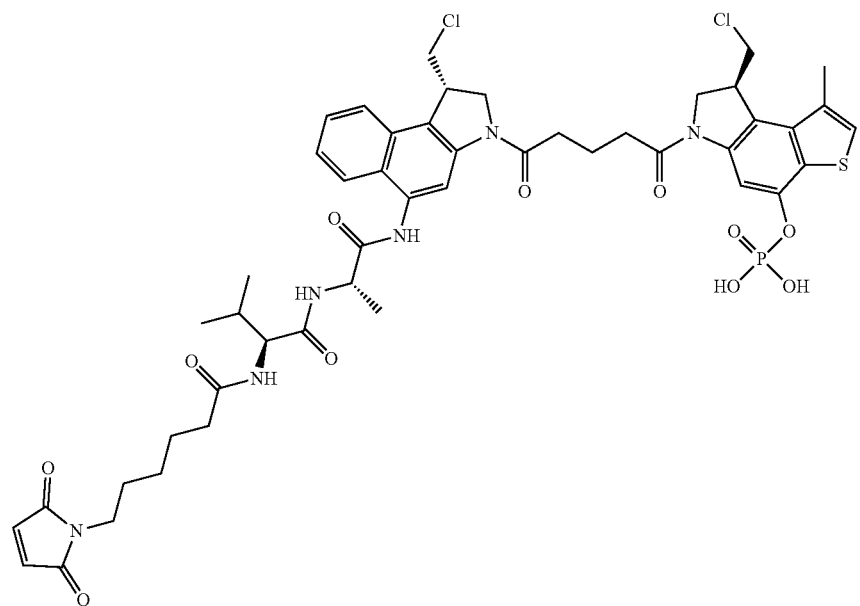
62
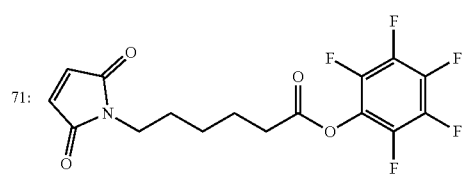
71:

Step 1: Synthesis of (S)-4-(benzyloxy)-8-(chloromethyl)-1-methyl-7,8-dihydro-6H-thieno[3,2-e]indole (63): To a stirred solution of compound 1 (300 mg, 0.676 mmol) in dry DCM (5 mL) was added dropwise 4.0 M HCl in EtOAc (5 mL) at 0° C. After addition, the mixture was stirred at r.t for 1.5 h. The mixture was concentrated in vacuum then co-evaporated with DCM once to give product 63 (260 mg, 100%) and was used as such in next step.

Step 2: Synthesis of tert-butyl (S)-5-(4-(benzyloxy)-8-(chloromethyl)-1-methyl-7,8-dihydro-6H-thieno[3,2-e]indol-6-yl)-5-oxopentanoate (63)

In a round bottom flask containing tert-butyl (S)-4-(benzyloxy)-8-(chloromethyl)-1-methyl-7,8-dihydro-6H-thieno[3,2-e]indole-6-carboxylate (1) (500 mg, 1.13 mmol) was added 25% TFA in DCM (10 mL). The reaction was stirred for 30 min. The reaction was concentrated and placed on under vacuum for 30 min to give the de-boc residue 63 which was taken up in 5 mL of DCM and used in the step below.

In a round bottom flask purged with $N_2$, containing 5-(tert-butoxy)-5-oxopentanoic acid (212 mg, 1.13 mmol)) in 5 mL of anhydrous DCM was added oxalyl chloride (0.101 mL, 1.13 mmol). To this solution was added 1 drop of DMF and the system was stirred for 3 hours. Noticed gas formation immediately. The reaction was concentrated by vacuum to give crude acid chloride 44. which was taken up in DCM and added to a round bottom flask containing the above described deprotected residue 63 and TEA (0.144 mL). The reaction was stirred at room temperature for 2 hours. The crude reaction mixture was concentrated by vacuum and taken up in 25 mL of DCM and transferred to a separatory funnel. Washed organic layer with 1M HCl (3×), water (3×), and brine (2×). Dried organic layer over sodium sulfate, filtered and concentrated the filtrate to a crude solid. The crude products was purified by silica gel chromatography (Gradient: 0% to 10% MeOH in DCM) to give 64 as a yellow solid (525 mg, 90%). LC-MS (Protocol A): m/z 514 [M+H]$^+$, retention time=2.43 minutes.

Step 3: Synthesis of tert-butyl (S)-5-((S)-2-((((9H-fluoren-9-yl)methoxy)carbonyl)amino)propanamido)-1-(chloromethyl)-1,2-dihydro-3H-benzo[e]indole-3-carboxylate (66).

In a round bottom flask tert-butyl (S)-5-amino-1-(chloromethyl)-1,2-dihydro-3H-benzo[e]indole-3-carboxylate (1000 mg, 3.0 mmol, 65) (prepared as described in WO 2015023355) in 15 mL of DCM was added (9H-fluoren-9-yl)methyl (S)-(1-chloro-1-oxopropan-2-yl)carbamate (991 mg, 3.0 mmol followed by 1.2 mL of Hunigs base. The reaction was stirred for 1 hour and concentrated to a crude glass. The crude reaction mixture was purified by silica gel chromatography (gradient: 0% to 10% MeOH in DCM) to give 66 as a white solid (1529 mg, 80%). LC-MS (Protocol A): m/z 626 [M+H]$^+$, retention time=2.32 minutes.

Step 4: Synthesis of (9H-fluoren-9-yl)methyl ((S)-1-(((S)-3-(5-((S)-4-(benzyloxy)-8-(chloromethyl)-1-methyl-7,8-dihydro-6H-thieno[3,2-e]indol-6-yl)-5-oxopentanoyl)-1-(chloromethyl)-2,3-dihydro-1H-benzo[e]indol-5-yl)amino)-1-oxopropan-2-yl)carbamate (67).

To a stirring solution of tert-butyl (S)-5-(4-(benzyloxy)-8-(chloromethyl)-1-methyl-7,8-dihydro-6H-thieno[3,2-e]indol-6-yl)-5-oxopentanoate (500 mg, 0.973 mmol, 64) in 10 mL of DCM was added 2.5 mL of TFA and the reaction was stirred for 3 hours. Upon completion the reaction was concentrated under vacuum to a pale white solid. The solid was then taken up in 5 mL of anhydrous DCM and oxalyl chloride (0.32 mL, 0.93 mmol). The reaction was stirred for 3 hours and concentrated under vacuum to a white solid.

tert-butyl (S)-5-((S)-2-((((9H-fluoren-9-yl)methoxy)carbonyl)amino)propanamido)-1-(chloromethyl)-1,2-dihydro-3H-benzo[e]indole-3-carboxylate (0.973 mmol, 66) was taken up in 25% TFA in DCM (5 mL) and stirred for 30 min. The reaction was concentrated under vacuum and taken back up in 5 mL of DCM. Hunigs base (0.32 mL) was added followed by the acid chloride previously described. The reaction was stirred for 2 hours. Upon completion the reaction mixture was concentrated under vacuum. The crude products was purified by silica gel chromatography (Gradient: 0% to 10% MeOH in DCM) to give 67 as a white solid (510 mg, 54%). %). LC-MS (Protocol A): m/z 965 [M+H]$^+$, retention time=2.61 minutes.

Step 5: Synthesis of tert-butyl ((S)-1-(((S)-1-(((S)-3-(5-((S)-4-(benzyloxy)-8-(chloromethyl)-1-methyl-7,8-dihydro-6H-thieno[3,2-e]indol-6-yl)-5-oxopentanoyl)-1-(chloromethyl)-2,3-dihydro-1H-benzo[e]indol-5-yl)amino)-1-oxopropan-2-yl)amino)-3-methyl-1-oxobutan-2-yl)carbamate (68).

To a stirring solution of (9H-fluoren-9-yl)methyl ((S)-1-(((S)-3-(5-((S)-4-(benzyloxy)-8-(chloromethyl)-1-methyl-7,8-dihydro-6H-thieno[3,2-e]indol-6-yl)-5-oxopentanoyl)-1-(chloromethyl)-2,3-dihydro-1H-benzo[e]indol-5-yl)amino)-1-oxopropan-2-yl)carbamate (500 mg, 0.518 mmol, 67) in 5 mL of DCM was added 5 mL of Diethylamine. The reaction was stirred for 3 hours and concentrated under vacuum to a yellow solid. The yellow crude solid was taken up in 10 mL of anyhdrous THF followed by 2,5-dioxopyrrolidin-1-yl (tert-butoxycarbonyl)-L-valinate (163 mg, 0.518 mmol) followed by TEA (0.2 mL). The reaction was stirred at 70 degrees Celsius for 4 hours. Upon completion the reaction mixture was concentrated under vacuum. The crude products was purified by silica gel chromatography (Gradient: 0% to 10% MeOH in DCM) to give 68 as a white solid (198 mg, 40%). %). LC-MS (Protocol A): m/z 942 [M+H]$^+$, retention time=2.49 minutes.

Step 6: Synthesis of tert-butyl ((S)-1-(((S)-1-(((S)-1-(chloromethyl)-3-(5-((S)-8-(chloromethyl)-4-hydroxy-1-methyl-7,8-dihydro-6H-thieno[3,2-e]indol-6-yl)-5-oxopentanoyl)-2,3-dihydro-1H-benzo[e]indol-5-yl)amino)-1-oxopropan-2-yl)amino)-3-methyl-1-oxobutan-2-yl)carbamate (69).

A stirring solution of tert-butyl ((S)-1-(((S)-1-(((S)-3-(5-((S)-4-(benzyloxy)-8-(chloromethyl)-1-methyl-7,8-dihydro-6H-thieno[3,2-e]indol-6-yl)-5-oxopentanoyl)-1-(chloromethyl)-2,3-dihydro-1H-benzo[e]indol-5-yl)amino)-1-oxopropan-2-yl)amino)-3-methyl-1-oxobutan-2-yl)carbamate (325 mg, 0.345 mmol, 68) in 7 mL of THF under nitrogen was cooled to 0 C using an ice bath. Palladium 10 wt. % on activated carbon (10 mg) was then added followed by the slow drop wise addition of 0.5 mL of 25% ammonium formate in water. The reaction was allowed to stir at 0 C. for 1 hour. Upon completion the reaction mixture was filtered through a pad of celite and the filtrate concentrated under vacuum. The crude products was purified by silica gel chromatography (gradient: 0% to 10% MeOH in DCM) to give 69 as a yellow solid (181 mg, 61%). LC-MS (Protocol A): m/z 852 [M+H]$^+$, retention time=2.18 minutes.

Step 7: Synthesis of tert-butyl ((S)-1-(((S)-1-(((S)-3-(5-((S)-4-((bis(benzyloxy)phosphoryl)oxy)-8-(chloromethyl)-1-methyl-7,8-dihydro-6H-thieno[3,2-e]indol-6-yl)-5-oxopentanoyl)-1-(chloromethyl)-2,3-dihydro-1H-benzo[e]indol-5-yl)amino)-1-oxopropan-2-yl)amino)-3-methyl-1-oxobutan-2-yl)carbamate (70).

To a stirring solution of tert-butyl ((S)-1-(((S)-1-(((S)-1-(chloromethyl)-3-(5-((S)-8-(chloromethyl)-4-hydroxy-1-methyl-7,8-dihydro-6H-thieno[3,2-e]indol-6-yl)-5-oxopentanoyl)-2,3-dihydro-1H-benzo[e]indol-5-yl)amino)-1-oxopropan-2-yl)amino)-3-methyl-1-oxobutan-2-yl)carbamate (165 mg, 0.193 mmol, 69) in 10 mL of THF and 10 mL of AcCN, carbon tetrachloride (2.04 mL, 21.0 mmol) was added followed by Huenig's base (1.12 mL, 6.45 mmol), dibenzylphosphite (320 mg, 1.16 mmol) and DMAP (catalytic). The reaction was allowed to stir at room temperature for 20 minutes. The reaction was concentrated to a crude glass. The crude reaction mixture was purified by silica gel chromatography (gradient: 0% to 10% MeOH in DCM) to give 70 as a white glass (51 mg, 24%). LC-MS (Protocol A): m/z 1113 [M–H]$^-$, retention time=2.50 minutes.

Step 8: Synthesis of (S)-8-(chloromethyl)-6-(5-((S)-1-(chloromethyl)-5-((S)-2-((S)-2-(6-(2,5-dioxo-2,5-dihydro-1H-pyrrol-1-yl)hexanamido)-3-methylbutanamido)propanamido)-1,2-dihydro-3H-benzo[e]indol-3-yl)-5-oxopentanoyl)-1-methyl-7,8-dihydro-6H-thieno[3,2-e]indol-4-yl dihydrogen phosphate (62).

In a round bottom flask equipped with a stir bar, tert-butyl ((S)-1-(((S)-1-(((S)-3-(5-((S)-4-((bis(benzyloxy)phosphoryl)oxy)-8-(chloromethyl)-1-methyl-7,8-dihydro-6H-thieno[3,2-e]indol-6-yl)-5-oxopentanoyl)-1-(chloromethyl)-2,3-dihydro-1H-benzo[e]indol-5-yl)amino)-1-oxopropan-2-yl)amino)-3-methyl-1-oxobutan-2-yl)carbamate (40 mg 0.036 mmol, 70) was taken up in 5 mL of DCM. TFA (2.5 mL) and 2 drops of thiophenol were added and the reaction was stirred for 6 hours. The crude material was concentrated under vacuum. The crude residue was taken up in 3 mL of DMF and pentafluorophenyl 6-(2,5-dioxo-2,5-dihydro-1H-pyrrol-1-yl)hexanoate (71) (13.6 mg, 0.036 mmol) was added followed by TEA (0.036 mmol). The reaction was stirred for 1 hour. The reaction was concentrated under vacuum and purified by HPLC Method to give 62 as a white solid (25 mg, 68%), retention time=7.115 minutes. LC-MS (Protocol A): m/z 1025 [M+H]$^+$, retention time=2.01 minutes Preparation of N~2~-acetyl-N~6~-[(9H-fluoren-9-ylmethoxy)carbonyl]-L-lysyl-L-valyl-N—5~-carbamoyl-N-{4-[({methyl[2-(methylamino)ethyl]carbamoyl}oxy)methyl]phenyl}-L-ornithinamide (74)

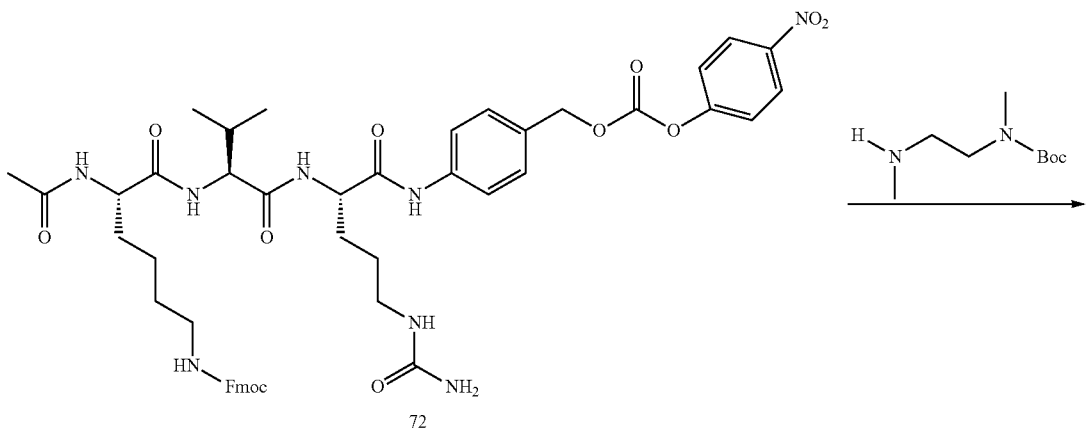

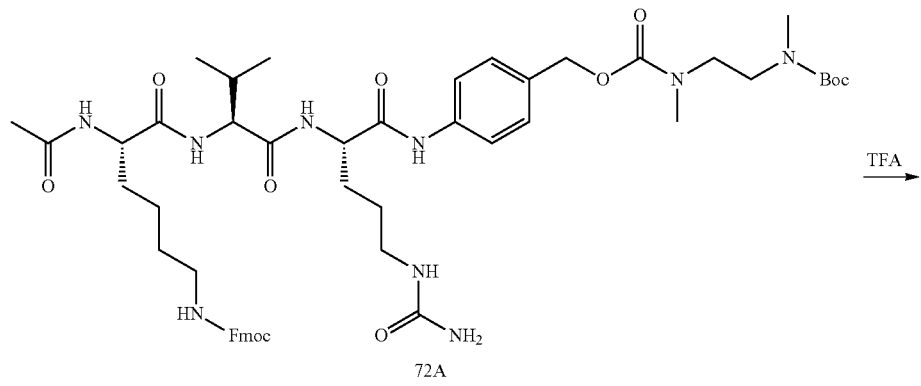

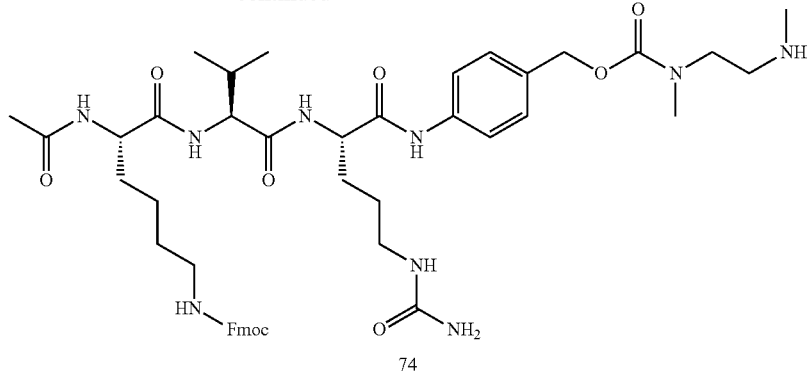

74

Step 1: Synthesis of N~2~-acetyl-N~6~-[(9H-fluoren-9-ylmethoxy)carbonyl]-L-lysyl-L-valyl-N~5~-carbamoyl-N-[4-(4,7,10,10-tetramethyl-3,8-dioxo-2,9-dioxa-4,7-diazaundec-1-yl)phenyl]-L-ornithinamide (72A): To a stirred solution of N~2~-acetyl-N~6~-[(9H-fluoren-9-ylmethoxy)carbonyl]-L-lysyl-L-valyl~N~5~-carbamoyl-N-[4-({[(4-nitrophenoxy)carbonyl]oxy}methyl)phenyl]-L-ornithinamide (72) (Prepared as described in U.S. Pat. No. 9,169,264) (1.00 g, 1.07 mmol) in DMF (20 mL) was added 38 [prepared as described *J. Med. Chem.* 1992, 33, 559-567] (241 mg, 1.28 mmol) at 0° C. under N₂ balloon. The resulting mixture was stirred at 0° C. for 30 mins. The mixture was poured into TBME (200 mL). The resulting white suspension was filtered and washed with TBME (200 mL) to afford the title compound 72A (750 mg, 71.3%) as a yellow solid Step 2: Synthesis of N~2~-acetyl-N~6~-[(9H-fluoren-9-ylmethoxy)carbonyl]-L-lysyl-L-valyl-N~5~-carbamoyl-N-{4-[({methyl[2-(methylamino)ethyl]carbamoyl}oxy)methyl]phenyl}-L-ornithinamide (74): To a stirred suspension of compound 72A (10.00 g, 10.1 mmol) in DCM(60.0 mL) was added TFA (50.0 mL) at 0° C. The resulting solution was stirred at 0° C. for 40 min. The resulting suspension was filtered. The filter cake was washed with TBME (200 mL) and dried in vacuum to dryness to afford crude product The crude product was purified by preparative-HPLC (Column: Phenomenex Synergi Max-RP 250×50 mm, 10 um, Gradient: 25% to 55% acetonitrile in water with 0.1% TFA in each phase over 17.5 min and hold for 8 min at 100% acetonitrile in water containing 0.1% TFA, Flow rate: 80 mL/min) to give the title compound 74 (5.2 g, 51.3% yield) as a white solid $^1$H NMR (400 MHz, DMSO-d6) □ 10.03 (s, 1H), 8.47 (br. s., 2H), 8.10 (d, J=7.0 Hz, 1H), 8.03 (d, J=7.8 Hz, 1H), 7.89 (d, J=7.5 Hz, 2H), 7.69 (d, J=7.3 Hz, 3H), 7.60 (d, J=8.5 Hz, 2H), 7.45-7.38 (m, 2H), 7.36-7.29 (m, 4H), 7.26 (t, J=5.4 Hz, 1H), 6.02 (br. s., 1H), 5.01 (s, 2H), 4.43-4.33 (m, 1H), 4.32-4.16 (m, 5H), 3.49 (t, J=6.0 Hz, 2H), 3.06-2.92 (m., 6H) 2.86 (s, 3H), 2.62-2.53 (m, 3H), 1.99 (dd, J=6.5, 13.3 Hz, 1H), 1.85 (s, 3H), 1.76-1.27 (m, 10H), 0.83 (d, J=6.8 Hz, 3H), 0.86 (d, J=6.8 Hz, 3H)

Preparation of LP: (2S,3S,4S,5R,6S)-6-(((S)-6-(5-((S)-4-(((2-((((4-((S)-2-((S)-2-((S)-2-acetamido-6-aminohexanamido)-3-methylbutanamido)-5-ureidopentanamido)benzyl)oxy)carbonyl)(methyl)amino)ethyl)(methyl)carbamoyl)oxy)-8-(chloromethyl)-1-methyl-7,8-dihydro-6H-thieno[3,2-e]indol-6-yl)-5-oxopentanoyl)-8-(chloromethyl)-1-methyl-7,8-dihydro-6H-thieno[3,2-e]indol-4-yl)oxy)-3,4,5-trihydroxytetrahydro-2H-pyran-2-carboxylic Acid (76)

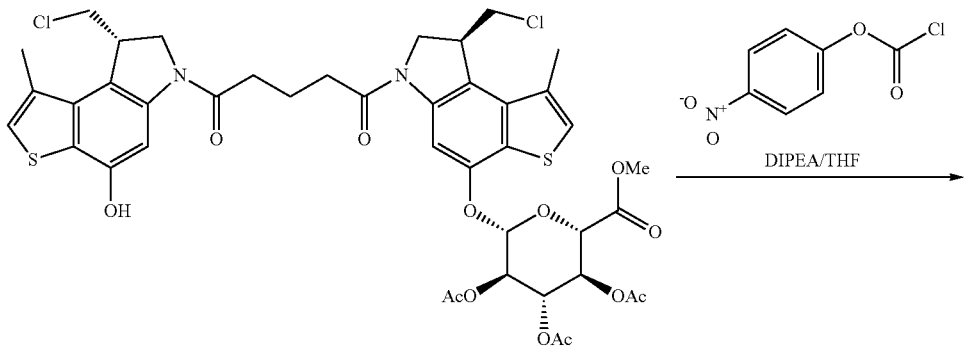

46

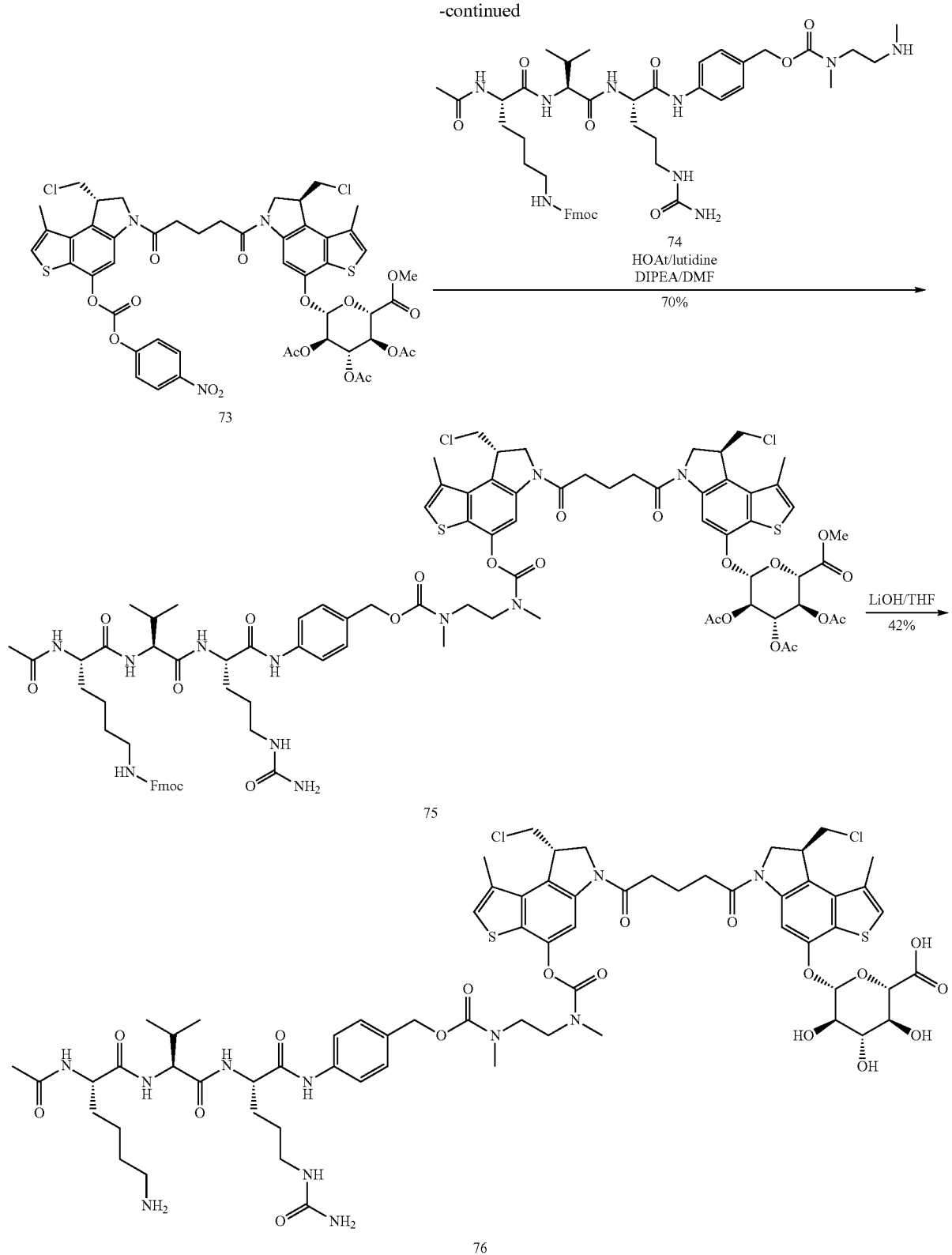
Step 1: Synthesis of (2S,3R,4S,5S,6S)-2-(((S)-8-(chloromethyl)-6-(5-((S)-8-(chloromethyl)-1-methyl-4-(((4-nitrophenoxy)carbonyl)oxy)-7,8-dihydro-6H-thieno[3,2-e]indol-6-yl)-5-oxopentanoyl)-1-methyl-7,8-dihydro-6H-thieno[3,2-e]indol-4-yl)oxy)-6-(methoxycarbonyl)tetrahydro-2H-pyran-3,4,5-triyl triacetate (73)
To a solution of 46 (120 mg, 0.13 mmol) in THF (5 mL) at 0° C., was added a solution of 4-nitrophenyl chloroformate (55 mg, 0.26 mmol) in DCM (0.5 mL), followed by Et₃N (109 uL, 0.78 mmol), and the mixture was stirred at 0° C. for 30 min. The mixture was concentrated in vacuum, and the residue was purified by reverse phase HPLC (Method C) to give the product 73 as white solid 109 mg (77%). LC-MS (Protocol B): m/z 1086.5 (m+H), retention time=1.24 min Step 2: Synthesis of (2S,3R,4S,5S,6S)-2-(((S)-6-(5-((S)-4-(((2-((((4-((9S,12S,15S)-9-acetamido-1-(9H-fluoren-9-yl)-12-isopropyl-3,10,13-trioxo-15-(3-ureidopropyl)-2-oxa-4,11,14-triazahexadecan-16-amido)benzyl)oxy)carbonyl)(methyl)amino)ethyl)(methyl)carbamoyl)oxy)-8-(chloromethyl)-1-methyl-7,8-dihydro-6H-thieno[3,2-e]indol-6-yl)-5-oxopentanoyl)-8-(chloromethyl)-1-methyl-7,8-dihydro-6H-thieno[3,2-e]indol-4-yl)oxy)-6-(methoxycarbonyl)tetrahydro-2H-pyran-3,4,5-triyl triacetate (75)

Compound 73 (50 mg, 0.046 mmol) was dissolved in DMF (2 mL), and to it was added 4-((9S,12S,15S)-9-acetamido-1-(9H-fluoren-9-yl)-12-isopropyl-3,10,13-trioxo-15-(3-ureidopropyl)-2-oxa-4,11,14-triazahexadecan-16-amido)benzyl methyl(2-(methylamino)ethyl)carbamate (74, 55 mg, 0.055 mmol), lutidine (0.021 mL, 0.18 mmol), DIPEA (0.032 mL, 0.18 mmol) and HOAt (6 mg, 0.046 mmol). The mixture was stirred at rt for 1 h. The mixture was concentrated in vacuum, and the residue was purified by reverse phase HPLC (Method C) to give the product 75 as white powder after freeze dry 72 mg (85%). LC-MS (Protocol B): m/z 1833.3 (M+H)retention time=1.17 min ¹H NMR (400 MHz, DMSO-d6) δ=10.02 (br. s., 1H), 8.22 (s, 1H), 8.19-8.13 (m, 1H), 8.10 (d, J=6.6 Hz, 1H), 8.02 (d, J=7.8 Hz, 1H), 7.89 (d, J=7.4 Hz, 2H), 7.69 (d, J=7.0 Hz, 3H), 7.57 (d, J=7.0 Hz, 2H), 7.54-7.38 (m, 5H), 7.37-7.30 (m, 3H), 7.26 (br. s., 3H), 5.99 (br. s., 1H), 5.74 (d, J=7.0 Hz, 1H), 5.64-5.49 (m, 1H), 5.20 (t, J=8.8 Hz, 1H), 5.13 (t, J=9.6 Hz, 1H), 5.04 (br. s., 1H), 5.00 (br. s., 1H), 4.81-4.70 (m, 1H), 4.39 (br.s., 2H), 4.32-4.11 (m, 14H), 3.95-3.80 (m, 3H), 3.62 (br. s., 1H), 3.56 (br. s., 1H), 3.48 (br. s., 2H), 3.12 (br. s., 1H), 3.03 (br. s., 2H), 3.00-2.91 (m, 6H), 2.88 (br. s., 3H), 2.82-2.67 (m, 4H), 2.67-2.55 (m, 7H), 2.10 (s, 1H), 2.08-1.91 (m, 14H), 1.85 (s, 3H), 1.79-1.64 (m, 2H), 1.61 (br. s., 2H), 1.54-1.32 (m, 5H), 1.31-1.23 (m, 2H), 1.23-1.12 (m, 2H), 0.84 (d, J=6.6 Hz, 3H), 0.87 (d, J=6.6 Hz, 3H).

Step 3. Preparation of LP: (2S,3S,4S,5R,6S)-6-(((S)-6-(5-((S)-4-(((2-((((4-((S)-2-((S)-2-((S)-2-acetamido-6-aminohexanamido)-3-methylbutanamido)-5-ureidopentanamido)benzyl)oxy)carbonyl)(methyl)amino)ethyl)(methyl)carbamoyl)oxy)-8-(chloromethyl)-1-methyl-7,8-dihydro-6H-thieno[3,2-e]indol-6-yl)-5-oxopentanoyl)-8-(chloromethyl)-1-methyl-7,8-dihydro-6H-thieno[3,2-e]indol-4-yl)oxy)-3,4,5-trihydroxytetrahydro-2H-pyran-2-carboxylic acid (76)

Compound 75 (44 mg, 0.024 mmol) was dissolved in DMF (1 mL) and THF (5 mL) and MeOH (1 mL), cooled to 0° C., LiOH.H₂O (10 mg, 0.24 mmol) was added and the mixture was stirred at 0° C. for 60 min. The mixture was acidified by adding HOAc (30 uL), and concentrated in vacuum. The residue was purified by reverse phase HPLC (Method C) to give 25.0 mg (66%) of the product 76 as white powder.

LC-MS (Protocol B): m/z 1471.1 (M+2H)⁺ retention time=0.75 min ¹H NMR (500 MHz, DMSO-d6) δ=8.09 (br. s., 2H), 7.97 (d, J=8.1 Hz, 1H), 7.68 (br. s., 2H), 7.48 (d, J=7.6 Hz, 1H), 7.44-7.39 (m, 1H), 7.39-7.31 (m, 2H), 7.22-7.12 (m, 1H), 5.97 (br. s., 1H), 5.45-5.32 (m, 2H), 5.18 (br. s., 1H), 5.06 (d, J=5.6 Hz, 1H), 4.98 (br. s., 1H), 4.92 (br. s., 1H), 4.31 (br. s., 1H), 4.26-4.05 (m, 8H), 3.82 (d, J=10.0 Hz, 1H), 3.76 (d, J=10.5 Hz, 1H), 3.70 (d, J=7.6 Hz, 1H), 3.66-3.57 (m, 1H), 3.57-3.44 (m, 5H), 3.43-3.36 (m, 2H), 3.36-3.28 (m, 3H), 3.12-3.07 (m, 2H), 3.05 (br. s., 1H), 3.00-2.91 (m, 2H), 2.88 (d, J=9.8 Hz, 3H), 2.80 (s, 2H), 2.72-2.59 (m, 4H), 2.59-2.37 (m, 22H), 2.02 (s, 2H), 1.97-1.83 (m, 3H), 1.78 (s, 3H), 1.69 (td, J=3.2, 6.4 Hz, 2H), 1.66-1.48 (m, 3H), 1.47-1.32 (m, 4H), 1.32-1.14 (m, 4H), 0.76 (d, J=6.4 Hz, 3H), 0.79 (d, J=5.9 Hz, 3H).

Preparation of 4-((S)-2-((S)-2-((S)-2-acetamido-6-aminohexanamido)-3-methylbutanamido)-5-ureidopentanamido)benzyl ((S)-8-(chloromethyl)-6-(5-((S)-8-(chloromethyl)-1-methyl-4-(((2S,3R,4S,5R,6R)-3,4,5-trihydroxy-6-(hydroxymethyl)tetrahydro-2H-pyran-2-yl)oxy)-7,8-dihydro-6H-thieno[3,2-e]indol-6-yl)-5-oxopentanoyl)-1-methyl-7,8-dihydro-6H-thieno[3,2-e]indol-4-yl) ethane-1,2-diylbis(methylcarbamate) (77)

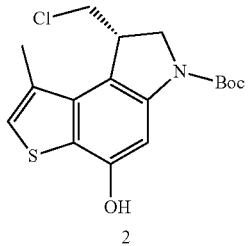

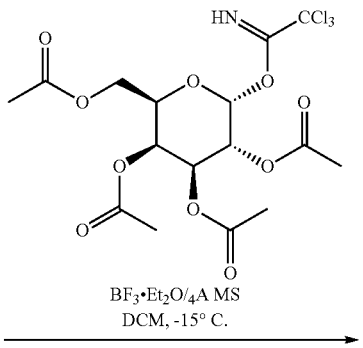

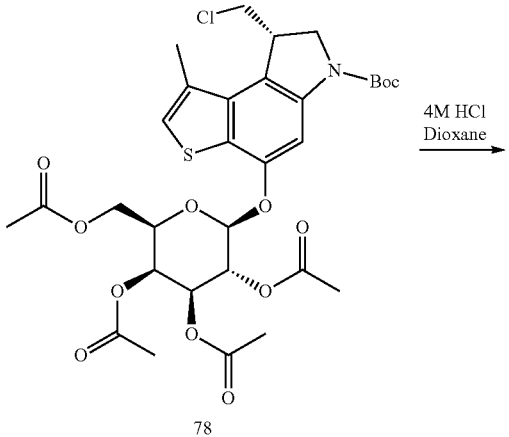

-continued
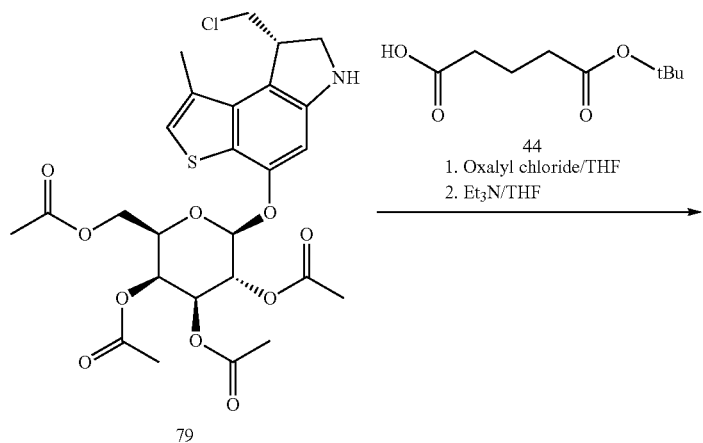
79
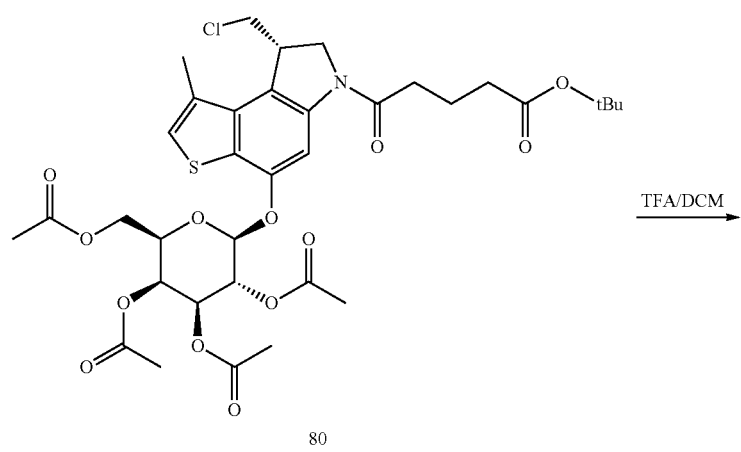
80
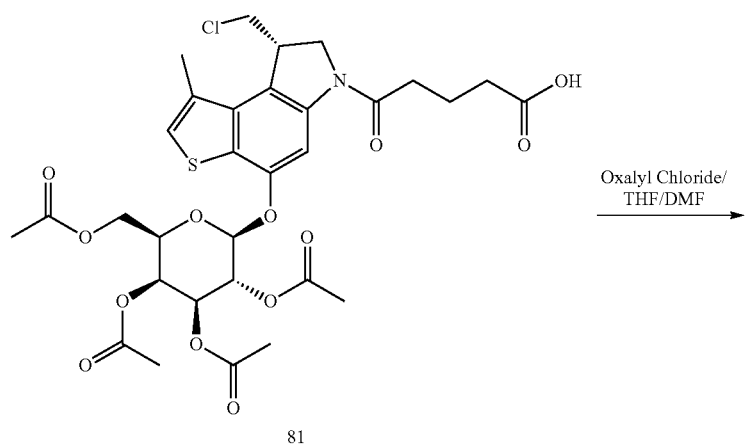
81

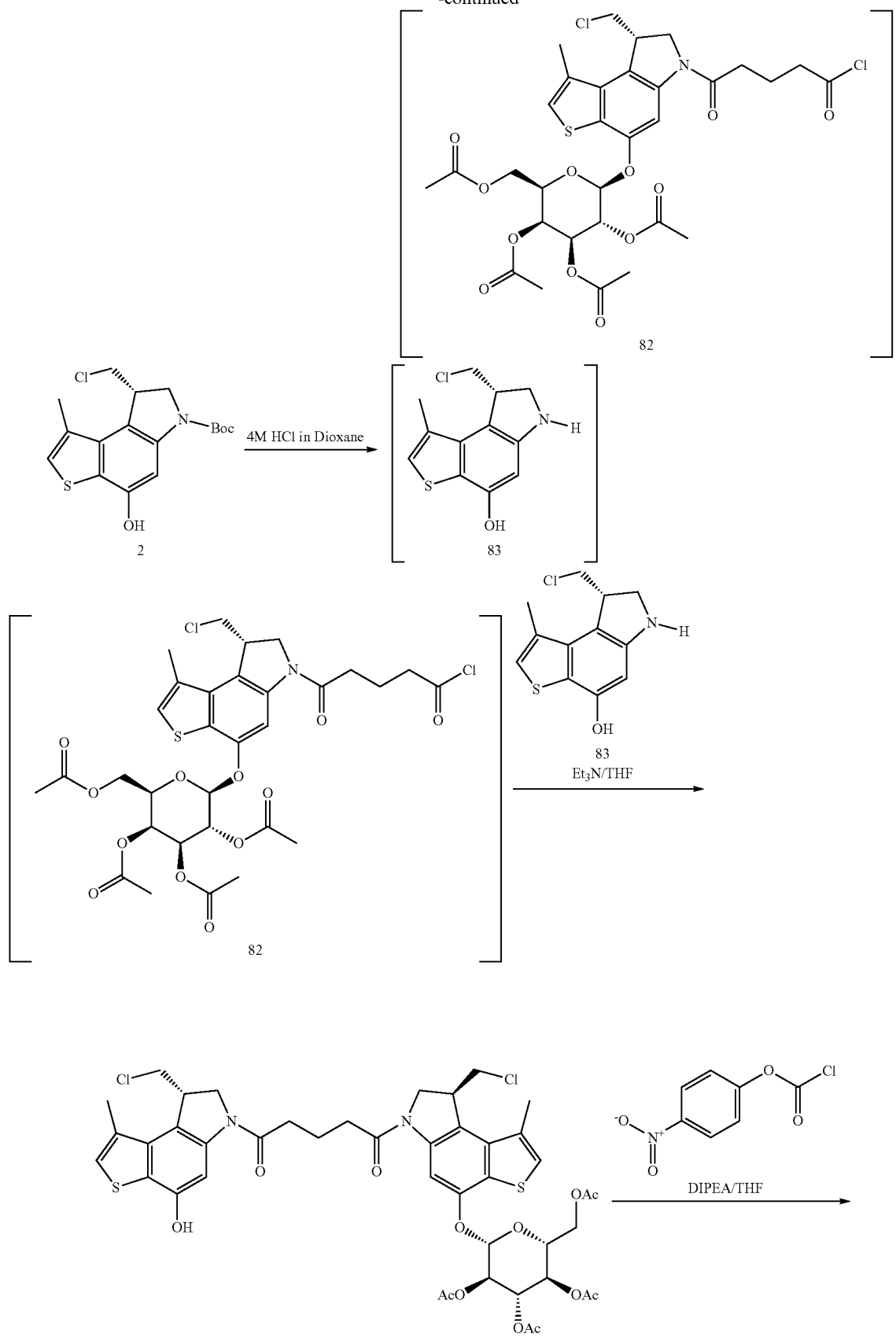

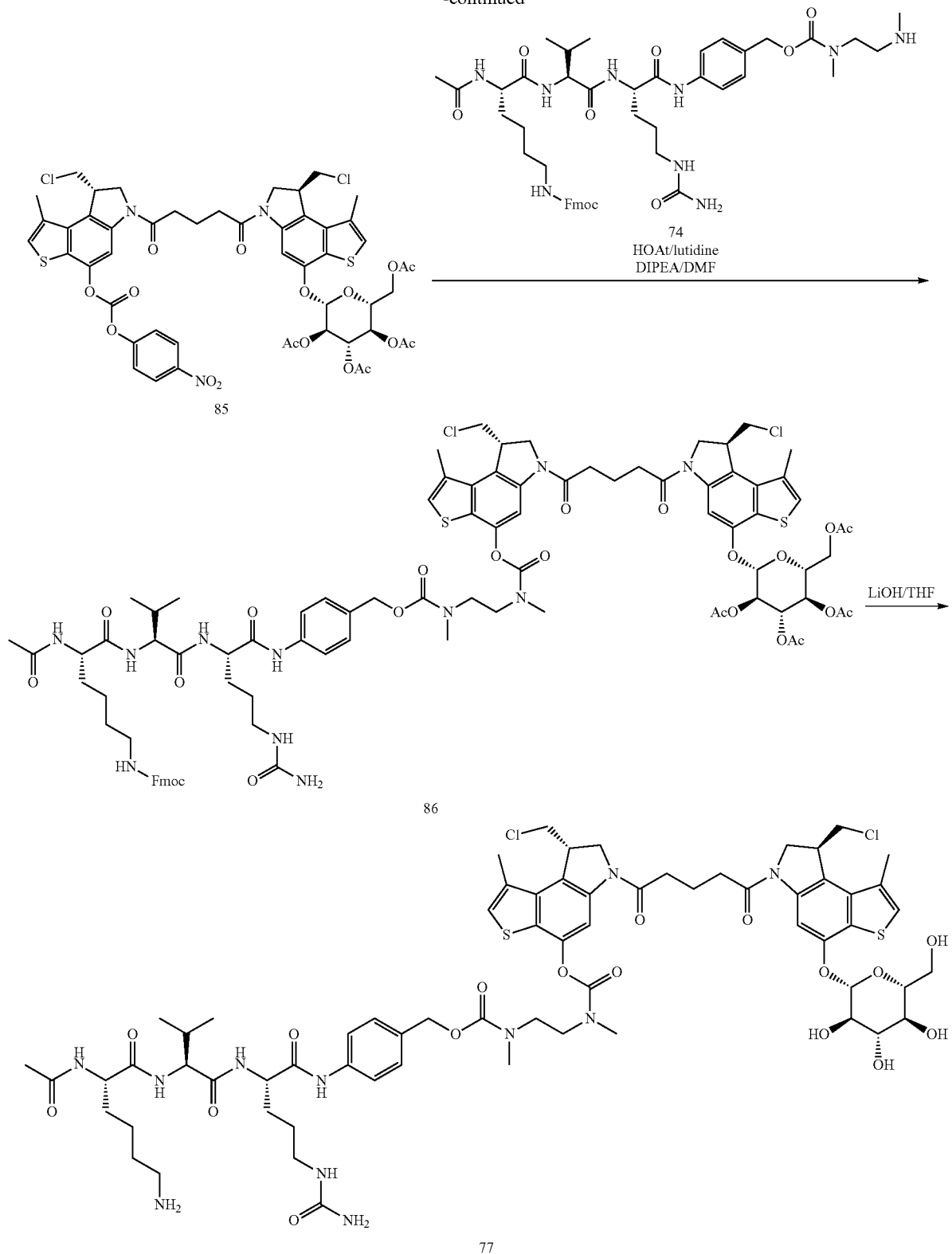
Step 1. Synthesis of (2R,3S,4S,5R,6S)-2-(acetoxymethyl)-6-(((S)-6-(tert-butoxycarbonyl)-8-(chloromethyl)-1-methyl-7,8-dihydro-6H-thieno[3,2-e]indol-4-yl)oxy)tetrahydro-2H-pyran-3,4,5-triyl Triacetate (78)
Compound 2 (300) mg, 0.85 mmol) was dissolved in DCM (30 mL), and 4A MS (1.5 g, powered, <5 micro, activated) was added and the mixture was stirred at room temperature for 30 min. To the reaction mixture, alpha-D- galactopanose, 2,3,4,6-tetraacetate 1-2,2,2-trichloroethanimidate (449 mg, 93%, 0.85 mmol) was added, and mixture was cooled to −15° C. and a solution of BF$_3$.Et$_2$O (0.052 mL, 0.42 mmol) in DCM (5 mL) was added slowly, and the reaction mixture was stirred at −15° C.--20° C. for 1 h. The reaction mixture was filtered off through a pad of Celite, washed with Acetone, concentrated to give a residue. The residue was treated with MeOH, and concentrated in vacuo to give 580 mg (100%) of product 78 as an off-white solid LC-MS (Protocol B): m/z: 706.4 (M+Na) retention time=1.09 min Step 2. Synthesis of (2R,3S,4S,5R,6S)-2-(acetoxymethyl)-6-(((S)-8-(chloromethyl)-1-methyl-7,8-dihydro-6H-thieno[3,2-e]indol-4-yl)oxy)tetrahydro-2H-pyran-3,4,5-triyl triacetate (79)

Compound 78 (580 mg, 0.85 mmol) was treated with a solution of 4M HCl in dioxane (5 mL) for 30 min and mixture was concentrated in vacuum to give the crude product 79 as green solid which was used without further purification LC-MS (Protocol B): m/z 584.3 (M+H), retention time=0.94 min. 1H NMR (400 MHz, METHANOL-d4) δ=7.53 (s, 1H), 7.22 (s, 1H), 5.57-5.46 (m, 3H), 5.34 (dd, J=2.0, 9.0 Hz, 1H), 4.53 (d, J=6.6 Hz, 2H), 4.42 (t, J=6.4 Hz, 1H), 4.25 (dt, J=6.4, 11.2 Hz, 2H), 4.18-4.01 (m, 5H), 3.74 (dd, J=8.6, 11.7 Hz, 2H), 3.69 (s, 14H), 2.68-2.58 (m, 4H), 2.23 (s, 3H), 2.19-2.14 (m, 2H), 2.14-2.07 (m, 7H), 2.07-1.94 (m, 6H), 1.33 (s, 3H).

Step 3. Synthesis of (2R,3S,4S,5R,6S)-2-(acetoxymethyl)-6-(((S)-6-(5-(tert-butoxy)-5-oxopentanoyl)-8-(chloromethyl)-1-methyl-7,8-dihydro-6H-thieno[3,2-e]indol-4-yl)oxy)tetrahydro-2H-pyran-3,4,5-triyl Triacetate (80)

A solution of 5-(tert-butoxy)-5-oxopentanoic acid (44, 191 mg, 1.02 mmol) in THF (10 mL) was cooled to 0° C. and oxalyl chloride (1.02 mL, 2M in DCM) was added followed by 1 drop of DMF. The mixture was stirred at 0° C. for 30 min, and concentrated in vacuum to give the corresponding acid chloride as wax. This was dissolved in THF (10 mL), and added to a solution of 79 (526 mg, 0.85 mmol) in THF (10 mL), and followed by Et$_3$N (0.354 mL, 2.54 mmol). The mixture was stirred at 0° C. for 30 min. The mixture was concentrated, and the residue was purified by silica gel chromatography using a gradient of 0% to 70% Ethyl Acetate in Heptanes to give the 448 mg (70%) product 80 as off-white solid LC-MS (Protocol B): m/z 754.4 (M+H), retention time=1.06 min Step 4. Synthesis of (2R,3S,4S,5R,6S)-2-(acetoxymethyl)-6-(((S)-8-(chloromethyl)-6-(5-((S)-8-(chloromethyl)-4-hydroxy-1-methyl-7,8-dihydro-6H-thieno[3,2-e]indol-6-yl)-5-oxopentanoyl)-1-methyl-7,8-dihydro-6H-thieno[3,2-e]indol-4-yl)oxy)tetrahydro-2H-pyran-3,4,5-triyl Triacetate (84)

A solution of compound 80 (448 mg, 0.59 mmol) was treated with DCM (3 mL) and TFA (2 mL) at rt for 1 h and the mixture was concentrated in vacuum to give the free acid 81 as green solid 212 mg. Acid 81 (167 mg, 0.24 mmol) was dissolved in THF (5 mL) and the solution cooled to 0° C. and oxalyl chloride (0.24 mL, 2M in DCM), followed by DMF (1 drop) were added. The mixture was stirred at 0° C. for 30 min, and concentrated in vacuum to give the corresponding acid chloride 82 which was used without further purification in next step A solution of compound 2 (102 mg, 0.28 mmol) in 4M HCl (2 mL) in dioxane was stirred at rt for 1 h and the mixture concentrated in vacuum to give compound 83 as a green solid which was dissolved in THF (5 mL) and cooled to 0° C. TEA (0.2 mL, 1.44 mmol) followed by a solution of crude acid chloride 82 in THF (5 mL) were added and the mixture was stirred at 0° C. for 20 min. The mixture was concentrated, and the residue was purified by silica gel chromatography using a gradient of 0% to 70% Acetone in Heptanes to give 196 mg (88%) of product 84 as a yellow solid LC-MS (Protocol B): m/z 933.5 (M+H), retention time=1.05 min. $^1$H NMR (400 MHz, DMSO-d6) δ=8.26 (s, 1H), 7.94 (s, 1H), 7.46 (s, 1H), 7.39 (s, 1H), 5.51 (d, J=7.8 Hz, 1H), 5.42-5.26 (m, 3H), 4.59-4.46 (m, 1H), 4.33-4.23 (m, 2H), 4.23-4.15 (m, 4H), 4.15-4.07 (m, 2H), 4.04 (s, 4H), 3.87 (dd, J=10.5, 18.0 Hz, 2H), 3.67 (t, J=9.8 Hz, 1H), 3.57 (t, J=10.1 Hz, 1H), 3.33 (s, 1H), 3.31 (s, 1H), 2.83-2.67 (m, 2H), 2.60 (dd, J=6.4, 16.2 Hz, 3H), 2.19 (s, 3H), 2.15-2.09 (m, 4H), 2.07 (s, 4H), 1.97 (s, 6H).

Step 5: Synthesis of (2R,3S,4S,5R,6S)-2-(acetoxymethyl)-6-(((S)-8-(chloromethyl)-6-(5-((S)-8-(chloromethyl)-1-methyl-4-(((4-nitrophenoxy)carbonyl)oxy)-7,8-dihydro-6H-thieno[3,2-e]indol-6-yl)-5-oxopentanoyl)-1-methyl-7,8-dihydro-6H-thieno[3,2-e]indol-4-yl)oxy)tetrahydro-2H-pyran-3,4,5-triyl Triacetate (85)

To a solution of 84 (100 mg, 0.107 mmol) in THF (5 mL) at 0° C. was added 4-nitrophenyl chloroformate (45 mg, 0.21 mmol), and followed by Et$_3$N (0.060 mL, 0.43 mmol). The mixture was stirred at 0° C. for 60 min. The mixture was concentrated in vacuum to give the crude product as yellow foam 142 mg, which was purified by reverse phase HPLC Method C) to give 50 mg (43%) of the product 85 as an off-white solid. LC-MS (Protocol B): m/z 1098.5 (M+H), retention time=1.05 min Step 6: Synthesis of (2S,3R,4S,5S,6R)-2-(((S)-6-(5-((S)-4-(((2-((((4-((9S,12S,15S)-9-acetamido-1-(9H-fluoren-9-yl)-12-isopropyl-3,10,13-trioxo-15-(3-ureidopropyl)-2-oxa-4,11,14-triazahexadecan-16-amido)benzyl)oxy)carbonyl)(methyl)amino)ethyl)(methyl)carbamoyl)oxy)-8-(chloromethyl)-1-methyl-7,8-dihydro-6H-thieno[3,2-e]indol-6-yl)-5-oxopentanoyl)-8-(chloromethyl)-1-methyl-7,8-dihydro-6H-thieno[3,2-e]indol-4-yl)oxy)-6-(acetoxymethyl)tetrahydro-2H-pyran-3,4,5-triyl triacetate (86): To a solution of 85 (50 mg, 0.045 mmol) in DMF (2 mL), was added 4-((9S,12S,15S)-9-acetamido-1-(9H-fluoren-9-yl)-12-isopropyl-3,10,13-trioxo-15-(3-ureidopropyl)-2-oxa-4,11,14-triazahexadecan-16-amido)benzyl methyl(2-(methylamino)ethyl)carbamate (7445 mg, 0.045 mmol) and DIPEA (0.024 mL, 0.136 mmol). The mixture was stirred at rt for 60 min, and purified using reverse phase HPLC (Method C) to give 26 mg (31%) of the product 86 as a white solid: LC-MS (Protocol B): m/z 1847.1 (M+H), retention time=1.06 min $^1$H NMR (400 MHz, DMSO-d6) δ=10.01 (br. s., 1H), 8.25 (s, 1H), 8.20-8.12 (m, 1H), 8.09 (d, J=6.6 Hz, 1H), 8.02 (d, J=8.2 Hz, 1H), 7.89 (d, J=7.8 Hz, 2H), 7.69 (d, J=7.0 Hz, 3H), 7.57 (d, J=7.4 Hz, 2H), 7.47-7.37 (m, 4H), 7.37-7.30 (m, 3H), 7.26 (br. s., 3H), 5.98 (br. s., 1H), 5.50 (d, J=7.0 Hz, 1H), 5.46-5.27 (m, 5H), 5.02 (d, J=19.1 Hz, 2H), 4.52 (br. s., 1H), 4.39 (br. s., 1H), 4.32-4.14 (m, 13H), 4.14-4.03 (m, 1H), 3.95-3.81 (m, 2H), 3.75-3.59 (m, 6H), 3.56 (br. s., 2H), 3.48 (br. s., 2H), 3.12 (br. s., 1H), 3.03 (br. s., 2H), 2.94 (s, 3H), 2.97 (s, 2H), 2.87 (br. s., 2H), 2.83-2.67 (m, 3H), 2.66-2.54 (m, 7H), 2.19 (s, 4H), 2.12 (s, 3H), 2.09-2.03 (m, 4H), 2.03-1.90 (m, 7H), 1.85 (s, 3H), 1.78 (t, J=6.4 Hz, 1H), 1.68 (d, J=7.8 Hz, 1H), 1.61 (br. s., 2H), 1.53-1.33 (m, 5H), 1.32-1.18 (m, 2H), 0.84 (d, J=7.0 Hz, 3H), 0.87 (d, J=6.6 Hz, 3H).

Step 7. Synthesis of LP: 4-((S)-2-((S)-2-((S)-2-acetamido-6-aminohexanamido)-3-methylbutanamido)-5-ureidopentanamido)benzyl ((S)-8-(chloromethyl)-6-(5-((S)-8-

(chloromethyl)-1-methyl-4-(((2S,3R,4S,5R,6R)-3,4,5-trihydroxy-6-(hydroxymethyl)tetrahydro-2H-pyran-2-yl)oxy)-7,8-dihydro-6H-thieno[3,2-e]indol-6-yl)-5-oxopentanoyl)-1-methyl-7,8-dihydro-6H-thieno[3,2-e]indol-4-yl) ethane-1,2-diylbis(methylcarbamate) (77): To a solution of 86 (24 mg, 0.013 mmol) in THF (2 mL) and MeOH (2 mL), at 0° C. was added a solution of LiOH (1M, 0.26 mL, 0.26 mmol) in water and the mixture was stirred at 0° C. to rt for 2 h. Acetic acid (20 uL) was added and the mixture was concentrated and the residue was purified by reverse phase HPLC (Method C) to give 14 mg (69%) of the product 77 as white foam: LC-MS (Protocol B): m/z 1456.9 (M+2H)+, retention time=0.75 min $^1$H NMR (500 MHz, DMSO-d6) δ=10.07-9.96 (m, 1H), 8.29-8.18 (m, 1H), 8.18-8.09 (m, 2H), 8.06 (d, J=8.1 Hz, 1H), 7.73 (d, J=8.6 Hz, 1H), 7.66 (br. s., 3H), 7.56 (d, J=7.8 Hz, 2H), 7.50 (d, J=9.3 Hz, 1H), 7.47-7.39 (m, 2H), 7.35 (d, J=7.6 Hz, 1H), 7.32-7.25 (m, 2H), 6.04 (br. s., 1H), 5.11 (d, J=6.4 Hz, 1H), 5.05 (br. s., 1H), 5.01 (br. s., 1H), 4.40 (br. s., 1H), 4.36-4.16 (m, 10H), 4.10 (d, J=11.7 Hz, 3H), 4.00 (br. s., 3H), 3.96-3.80 (m, 10H), 3.77 (br. s., 4H), 3.73-3.55 (m, 11H), 3.52 (br. s., 1H), 3.48 (br. s., 3H), 3.12 (br. s., 1H), 3.05 (br. s., 2H), 3.01-2.91 (m, 4H), 2.88 (br. s., 2H), 2.86-2.72 (m, 4H), 2.72-2.53 (m, 13H), 2.45 (t, J=7.5 Hz, 1H), 2.06-1.92 (m, 3H), 1.86 (s, 4H), 1.71-1.56 (m, 3H), 1.56-1.42 (m, 4H), 1.42-1.23 (m, 4H), 0.85 (dd, J=6.6, 14.7 Hz, 6H).

Preparation of 4-((S)-2-((S)-2-((((9H-fluoren-9-yl)methoxy)carbonyl)amino)-3-methylbutanamido)-5-ureidopentanamido)benzyl methyl(2-(methylamino)ethyl)carbamate (96)

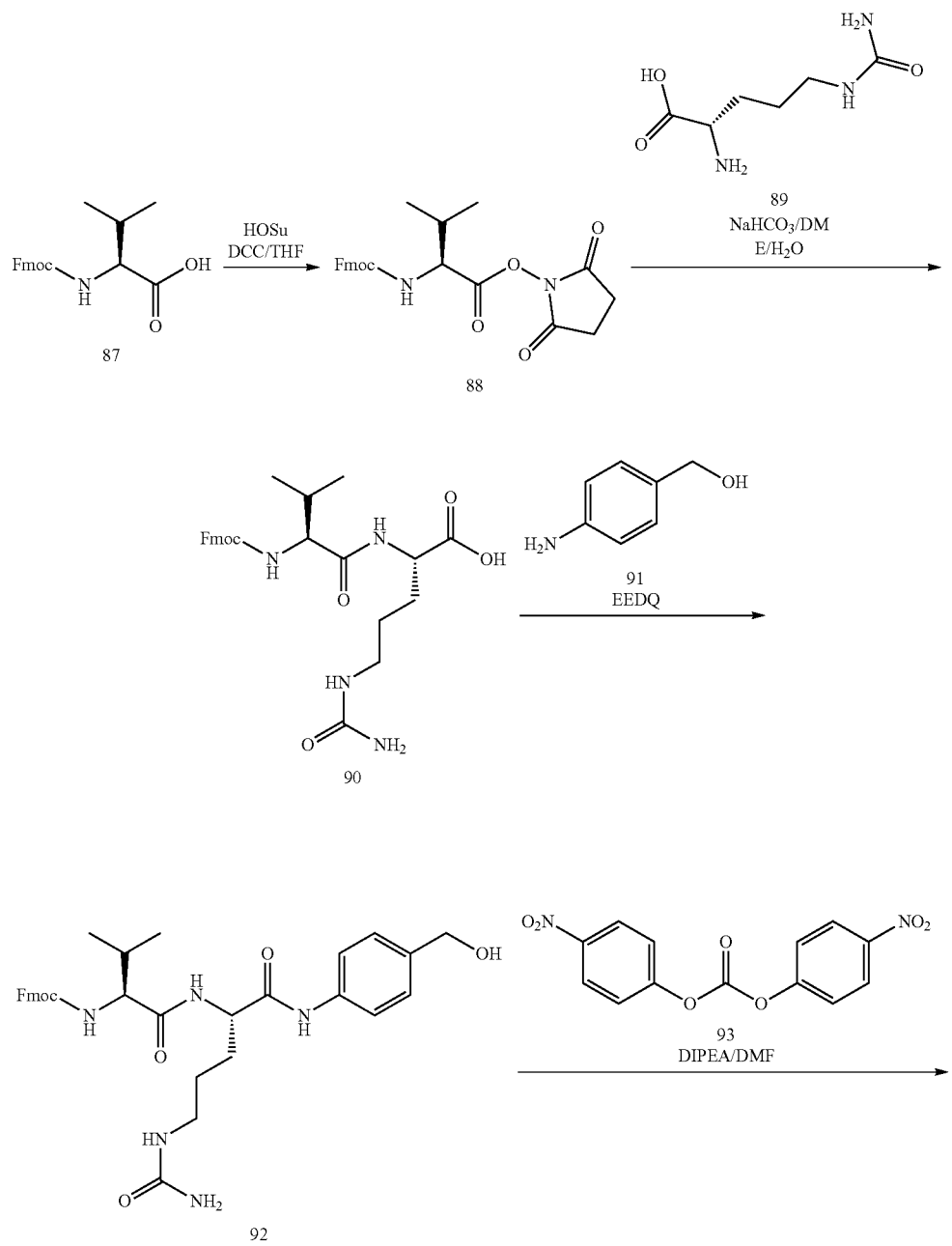

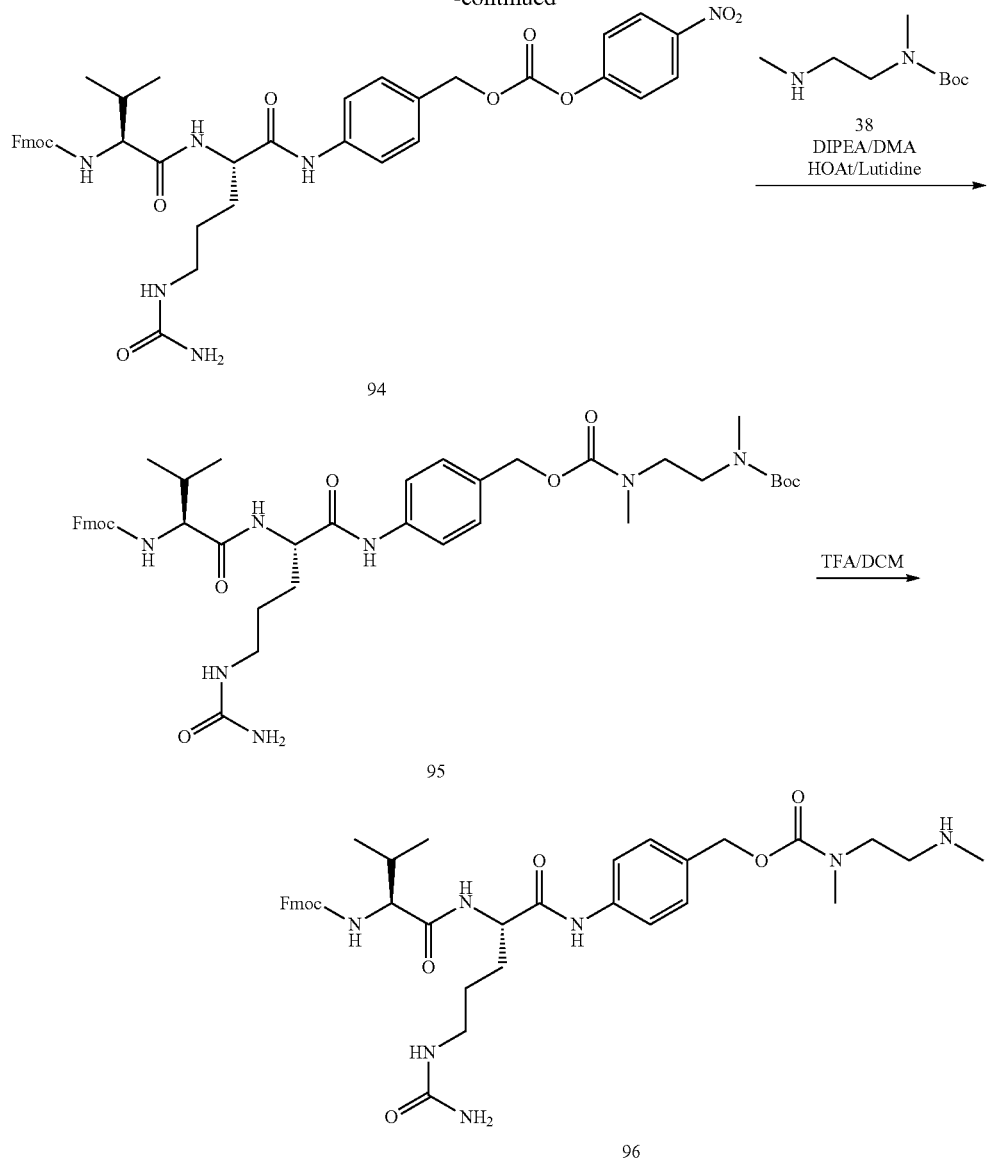

Step 1. Synthesis of 2,5-dioxopyrrolidin-1-yl (((9H-fluoren-9-yl)methoxy)carbonyl)-L-valinate (88)

To a solution of compound 87 (150 g, 0.442 mol) and HOSu (56 g, 0.487 mol) in THF (1800 mL) was added DCC (100 g, 0.487 mol) in portions under ice-bath. After the addition, the reaction was stirred at room temperature overnight. The reaction was cooled to −5° C., filtered and washed with cold THF, the filtrate was concentrated in vacuum and the residue was re-crystallized from MTBE to give compound 88 as white solid 175 g (91%).

Step 2. Synthesis of (S)-2-((S)-2-((((9H-fluoren-9-yl)methoxy)carbonyl)amino)-3-methylbutanamido)-5-ureidopentanoic acid (90)

To a solution of compound 89 (40.14 g, 0.229 mol) and NaHCO₃ (19.23 g, 0.229 mol) in water (750 mL) was added the solution of compound 88 (100 g, 0.229 mol) in DME (750 mL) dropwise under ice-bath. During the addition, a white suspension was formed. Additional THF (400 mL) was added to improve the solubility. After addition, the solution was stirred at 25-30° C. for 2 days. To the reaction was added saturated aq. K₂CO₃ to adjust pH to 8-9, then extracted with EtOAc (500 mL×5). The aqueous layer was adjusted pH to 3-4 with aq. citric acid. A gelatinous material was formed and filtered. The wet cake was dissolved in THF (1.5 L). Methanol was added until the solid was dissolved. The solution was concentrated in vacuum to remove 30% of solvent and then cooled to room temperature. TBME (2 L) was added to the solution and the mixture was stirred at room temperature overnight. The mixture was filtered and the wet cake was dried in vacuum to give compound 90 as a white solid 60 g (53%).

Step 3. Synthesis of (9H-fluoren-9-yl)methyl ((S)-1-(((S)-1-((4-(hydroxymethyl)phenyl)amino)-1-oxo-5-ureidopentan-2-yl)amino)-3-methyl-1-oxobutan-2-yl)carbamate (92)

To the suspension of compound 90 (70 g, 0.141 mol) in DCM/MeOH (1 L/500 mL) was added compound 91 (34.7 g, 0.282 mol) followed by EEDQ (69.7 g, 0.282 mol). The mixture was stirred at 40° C. overnight. The reaction mixture was filtered and the wet cake was suspended in EtOAc/TBME (500 mL/200 mL) and stirred for 30 min, then filtered. The solid was washed with EtOAc/TBME to provide compound 92 as off-white solid 65 g (77%). ¹H NMR (400 MHz, DMSO-d6) δ=9.98 (s, 1H), 8.11 (d, 1H), 7.87 (d, 2H), 7.77 (m, 2H), 7.52 (d, 2H), 7.39 (m, 3H), 7.30 (m, 2H), 7.21 (d, 2H), 5.97 (m, 1H), 5.41 (s, 2H), 5.10 (m, 1H), 4.42 (m, 3H), 4.22 (m, 3H), 3.90 (m, 1H), 2.93 (m, 2H), 1.98 (m, 1H), 1.50 (m, 2H), 1.30 (m, 2H), 0.84 (m, 6H).

Step 4. Synthesis of (9H-fluoren-9-yl)methyl ((S)-3-methyl-1-(((S)-1-((4-((((4-nitrophenoxy)carbonyl)oxy) methyl)phenyl)amino)-1-oxo-5-ureidopentan-2-yl)amino)-1-oxobutan-2-yl)carbamate (94)

To a solution of (9H-fluoren-9-yl)methyl ((S)-1-(((S)-1-((4-(hydroxymethyl)phenyl)amino)-1-oxo-5-ureidopentan-2-yl)amino)-3-methyl-1-oxobutan-2-yl)carbamate (3.74 g, 8.31 mmol, 92) in anhydrous DMF (120 mL) was added bis(4-nitrophenyl) carbonate (3.78 g, 12.4 mmol, 93) in portions, followed by DIPEA (1.21 g, 9.32 mmol) at 0° C. dropwise. The reaction mixture was stirred at room temperature overnight. TLC (MeOH: CH₂CH₂Cl₂=1:10) showed that the reaction was completed. The reaction mixture was added dropwise to MTBE (2.5 L) with stirring. The crude product was collected by filtration. The filtrate cake was washed with MTBE and dried under high vacuum to afford compound 94 as brown solid 2.7 g (57%).

Step 5. Synthesis of 4-((S)-2-((S)-2-((((9H-fluoren-9-yl) methoxy)carbonyl)amino)-3-methylbutanamido)-5-ureidopentanamido)benzyl tert-butyl ethane-1,2-diylbis(methylcarbamate) (95)

To a solution of compound 94 (1.7 g, 2.217 mmol) in DMA (15 mL) was added HOAT (332 mg, 2.44 mmol), 2,6-lutidine (950 mg, 8.87 mmol) at 0° C. The mixture was stirred at 0° C. for 5 minutes. Then tert-butyl methyl(2-(methylamino)ethyl)carbamate (38, 459 mg, 2.44 mmol) was added to the mixture at 0° C. and followed by DIPEA (860 mg, 6.65 mmol) at 0° C. The mixture was stirred at rt for 1 h. and poured into TBME (800 mL) and stirred for 30 min, filtered and the filter cake was concentrated in vacuum to give the crude product (1.06 g) as a yellow solid. The crude product was purified by silica gel chromatography (Gradient: DCM:MeOH=100:1-10:1) to give the product 95 as a white solid 600 mg (33%).

Step 6. Synthesis of 4-((S)-2-((S)-2-((((9H-fluoren-9-yl) methoxy)carbonyl)amino)-3-methylbutanamido)-5-ureidopentanamido)benzyl methyl(2-(methylamino)ethyl)carbamate (96)

To a stirred a solution of compound 95 (600 mg, 0.735 mmol) in dry DCM (10 mL) was added TFA (5 mL) at 0° C. and stirred at 0° C. for 1 h. The mixture was concentrated in vacuum to give the title compound 96 as a white solid 550 mg (100%). ¹H NMR (400 MHz, DMSO-d6) δ=10.09 (br, 1H), 8.40 (s, 2H), 8.14 (d, 1H), 7.90 (d, 2H), 7.74 (m, 2H), 7.61 (d, 2H), 7.43 (m, 3H), 7.33 (m, 4H), 6.00 (s, 1H), 5.43 (s, 2H), 5.02 (s, 2H), 4.42-4.23 (m, 4H), 3.93 (m, 1H), 3.50 (m, 2H), 3.08-2.94 (m, 4H), 2.88 (s, 3H), 2.59 (m, 3H), 1.99 (m, 1H), 1.69-1.59 (m, 2H), 1.46-1.39 (m, 2H), 0.90-0.85 (m, 6H).

Alternate Preparation of (2S,3S,4S,5R,6S)-6-(((S)-8-(chloromethyl)-6-(5-((S)-8-(chloromethyl)-4-(((2-((((4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosan-27-amido)benzyl)oxy)carbonyl) (methyl)amino)-ethyl)(methyl)carbamoyl)oxy)-1-methyl-7,8-dihydro-6H-thieno[3,2-e]indol-6-yl)-5-oxopentanoyl)-1-methyl-7,8-dihydro-6H-thieno[3,2-e]indol-4-yl)oxy)-3,4,5-trihydroxytetrahydro-2H-pyran-2-carboxylic Acid (49)

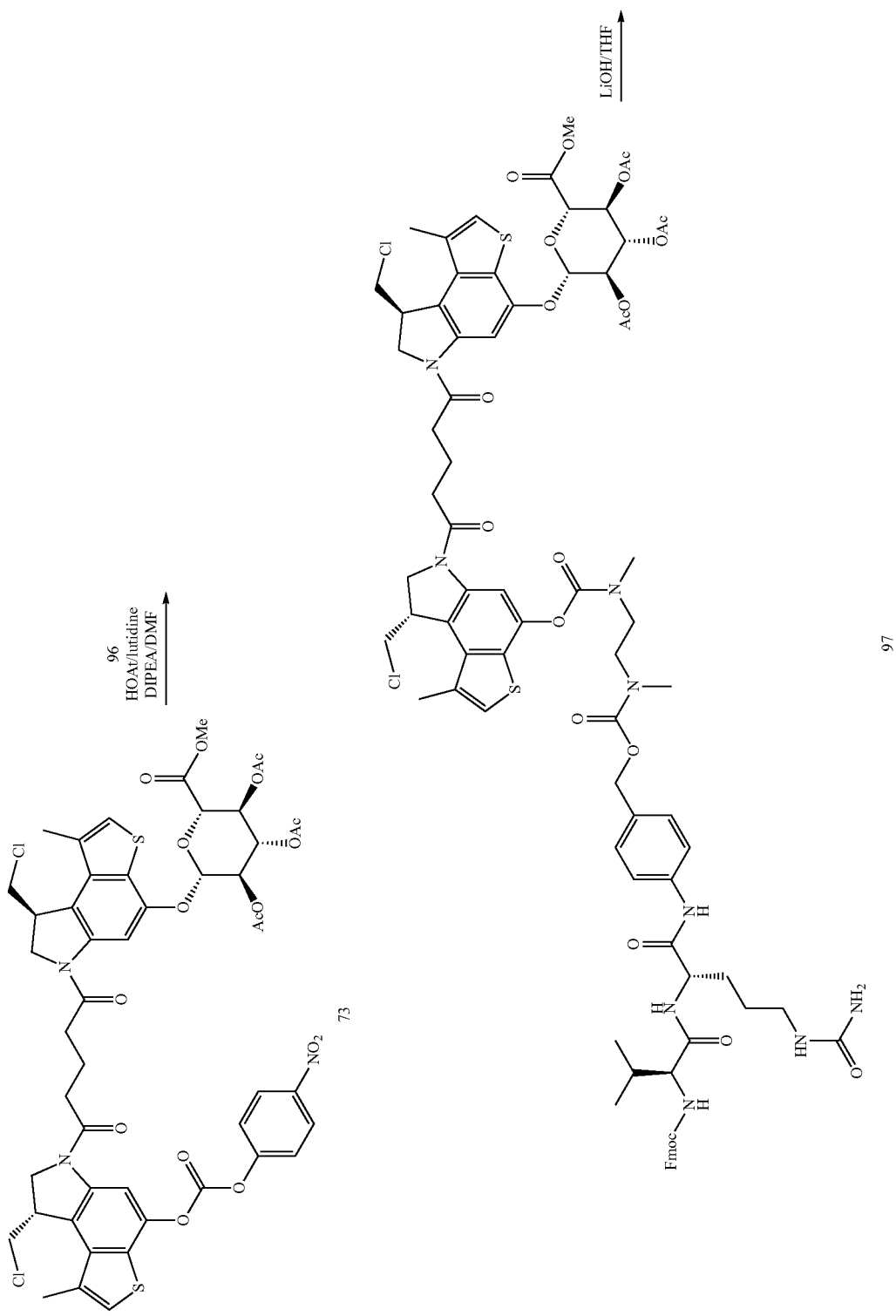

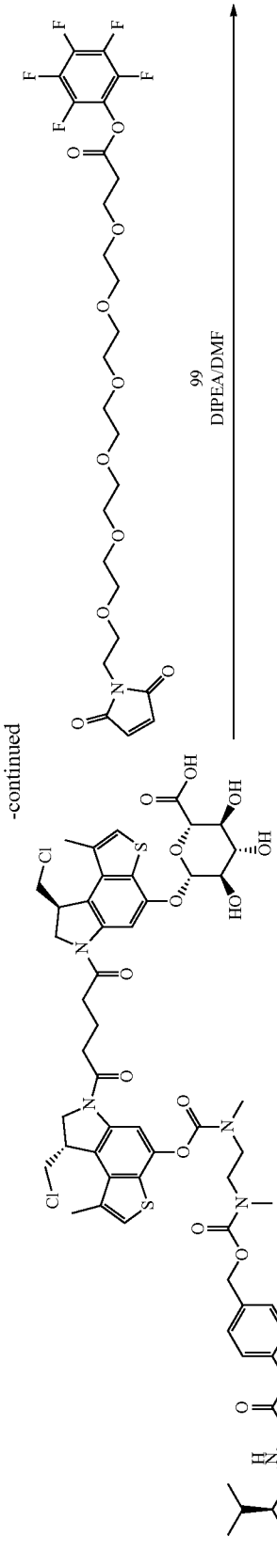
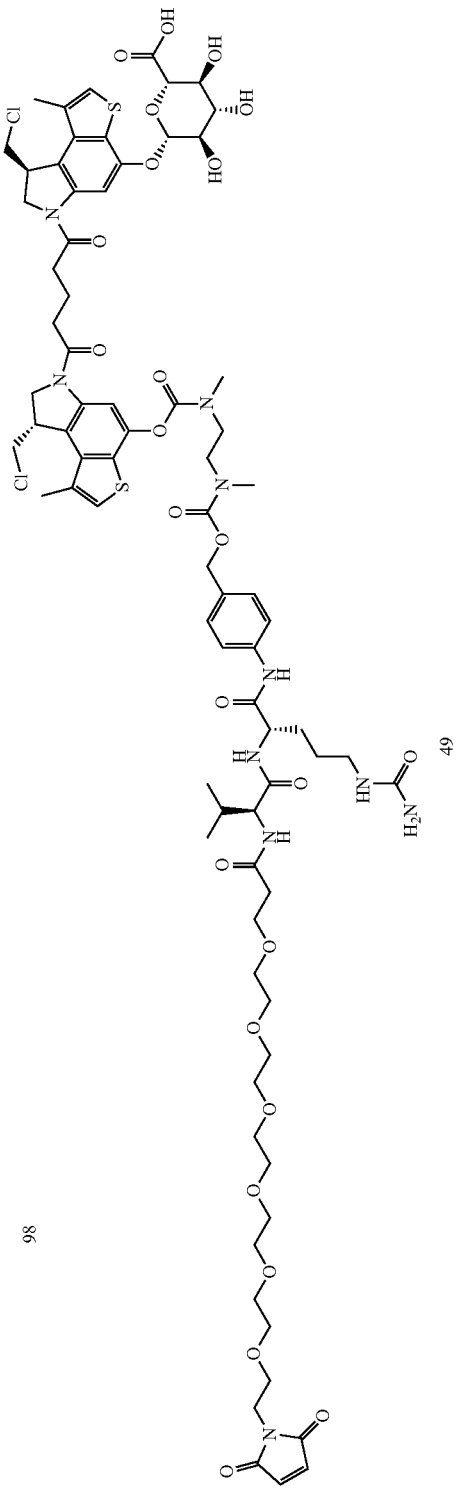

Step 1: Synthesis of (2S,3R,4S,5S,6S)-2-(((S)-6-(5-((S)-4-(((2-(((((4-((S)-2-((S)-2-((((9H-fluoren-9-yl)methoxy)carbonyl)amino)-3-methylbutanamido)-5-ureidopentanamido)benzyl)oxy)carbonyl)(methyl)amino)ethyl)(methyl)carbamoyl)oxy)-8-(chloromethyl)-1-methyl-7,8-dihydro-6H-thieno[3,2-e]indol-6-yl)-5-oxopentanoyl)-8-(chloromethyl)-1-methyl-7,8-dihydro-6H-thieno[3,2-e]indol-4-yl)oxy)-6-(methoxycarbonyl)tetrahydro-2H-pyran-3,4,5-triyl triacetate (97)

To a solution of compound 73 (26 mg, 0.024 mmol) in DMF (1.5 mL), Fmoc-VCPABC-DMEA linker 96 (24 mg, 0.029 mmol), 2,6-lutidine (0.0167 mL, 0.14 mmol), DIPEA (0.0253 mL, 0.14 mmol) and HOAt (3.3 mg, 0.024 mmol) were added. The mixture was stirred at rt for 30 min, and concentrated in vacuum to give a residue. The crude was subjected to HPLC purification (Method C) to give the product 97 as white solid 33 mg (83%). LC-MS (Protocol B): m/z 1660.9 (M+H), retention time=1.11 min.

Step 2: Synthesis of (2S,3S,4S,5R,6S)-6-(((S)-6-(5-((S)-4-(((2-(((((4-((S)-2-((S)-2-amino-3-methylbutanamido)-5-ureidopentanamido)benzyl)oxy)carbonyl)(methyl)amino)ethyl)(methyl)carbamoyl)oxy)-8-(chloromethyl)-1-methyl-7,8-dihydro-6H-thieno[3,2-e]indol-6-yl)-5-oxopentanoyl)-8-(chloromethyl)-1-methyl-7,8-dihydro-6H-thieno[3,2-e]indol-4-yl)oxy)-3,4,5-trihydroxytetrahydro-2H-pyran-2-carboxylic acid (98): To a solution of 97 (46 mg, 0.028 mmol) in THF (3 mL) and MeOH (3 mL), cooled to 0° C., was added a solution of LiOH.H$_2$O (12 mg, 0.28 mmol) in water (0.5 mL). The mixture was stirred at 0° C. for 1 h. AcOH (0.03 mL) was added to neutralize the mixture, and concentrated in vacuum to give a white solid residue. It was purified by HPLC (Method C) to give the product 98 as off-white solid 28 mg (72%). LC-MS (Protocol B): m/z 1300.6 (M+H), retention time=0.78 min. $^1$H NMR (400 MHz, DMF) δ=10.33-10.21 (m, 1H), 8.84 (d, J=7.4 Hz, 1H), 8.63 (br. s., 3H), 8.41-8.28 (m, 2H), 8.05 (s, 1H), 7.81-7.63 (m, 2H), 7.57-7.41 (m, 3H), 7.38 (br. s., 2H), 6.52 (br. s., 1H), 5.39 (d, J=6.6 Hz, 1H), 5.17 (br. s., 1H), 5.12 (br. s., 1H), 4.74 (br. s., 1H), 4.48-4.28 (m, 5H), 4.24 (br. s., 1H), 4.09 (s, 4H), 4.04-3.89 (m, 2H), 3.84-3.67 (m, 6H), 3.67-3.52 (m, 4H), 3.32 (s, 9H), 3.26 (br. s., 2H), 3.19 (br. s., 1H), 3.14-3.04 (m, 4H), 3.00 (s, 2H), 2.94 (br. s., 2H), 2.85 (br. s., 2H), 2.79-2.68 (m, 5H), 2.62 (s, 4H), 2.64 (s, 3H), 2.42-2.29 (m, 1H), 2.23-2.05 (m, 11H), 1.92 (br. s., 1H), 1.78 (br. s., 1H), 1.60 (br. s., 2H), 1.15 (br. S., 6H).

Step 3: Synthesis of (2S,3S,4S,5R,6S)-6-(((S)-8-(chloromethyl)-6-(5-((S)-8-(chloromethyl)-4-(((2-(((((4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosan-27-amido)benzyl)oxy)carbonyl)(methyl)amino)ethyl)(methyl)carbamoyl)oxy)-1-methyl-7,8-dihydro-6H-thieno[3,2-e]indol-6-yl)-5-oxopentanoyl)-1-methyl-7,8-dihydro-6H-thieno[3,2-e]indol-4-yl)oxy)-3,4,5-trihydroxytetrahydro-2H-pyran-2-carboxylic acid (49): To a solution of 98 (10 mg, 0.007 mmol) was dissolved in DMF (1 mL), was added perfluorophenyl 1-(2,5-dioxo-2,5-dihydro-1H-pyrrol-1-yl)-3,6,9,12,15,18-hexaoxahenicosan-21-oate (5.6 mg, 0.009 mmol, 99) and DIPEA (0.007 mL, 0.042 mmol). The mixture was stirred at rt for 30 min. The mixture was purified by HPLC (Method C) to give the product 49 as white foam 10 mg (82%). LC-MS (Protocol B): m/z 1715.7 (M+H), retention time=0.89 min. 1H NMR (400 MHz, ACETONITRILE-d3) δ=8.21 (br. s., 2H), 7.56 (d, J=7.4 Hz, 1H), 7.31-7.10 (m, 4H), 6.78 (s, 2H), 5.25 (br. S., 1H), 5.11 (br. s., 1H), 5.02 (br.s., 1H), 4.50 (br. S., 1H), 4.18 (br. s., 2H), 3.77 (br. s., 2H), 3.71 (br. s., 3H), 3.66-3.42 (m), 3.37-3.24 (m, 4H), 3.16 (br. s., 1H), 3.12-2.95 (m, 4H), 2.93 (s, 2H), 2.77-2.47 (m, H), 2.22-2.02 (m, 4H), 1.51 (br. s., 2H), 0.95 (br. S., 6H).

Preparation of 4-((S)-2-((S)-2-((S)-2-acetamido-6-aminohexanamido)-3-methylbutanamido)-5-ureidopentanamido)benzyl ((S)-8-(chloromethyl)-6-(5-((S)-8-(chloromethyl)-1-methyl-4-(phosphonooxy)-7,8-dihydro-6H-thieno[3,2-e]indol-6-yl)-5-oxopentanoyl)-1-methyl-7,8-dihydro-6H-thieno[3,2-e]indol-4-yl) ethane-1,2-diylbis(methylcarbamate) (100)

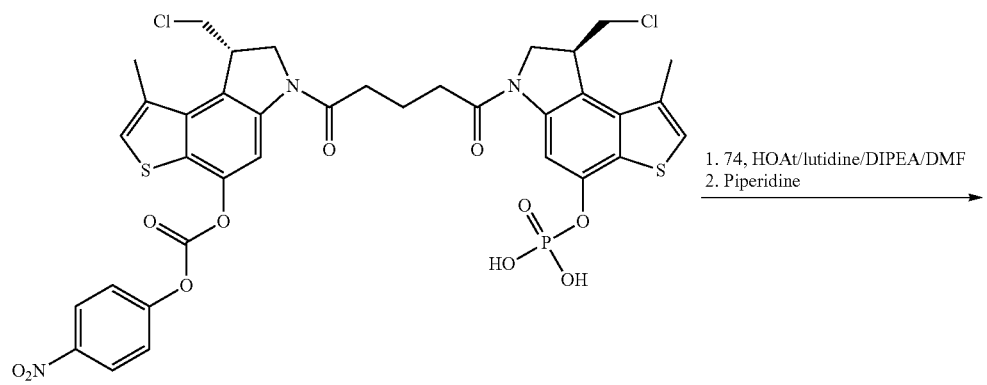

1. 74, HOAt/lutidine/DIPEA/DMF
2. Piperidine

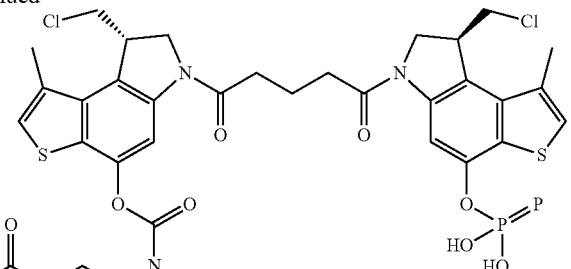
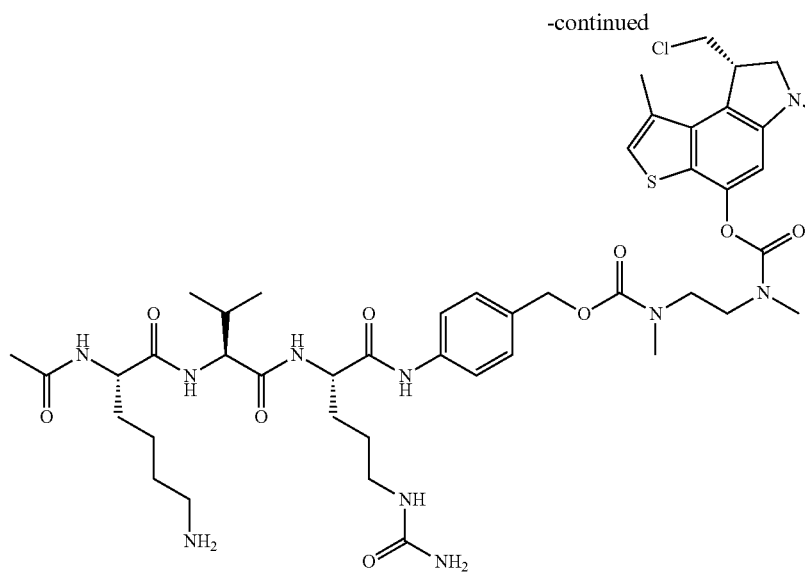

100

Step 1: Synthesis of 4-((S)-2-((S)-2-((S)-2-acetamido-6-aminohexanamido)-3-methylbutanamido)-5-ureidopentanamido)benzyl ((S)-8-(chloromethyl)-6-(5-((S)-8-(chloromethyl)-1-methyl-4-(phosphonooxy)-7,8-dihydro-6H-thieno[3,2-e]indol-6-yl)-5-oxopentanoyl)-1-methyl-7,8-dihydro-6H-thieno[3,2-e]indol-4-yl) ethane-1,2-diylbis(methylcarbamate) (100): To a solution of 55 (35 mg, 0.041 mmol) in DMF (3 mL), was added 74 (45 mg, 0.045 mmol), lutidine (0.019 mL, 0.16 mmol), DIPEA (0.029 mL, 0.16 mmol) and HOAt (5.6 mg, 0.041 mmol). The mixture was stirred at rt for 3 h. To the resulting mixture, piperidine (0.3 mL, 3 mmol) was stirred at rt for 20 min. The mixture was concentrated in vacuum, and the residue was purified by HPLC (Method C) to give the product 100 as white powder after freeze dry 35 mg (62%). LC-MS (Protocol B): m/z 1374.8 (M+H), retention time=0.92 min. $^1$H NMR (400 MHz, DMSO-d6) δ=8.45 (d, J=13.7 Hz, 1H), 8.14 (s, 1H), 8.17 (s, 1H), 8.05 (d, J=7.4 Hz, 1H), 7.76 (br. s., 3H), 7.58 (d, J=8.2 Hz, 1H), 7.52-7.39 (m, 2H), 7.30-7.16 (m, 1H), 6.09 (br. s., 1H), 5.15-4.94 (m, 2H), 4.40 (br. s., 1H), 4.35-4.08 (m, 8H), 3.95-3.79 (m, 2H), 3.69 (br. s., 1H), 3.60 (d, J=10.5 Hz, 3H), 3.49 (br. s., 3H), 3.13 (br. s., 1H), 3.06 (br. s., 1H), 3.03-2.91 (m, 4H), 2.88 (s, 2H), 2.76 (br. s., 4H), 2.61 (d, J=6.6 Hz, 2H), 2.56 (s, 6H), 1.98 (m, 3H), 1.86 (s, 3H), 1.65 (m, 3H), 1.58-1.49 (m, 3H), 1.46 (m, 2H), 1.40-1.20 (m, 3H), 0.85 (m, 6H).

As noted herein, the described compounds in Tables 1 and 2 may exist in their acetate or phenol prodrug stage, which both rapidly convert into the bis cyclopropyl active drug species. This interconversion occurs rapidly in the assay medium. Hence, all three compound forms are functionally equivalent and result in the same growth inhibitory values in cancer cell proliferation assays. Thus describing compounds as "bis-acetates" also entails the description as their functionally equivalent phenol- and bis cyclopropyl species.

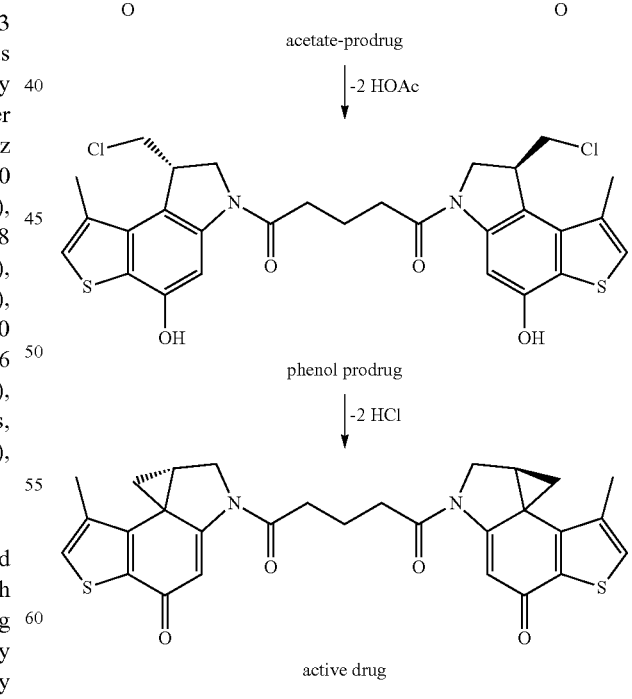

The following payloads were prepared. All payloads were prepared either using the general procedures A and B or by indicated methods

TABLE 1

Examples of Payloads

| Structure | Compound ID | LC-MS Retention time (Method) | m/z [M + H]+ |
|---|---|---|---|
| 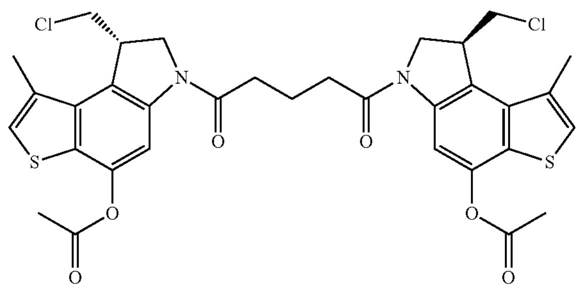 [SMILES: CC(=O)Oc1cc2c(c3c(C)csc13)[C@H](CCl)CN2C(=O)CCCC(=O)N1C[C@@H](CCl)c2c1cc(OC(C)=O)c1scc(C)c21] | 24 | 1.11 min (Protocol B) | 687.2 |
| 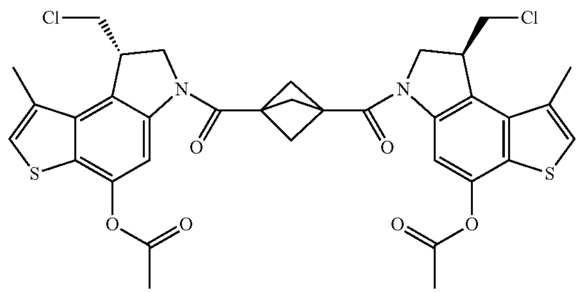 [SMILES: CC(=O)Oc1cc2c(c3c(C)csc13)[C@H](CCl)CN2C(=O)C12CC(C(=O)N3C[C@@H](CCl)c4c3cc(OC(C)=O)c3scc(C)c43)(C1)C2] | 7 | 1.12 min (Protocol B) | 711.1 |
| 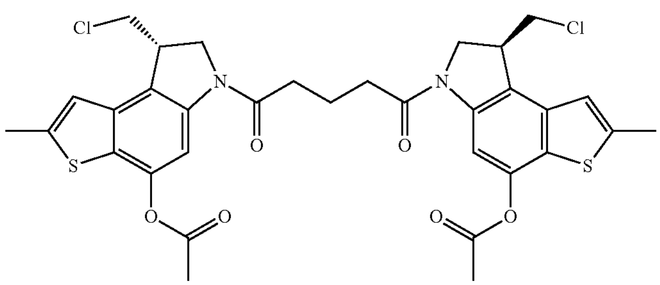 | 26 | 1.11 min (Protocol B) | 687.2 |
| 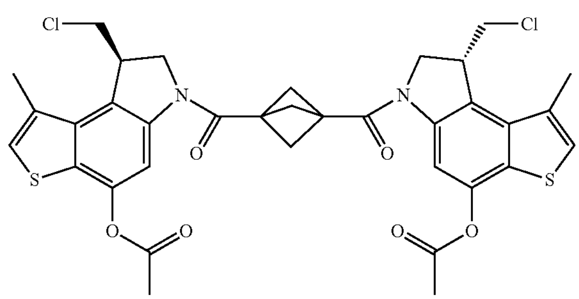 [SMILES: CC(=O)Oc1cc2c(c3c(C)csc13)[C@@H](CCl)CN2C(=O)C12CC(C(=O)N3C[C@H](CCl)c4c3cc(OC(C)=O)c3scc(C)c43)(C1)C2] | 12 | 1.12 min (Protocol B) | 711.1 |
| 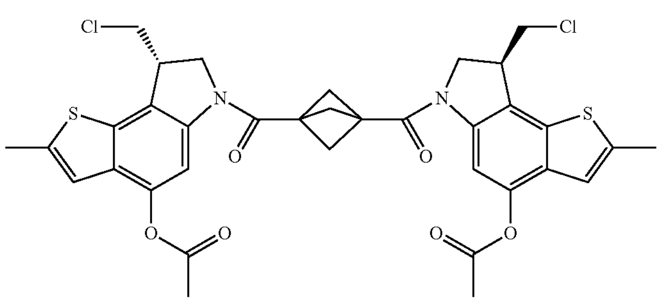 | 17 | 1.12 min (Protocol B) | 711 |

TABLE 1-continued

Examples of Payloads

| Structure | Compound ID | LC-MS Retention time (Method) | m/z [M + H]+ |
|---|---|---|---|
| 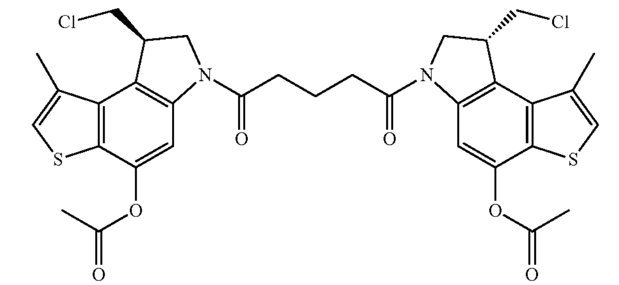 [SMILES: CC(=O)Oc1cc2c(c3c(C)csc13)[C@@H](CCl)CN2C(=O)CCCC(=O)N1C[C@H](CCl)c2c1cc(OC(C)=O)c1scc(C)c21] | 25 | 1.11 min (Protocol B) | 687.1 |
| 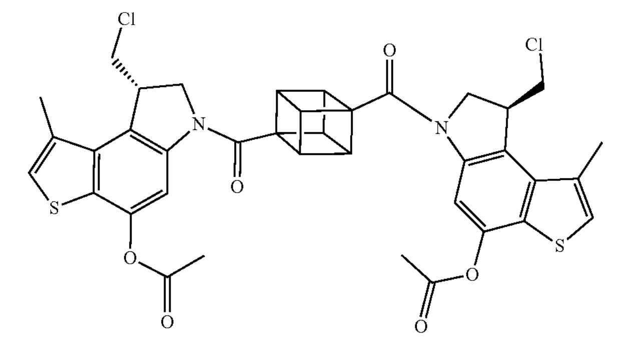 [SMILES: CC(=O)Oc1cc2c(c3c(C)csc13)[C@H](CCl)CN2C(=O)C12C3C4C1C1C2C3C41C(=O)N1C[C@@H](CCl)c2c1cc(OC(C)=O)c1scc(C)c21] | 60 | 2.39 min (Protocol A) | 747 |
| 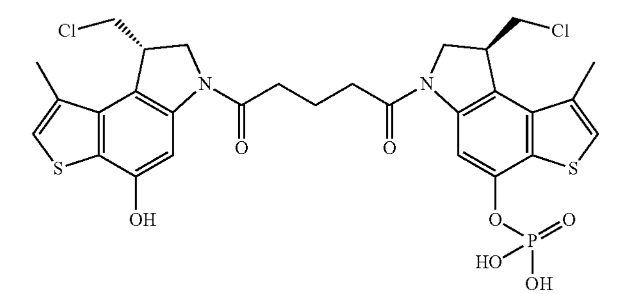 [SMILES: Cc1csc2c(O)cc3c(c12)[C@H](CCl)CN3C(=O)CCCC(=O)N1C[C@@H](CCl)c2c1cc(OP(=O)(O)O)c1scc(C)c21] | 61 | 0.93 min (Protocol B) | 683 |
| 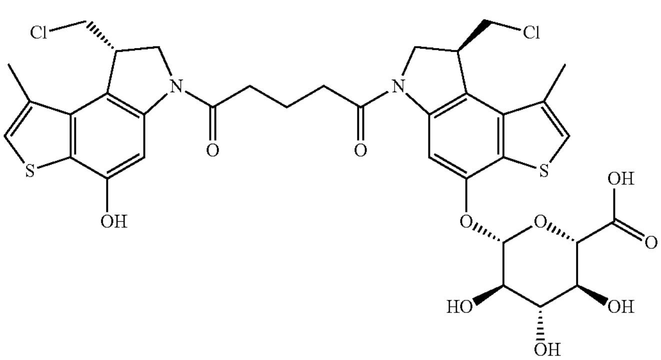 [SMILES: Cc1csc2c(O)cc3c(c12)[C@H](CCl)CN3C(=O)CCCC(=O)N1C[C@@H](CCl)c2c1cc(O[C@@H]1O[C@H](C(=O)O)[C@@H](O)[C@H](O)[C@H]1O)c1scc(C)c21] | 57 | 0.9 min (Protocol B) | 779 |

TABLE 1-continued

Examples of Payloads

| Structure | Compound ID | LC-MS Retention time (Method) | m/z [M + H]+ |
|---|---|---|---|
| 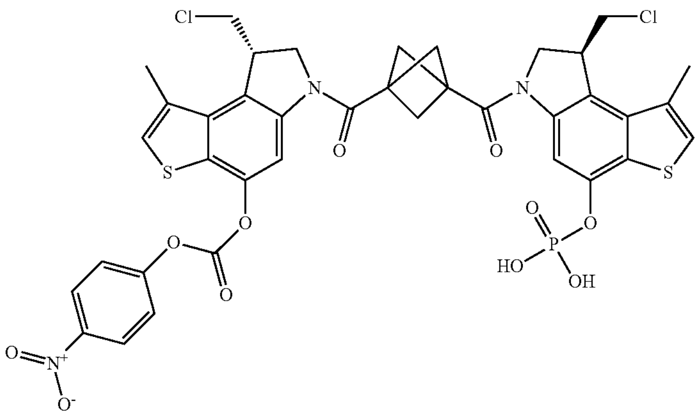 [SMILES: Cc1csc2c(OC(=O)Oc3ccc([N+](=O)[O-])cc3)cc3c(c12)[C@H](CCl)CN3C(=O)C12CC(C(=O)N3C[C@@H](CCl)c4c3cc(OP(=O)(O)O)c3scc(C)c43)(C1)C2] | 33 | 1.86 min (Protocol A) | 872 |
| 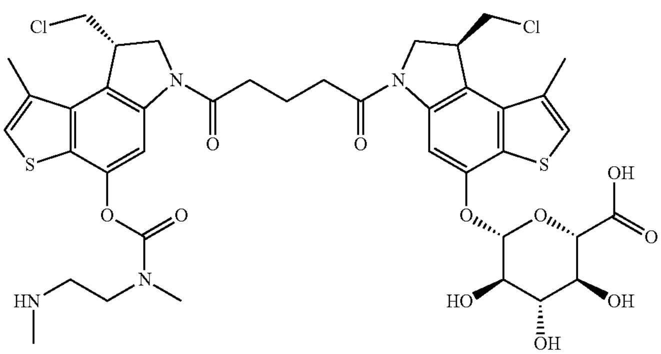 [SMILES: CNCCN(C)C(=O)Oc1cc2c(c3c(C)csc13)[C@H](CCl)CN2C(=O)CCCC(=O)N1C[C@@H](CCl)c2c1cc(O[C@@H]1O[C@H](C(=O)O)[C@@H](O)[C@H](O)[C@H]1O)c1scc(C)c21] | 59 | 0.74 min (Protocol B) | 893 |
| 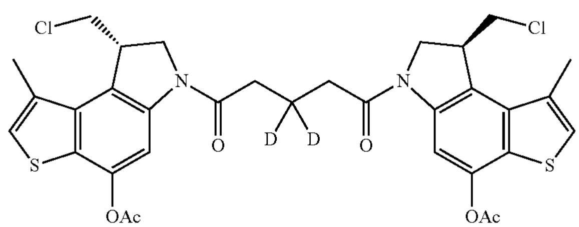 [SMILES: [2H]C([2H])(CC(=O)N1C[C@@H](CCl)c2c1cc(OC(C)=O)c1scc(C)c21)CC(=O)N1C[C@@H](CCl)c2c1cc(OC(C)=O)c1scc(C)c21] | 87 | 2.25 min (Protocol A) | 689.3 |
| 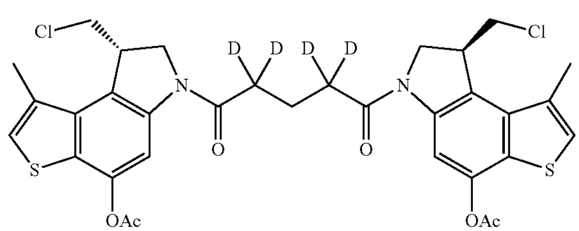 [SMILES: [2H]C([2H])(CC([2H])([2H])C(=O)N1C[C@@H](CCl)c2c1cc(OC(C)=O)c1scc(C)c21)C(=O)N1C[C@@H](CCl)c2c1cc(OC(C)=O)c1scc(C)c21] | 88 | 2.25 min (Protocol A) | 691.3 |
| 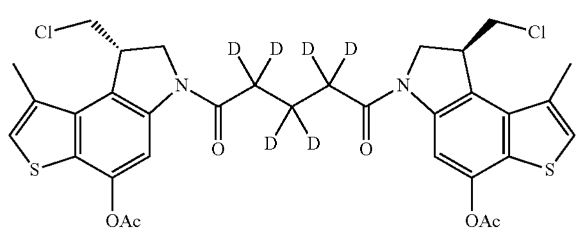 [SMILES: [2H]C([2H])(C(=O)N1C[C@@H](CCl)c2c1cc(OC(C)=O)c1scc(C)c21)C([2H])([2H])C([2H])([2H])C(=O)N1C[C@@H](CCl)c2c1cc(OC(C)=O)c1scc(C)c21] | 89 | 2.25 min (Protocol A) | 693.3 |

TABLE 2

The following payloads are prepared using the general synthetic procedures A and B.

Structure

TABLE 2-continued
The following payloads are prepared using the general synthetic procedures A and B.
Structure
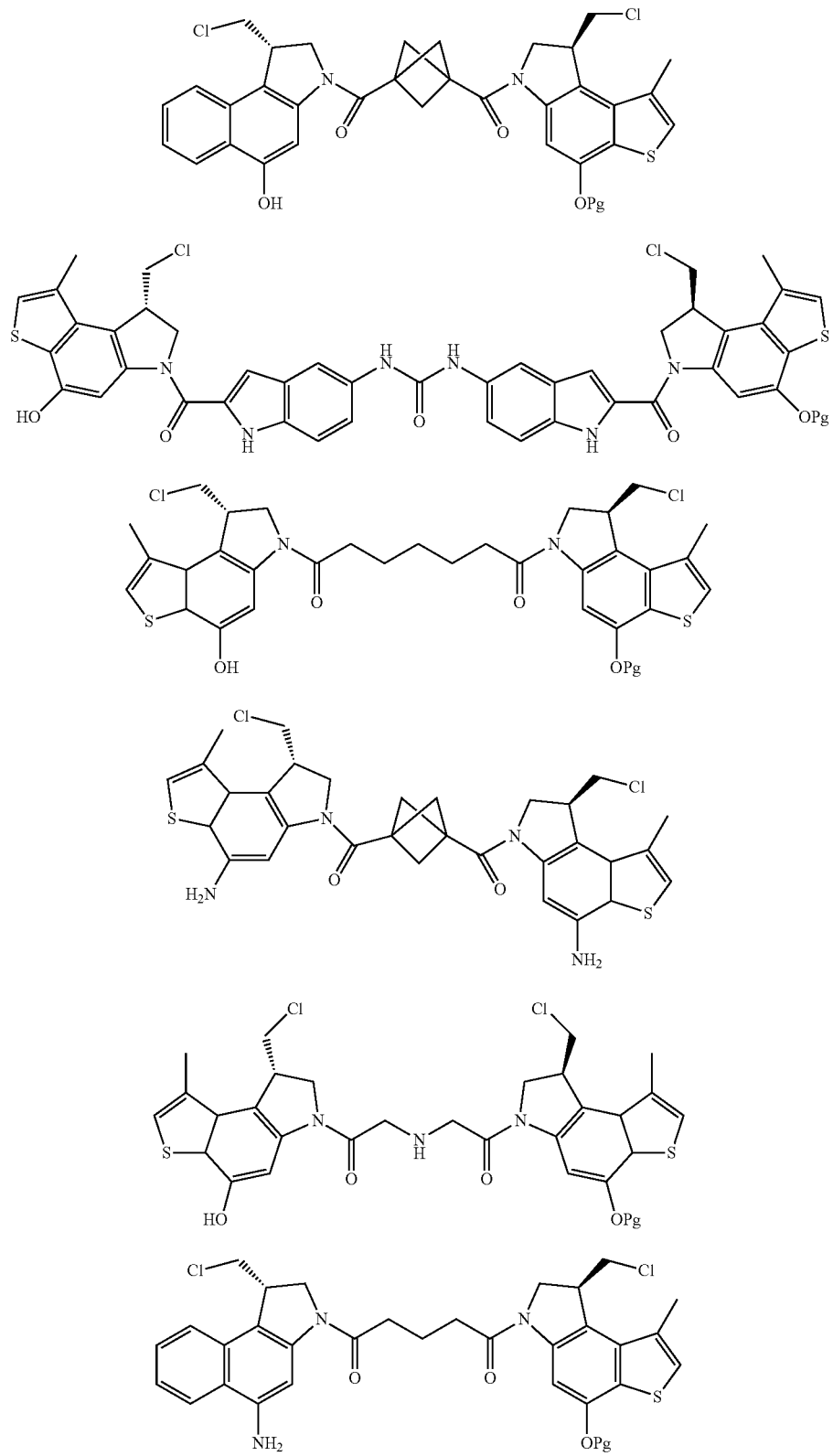

TABLE 2-continued

The following payloads are prepared using the general synthetic procedures A and B.

Structure

TABLE 2-continued
The following payloads are prepared using the general synthetic procedures A and B.
Structure
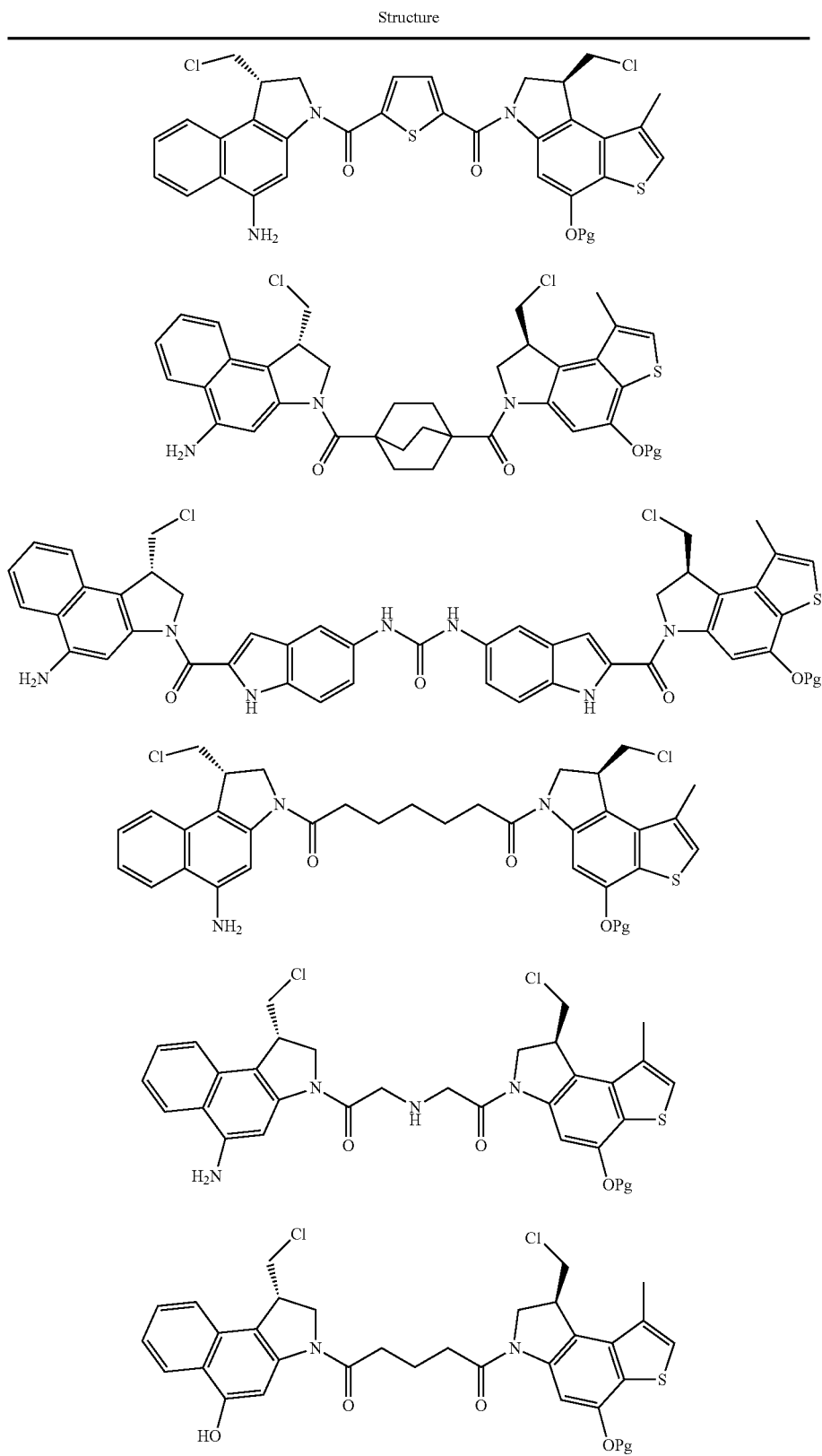

TABLE 2-continued

The following payloads are prepared using the general synthetic procedures A and B.

Structure

In the above examples, the variable Pg is H, acyl, phosphate $PO_3H_2$, a carbohydrate, an amino acid or a peptide (and in particular a peptide that is cleaved by proteases, such as cathepsins and matrix metalloproteinases).

The following linker/payloads were prepared:

TABLE 3

Prepared Linker-Payloads

| Structure | Compound ID | LC-MS Retention time (Method) | Observed Ion in Mass. Spec. |
| --- | --- | --- | --- |
| (structure) | 41 | 1.61 minutes (Protocol A) | 1642 [M + 2H] |
| (structure) | 49 | 0.89 minutes (Protocol B) | 1714 [M + 2H] |

TABLE 3-continued

Prepared Linker-Payloads

| Structure | Compound ID | LC-MS Retention time (Method) | Observed Ion in Mass. Spec. |
|---|---|---|---|
| 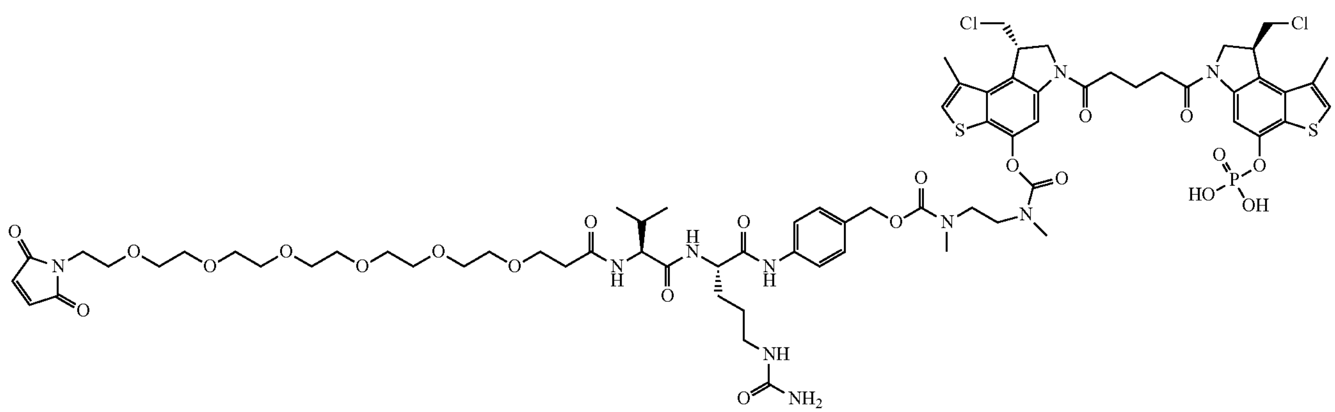 [SMILES: Cc1csc2c(OC(=O)N(C)CCN(C)C(=O)OCc3ccc(NC(=O)[C@H](CCCNC(N)=O)NC(=O)[C@@H](NC(=O)CCOCCOCCOCCOCCOCCOCCN4C(=O)C=CC4=O)C(C)C)cc3)cc3c(c12)[C@H](CCl)CN3C(=O)CCCC(=O)N1C[C@@H](CCl)c2c1cc(OP(=O)(O)O)c1scc(C)c21] | 56 | 0.95 minutes (Protocol B) | 1618 [M + 2H] |

TABLE 3-continued

Prepared Linker-Payloads

| Compound ID | Structure | LC-MS Retention time (Method) | Observed Ion in Mass. Spec. |
|---|---|---|---|
| 62 | 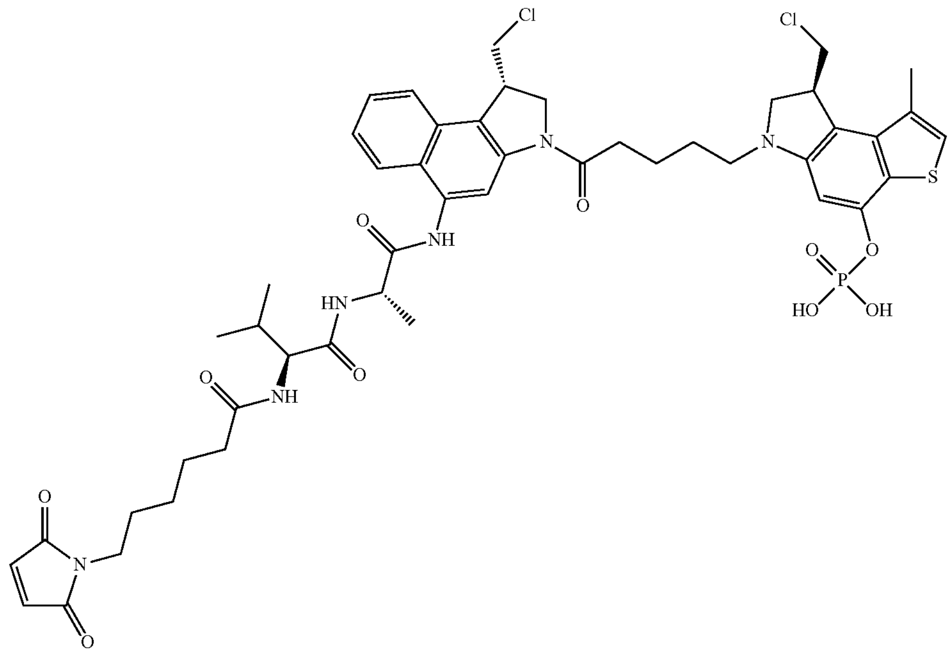 [SMILES: Cc1csc2c(OP(=O)(O)O)cc3c(c12)[C@H](CCl)CN3CCCCC(=O)N1C[C@@H](CCl)c2c1cc(NC(=O)[C@H](C)NC(=O)[C@@H](NC(=O)CCCCCN1C(=O)C=CC1=O)C(C)C)c1ccccc21] | 2.01 min (Protocol A) | 1026 [M + 2H] |

TABLE 3-continued
Prepared Linker-Payloads
| Structure | Compound ID | LC-MS Retention time (Method) | Observed Ion in Mass. Spec. |
|---|---|---|---|
| 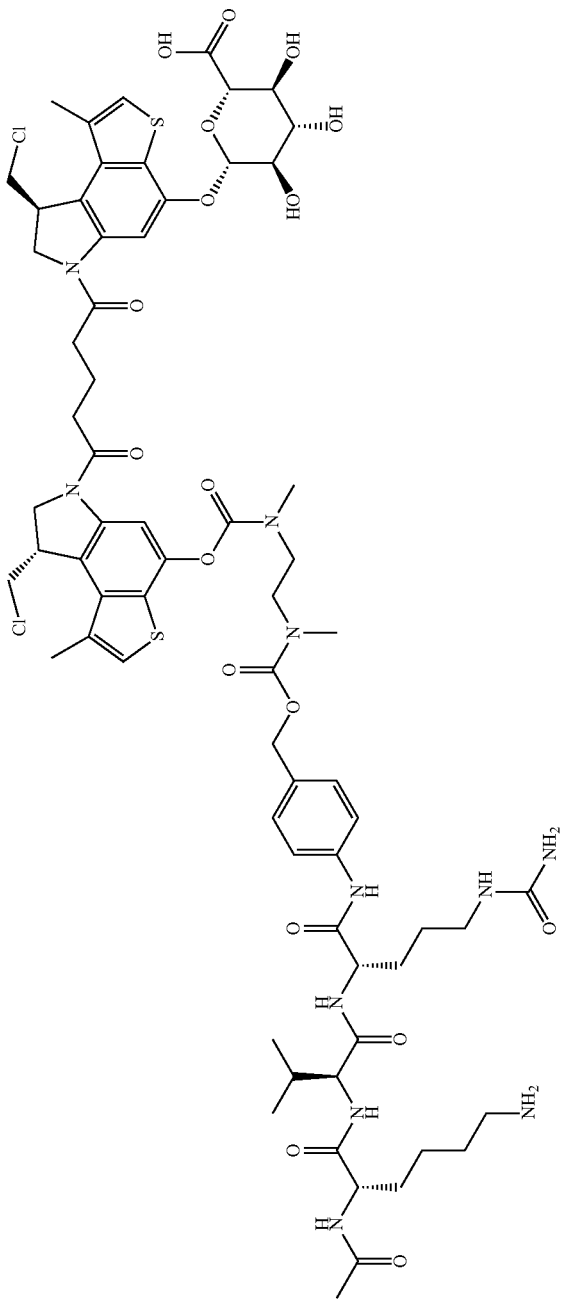 | 76 | 0.75 min (Protocol B) | 1471.1 (M + 2H)+ |

TABLE 3-continued
Prepared Linker-Payloads
| Compound ID | Structure | LC-MS Retention time (Method) | Observed Ion in Mass. Spec. |
|---|---|---|---|
| 77 | 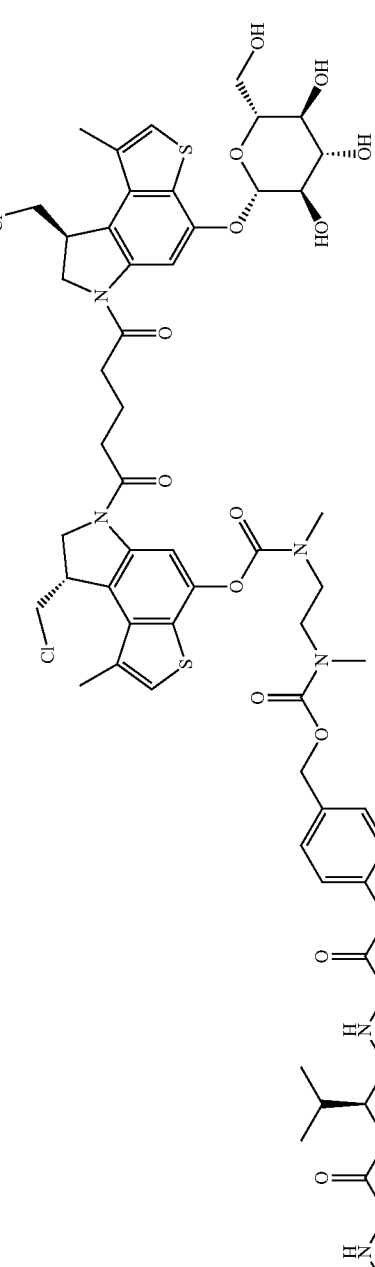 | 0.75 min (Protocol B) | 1456.9 (M + 2H)+ |

TABLE 3-continued
Prepared Linker-Payloads
| Structure | Compound ID | LC-MS Retention time (Method) | Observed Ion in Mass. Spec. |
|---|---|---|---|
| 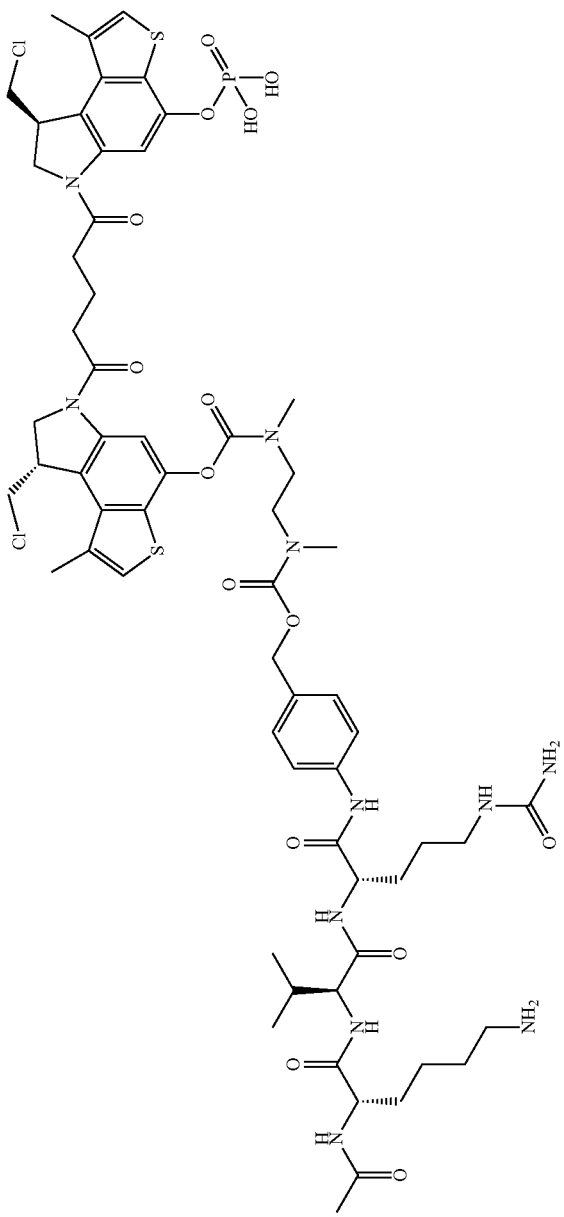 | 100 | 0.92 min (Protocol B) | 1374.8 (M + 2H)+ |

Table 4: The following linker/payloads are prepared using the procedure described above for preparation of linker/payload analogs shown in Table 3.
TABLE 4
Additional Linker/Payloads
Linker Structures for Table 4
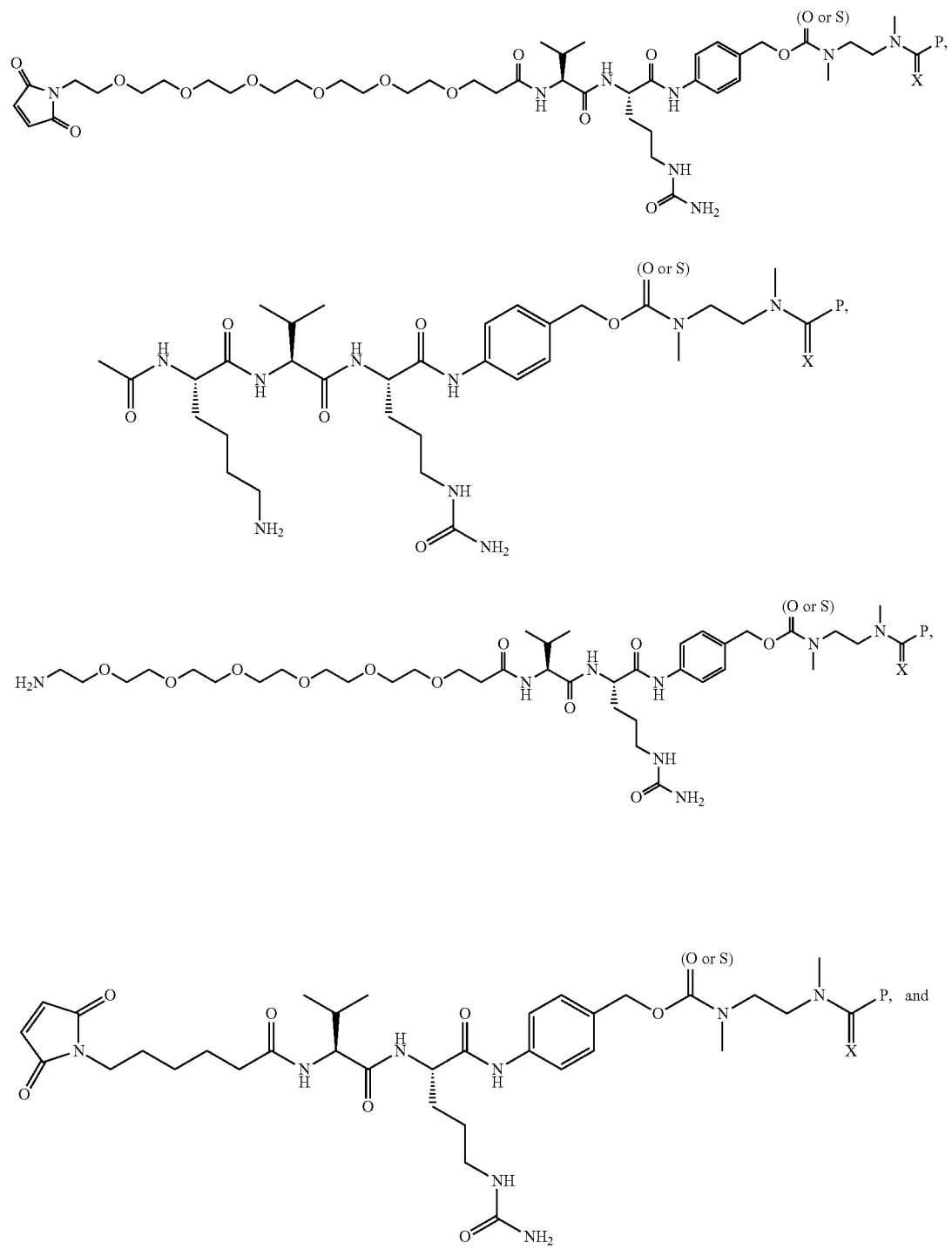

TABLE 4-continued

Additional Linker/Payloads

Linker Structures for Table 4

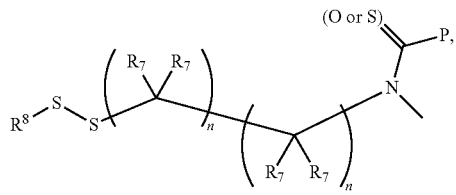

where
P represents the point of attachment to said payload,
each $R^7$ is independently H or —$C_1$-$C_{20}$ alkyl,
$R^8$ is —$C_1$-$C_{20}$ alkyl, —$C_6$-$C_{14}$ aryl or —$C_6$-$C_{14}$ heteroaryl,
n = 0-20, and
m = 0-20.

The attachment points of the above linker structures are indicated and are located at the payload phenol:

Payload Structure (P)

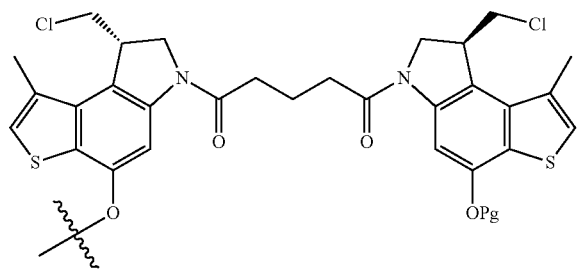

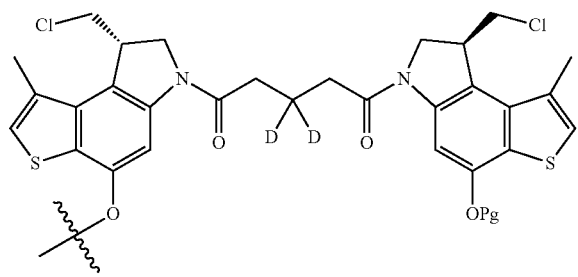

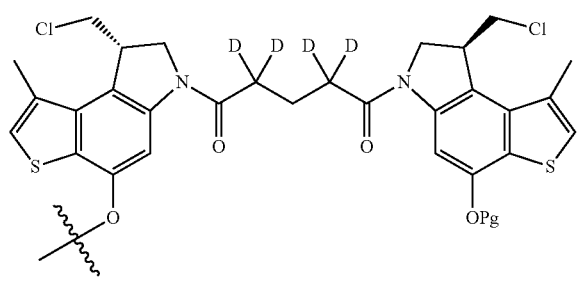

| Payload Structure (P) |
|---|
| 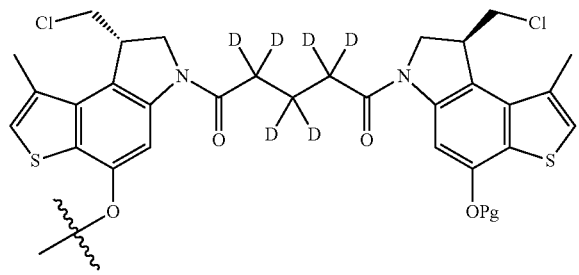 |
| 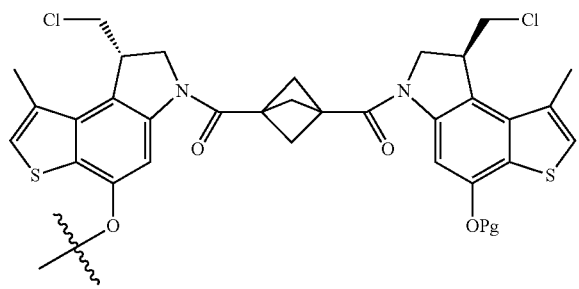 |
| 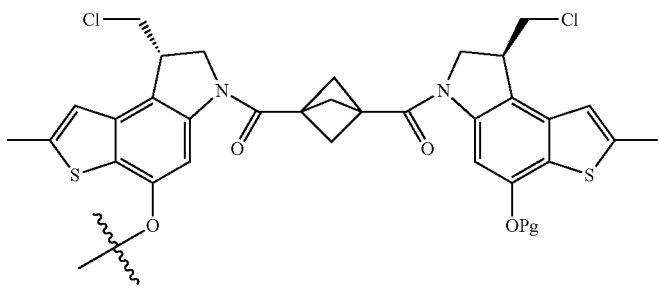 |
| 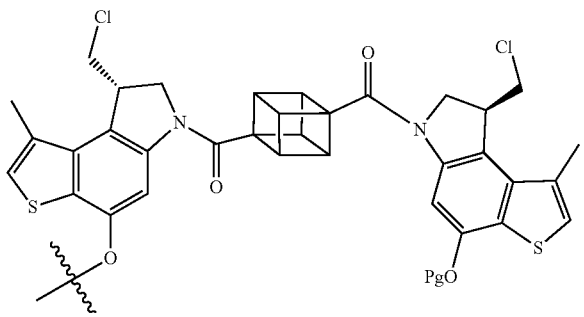 |
| 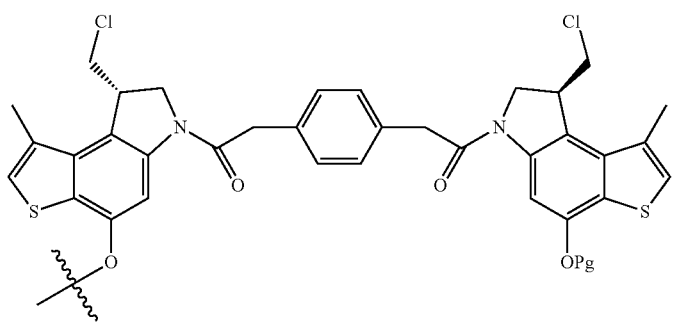 |

| Payload Structure (P) |
|---|
| 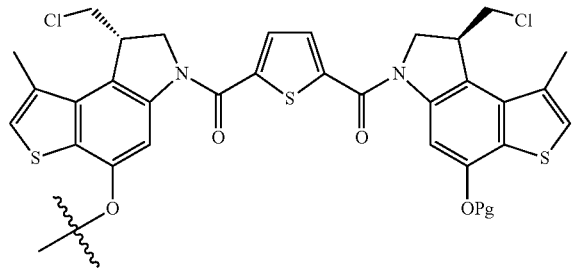 |
| 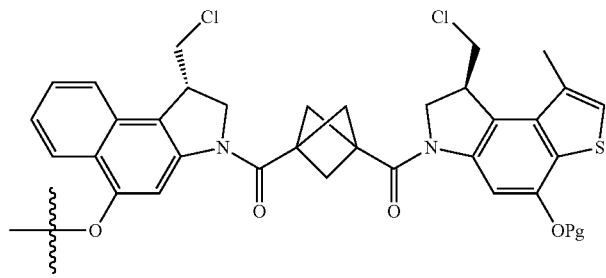 |
| 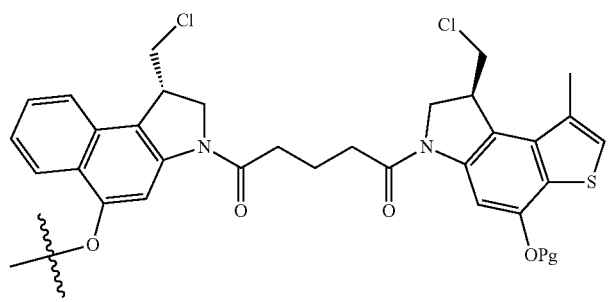 |
| 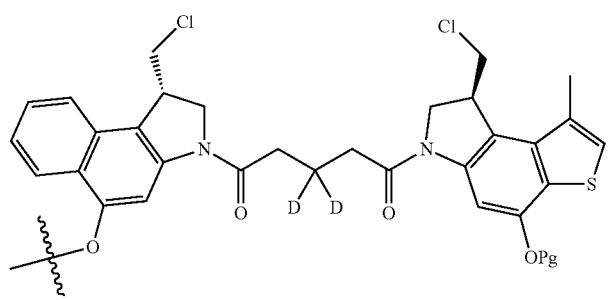 |
| 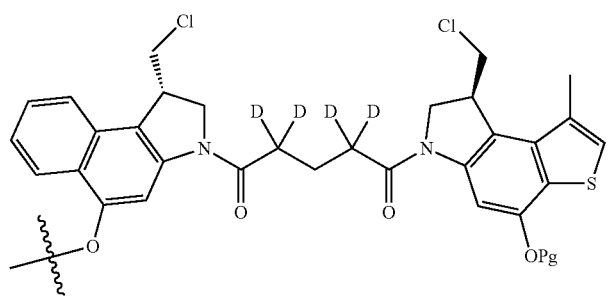 |

| Payload Structure (P) |
|---|
| 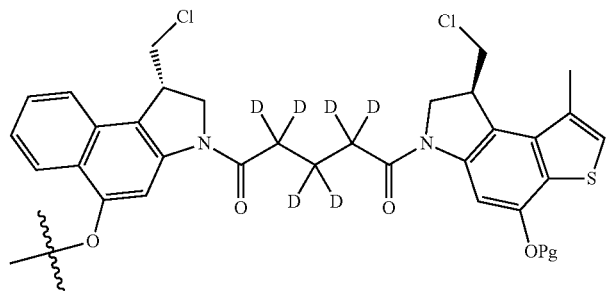 |
| 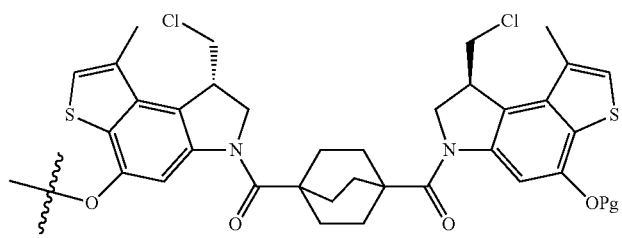 |
| 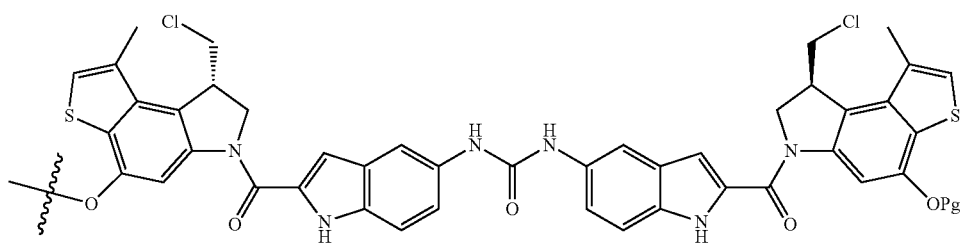 |
| 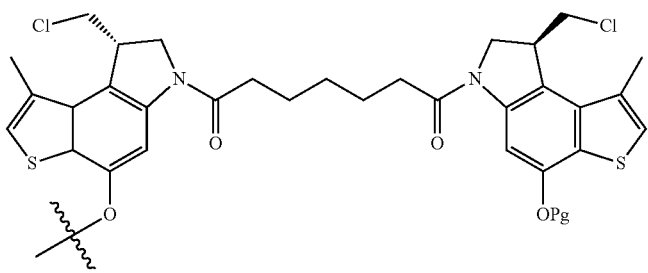 |
| 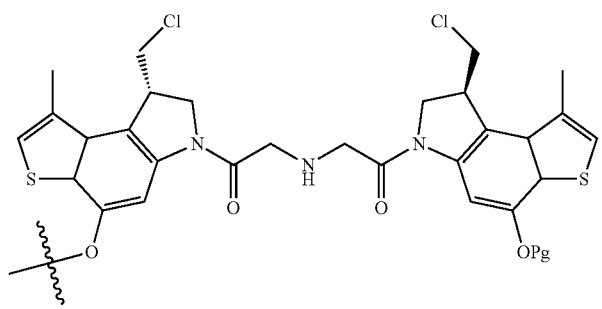 |

In Table 4, Pg is H, acyl, phosphate PO$_3$H$_2$, a carbohydrate, an amino acid or a peptide (in particular a peptide that is cleaved by proteases, such as cathepsins and matrix metalloproteinases).
TABLE 5
Additional Linker-Payloads
Linker Structures for Table 5
from:
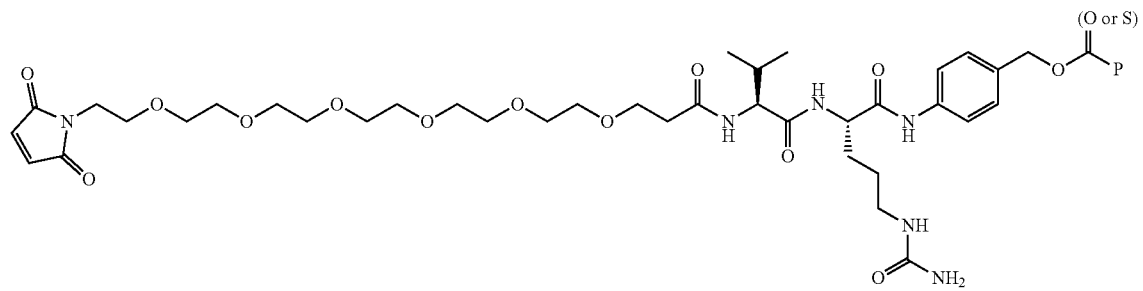
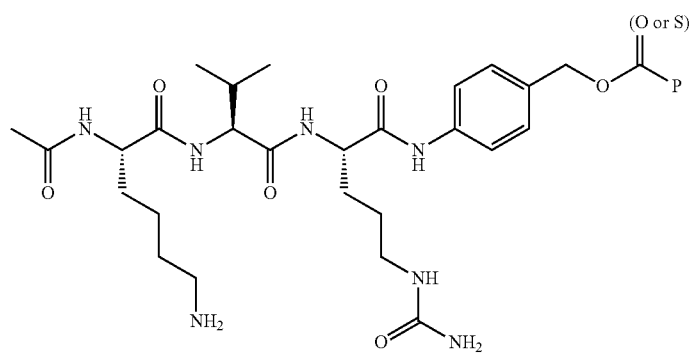
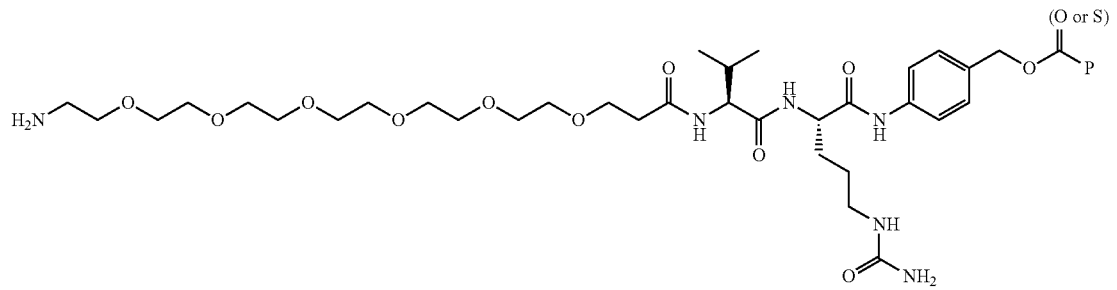
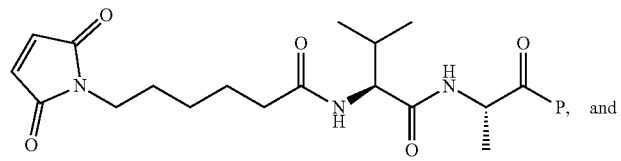

TABLE 5-continued
Additional Linker-Payloads
Linker Structures for Table 5
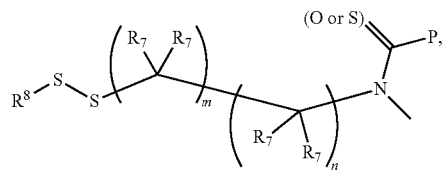
where
P represents the point of attachment to said payload,
each $R^7$ is independently H or —$C_1$-$C_{20}$ alkyl,
$R^8$ is —$C_1$-$C_{20}$ alkyl, —$C_6$-$C_{14}$ aryl or —$C_6$-$C_{14}$ heteroaryl,
n = 0-20, and
m = 0-20.
The attachment points of the above linker structures are located at the aniline N function:
Payload Structure (P)
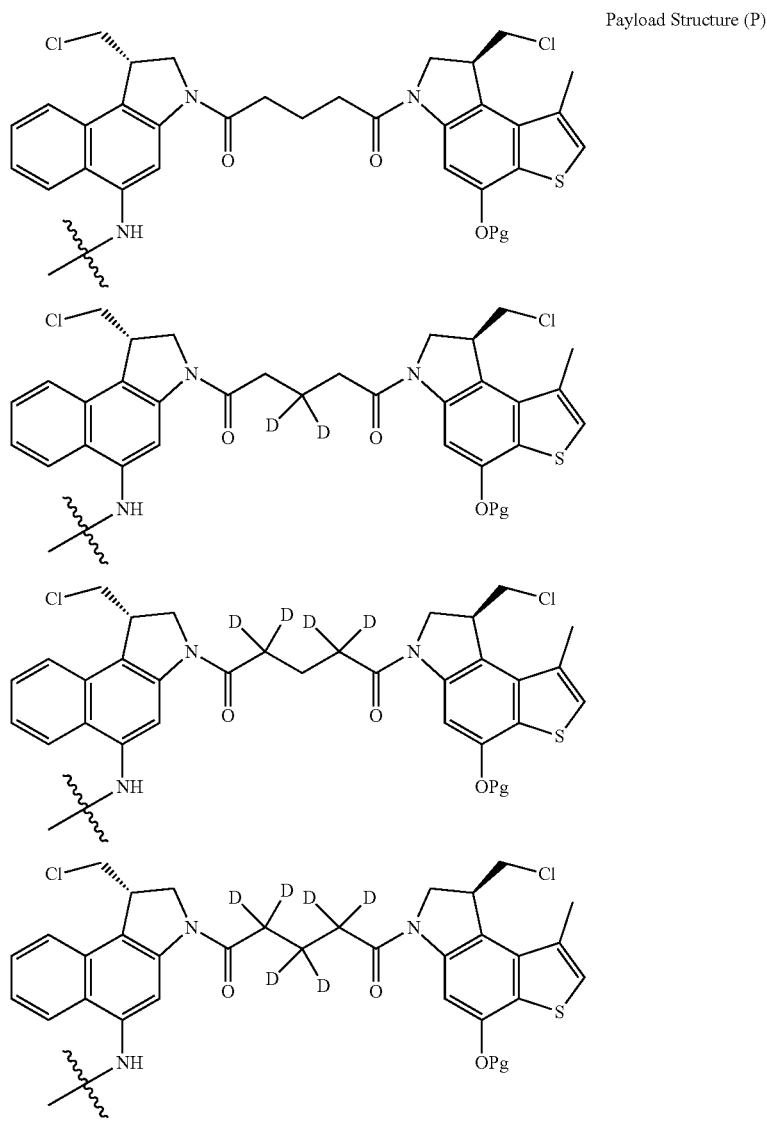

-continued
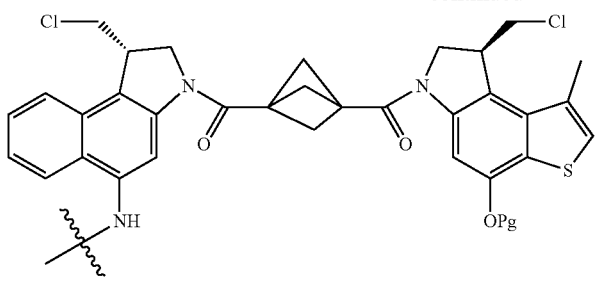
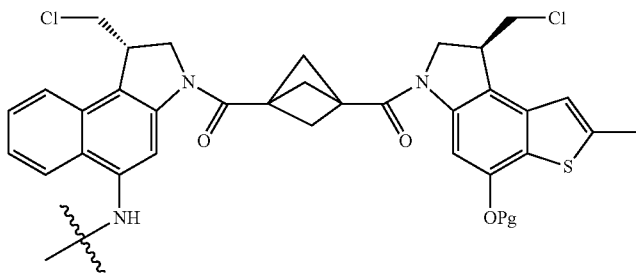
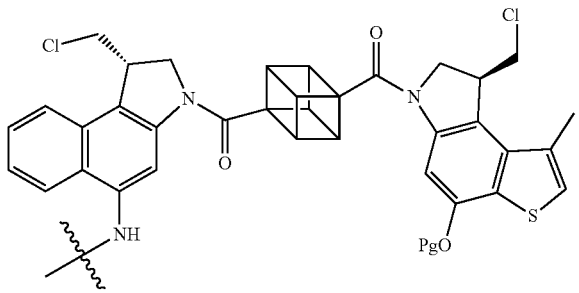
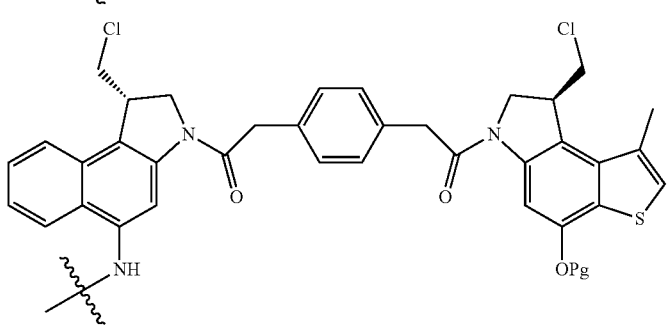
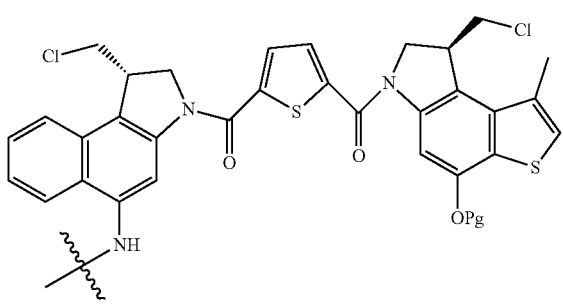
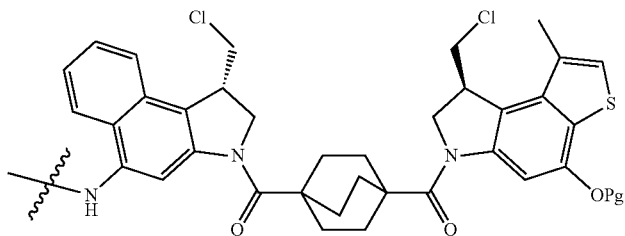

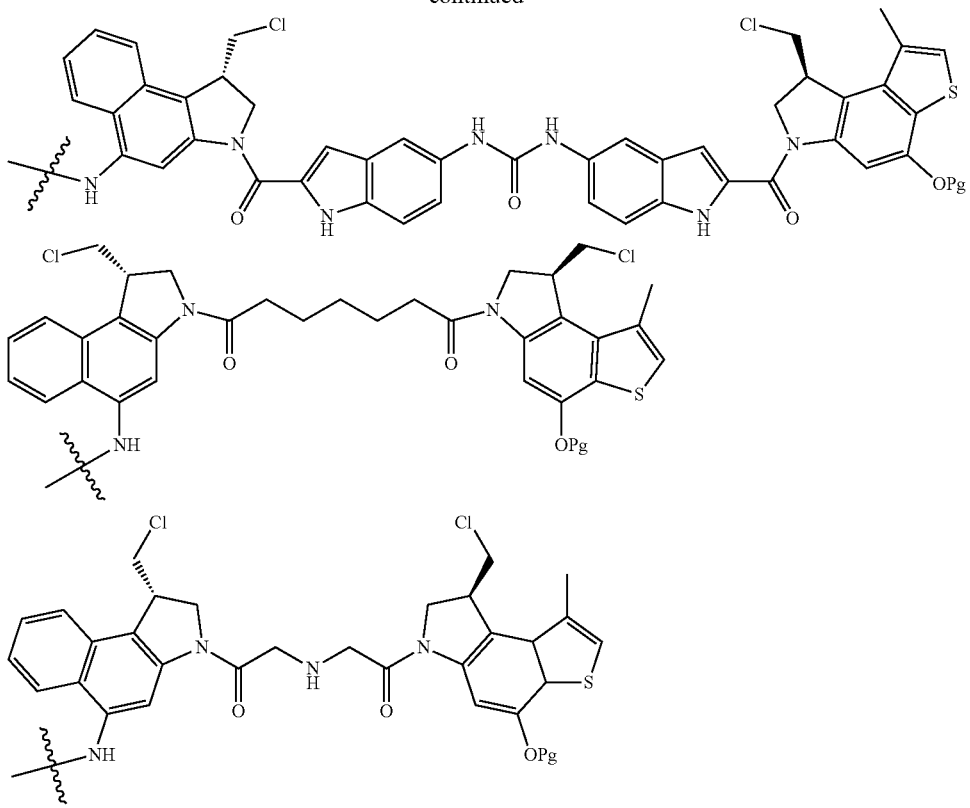

In Table 5, Pg is H, acyl, phosphate POH, a carbohydrate, an amino acid or a peptide (in particular a peptide that is cleaved by proteases, such as cathepsins and matrix metalloproteinases).

Experimental Procedures for Biological Assessment of Payloads and Antibody Drug Conjugates Cell Lines for Payload Viability Assays Cancer cell lines were obtained from ATCC (Manassas, Va.). N87 (human gastric carcinoma derived from metastatic liver site). HL60 (leukemia) and MDA-MB-361 DYT2 (human breast carcinoma MDA-MB-361) were grown in RPMI 1640 media. All media were supplemented with 10% fetal bovine serum, 1% sodium pyruvate, and 1% L-glutamine (Invitrogen, Grand Island, N.Y.). Human umbilical vein endothelial cells (HUVEC) were obtained from Lonza (Allendale, N.J.) and maintained in EGM2 media supplemented with EGM-2 SingleQuots (Lonza #CC-4176). All cells were maintained in a humidified incubator (37° C., 5% $CO_2$).

Cytotoxicity Assay Procedure for Payloads

Cells in 100 μl medium were cultured in a 96-well plate. Cancer cell lines treated with the indicated compounds by adding 50 μl of 3× stocks in duplicate at 10 concentrations. Cells were incubated with compounds for four days, then 30 μl of CellTiter® 96 AQueous One MTS Solution (Promega Cat #G3582) was added to the cells, incubated 1.5 hr at 37° C., then absorbance measured at 490 nm on a Victor plate reader (Perkin Elmer, Waltham, Mass.). Relative cell viability was determined as a percentage of untreated control wells. IC50 values were calculated using four parameter logistic model #203 with XLfit v4.2 (IDBS, Guildford, Surry, UK).

Cytotoxicity Assay Procedure for Anti-IL13Rα2 ADCs

Cell lines used: A375 (melanoma), PC3MM2 (prostate), PC3 (prostate)

Cells were seeded into 96-well plate overnight before expose to increasing concentrations of anti-IL13Rα2 ADCs or control ADCs. After four days, viability of each culture was assessed against control cells. $IC_{50}$ values were calculated by logistic non-linear regression.

Cytotoxcity Assays Procedure for Anti-CD33 ADCs

Human AML cell lines (HL60, NB4, HEL92.1.7, and Raji) were obtained from American Type Culture Collection (Manassas, Va.). The cells were grown in RPMI media, supplemented with 10% FBS, 1% Pen/Strep and L-Glutamine Mixture, 1 mM sodium pyruvate, 10 mM HEPES, and 0.27% glucose (Life Technology, Carlsbad, Calif.). Cell lines were tested for their endogenous activity levels of P-glycoprotein, multidrug resistance protein, and breast cancer resistance protein were determined using a commercial flow cytometric kit (eFLUXX-ID; ENZO Life Sciences, Plymouth Meeting, Pa.).

For cytotox assays, cells were plated in a 96-well opaque plates (Corning) and treated with varying concentrations of compounds for 4 days. Viability was determined by using a CellTiter Glo luminescent cell viability assay kit (Promega, Madison, Wis.) and measured using a Victor X3 plate reader (Perkin Elmer Waltham, Mass.). The data were normalized to the control group (DMSO or PBS). $IC_{50}$ values were defined as the concentration that causes 50% growth inhibition. $IC_{50}$ values were calculated using a logistic nonlinear regression, model no. 203 with XL fit v4.2 (IDBS, Guldford, Surry, UK). All experimental points were setup in two replicate wells and independently performed in duplicate.

Cytotoxcity Assays for Anti-Trastuzumab ADCs

Target expressing N87 (gastric cancer), MDA-MB-361-DYT2 (breast cancer)) or non-expressing (HT-29) cells were seeded in 96-well cell culture plates for 24 hours before treatment. Cells were treated with 3-foldserially diluted antibody-drug conjugates Cell viability was determined by CellTiter 96® AQ$_{ueous}$ One Solution Cell Proliferation MTS Assay (Promega, Madison Wis.) 96 hours after treatment. Relative cell viability was determined as percentage of untreated control. IC$_{50}$ values were calculated using a four parameter logistic model #203 with XLfit v4. 2 (IDBS, Guildford, Surry, UK).

Results of cytotoxicity of payloads and ADCs are shown in Tables 6 and 10

TABLE 6

Exemplifeid Free Payload Potencies:

| Compound ID | N87 [nM] | HL60 [nM] | DYT2 [nM] |
|---|---|---|---|
| 24 | 0.024 | <0.005 | 0.171 |
| 7 | 0.022 | <0.005 | 0.185 |
| 26 | 0.263 | 0.014 | 1.670 |
| 12 | 2.258 | 0.180 | 5.077 |
| 17 | 1.296 | 0.084 | 6.062 |
| 25 | 41.600 | NA | >100 |
| 60 | 0.122 | 0.009 | 0.079 |
| 61 | 13.646 | 0.806 | 28.587 |
| 57 | 11.020 | 0.873 | 37.588 |
| 87 | 0.036 | 0.349 | 0.002 |
| 88 | 0.041 | 0.41 | 0.004 |
| 89 | 0.041 | 0.302 | 0.002 |

Exemplification of Antibody Drug Conjugates

Method D: General Procedure for Conjugation of Antibody with Linker-Payload Via Internal Disulfides A solution of therapeutic antibody in Dulbecco's Phosphate Buffered Saline (PBS, Lonza, pH 7.4) was reduced by addition of 3.0-3.5 equivalents of tris(2-carboxyethyl)phosphine hydrochloride (TCEP, 5 mM solution in PBS). The reaction was incubated at 37° C. for 1-2 h and then allowed to cool to ambient temperature. Conjugation was performed by addition of 7 equivalents of linker-payload [10 mM solution in N,N-dimethylacetamide (DMA)]. Additional DMA was added to reaction mixture to achieve 15% (v/v) total organic solvent component in final reaction mixture. The reaction was incubated for 1 h at ambient temperature. After 1 h at ambient temperature, crude reaction was either buffer exchanged PBS via GE Sephadex desalting columns or the excess linker-payload was quenched via addition of 10 equivalents of cysteine (20 mM solution in PBS). In either case, crude material was then purified by size exclusion chromatography (SEC, Protocol C). The monomeric fractions were pooled and concentrated if necessary to give the ADC.

Method E: Site-Specific Conjugation of Linker-Payloads to a Trastuzumab Antibody Containing Engineered Cysteine Residues A solution of therapeutic antibody containing an engineered cysteine residue (Kabat numbering, see WO2013093809) was prepared in 50 mM phosphate buffer, pH 7.4. PBS, EDTA (0.5 M stock), and TCEP (0.5 M stock) were added such that the final protein concentration was ~10 mg/mL, the final EDTA concentration was ~20 mM, and the final TCEP concentration was approximately ~6.6 mM (100 molar eq.). The reaction was allowed to stand at rt for 2-48 h and then buffer exchanged into PBS using GE PD-10 Sephadex G25 columns per the manufacturer's instructions. Alternative methods such as diafiltration or dialysis are also useful in particular circumstances. The resulting solution was treated with approximately 50 equivalents of dehydroascorbate (50 mM stock in 1:1 EtOH/water). The antibody was allowed to stand at 4° C. overnight and subsequently buffer exchanged into PBS using GE PD-10 Sephadex G25 columns per the manufacturer's instructions. Again, alternative methods such as diafiltration or dialysis are also useful in particular circumstances.

Conjugation to the antibody thus prepared was performed by addition of 10 equivalents of linker-payload [10 mM solution in N,N-dimethylacetamide (DMA)]. Additional DMA was added to reaction mixture to achieve 15% (v/v) total organic solvent component in final reaction mixture. In some instances, additional PBS was added to achieve final total antibody concentration in the reaction of 5-10 mg/mL. After 1-2 h at rt, the reaction mixture was buffer exchanged into PBS (per above) and purified by size exclusion chromatography (SEC, Protocol D). The monomeric fractions were pooled and concentrated if necessary to give the ADC. In some instances, the ADC was then subsequently incubated after SEC purification with 0.5-1.0 g Bio-Beads SM-2 adsorbent (Bio-Rad) at 23-37 C for 4-18 h, filtered, and then concentrated if required.

Method F: Enzyme Mediated Conjugation to Antibody Carrying Reactive Glutamine Residues:

Therapeutic antibody carrying transglutamine enzyme-reactive glutamine residues was dialyzed into sterile water (Lonza). The transglutaminase mediated conjugation was carried out by mixing 5.0-15 mg/mL transglutaminase reactive glutamine containing antibody in water with 30 mM Potassium Phosphate pH7.4 DILUT-IT Dissolution Media Concentrate (J. T. Baker), 150 mM sodium chloride (NaCl), 15.0-20.0-fold molar excess of amino alkyl linker carrying payload (10-30 mM solution in DMSO), and 30-60 mg/mL transglutaminase enzyme powder (Ajinomoto Activa TI). Additionally, DMSO was added to reaction mixture to achieve 5-10% (v/v) total organic solvent component in final reaction mixture. In some instances, additional water was added to achieve final total antibody concentration in the reaction of 5-10 mg/mL. The resulting mixture was incubated at ambient temperature for 5-6 hours. Next, another 30-60 mg/mL of transglutaminase solid was added and the mixture further incubated at ambient temperature for an additional 18 hours. After overnight, the crude reaction was buffer exchanged into Dulbecco's phosphate buffered saline (PBS, pH7.4, Lonza) using GE Healthcare Sephadex buffer exchange columns per manufacturer's instructions. Crude material was purified either by size exclusion chromatography (SEC, Protocol D) or hydrophobic interaction chromatography (HIC, Protocol G). After purification, the monomeric fractions were pooled and concentrated if necessary to give the ADC. In examples where ADC was purification by HIC, the pooled fractions were then buffer exchanged into Dulbecco's phosphate buffered saline (PBS, pH7.4, Lonza) using GE Healthcare Sephadex buffer exchange columns per manufacturer's instructions. In some instances, the ADC was then subsequently incubated after purification with 0.5-1.0 g Bio-Beads SM-2 adsorbent (Bio-Rad) at 23-37 C for 4-18 h, filtered, and then concentrated if required.

The ADC was characterized via size exclusion chromatography (SEC) and hydrophobic interaction chromatography (HIC) for purity, and liquid chromatography electrospray ionization tandem mass spectrometry (LC-ESI MS) to calculate drug-antibody ratio (DAR, loading).

Protocol C: Column: Agilent Poroshell 300SB-C8, 75×2.1 mm, 2.6 μm; Mobile phase A:0.1% formic acid in water (v/v); Mobile phase B: 0.1% formic acid in acetonitrile (v/v); Gradient: Initial Conditions: 20% B to 45% B over 4 minutes; Flow rate: 1.0 mL/minute. Temperature: 60° C.; Detection: 220 nm; MS (+) range 400-2000 Da; Injection volume: 10 μL; Instrument: Agilent 1100 LC, Waters MicromassZQ MS. Deconvolution was performed using MaxEnt1.

Protocol D: Column: GE Superdex 200 (10/300 GL); Mobile phase: Phosphate buffered saline (PBS, 1×, pH 7.4); Isocratic; Flow rate: 1.0 mL/minute. Temperature: room temperature; Instrument: GE Akta Explorer.

Protocol E: Column=Waters BEH300-C4, 2.1×100 mm (P/N=186004496); Instrument=Acquity UPLC with an SQD2 mass spec detector; Flow rate=0.7 mL/min; Temperature=80° C.; Buffer A=water+0.1% formic acid; Buffer B=acetonitrile+0.1% formic acid. The gradient runs from 3% B to 95% B over 2 minutes, holds at 95% B for 0.75 min, and then re-equilibrates at 3% B. The sample is reduced with TCEP or DTT immediately prior to injection. The eluate is monitored by LCMS (400-2000 daltons) and the protein peak is deconvoluted using MaxEnt1. DAR is reported as a weight average loading as has been previously described.

Protocol F: Column: TSKGel Butyl NPR, 4.6 mm×3.5 cm (P/N=S0557-835); Buffer A=1.5 M ammonium sulfate containing 10 mM phosphate, pH 7; Buffer B=10 mM phosphate, pH 7+20% isopropyl alcohol; Flow rate=0.8 mL/min; Temperature=ambient; Gradient=0% B to 100% B over 12 minutes, hold at 100% B for 2 minutes, then re-equilibrate at 100% A; Instrument: Agilent 1100 HPLC.

Protocol G: Column: GE HiTrap Butyl HP, 5 mL; Mobile phases: 1M potassium phosphate, 50 mM Tris-HCl, pH7 (Buffer A); 50 mM Tris-HCl, pH7 (Buffer B); Gradient elution: 0-100% Buffer B over 10-20 column volumes; Flow rate: 5.0 mL/minute. Temperature: room temperature; Instrument: GE Akta Explorer.

TABLE 7
Structure of ADC and Payload Linkers used to prepare them
| ADC# | Structure | LP used for synthesis |
|---|---|---|
| ADC#1 | 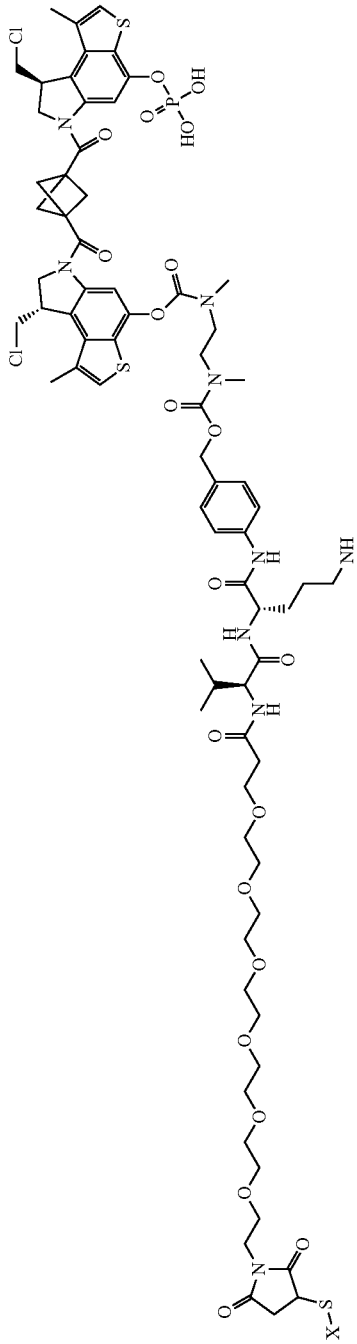 | 41 |
| ADC#2 | 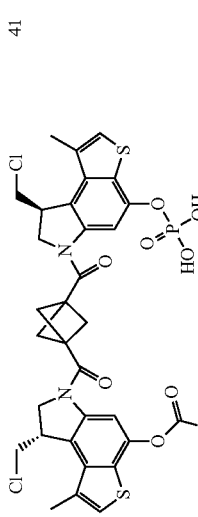 | 76 |

TABLE 7-continued
Structure of ADC and Payload Linkers used to prepare them
| ADC# | Structure | LP used for synthesis |
|---|---|---|
| ADC#3 | 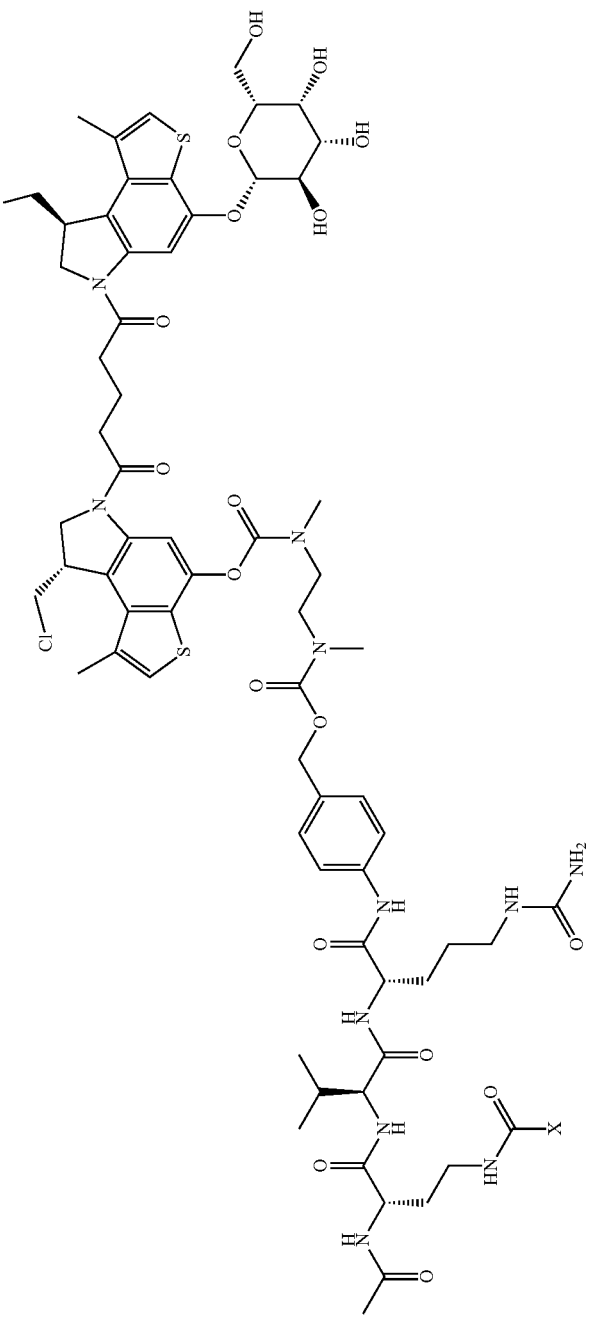 | 77 |
| ADC#4 | 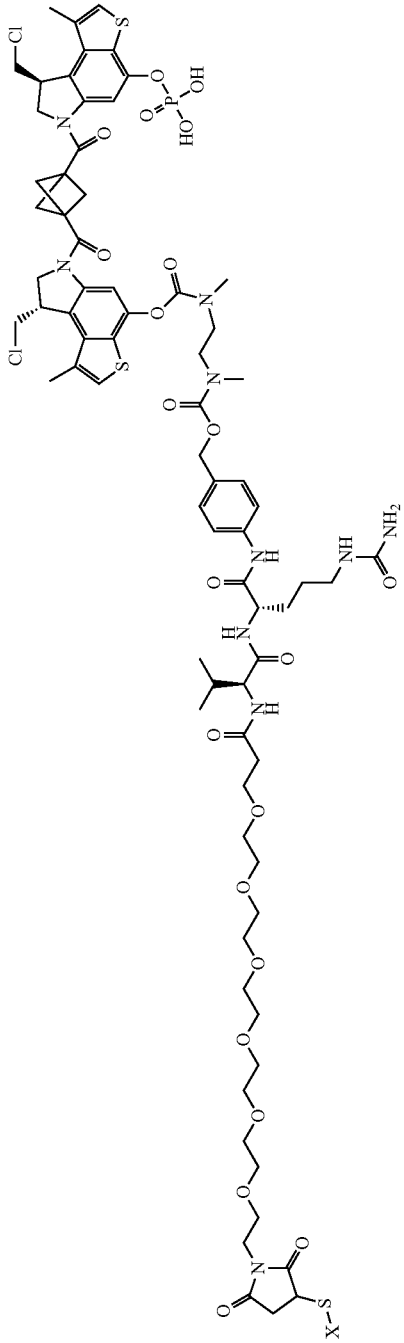 | 41 |

TABLE 7-continued
Structure of ADC and Payload Linkers used to prepare them
| ADC# | Structure | LP used for synthesis |
|---|---|---|
| ADC#5 | 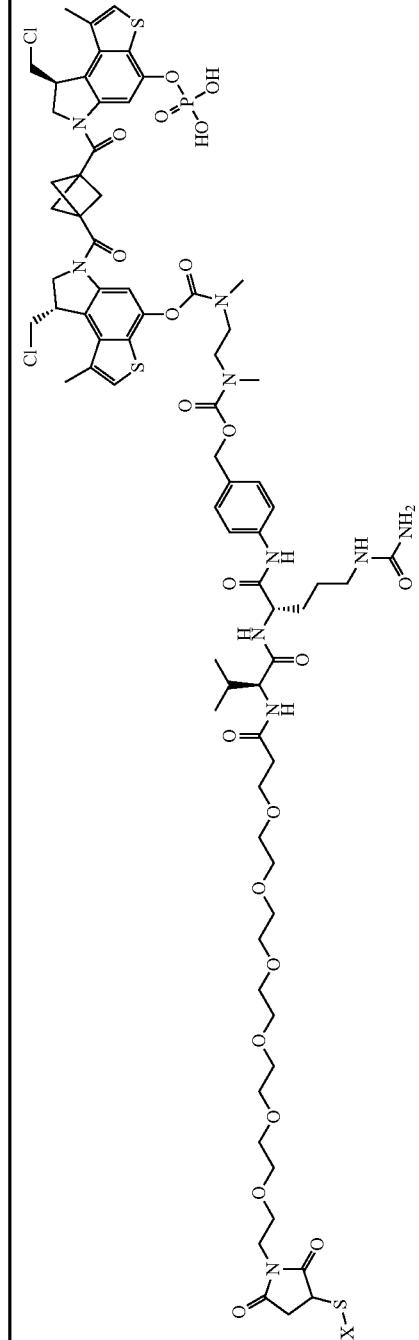 | 41 |
| ADC#6 | 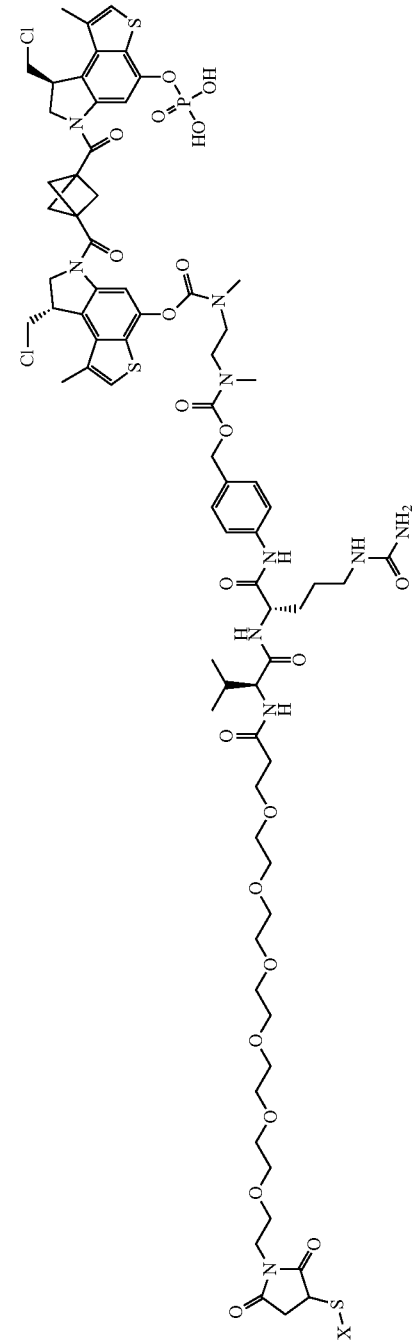 | 41 |

X=In the above table, "X" indicates the antibody used for conjugation as denoted in Table 5.

TABLE 8

General Method for Preparation of ADCs

| ADC# | General Method for preparation | Antibody used | Linker-payload used | Theoretical MW (increase) |
|---|---|---|---|---|
| ADC#1 | D | IL13Rα2-AB08-v1.0 | 41 | 1640 |
| ADC#2 | F | Trastuzumab-H16-K222R-hG1 | 76 | 1450 |
| ADC#3 | F | Trastuzumab-H16-K222R-hG1 | 77 | 1436 |
| ADC#4 | E | CD33-11A1-v1417-hG1-(C) | 41 | 1640 |
| ADC#5 | E | CD33-11A1-v1417-K334C-K392C-hG1-(C334 + C392) | 41 | 1640 |
| ADC#6 | E | CD33-11A1-v1417-K334C-hG1-(C334) | 41 | 1640 |

TABLE 9

Purification method and Analytical Characterization of ADCs

| ADC# | Purification method | Isolated yield | HIC retention time (Method F) | Observed mass for the Heavy Chain (HC) portion | Drug per Antibody ratio (DAR) (LC/MS Method) (protocol E) | Drug per Antibody ratio (DAR) (HIC Method) (Protocol F) |
|---|---|---|---|---|---|---|
| ADC#1 | Protocol D | 18% | NA | 1642 | 2.1 | NA |
| ADC#2 | Protocol D | 36% | 5.43 | 1450 | 1.5 | 1.7 |
| ADC#3 | Protocol D | 34% | 5.48 | 1436 | 1.8 | 1.9 |
| ADC#4 | Protocol D | 52% | 6.20 | 1641 | 2.8 | 2.6 |
| ADC#5 | Protocol D | 72% | 5.34 | 1639 | 3.6 | 3.5 |
| ADC#6 | Protocol D | 73% | 5.41 | 1640 | 2.0 | 2.0 |

TABLE 10

In vitro Cytotoxicity data for ADCs #1-6 in Antigen +ve and Antigen −ve cell lines

| ADC# | N87 (+ve) | MDA-MB-361-DYT2 | HT29 (−ve) | A375 (+ve) | PC3MM2 (+ve) | PC3 (−ve) | HL-60 (+ve) | HEL 92.1.7 (+ve) | Raji (−ve) |
|---|---|---|---|---|---|---|---|---|---|
| ADC#1 |  |  |  | 0.9 | 0.5 | >1000 |  |  |  |
| ADC#2 | 0.6 | >470 | >470 |  |  |  |  |  |  |
| ADC#3 | 0.4 | >470 | >470 |  |  |  |  |  |  |
| ADC#4 |  |  |  |  |  |  | 1.7 | <0.5 | 3040.7 |
| ADC#5 |  |  |  |  |  |  | 1.5 | 0.6 | >10,000 |
| ADC#6 |  |  |  |  |  |  | 2.1 | 0.6 | >10,000 |

The following ADC's are prepared, including the linker/payloads shown in Tables 4 and 5 conjugated to antibodies of interest using the appropriate conjugation method:

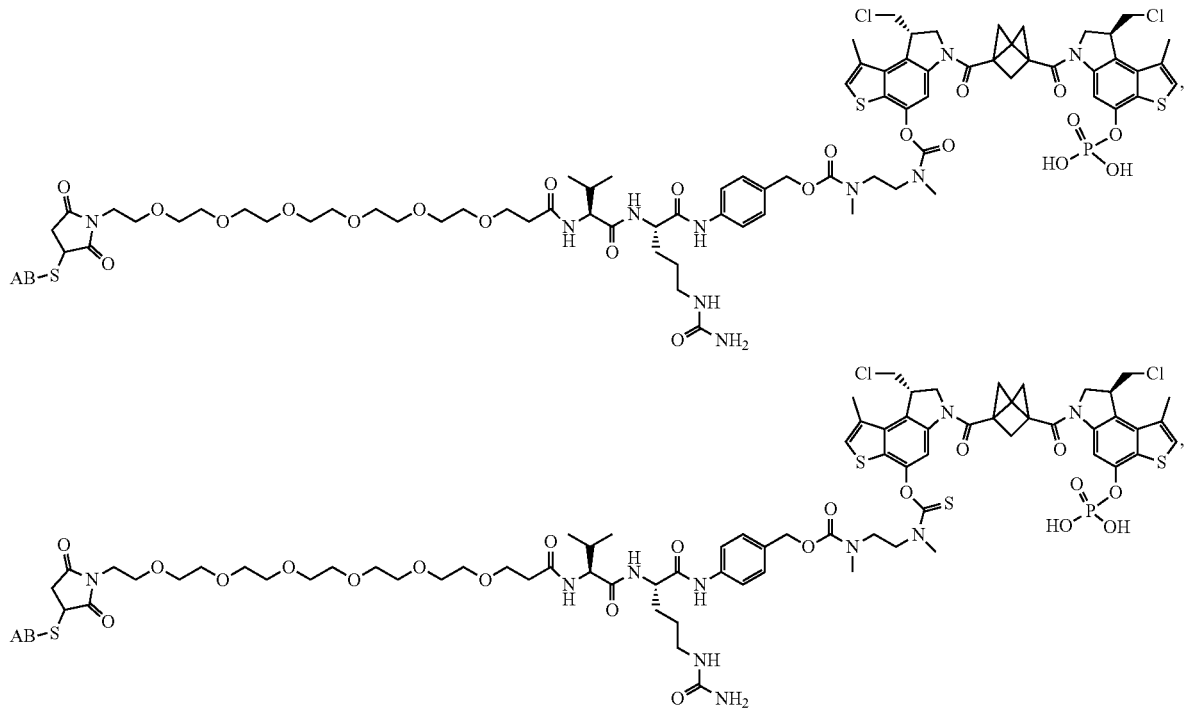

209
210
-continued
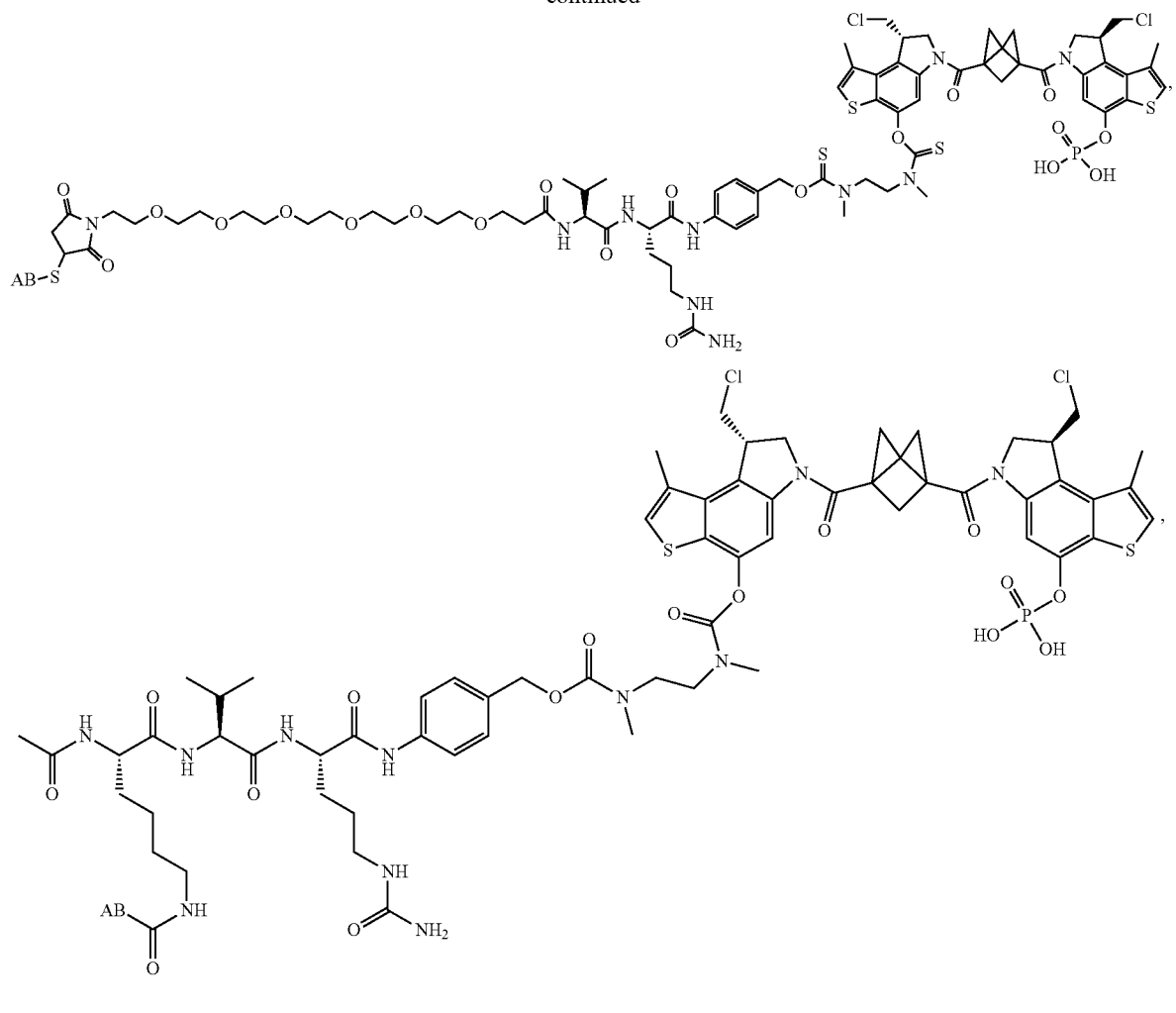
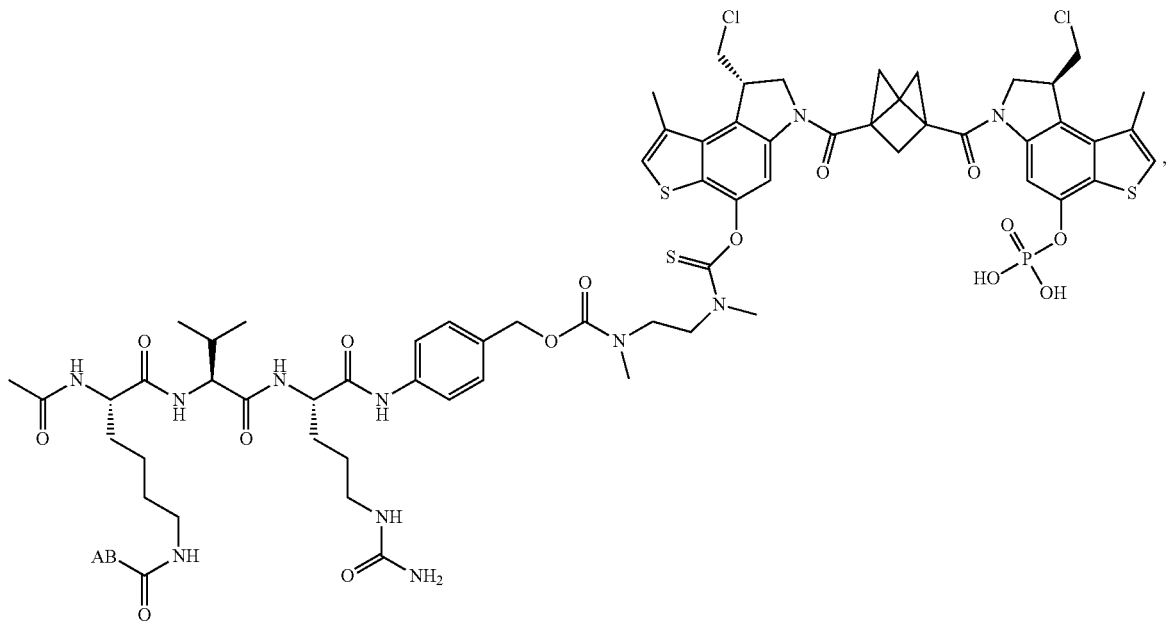

211 212
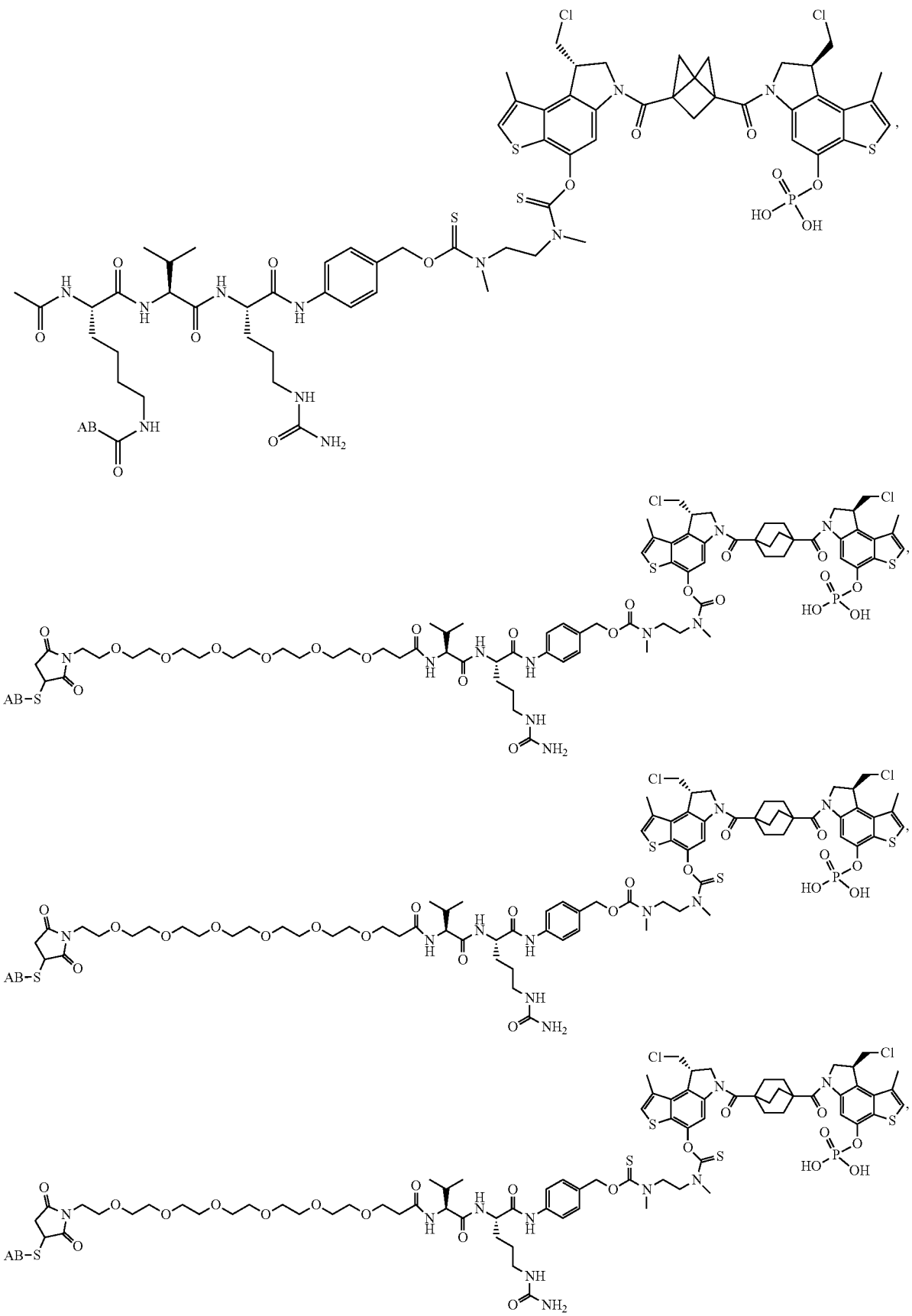

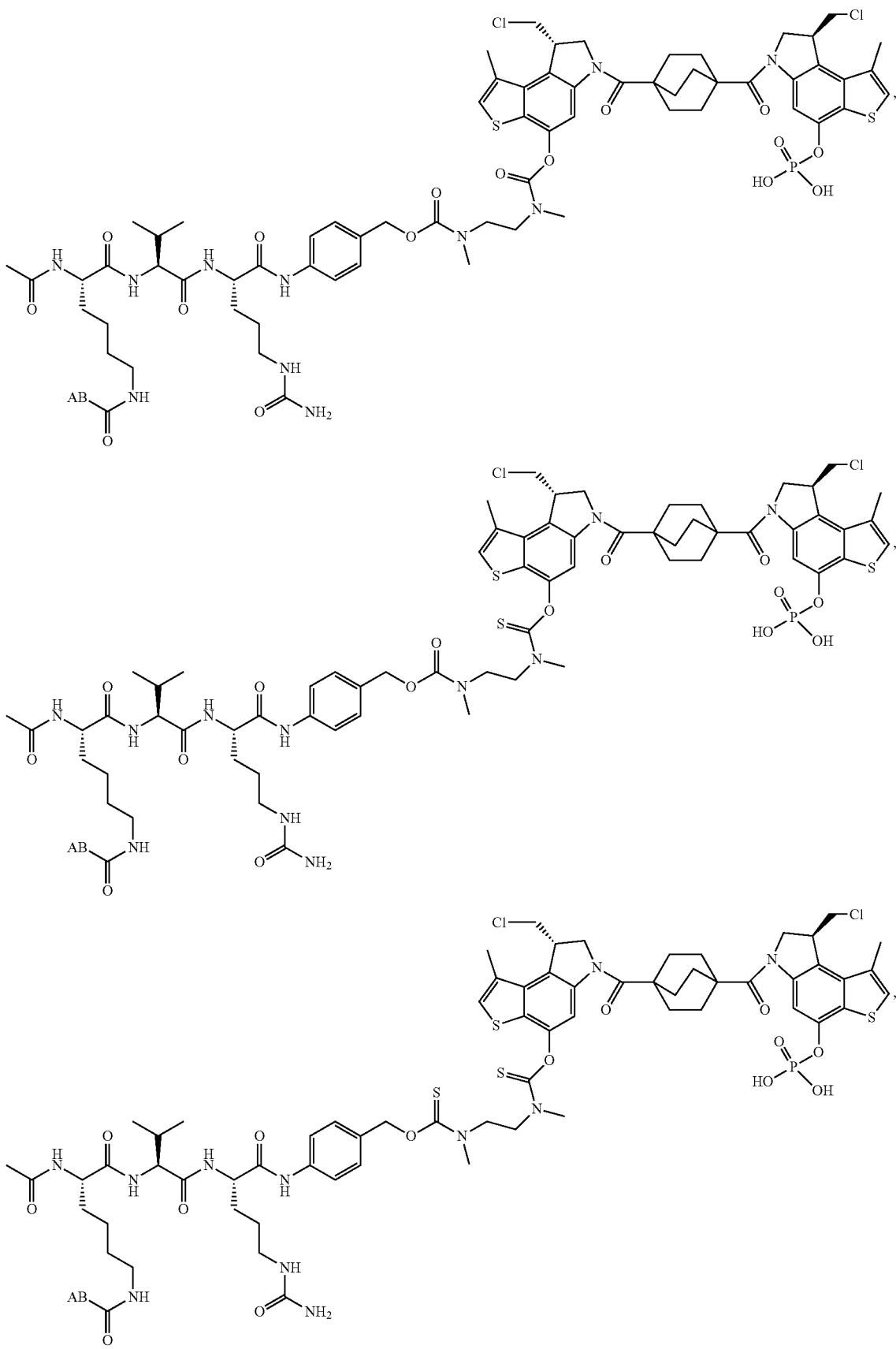

215 216
-continued
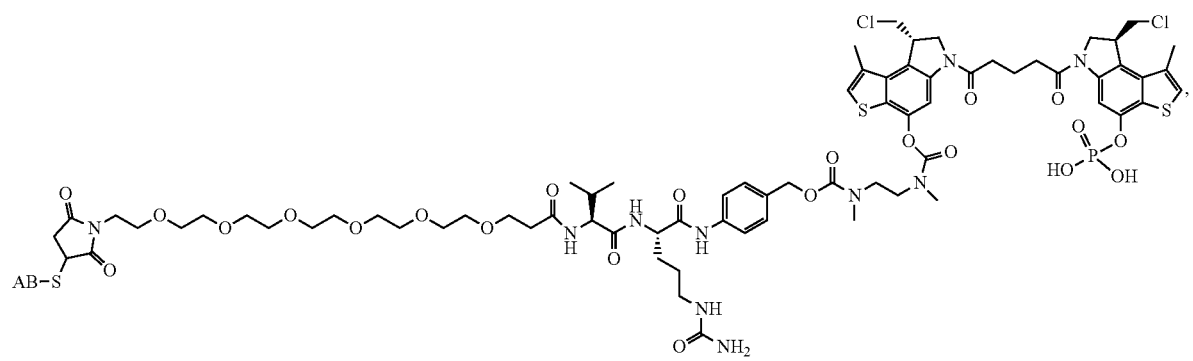
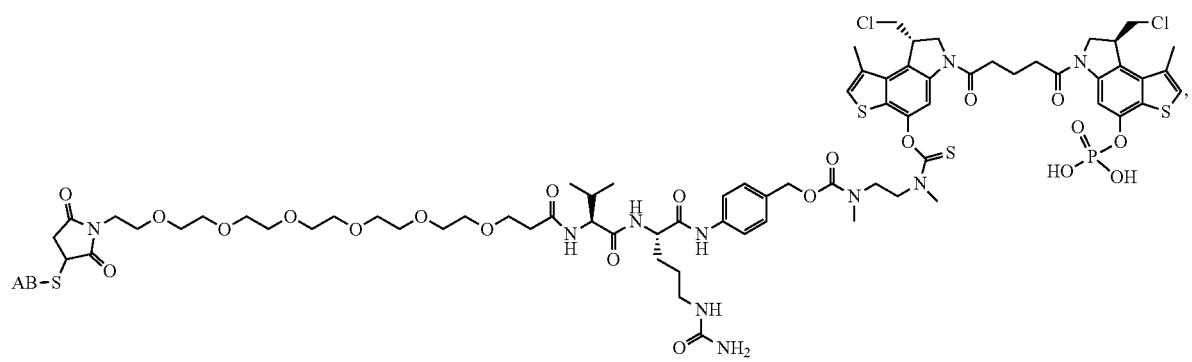
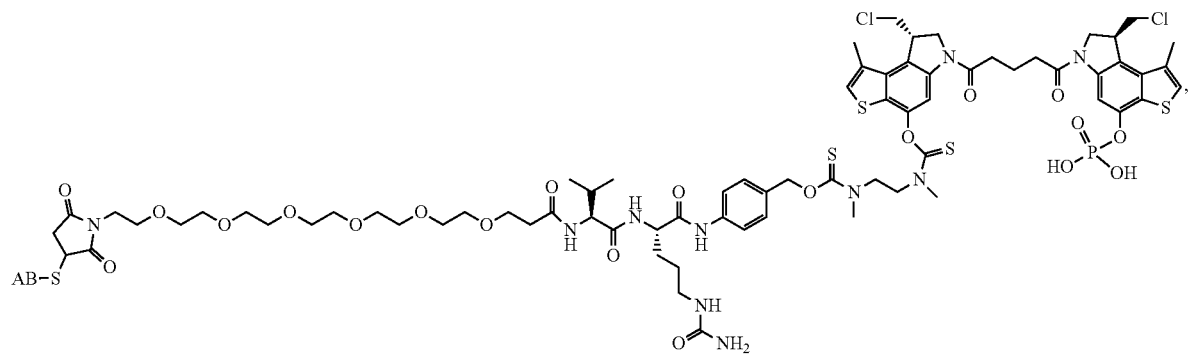
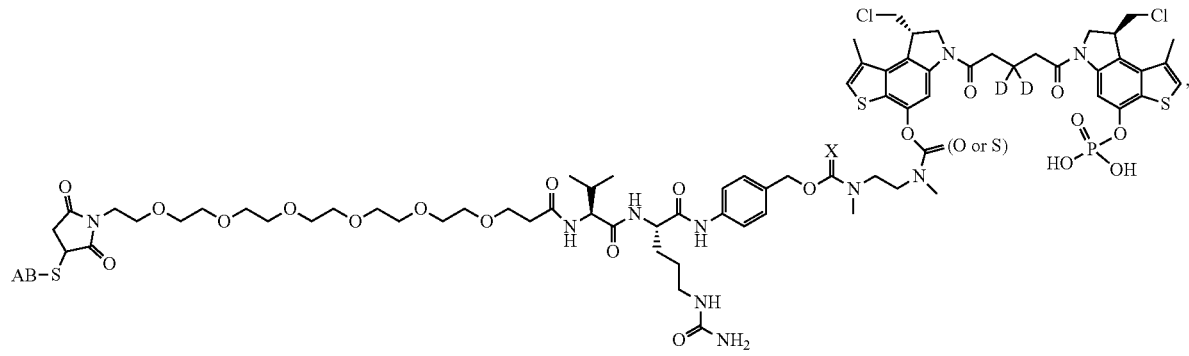

217
-continued
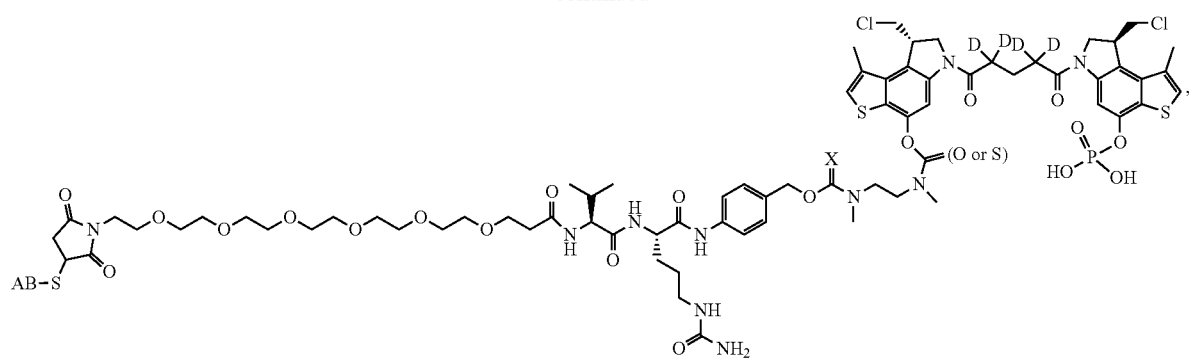
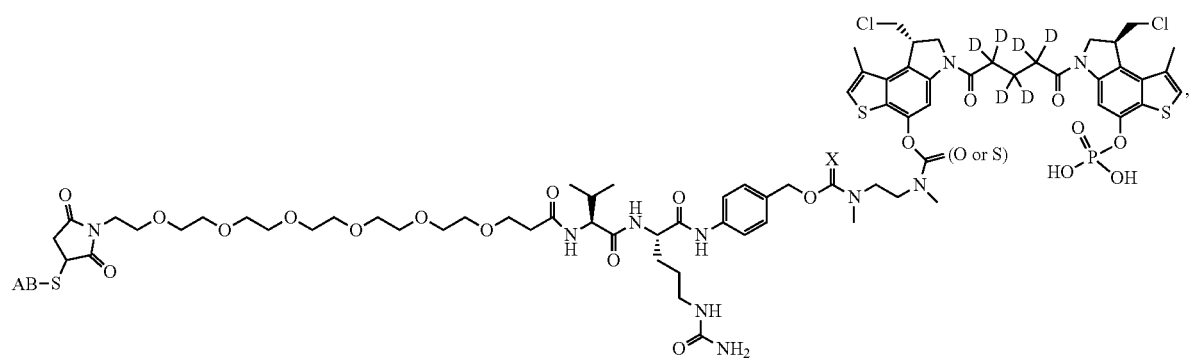
218
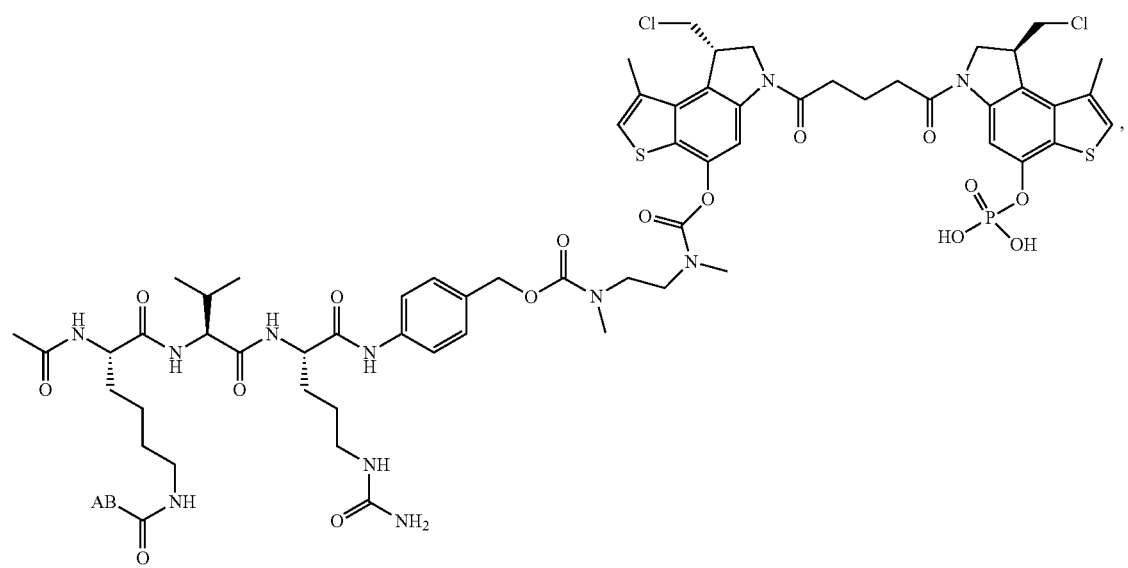

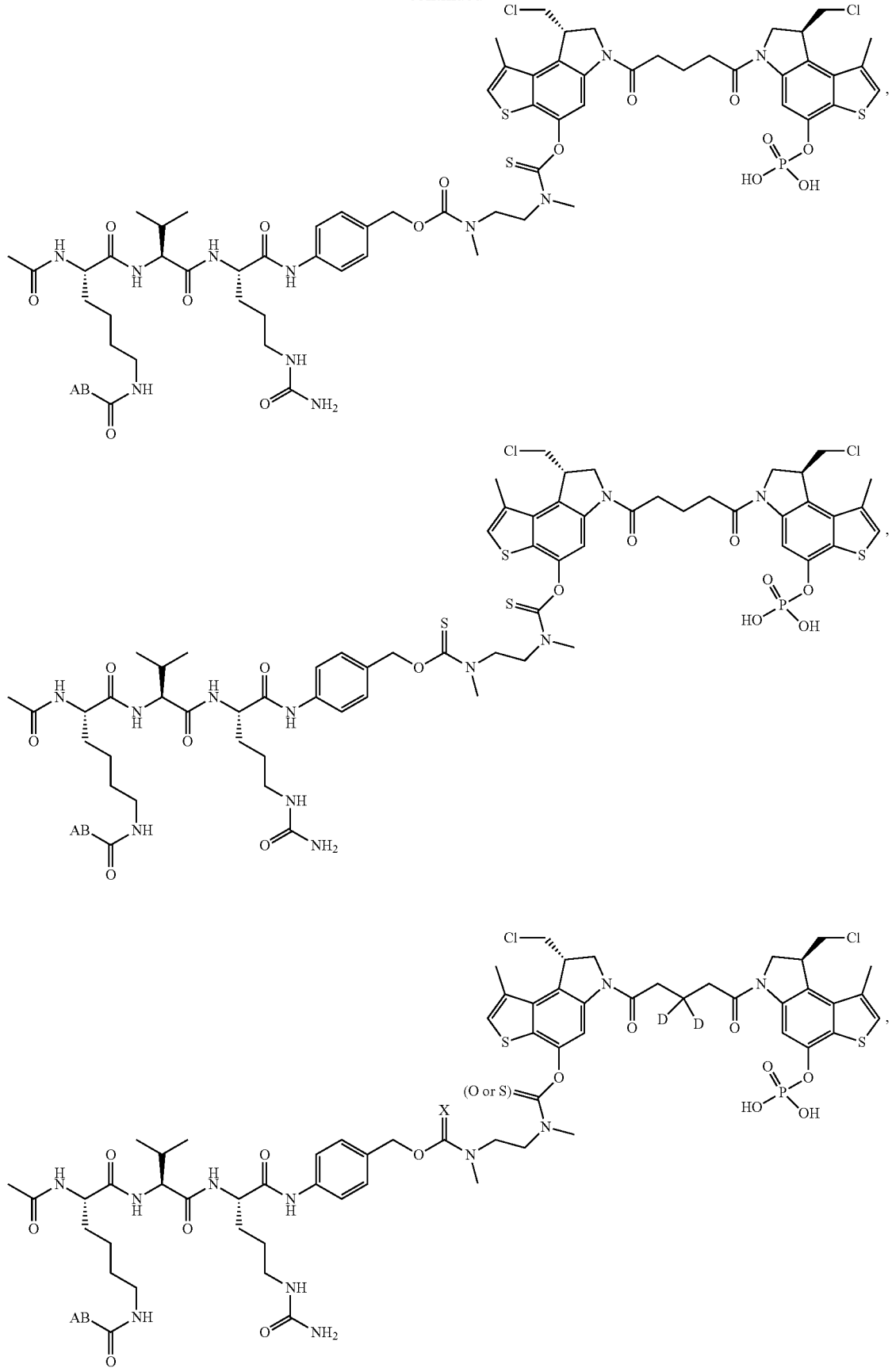

-continued
221
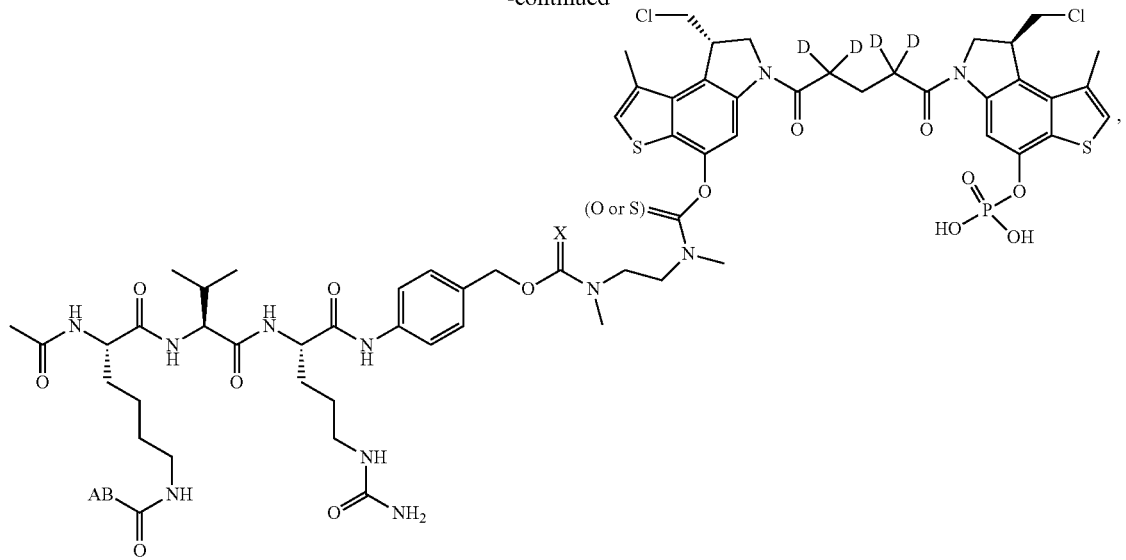
222
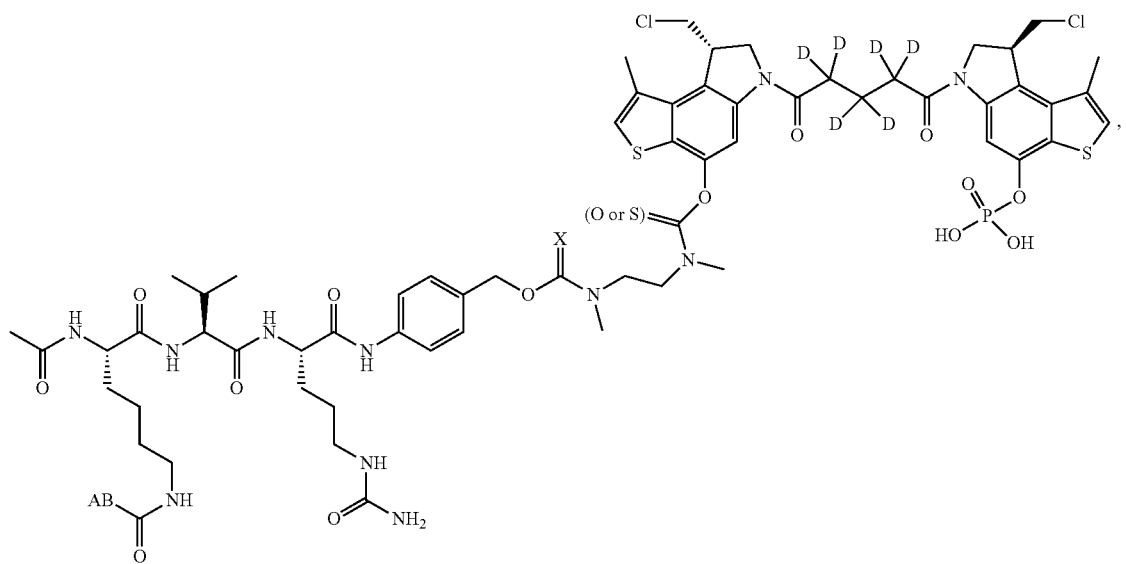
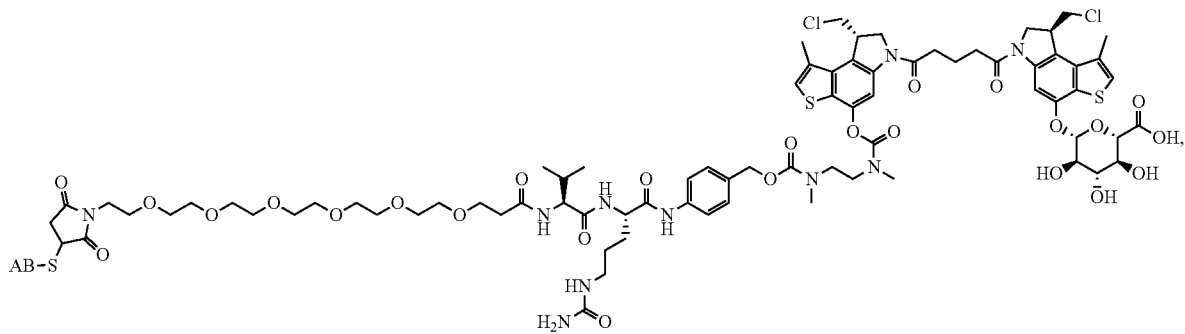

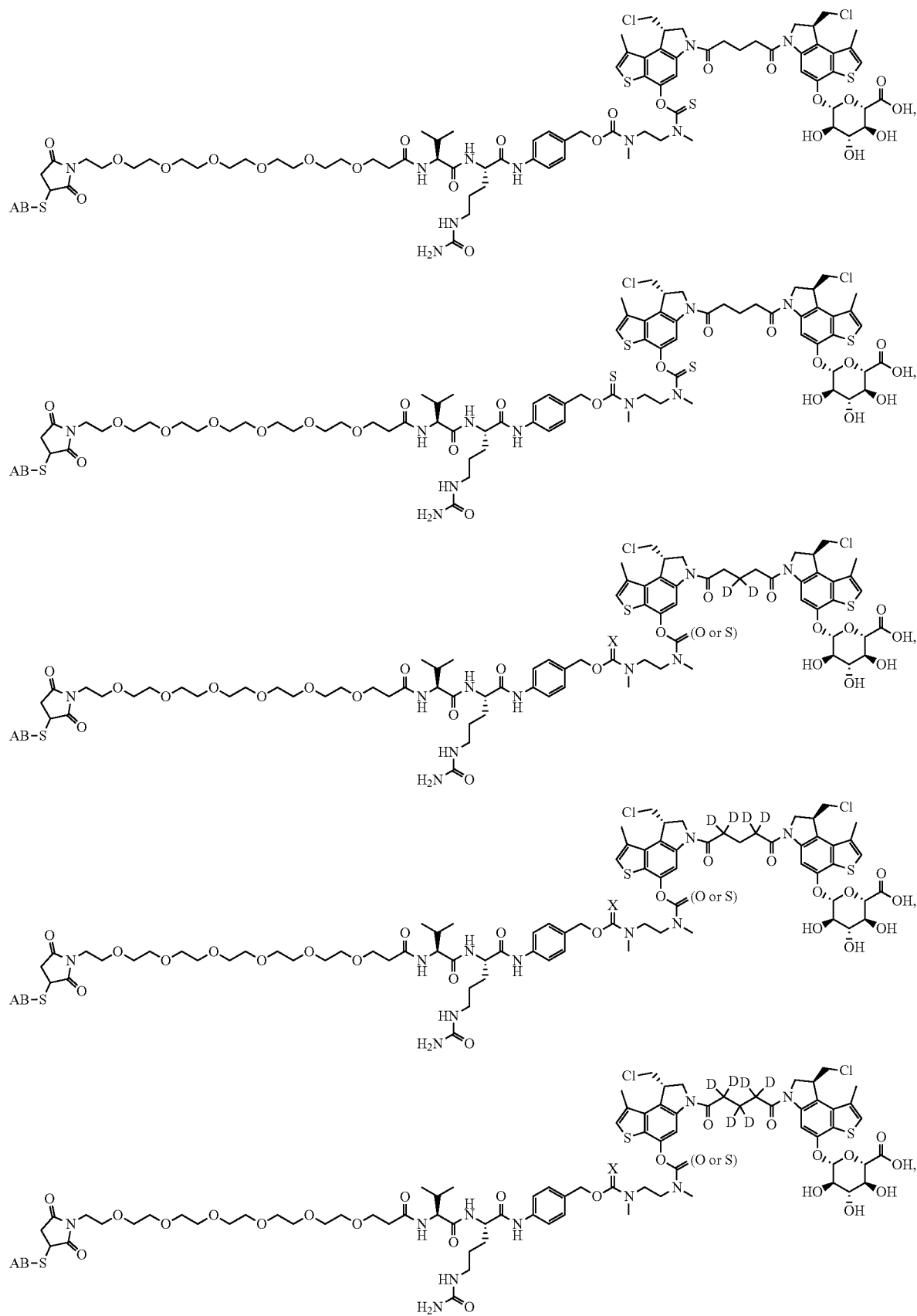

225
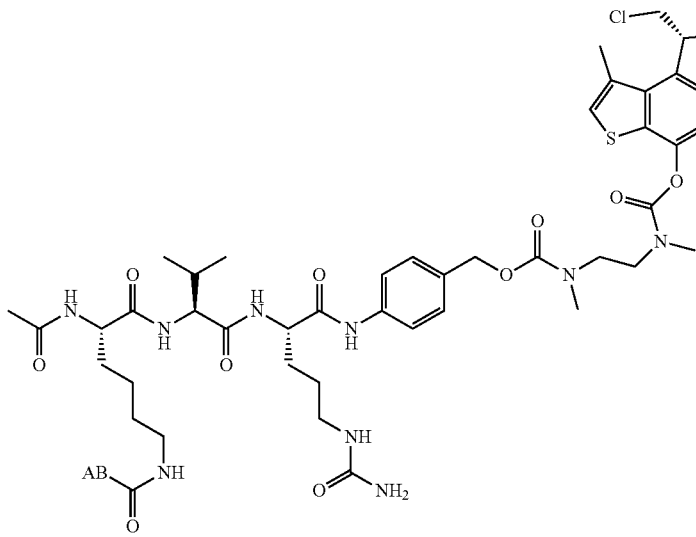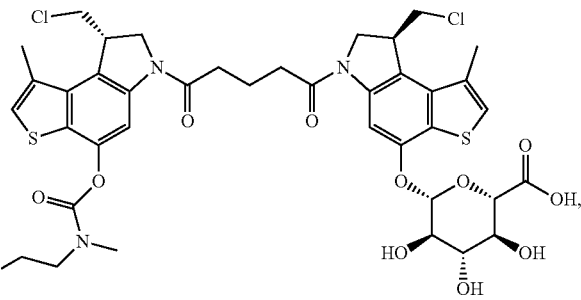
226
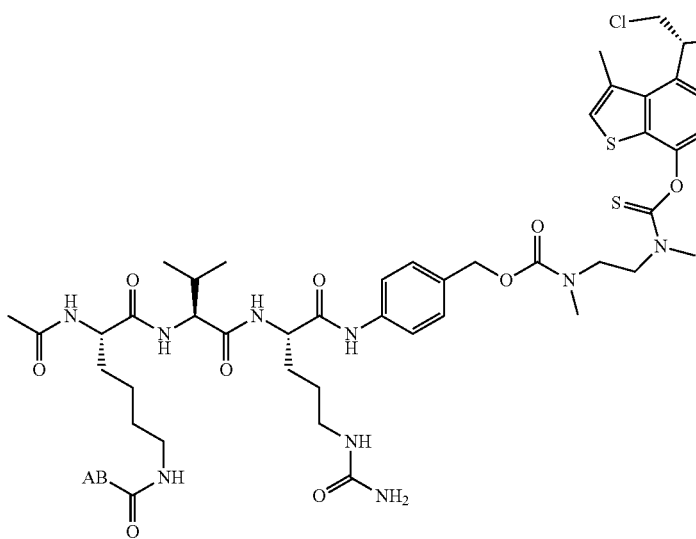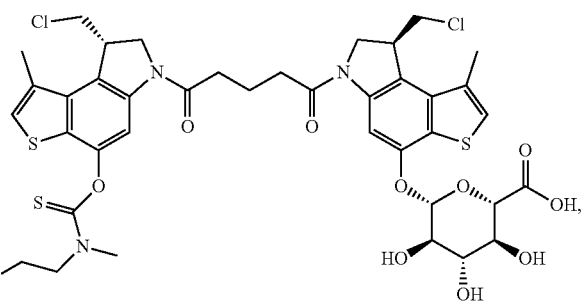
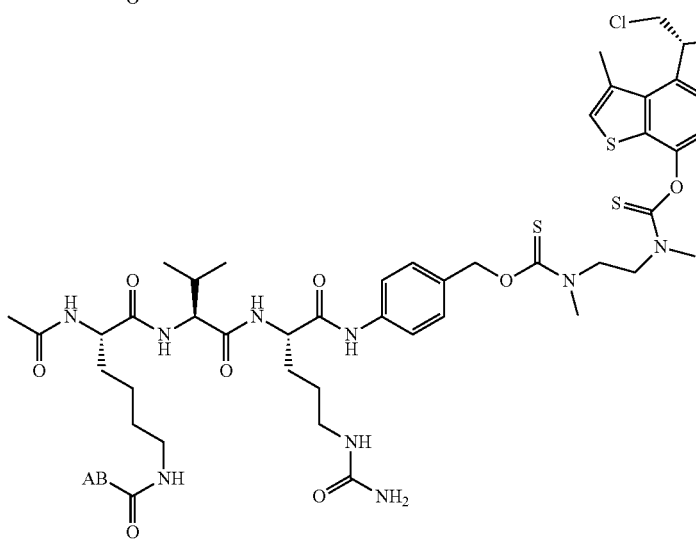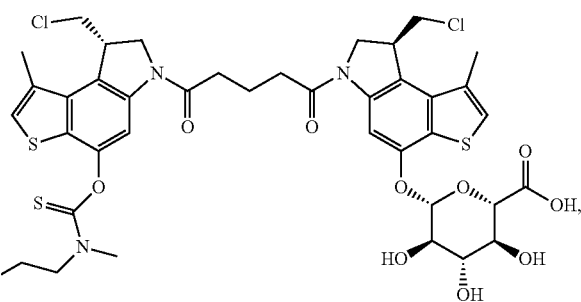

227
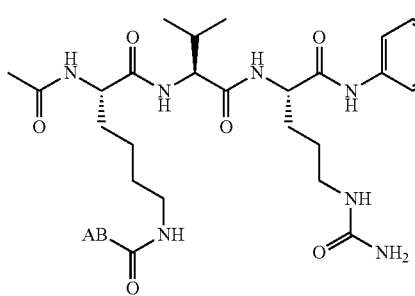
228
-continued
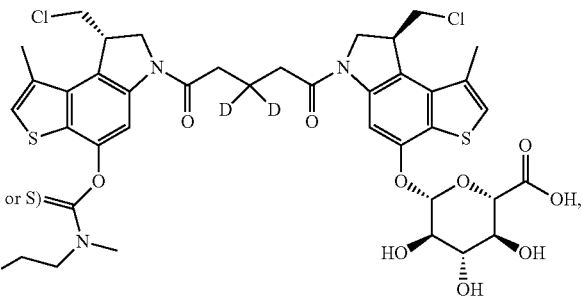
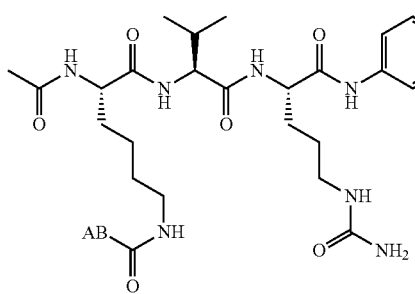
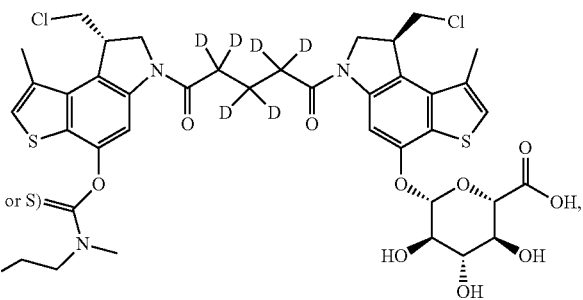
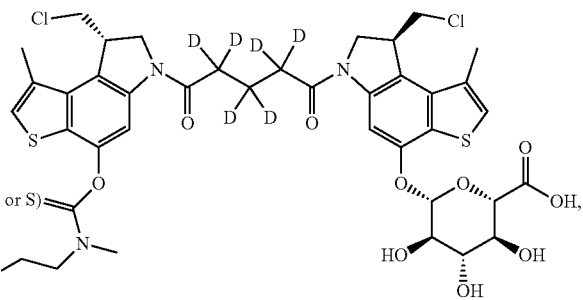
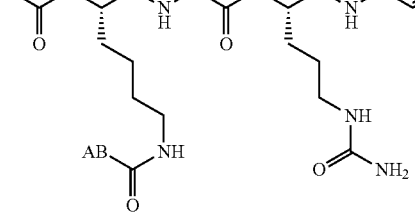

229
230
-continued
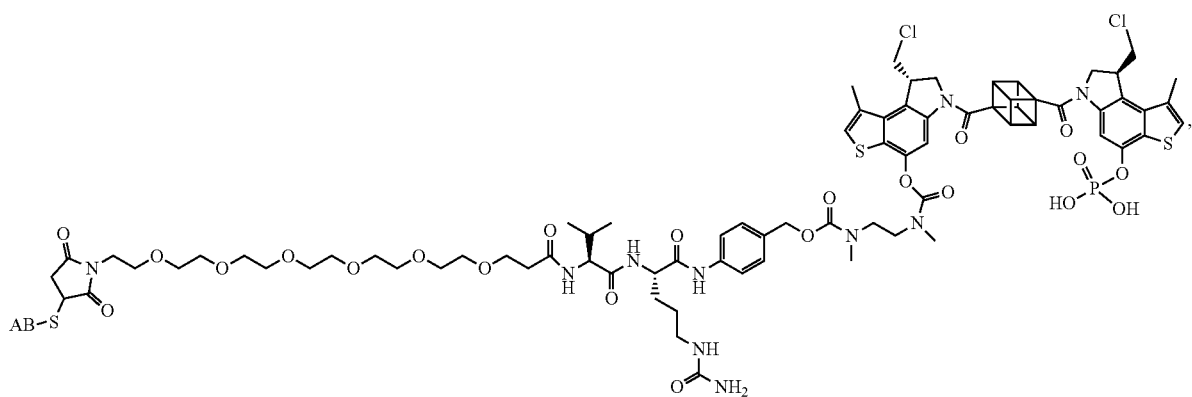
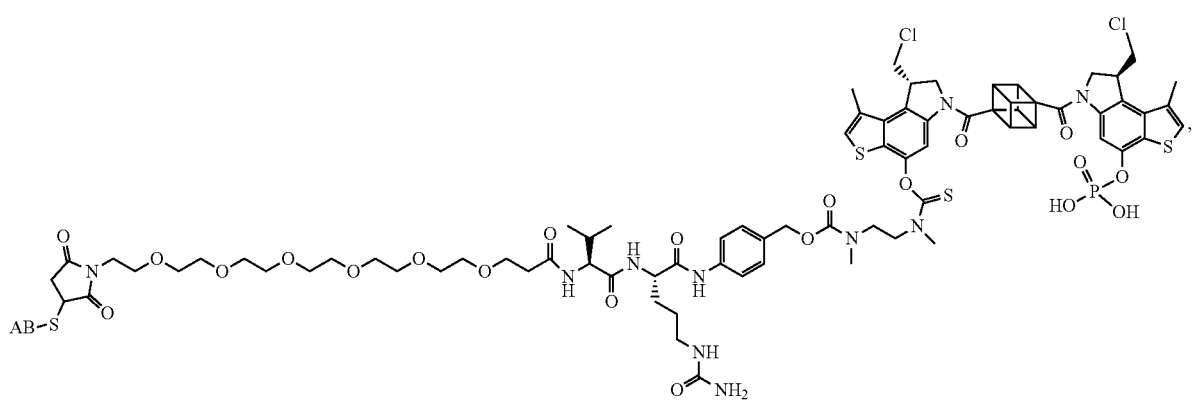
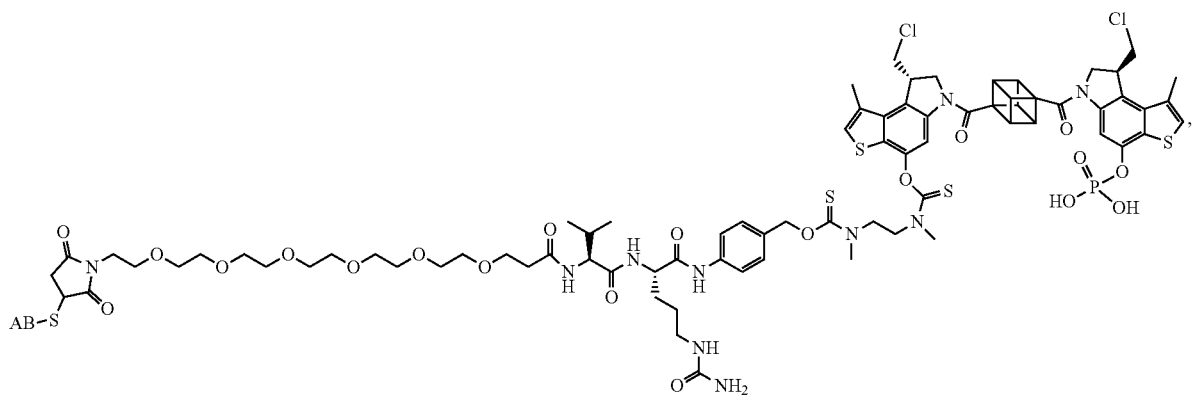

231
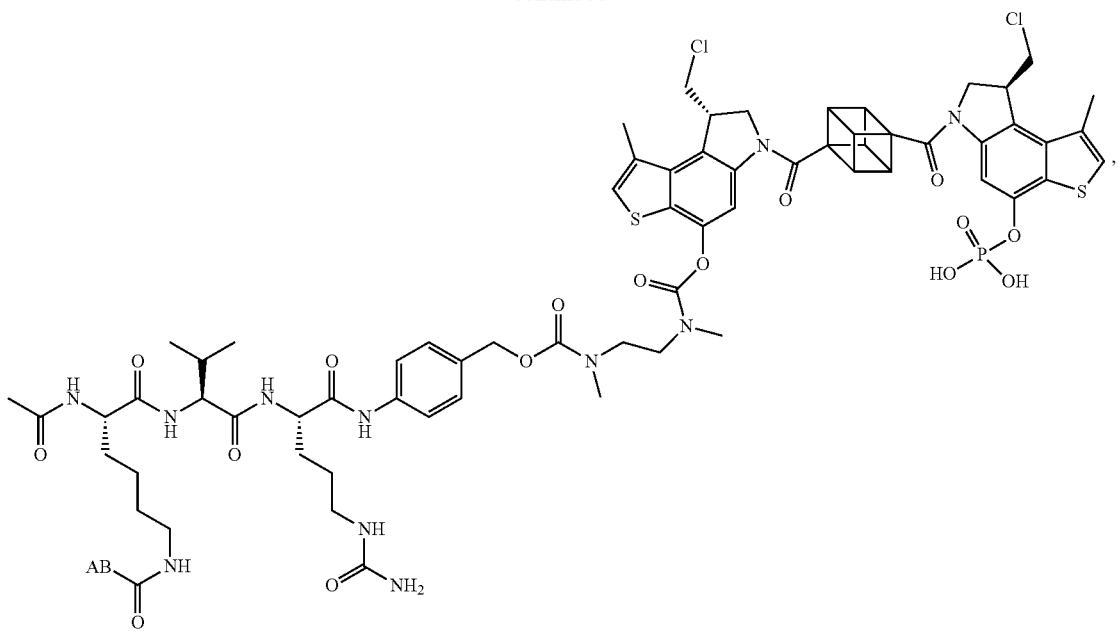
232
-continued
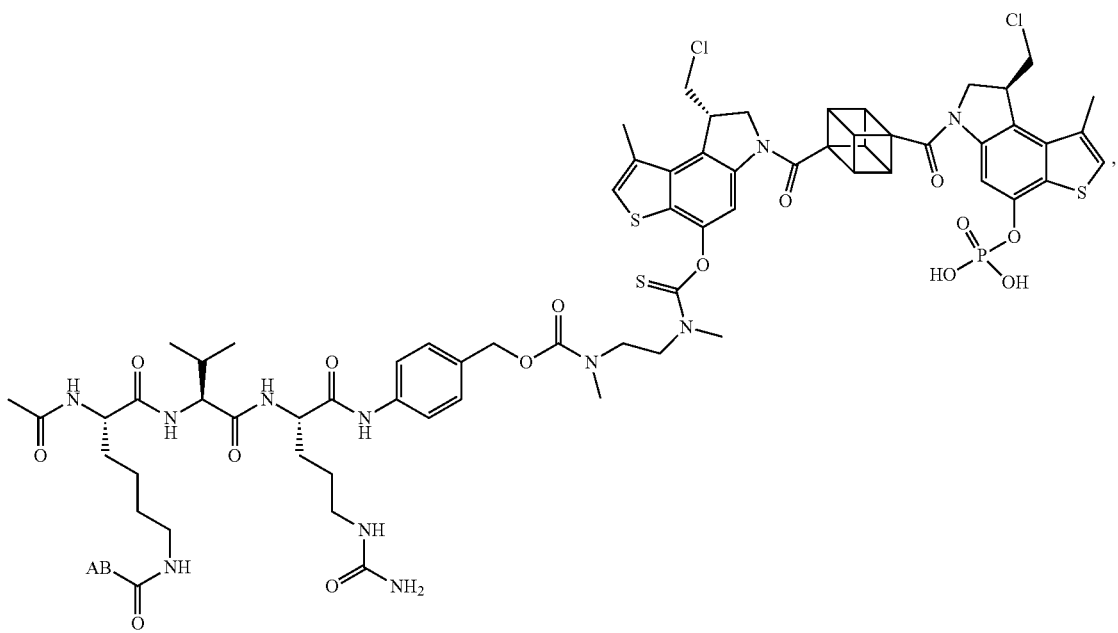

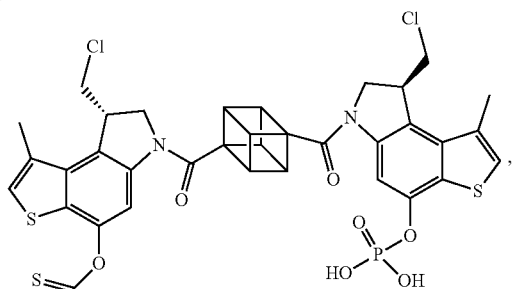
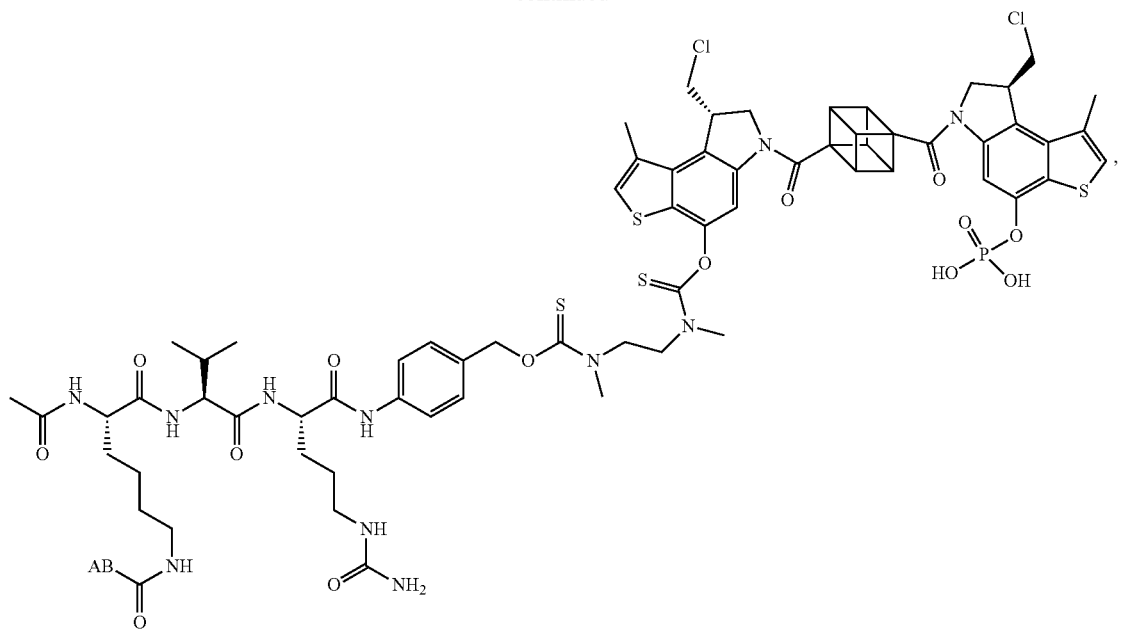
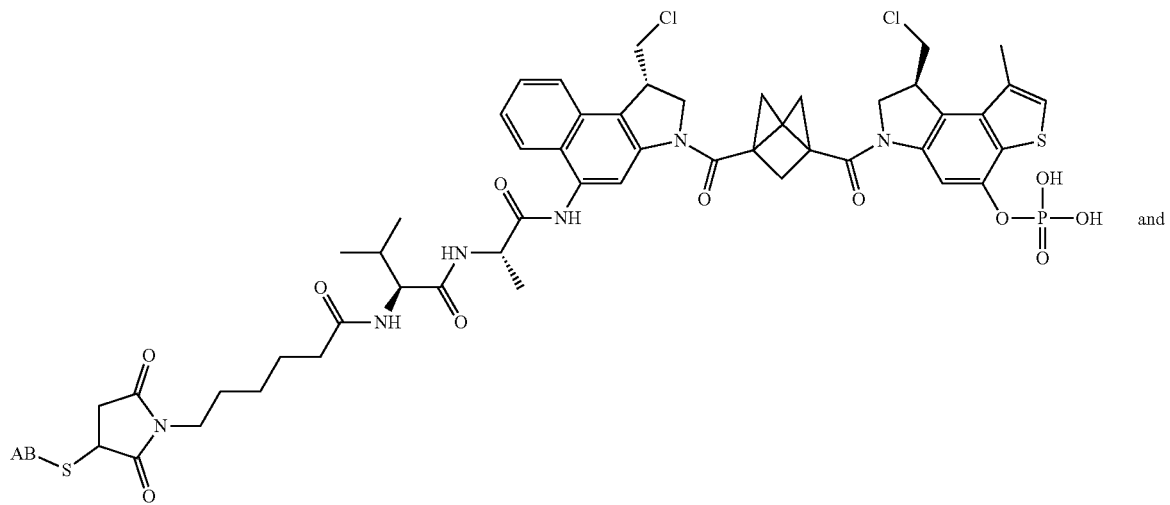
and
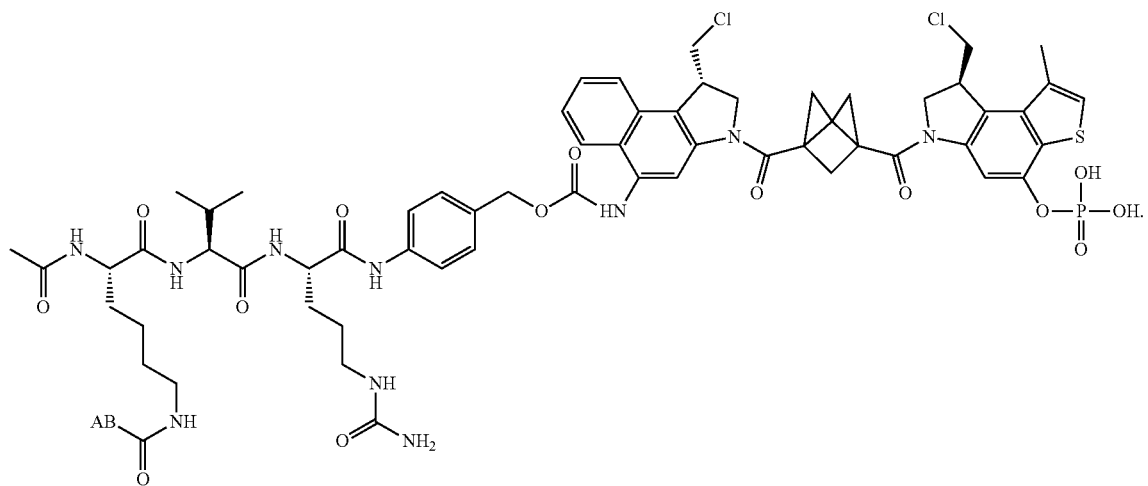

We claim:
1. A method of treating cancer comprising administering to a patient in need thereof a therapeutically effective amount of a compound of Formula (IIIA):

$$AB\text{-}(L\text{-}P)_{1\text{-}20} \quad \text{(IIIA)}$$

or a pharmaceutically acceptable salt or solvate thereof, wherein:
AB is an antibody:
P is:

$$F^1\text{-}L^1\text{-}T\text{-}L^2\text{-}F^2$$

wherein:
$F^1$ and $F^2$ are each independently selected from ring systems A, B, C and D:

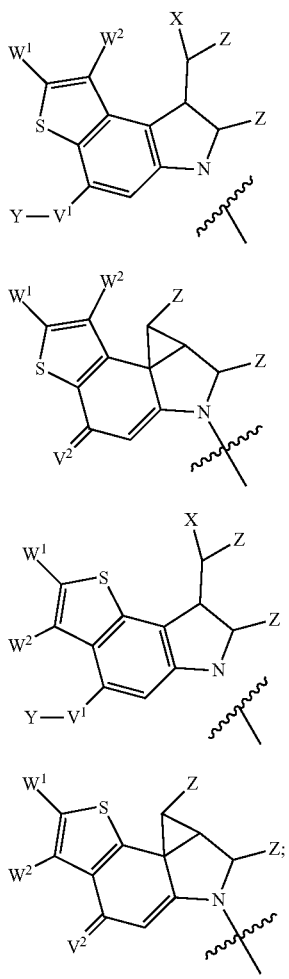

(Ring System A)

(Ring System B)

(Ring System C)

(Ring System D)

where:
each R is independently selected from the group consisting of H, —$C_1$-$C_{20}$ alkyl, —$C_2$-$C_6$ alkenyl, —$C_2$-$C_6$ alkynyl, halo, deuterium, hydroxyl, alkoxy, —$NH_2$, —NH($C_1$-$C_8$ alkyl), —N($C_1$-$C_8$ alkyl)$_2$, —$NO_2$, —$C_6$-$C_{14}$ aryl and —$C_6$-$C_{14}$ heteroaryl, or wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —$NO_2$ or —$C_1$-$C_{10}$ heterocyclyl, for each ring system in which R appears:

each $V^1$ is independently a bond, O, N(R) or S, for each ring system in which $V^1$ appears:

each $V^2$ is independently O, N(R) or S, for each ring system in which $V^2$ appears:

$W^1$ and $W^2$ are each independently H, —$C_1$-$C_5$ alkyl, -phenyl, —C(O)OR, —C(O)SR, —C(O)NHN(R)$_2$ or —C(O)N(R)$_2$ for each ring system in which $W^1$ and $W^2$ appear;

each X is independently selected from —OH, —O-acyl, azido, halo, cyanate, thiocyanate, isocyanate, thioisocyanate, or

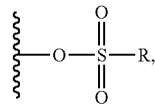

for each ring system in which X appears;

each Y is independently selected from a bond, H, —C(O)$R^A$, —C(S)$R^A$, —C(O)O$R^A$, —S(O)$_2$O$R^A$, —C(O)N($R^A$)$_2$, —C(S)N($R^A$)$_2$, glycosyl, —$NO_2$, —P(O)(O$R^A$)$_2$, an amino acid and a peptide for each ring system in which Y appears, wherein each $R^A$ is independently selected from H, —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl, —$C_1$-$C_{20}$ alkylN(R)$_2$, —$C_1$-$C_{20}$ alkylene, —$C_1$-$C_8$ heteroalkylene, —$C_6$-$C_{14}$ arylene, aralkylene, —$C_1$-$C_{10}$ heterocyclo, —$C_3$-$C_8$ carbocyclo and —$C_1$-$C_{20}$ alkylN(R)—, and $R^F$ where said $R^A$ is optionally substituted with 1 to 3 substituents independently selected from R, and wherein at least one Y-containing Ring System is present and is divalent and is bonded to L, $R^F$ is —N($R^6$)QN($R^5$)C(O)— and is bonded to L at the carbonyl adjacent N($R^5$), wherein $R^5$ and $R^6$ are each independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl and —$C_3$-$C_8$ carbocyclyl, or $R^5$ or $R^6$ loins with a substituted carbon on Q to form a —$C_1$-$C_{10}$ heterocyclic or —$C_6$-$C_{14}$ heteroaryl ring, or $R^5$ and $R^6$ join together to form a —$C_1$-$C_{10}$ heterocyclic or —$C_6$-$C_{14}$ heteroaryl ring system, and where Q is —$C_1$-$C_8$ alkylene-, —$C_1$-$C_8$ heteroalkylene-, —$C_6$-$C_{14}$ arylene-, -aralkylene-, —$C_1$-$C_{10}$ heterocyclo- or —$C_3$-$C_8$ carbocyclo-, wherein Q, $R^5$ and $R^6$ are each independently optionally substituted with 1 to 3 substituents independently selected from R:

each Z is independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo, and wherein said $C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo are each optionally substituted with 1 to 3 substitutents independently selected from R, for each ring system in which Z appears:

$L^1$ and $L^2$ are each independently selected from a direct bond

T is
—C(A$^1$)X$^1$-T$^2$-X$^1$C(B$^1$)—, where T$^2$ is:

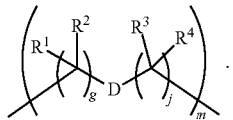

wherein each X$^1$ is independently a bond, —NR$^E$—, —O— or —S—, wherein A$^1$ and B$^1$ are each independently =O or =S, wherein R$^1$, R$^2$, R$^3$, and R$^4$ are each independently R$^E$ or R$^1$ and R$^2$ form a ring system, or R$^3$ and R$^4$ form a ring system, or both R$^1$ and R$^2$, and R$^3$ and R$^4$, each independently form ring systems, or R$^1$ and R$^3$ form a ring system, or R$^2$ and R$^4$ form a ring system, or both R$^1$ and R$^3$, and R$^2$ and R$^4$, each independently form ring systems, where said ring systems are independently selected from —C$_1$-C$_{10}$ heterocyclyl or —C$_3$-C$_8$ carbocyclycl, or R$^1$, R$^2$, R$^3$ and R$^4$ are each bonds to different carbons on D, wherein q and j are each independently an integer from 0 to 50 and m is an integer from 1 to 50, and wherein D is selected from the group consisting of —C$_1$-C$_{10}$ heterocyclo and —C$_3$-C$_8$ carbocyclo, where said —C$_1$-C$_{10}$ heterocyclo and —C$_3$-C$_8$ carbocyclo are optionally substituted with —R$^E$, —C(O)R$^E$, —C(O)OR$^E$, —N(R$^E$)$_2$, —N(R)C(O)R$^E$ or —N(R)C(O)OR$^E$, and D is additionally optionally substituted by 1 to 2 R, wherein each R$^E$ is independently selected from the group consisting of H, —C$_1$-C$_8$ alkyl, —C$_1$-C$_8$ heteroalkyl, -aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, and —C(O)-halo, and wherein each R$^E$ is optionally substituted with 1 to 3 substitutents independently selected from R;

L is L$^A$-L$^B$-(L$^C$)$_{1-3}$ wherein an L$^C$ is bound to Y;
L$^A$ is selected from: a bond to AB, —NR-(bond to AB), -heteroaryl-(bond to AB),

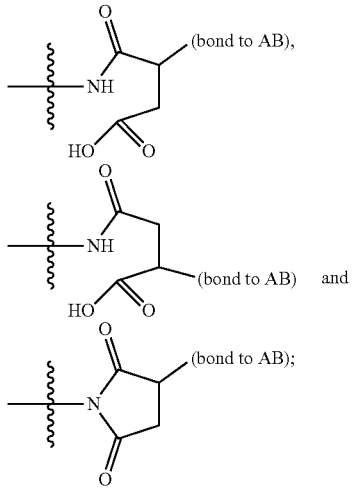

L$^B$ is L$^{B1}$-L$^{B2}$-L$^{B3}$
wherein L$^{B1}$ is absent or is one or more components selected from the group consisting of —C(O)—, —C(S)—, —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-6}$—, —C(O)C$_1$-C$_6$alkylNRC(O)—, —C(O)C$_1$-C$_6$alkyl(OCH$_2$CH$_2$)$_{1-6}$—, —C$_1$-C$_6$alkyl(OCH$_2$CH$_2$)$_{1-6}$-C(O)—, —C$_1$-C$_6$alkyl-S—S—C$_1$-C$_6$alkylNRC(O)CH$_2$—, —C$_1$-C$_6$alkyl(OCH$_2$CH$_2$)$_{1-6}$NRC(O)CH$_2$—, —C(O)C$_1$-C$_6$alkyl-NRC(O)C$_{1-6}$alkyl-, —N=CR-phenyl-O—C$_1$-C$_6$alkyl-, —N=CR-phenyl-O—C$_1$-C$_6$alkyl-C(O)—, —C(O)—C$_1$-C$_6$alkyl(OCH$_2$CH$_2$)$_{1-6}$NRC(O)—, —C(O)C$_1$-C$_6$alkyl-phenyl(NR—C(O)C$_1$-C$_6$alkyl)$_{1-4}$-, —C(O)C$_1$-C$_6$alkyl(OCH$_2$CH$_2$)$_{1-6}$—NRC(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl- and (—CH$_2$—CH$_2$—O—)$_{1-20}$;

L$^{B2}$ is AA$_{0-12}$, wherein AA is a natural amino acid- or a non-natural amino acid;

L$^{B3}$ is p-aminobenzoic acid, p-aminobenzyloxycarbonyl, —C(O)(CH$_2$)$_{0-50}$C(O)— or absent, L$^C$ is absent or is independently selected from the group consisting of —C$_1$-C$_6$alkylene-, —NRC$_3$-C$_8$-heterocyclylNR—, —NRC$_3$-C$_3$-carbocyclylNR—, —NRC$_1$-C$_6$alkylNR—, —NRC$_1$-C$_6$alkylene-, —S—, —NR—, —NRNR—, —O(CR$_2$)$_{1-4}$S—S(CR$_2$)$_{1-4}$N(R)—, —NRC$_1$-C$_6$-alkylenephenyleneNR—, —NRC$_1$-C$_6$alkylenephenyleneSO$_2$NR—, —OC$_1$-C$_6$alkylS-SC$_1$-C$_6$alkylC(COOR)NR—,

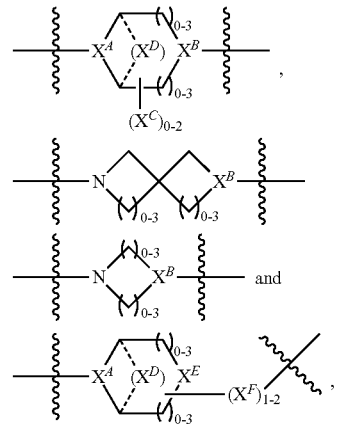

wherein
X$^A$ is CR or N,
X$^B$ is CH, CR(C(R)$_2$)$_{1-3}$NR, CR(C(R)$_2$)$_{1-30}$, CR(C(R)$_2$)$_{1-3}$C(O)NR, CR—(C(R)$_2$)$_{1-3}$C(O)NRNR, CR(C(R)$_2$)$_{1-3}$SO$_2$NR, CR(C(R)$_2$)$_{1-3}$NRNR, CR(C(R)$_2$)$_{1-3}$NRC(O) or N,
each X$^C$ is R;
each X$^D$ is —(CH$_2$)$_{1-5}$—, or is absent;
X$^E$ is O, S, C(R)$_2$, C(R)(C(R)$_2$)$_{1-3}$—NR$_2$ or NR, and
each X$^F$ is (C(R)$_2$)$_{1-3}$—NR or C(R)$_2$—(C(R)$_2$)$_{1-3}$—O.

2. A method of treating cancer comprising administering to a patient in need thereof a therapeutically effective amount of a compound of Formula (IIIB):

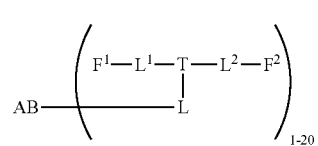

(Formula IIIB)

or a pharmaceutically acceptable salt or solvate thereof, wherein:

AB is an antibody;

$F^1$ and $F^2$ are each independently selected from ring systems A, B, C and D:

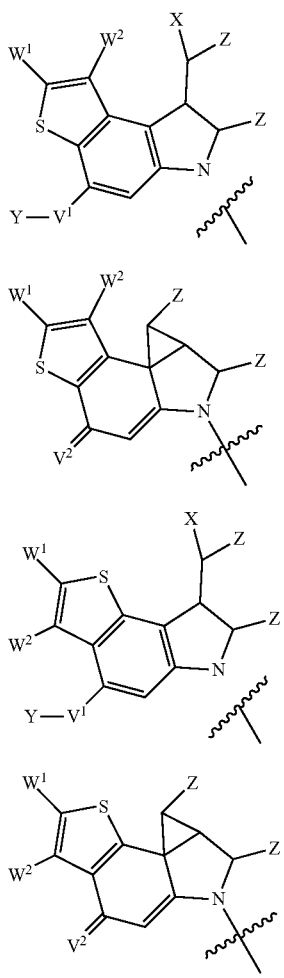

(Ring System A)

(Ring System B)

(Ring System C)

(Ring System D)

where:

each R is independently selected from the group consisting of H, —$C_1$-$C_{20}$ alkyl, —$C_2$-$C_6$ alkenyl, —$C_2$-$C_6$ alkynyl, halo, deuterium, hydroxyl, alkoxy, —$NH_2$, —NH($C_1$-$C_8$ alkyl), —N($C_1$-$C_8$ alkyl)$_2$, —$NO_2$, —$C_6$-$C_{14}$ aryl and —$C_6$-$C_{14}$ heteroaryl, or wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —$NO_2$ or —$C_1$-$C_{10}$ heterocyclyl, for each ring system in which R appears:

each $V^1$ is independently a bond, O, N(R) or S, for each ring system in which $V^1$ appears;

each $V^2$ is independently O, N(R) or S, for each ring system in which $V^2$ appears;

$W^1$ and $W^2$ are each independently H, —$C_1$-$C_5$ alkyl, -phenyl, —C(O)OR, —C(O)SR, —C(O)NHN(R)$_2$ or —C(O)N(R)$_2$ for each ring system in which $W^1$ and $W^2$ appear;

each X is independently —OH, —O-acyl, azido, halo, cyanate, thiocyanate, isocyanate, thioisocyanate, or

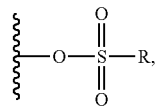

for each ring system in which X appears:

each Y is independently selected from the group consisting of H, —$C_1$-$C_6$ alkyl-$R^A$ —C(O)$R^A$, —C(S)$R^A$, —C(O)O$R^A$, —S(O)$_2$O$R^A$, —C(O)N($R^A$)$_2$, —C(S)N($R^A$)$_2$, glycosyl, —NO, —PO(O$R^A$)$_2$, an amino acid and a peptide for each ring system in which Y appears, wherein each $R^A$ is independently selected from the group consisting of H, —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl and —$C_1$-$C_{20}$ alkylN(R)$_2$, wherein said —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl and —$C_1$-$C_{20}$ alkylN(R)$_2$ are optionally substituted with 1 to 3 substitutents independently selected from R;

each Z is independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo, and wherein said $C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo are each optionally substituted with 1 to 3 substituents independently selected from R, for each ring system in which Z appears;

$L^1$ and $L^2$ are each independently selected from a direct bond

T is:

$C(A^1)X^1$-$T^2$-$X^1C(B^1)$—, where $T^2$ is:

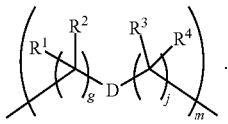

wherein each $X^1$ is independently a bond, —$NR^E$—, —O— or —S—, wherein $A^1$ and $B^1$ are each independently =O or =S, wherein $R^1$, $R^2$, $R^3$, and $R^4$ are each independently $R^E$ or $R^1$ and $R^2$ form a ring system, or $R^3$ and $R^4$ form a ring system, or both $R^1$ and $R^2$, and $R^3$ and $R^4$ each independently form ring systems, or $R^1$ and $R^3$ form a ring system, or $R^2$ and $R^4$ form a ring system, or both $R^1$ and $R^3$, and $R^2$ and $R^4$ each independently form ring systems, where the ring systems are independently selected from —$C_1$-$C_{10}$ heterocyclyl or —$C_3$-$C_8$ carbocyclycl, or $R^1$, $R^2$, $R^3$ and $R^4$ are each bonds to different carbons on D, wherein q and j are each independently an integer from 0 to 50 and m is an integer from 1 to 50, and wherein D is selected from the group consisting of —$C_1$-$C_{10}$ heterocyclo and —$C_3$-$C_8$ carbocyclo, where said —$C_1$-$C_{10}$ heterocyclo and —$C_3$-$C_8$ carbocyclo are substituted with one member of the group selected from N($R^E$)C(O)— where the carbonyl is bonded to L, and —C(O)— where the carbonyl is bonded to L, and additionally optionally substituted by 1 to 2 R;

where each $R^E$ is independently selected from the group consisting of H, —$C_1$-$C_8$ alkyl, —$C_1$-$C_8$ heteroalkyl, -aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, and —C(O)-halo, and wherein each $R^E$ is optionally substituted with 1 to 3 substitutents independently selected from R:

L is $L^A$-$L^B$-($L^C$)$_{1-3}$ wherein an $L^C$ is bound to $T^2$;

$L^A$ is selected from: a bond to AB, —NR-(bond to AB), -heteroaryl-(bond to AB),

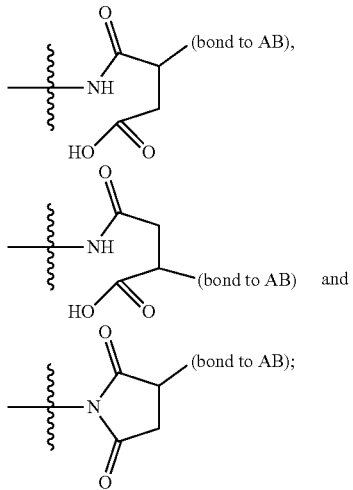

$L^B$ is $L^{B1}$-$L^{B2}$-$L^{B3}$ wherein $L^{B1}$ is absent or is one or more components selected from the group consisting of —C(O)—, —C(S)—, —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-6}$—, —C(O)$C_1$-$C_6$alkylNRC(O)—, —C(O)$C_1$-$C_6$alkyl(OCH$_2$CH$_2$)$_{1-6}$—, —$C_1$-$C_6$alkyl(OCH$_2$CH$_2$)$_{1-6}$-C(O)—, —$C_1$-$C_6$alkyl-S—S—$C_1$-$C_6$alkylNRC(O)CH$_2$—, —$C_1$-$C_6$alkyl(OCH$_2$CH$_2$)$_{1-6}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR-phenyl-O—$C_1$-$C_6$alkyl-C(O)—, —C(O)—$C_1$-$C_6$alkyl(OCH$_2$CH$_2$)$_{1-6}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-6}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl- and (—CH$_2$—CH$_2$—O—)$_{1-20}$;

$L^{B2}$ is AA$_{0-12}$, wherein AA is a natural amino acid- or a non-natural amino acid;

$L^{B3}$ is p-aminobenzoic acid, p-aminobenzyloxycarbonyl, —C(O)(CH$_2$)$_{0-50}$C(O)— or absent;

$L^C$ is absent or is independently selected from the group consisting of —$C_1$-$C_6$alkylene-, —NR$C_3$-$C_3$-heterocyclylNR—, —NR$C_3$-$C_3$-carbocyclylNR—, —NR$C_1$-$C_6$alkylNR—, —NR$C_1$-$C_6$alkylene-, —S—, —NR—, —NRNR—, —O(CR$_2$)$_{1-4}$S—S(CR$_2$)$_{1-4}$N(R)—, —NR$C_1$-$C_6$-alkylenephenyleneNR—, —NR$C_1$-$C_6$alkylenephenyleneSO$_2$NR—, —O$C_1$-$C_6$alkylS-S$C_1$-$C_6$alkylC(COOR)NR—, —NRC(COOR)$C_1$-$C_6$alkylS-S$C_1$-$C_6$alkylO—,

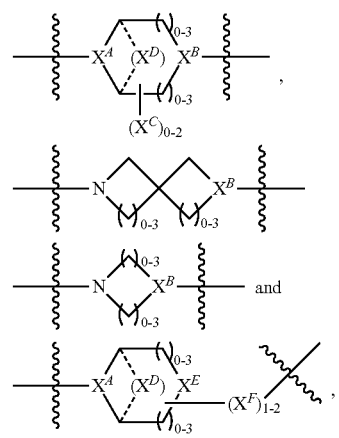

wherein
$X^A$ is CR or N,
$X^B$ is CH, CR(C(R)$_2$)$_{1-3}$NR, CR(C(R)$_2$)$_{1-3}$O, CR(C(R)$_2$)$_{1-3}$C(O)NR, CR—(C(R)$_2$)$_{1-3}$C(O)NRNR, CR(C(R)$_2$)$_{1-3}$SO$_2$NR, CR(C(R)$_2$)$_{1-3}$NRNR, CR(C(R)$_2$)$_{1-3}$NRC(O) or N;
each $X^C$ is R;
each $X^D$ is —(CH$_2$)$_{1-5}$—, or is absent;
$X^E$ is O, S, C(R)$_2$, C(R)(C(R)$_2$)$_{1-3}$—NR$_2$ or NR, and
each $X^F$ is (C(R)$_2$)$_{1-3}$—NR or C(R)$_2$—(C(R)$_2$)$_{1-3}$—O.

3. The method of claim 1 wherein said cancer is bladder cancer, breast cancer, cervical cancer, colon cancer, endometrial cancer, kidney cancer, lung cancer, esophageal cancer, ovarian cancer, prostate cancer, pancreatic cancer, skin cancer, stomach (gastric) cancer, testicular cancer, leukemias or lymphomas.

4. The method of claim 2 wherein said cancer is bladder cancer, breast cancer, cervical cancer, colon cancer, endometrial cancer, kidney cancer, lung cancer, esophageal cancer, ovarian cancer, prostate cancer, pancreatic cancer, skin cancer, stomach (gastric) cancer, testicular cancer, leukemias or lymphomas.

* * * * *